United States Patent
Collins et al.

(10) Patent No.: US 8,530,468 B2
(45) Date of Patent: Sep. 10, 2013

(54) BICYCLYLARYL-ARYL-AMINE COMPOUNDS AND THEIR USE

(75) Inventors: Ian Collins, London (GB); John Charles Reader, Cambridge (GB); David Hugh Williams, Cambridge (GB); Sukhbinder Singh Klair, Cambridge (GB); Jane Elizabeth Scanlon, Cambridge (GB); Nelly Piton, Cambridge (GB); Michael Cherry, Cambridge (GB)

(73) Assignee: Cancer Research Technology Limited, London (GB)

( * ) Notice: Subject to any disclaimer, the term of this patent is extended or adjusted under 35 U.S.C. 154(b) by 138 days.

(21) Appl. No.: 12/918,266

(22) PCT Filed: Feb. 19, 2009

(86) PCT No.: PCT/GB2009/000438
§ 371 (c)(1),
(2), (4) Date: Aug. 18, 2010

(87) PCT Pub. No.: WO2009/103966
PCT Pub. Date: Aug. 27, 2009

(65) Prior Publication Data
US 2010/0331328 A1 Dec. 30, 2010

Related U.S. Application Data

(60) Provisional application No. 61/029,621, filed on Feb. 19, 2008.

(30) Foreign Application Priority Data

Feb. 19, 2008 (GB) .................. 0803018.1

(51) Int. Cl.
*A61K 31/497* (2006.01)
*A61K 31/5377* (2006.01)
*C07D 401/12* (2006.01)
*C07D 401/14* (2006.01)
*C07D 413/14* (2006.01)

(52) U.S. Cl.
USPC .................. 514/235.2; 514/255.05; 544/120; 544/405

(58) Field of Classification Search
None
See application file for complete search history.

(56) References Cited

U.S. PATENT DOCUMENTS

| | | | |
|---|---|---|---|
| 8,058,045 B2 | 11/2011 | Collins et al. | |
| 2010/0311730 A1 | 12/2010 | Collins et al. | |
| 2012/0040967 A1 | 2/2012 | Collins et al. | |

FOREIGN PATENT DOCUMENTS

| | | |
|---|---|---|
| WO | WO 03/032984 | 4/2003 |
| WO | WO 03/035065 | 5/2003 |
| WO | WO 03/093297 | 11/2003 |
| WO | WO 03/101444 | 12/2003 |
| WO | WO 2005/011597 | 2/2005 |
| WO | WO 2005/034869 | 4/2005 |
| WO | WO 2005/037285 | 4/2005 |
| WO | WO 2005/121126 | 12/2005 |
| WO | WO 2006/039718 | 4/2006 |
| WO | WO 2007/000240 | 1/2007 |
| WO | WO 2008/077554 | 7/2008 |
| WO | WO 2008/115369 | 9/2008 |
| WO | WO 2009/044162 | 4/2009 |
| WO | WO 2009/103966 | 8/2009 |

OTHER PUBLICATIONS

Balaint and Vousden, 2001, "Activation and activities of the p53 tumour suppressor protein," *Br. J. Cancer*, vol. 85, pp. 1813-1823.
Bartek and Lukas, 2003, "Chk1 and Chk2 kinases in checkpoint control and cancer," *Cancer Cell*, vol. 3, pp. 421-429.
Carson and Lois, 1995, "Cancer progression and p53," *Lancet*, vol. 346, pp. 1009-1011.
Dixon and Norbury, 2002, "Therapeutic exploitation of checkpoint defects in cancer cells lacking p53 function," *Cell Cycle*, vol. 1, pp. 362-368.
Greenblatt et al., 1994, "Mutations in the p53 tumor suppressor gene: clues to cancer etiology and molecular pathogenesis," *Cancer Res.*, vol. 54, pp. 4855-4878.
Itoh et al., 2002, "Efficient synthesis of substituted 2-aminopyrazines: FeCl3-promoted condensation of hydroxyiminoketones with aminoacetonitriles", *Tetrahedron Lett.*, vol. 43, pp. 9287-9290.

(Continued)

*Primary Examiner* — Emily Bernhardt
(74) *Attorney, Agent, or Firm* — Swanson & Bratschun, L.L.C.

(57) ABSTRACT

The present invention pertains generally to the field of therapeutic compounds, and more specifically to certain bicyclylaryl-aryl-amines compounds of the following formula (referred to herein as BCAA compounds), which, inter alia, inhibit Checkpoint Kinase 1 (CHK1) kinase function. The present invention also pertains to pharmaceutical compositions comprising such compounds, and the use of such compounds and compositions, both in vitro and in vivo, to inhibit CHK1 kinase function, and in the treatment of diseases and conditions that are mediated by CHK1, that are ameliorated by the inhibition of CHK1 kinase function, etc., including proliferative conditions such as cancer, etc., optionally in combination with another agent, for example, (a) a DNA topoisomerase I or II inhibitor; (b) a DNA damaging agent; (c) an antimetabolite or TS inhibitor; (d) a microtubule targeted agent; and (e) ionising radiation:

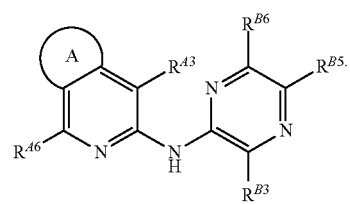

19 Claims, No Drawings

(56) References Cited

OTHER PUBLICATIONS

Liu et al., 2000, "Chk1 is an essential kinase that is regulated by Atr and required for the G(2)/M DNA damage checkpoint," *Genes Dev.*, vol. 14, pp. 1448-1459.

Sanchez et al., 1997, "Conservation of the Chk1 checkpoint pathway in mammals: linkage of DNA damage to Cdk regulation through Cdc25," *Science*, vol. 277, pp. 1497-1501.

Sorensen et al., 2005, "Cell-cycle checkpoint kinase Chk1 is required for mammalian homologous recombination repair," *Nat. Cell Biol.*, vol. 7, pp. 195-201.

Tao and Lin, 2006, "Chk1 inhibitors for novel cancer treatment," *Anti-Cancer Agents in Medicinal Chemistry*, vol. 6, pp. 377-388.

Wang et al., 1996, "UCN-01: a potent abrogator of G2 checkpoint function in cancer cells with disrupted p53," *J. Natl. Cancer Inst.*, vol. 8, pp. 956-965.

Weinert and Hartwell, 1989, "Control of G2 delay by the rad9 gene of *Saccharomyces cerevisiae*," *J. Cell Sci. Suppl.*, vol. 12, pp. 145-148.

White et al., 1967, "Gattermann reaction of 3,5-dimethoxyphenylacetonitrile. Synthesis of 6,8-dioxyisoquinolines" *J. Org. Chem.*, vol. 32, pp. 2689-2692.

Xiao et al., 2006, "Differential roles of checkpoint kinase 1, checkpoint kinase 2, and mitogen-activated protein kinase-activated protein kinase 2 in mediating DNA damage-induced cell cycle arrest: implications for cancer therapy," *Mol. Cancer Ther.*, vol. 5, pp. 1935-1943.

Zachos et al., 2003, "Chk1-deficient tumour cells are viable but exhibit multiple checkpoint and survival defects," *EMBO J.*, vol. 22, pp. 713-723.

Zhao et al., 2002, "Disruption of the checkpoint kinase 1/cell division cycle 25A pathway abrogates ionizing radiation-induced S and G2 checkpoints," *Proc. Natl. Acad. Sci. USA*, vol. 99, pp. 14795-14800.

International Search Report (ISR) and Written Opinion of International Searching Authority (WOISA) for PCT/GB2008/003362.

International Preliminary Report on Patentability (IPRP) for PCT/GB2008/003362.

International Search Report (ISR) and Written Opinion of International Searching Authority (WOISA) for PCT/GB2009/000438, (2010).

International Preliminary Report on Patentability (IPRP) for PCT/GB2009/000438, (2009).

UK Search Report for GB 0719644.7, (2008).

UK Search Report for GB 0803018.1, (2008).

Durola et al., 2007, "A New Family of Biisoquinoline Chelates", *Eur. J. Org. Chem.*, Issue 1, pp. 125-135.

Walton et al., Jan. 2010, "The Preclinical Pharmacology and Therapeutic Activity of the Novel CHK1 Inhibitor SAR-020106", Mol. Cancer Ther., vol. 9, No. 1, pp. 89 100.

BICYCLYLARYL-ARYL-AMINE COMPOUNDS AND THEIR USE

RELATED APPLICATIONS

This application a 35 U.S.C. §371 national phase application of PCT/GB2009/000438, filed Feb. 19, 2009. PCT/GB2009/000438 is a non-provisional application claiming priority to U.S. provisional patent application No. 61/029,621 filed Feb. 19, 2008 and United Kingdom patent application number 0803018.1 filed Feb. 19, 2008. Each of these application is incorporated herein by reference in their entirety.

TECHNICAL FIELD

The present invention pertains generally to the field of therapeutic compounds, and more specifically to certain bicyclylaryl-aryl-amine compounds (referred to herein as BCAA compounds), which, inter alia, inhibit Checkpoint Kinase 1 (CHK1) kinase function. The present invention also pertains to pharmaceutical compositions comprising such compounds, and the use of such compounds and compositions, both in vitro and in vivo, to inhibit CHK1 kinase function, and in the treatment of diseases and conditions that are mediated by CHK1, that are ameliorated by the inhibition of CHK1 kinase function, etc., including proliferative conditions such as cancer, etc., optionally in combination with another agent, for example, (a) a DNA topoisomerase I or II inhibitor; (b) a DNA damaging agent; (c) an antimetabolite or TS inhibitor; (d) a microtubule targeted agent; and (e) ionising radiation.

Incorporated by reference herein in its entirety is the Sequence Listing entitled "Sequence_Listing.txt", created Aug. 17, 2010, size of 1 kilobytes.

BACKGROUND

A number of patents and publications are cited herein in order to more fully describe and disclose the invention and the state of the art to which the invention pertains. Each of these references is incorporated herein by reference in its entirety into the present disclosure, to the same extent as if each individual reference was specifically and individually indicated to be incorporated by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

This disclosure includes information that may be useful in understanding the present invention. It is not an admission that any of the information provided herein is prior art or relevant to the presently claimed invention, or that any publication specifically or implicitly referenced is prior art.

Checkpoint Kinase 1 (CHK1)

Progression through the cell division cycle is a tightly regulated process and is monitored at several positions known as cell cycle checkpoints (see, e.g., Weinert and Hartwell, 1989; Bartek and Lukas, 2003). These checkpoints are found in all four stages of the cell cycle; G1, S (DNA replication), G2 and M (Mitosis) and they ensure that key events which control the fidelity of DNA replication and cell division are completed correctly. Cell cycle checkpoints are activated by a number of stimuli, including DNA damage and DNA errors caused by defective replication. When this occurs, the cell cycle will arrest, allowing time for either DNA repair to occur or, if the damage is too severe, for activation of cellular processes leading to controlled cell death.

All cancers, by definition, have some form of aberrant cell division cycle. Frequently, the cancer cells possess one or more defective cell cycle checkpoints, or harbour defects in a particular DNA repair pathway. These cells are therefore often more dependent on the remaining cell cycle checkpoints and repair pathways, compared to non-cancerous cells (where all checkpoints and DNA repair pathways are intact). The response of cancer cells to DNA damage is frequently a critical determinant of whether they continue to proliferate or activate cell death processes and die. For example, tumour cells that contain a mutant form(s) of the tumour suppressor p53 are defective in the G1 DNA damage checkpoint. Thus inhibitors of the G2 or S-phase checkpoints are expected to further impair the ability of the tumour cell to repair damaged DNA.

Many known cancer treatments cause DNA damage by either physically modifying the cell's DNA or disrupting vital cellular processes that can affect the fidelity of DNA replication and cell division, such as DNA metabolism, DNA synthesis, DNA transcription and microtubule spindle formation. Such treatments include for example, radiotherapy, which causes DNA strand breaks, and a variety of chemotherapeutic agents including topoisomerase inhibitors, antimetabolites, DNA-alkylating agents, and platinum-containing cytotoxic drugs. A significant limitation to these genotoxic treatments is drug resistance. One of the most important mechanisms leading to this resistance is attributed to activation of cell cycle checkpoints, giving the tumour cell time to repair damaged DNA. By abrogating a particular cell cycle checkpoint, or inhibiting a particular form of DNA repair, it may therefore be possible to circumvent tumour cell resistance to the genotoxic agents and augment tumour cell death induced by DNA damage, thus increasing the therapeutic index of these cancer treatments.

CHK1 is a serine/threonine kinase involved in regulating cell cycle checkpoint signals that are activated in response to DNA damage and errors in DNA caused by defective replication (see, e.g., Bartek and Lukas, 2003). CHK1 transduces these signals through phosphorylation of substrates involved in a number of cellular activities including cell cycle arrest and DNA repair. Two key substrates of CHK1 are the Cdc25A and Cdc25C phosphatases that dephosphorylate CDK1 leading to its activation, which is a requirement for exit from G2 into mitosis (M phase) (see, e.g., Sanchez et al., 1997). Phosphorylation of Cdc25C and the related Cdc25A by CHK1 blocks their ability to activate CDK1, thus preventing the cell from exiting G2 into M phase. The role of CHK1 in the DNA damage-induced G2 cell cycle checkpoint has been demonstrated in a number of studies where CHK1 function has been knocked out (see, e.g., Liu et al., 2000; Zhao et al., 2002; Zachos et al., 2003).

The reliance of the DNA damage-induced G2 checkpoint upon CHK1 provides one example of a therapeutic strategy for cancer treatment, involving targeted inhibition of CHK1. Upon DNA damage, the p53 tumour suppressor protein is stabilised and activated to give a p53-dependent G1 arrest, leading to apoptosis or DNA repair (Balaint and Vousden, 2001). Over half of all cancers are functionally defective for p53, which can make them resistant to genotoxic cancer treatments such as ionising radiation (IR) and certain forms of chemotherapy (see, e.g., Greenblatt et al., 1994; Carson and Lois, 1995). These p53 deficient cells fail to arrest at the G1 checkpoint or undergo apoptosis or DNA repair, and consequently may be more reliant on the G2 checkpoint for viability and replication fidelity. Therefore abrogation of the G2 checkpoint through inhibition of the CHK1 kinase function may selectively sensitise p53 deficient cancer cells to genotoxic cancer therapies, and this has been demonstrated (see, e.g., Wang et al., 1996; Dixon and Norbury, 2002).

In addition, CHK1 has also been shown to be involved in S phase cell cycle checkpoints and DNA repair by homologous recombination. Thus, inhibition of CHK1 kinase in those cancers that are reliant on these processes after DNA damage, may provide additional therapeutic strategies for the treatment of cancers using CHK1 inhibitors (see, e.g., Sorensen et al., 2005). Recent data using CHK1 selective siRNA supports the selective inhibition of CHK1 as a relevant therapeutic approach, and suggests that combined inhibition with certain other checkpoint kinases provides no additional benefit and may be non-productive (see, e.g., Xiao et al., 2006). Small-molecule selective inhibitors of CHK1 kinase function from various chemical classes have been described (see, e.g., Tao and Lin, 2006).

SUMMARY OF THE INVENTION

One aspect of the invention pertains to certain bicyclylaryl-aryl-amine compounds (referred to herein as BCAA compounds), as described herein.

Another aspect of the invention pertains to a composition (e.g., a pharmaceutical composition) comprising a BCAA compound, as described herein, and a pharmaceutically acceptable carrier or diluent.

Another aspect of the invention pertains to method of preparing a composition (e.g., a pharmaceutical composition) comprising the step of admixing a BCAA compound, as described herein, and a pharmaceutically acceptable carrier or diluent.

Another aspect of the present invention pertains to a method of inhibiting CHK1 kinase function in a cell, in vitro or in vivo, comprising contacting the cell with an effective amount of a BCAA compound, as described herein.

In one embodiment, the method further comprises contacting the cell with one or more other agents selected from: (a) a DNA topoisomerase I or II inhibitor; (b) a DNA damaging agent; (c) an antimetabolite or TS inhibitor; (d) a microtubule targeted agent; and (e) ionising radiation.

Another aspect of the present invention pertains to a method of regulating (e.g., inhibiting) cell proliferation (e.g., proliferation of a cell), inhibiting cell cycle progression, promoting apoptosis, or a combination of one or more these, in vitro or in vivo, comprising contacting a cell with an effective amount of a BCAA compound, as described herein.

In one embodiment, the method further comprises contacting the cell with one or more other agents selected from: (a) a DNA topoisomerase I or II inhibitor; (b) a DNA damaging agent; (c) an antimetabolite or TS inhibitor; (d) a microtubule targeted agent; and (e) ionising radiation.

Another aspect of the present invention pertains to a method of treatment comprising administering to a subject in need of treatment a therapeutically-effective amount of a BCAA compound, as described herein, preferably in the form of a pharmaceutical composition.

In one embodiment, the method further comprises administering to the subject one or more other agents selected from: (a) a DNA topoisomerase I or II inhibitor; (b) a DNA damaging agent; (c) an antimetabolite or TS inhibitor; (d) a microtubule targeted agent; and (e) ionising radiation.

Another aspect of the present invention pertains to a BCAA compound as described herein for use in a method of treatment of the human or animal body by therapy.

In one embodiment, the method of treatment comprises treatment with both (i) a BCAA compound and (ii) one or more other agents selected from: (a) a DNA topoisomerase I or II inhibitor; (b) a DNA damaging agent; (c) an antimetabolite or TS inhibitor; (d) a microtubule targeted agent; and (e) ionising radiation.

Another aspect of the present invention pertains to use of a BCAA compound, as described herein, in the manufacture of a medicament for use in treatment.

In one embodiment, the treatment comprises treatment with both (i) a medicament comprising a BCAA compound and (ii) one or more other agents selected from: (a) a DNA topoisomerase I or II inhibitor; (b) a DNA damaging agent; (c) an antimetabolite or TS inhibitor; (d) a microtubule targeted agent; and (e) ionising radiation.

In one embodiment, the treatment is treatment of a disease or condition that is mediated by CHK1.

In one embodiment, the treatment is treatment of a disease or condition that is ameliorated by the inhibition of CHK1 kinase function.

In one embodiment, the treatment is treatment of a proliferative condition.

In one embodiment, the treatment is treatment of cancer.

In one embodiment, the treatment is treatment of: p53 negative cancer.

In one embodiment, the treatment is treatment of: lung cancer, breast cancer, ovarian cancer, colorectal cancer, melanoma, or glioma.

Another aspect of the present invention pertains to a kit comprising (a) a BCAA compound, as described herein, preferably provided as a pharmaceutical composition and in a suitable container and/or with suitable packaging; and (b) instructions for use, for example, written instructions on how to administer the compound.

In one embodiment, the kit further comprises one or more other agents selected from: (a) a DNA topoisomerase I or II inhibitor; (b) a DNA damaging agent; (c) an antimetabolite or TS inhibitor; and (d) a microtubule targeted agent.

Another aspect of the present invention pertains to a BCAA compound obtainable by a method of synthesis as described herein, or a method comprising a method of synthesis as described herein.

Another aspect of the present invention pertains to a BCAA compound obtained by a method of synthesis as described herein, or a method comprising a method of synthesis as described herein.

Another aspect of the present invention pertains to novel intermediates, as described herein, which are suitable for use in the methods of synthesis described herein.

Another aspect of the present invention pertains to the use of such novel intermediates, as described herein, in the methods of synthesis described herein.

As will be appreciated by one of skill in the art, features and preferred embodiments of one aspect of the invention will also pertain to other aspect of the invention.

DETAILED DESCRIPTION OF THE INVENTION

Compounds

One aspect of the present invention relates to certain bicyclylaryl-aryl-amines (for convenience, collectively referred to herein as "bicyclylaryl-aryl compounds" or "BCAA compounds") which are related to pyrazin-2-yl-pyridin-2-yl-amines.

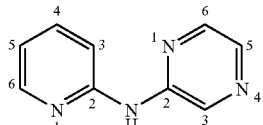

Pyrazin-2-yl-pyridin-2-yl-amine

More particularly, the compounds are related to the following compounds:

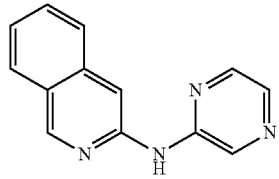

Isoquinolin-3-yl-pyrazin-2-yl-amine

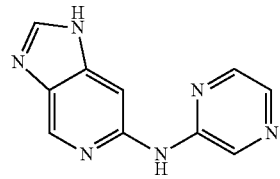

(1H-Imidazo[4,5-c]pyridin-6-yl)-pyrazin-2-yl-amine

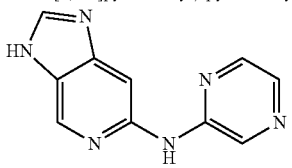

(3H-Imidazo[4,5-c]pyridin-6-yl)-pyrazin-2-yl-amine

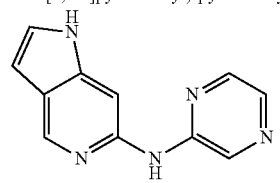

Pyrazin-2-yl-(1H-pyrrolo[3,2-c]pyridin-6-yl)-amine

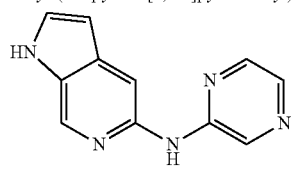

Pyrazin-2-yl-(1H-pyrrolo[2,3-c]pyridin-5-yl)-amine

In one embodiment, the compounds are selected from compounds of the following formula, and pharmaceutically acceptable salts, hydrates, and solvates thereof:

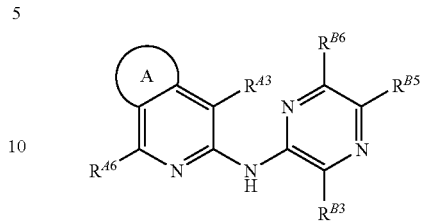

wherein the ring denoted A is independently selected from:

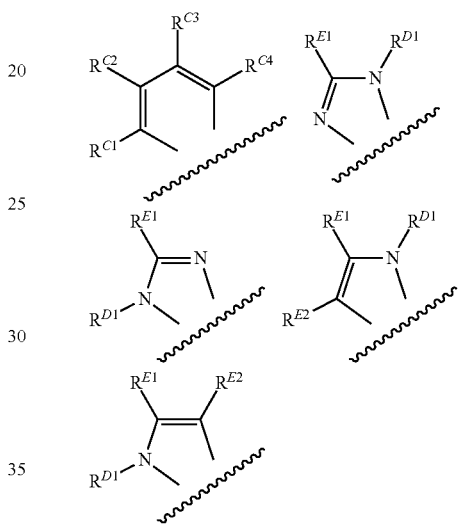

and wherein:
  each of —$R^{C1}$, —$R^{C2}$, —$R^{C3}$, and —$R^{C4}$ is independently —H or -$Q^C$;
  —$R^{D1}$ is independently —H or -$Q^D$;
  each of —$R^{E1}$ and —$R^{E2}$ is independently —H or -$Q^E$;
and wherein:
  —$R^{A3}$ is independently —H or -$Q^{A3}$;
  —$R^{A6}$ is independently —H or -$Q^{A6}$;
  —$R^{B3}$ is independently —H or -$Q^{B3}$;
  —$R^{B5}$ is independently —H or -$Q^{B5}$;
  —$R^{B6}$ is independently —H or -$Q^{B6}$.

Optional Provisos

In one or more aspects of the present invention (e.g., compounds, compositions, compounds for use in therapy, use of compounds in the manufacture of a medicament, methods, methods of treatment, etc.), the compounds are optionally as defined herein, but with one or more optional provisos, as defined herein.

In one embodiment, the proviso is that the compound is not the following compound, which is shown on page 117 (No 197) in WO 2007/000240 and is allegedly useful for the treatment and/or prevention of diseases associated with Rho-kinase and/or Rho-kinase mediated phosphorylation of myosin light chain phosphatase.

| Structure | Name | CAS Registry No. |
|---|---|---|
| 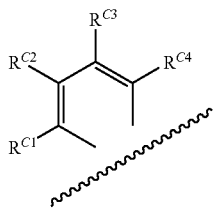 | [6-(Piperidin-4-yloxy)-isoquinolin-3-yl]-pyrazin-2-yl-amine hydrochloride salt | 918490-87-6 |

In one embodiment, the proviso is that the compound is not [6-(piperidin-4-yloxy)-isoquinolin-3-yl]-pyrazin-2-yl-amine hydrochloride salt.

In one embodiment, the proviso is that the compound is not [6-(piperidin-4-yloxy)-isoquinolin-3-yl]-pyrazin-2-yl-amine, or a salt, hydrate, or solvate thereof.

In one or more aspects of the present invention (e.g., compounds for use in therapy, use of compounds in the manufacture of a medicament, methods of treatment, etc.), the compounds are optionally as defined herein, but without the above proviso.

For example, a reference to a particular group of compounds "without the recited proviso" (e.g., for use in therapy) is intended to be a reference to the compounds as defined, but wherein the definition no longer includes the indicated proviso. In such cases, it is as if the indicated proviso has been deleted from the definition of compounds, and the definition has been expanded to encompass those compounds which otherwise would have been excluded by the indicated proviso.

The Fused Ring

In one embodiment, the ring denoted A is independently:

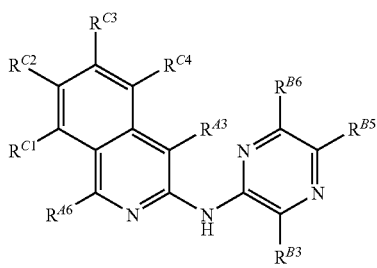

as in, for example:

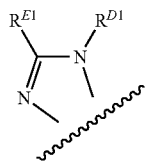

In one embodiment, the ring denoted A is independently selected from:

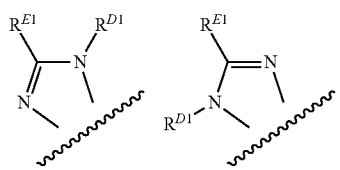

as in, for example:

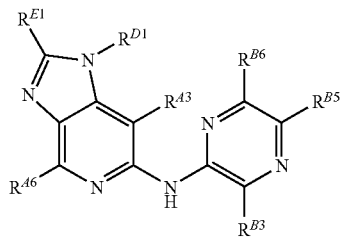

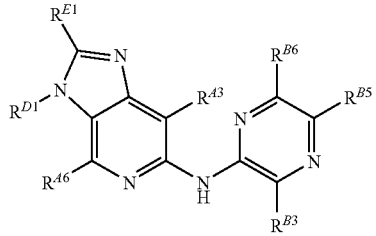

In one embodiment, the ring denoted A is independently:

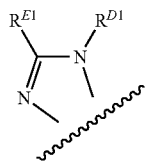

In one embodiment, the ring denoted A is independently:

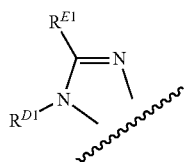

In one embodiment, the ring denoted A is independently selected from:

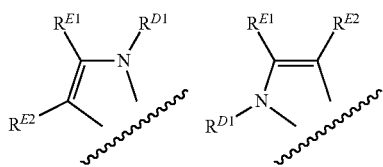

as in, for example:

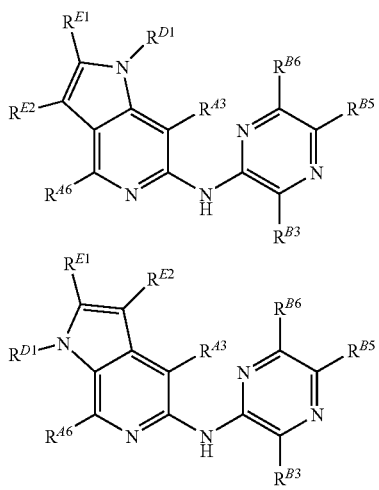

In one embodiment, the ring denoted A is independently:

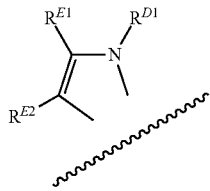

In one embodiment, the ring denoted A is independently:

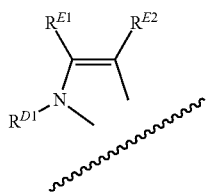

The Group —$R^{A3}$
In one embodiment, —$R^{A3}$ is independently —H or -$Q^{A3}$.
In one embodiment, —$R^{A3}$ is independently —H.
In one embodiment, —$R^{A3}$ is independently -$Q^{A3}$.
The Group —$R^{A6}$
In one embodiment, —$R^{A6}$ is independently —H or -$Q^{A6}$.
In one embodiment, —$R^{A6}$ is independently —H.
In one embodiment, —$R^{A6}$ is independently -$Q^{A6}$.
The Group —$R^{B3}$
In one embodiment, —$R^{B3}$ is independently —H or -$Q^{B3}$.
In one embodiment, —$R^{B3}$ is independently —H.
In one embodiment, —$R^{B3}$ is independently -$Q^{B3}$.

The Group —$R^{B5}$
In one embodiment, —$R^{B5}$ is independently —H or -$Q^{B5}$.
In one embodiment, —$R^{B5}$ is independently —H.
In one embodiment, —$R^{B5}$ is independently -$Q^{B5}$.
The Group —$R^{B6}$
In one embodiment, —$R^{B6}$ is independently —H or -$Q^{B6}$.
In one embodiment, —$R^{B6}$ is independently —H.
In one embodiment, —$R^{B6}$ is independently -$Q^{B6}$.
The Groups —$R^{C1}$, —$R^{C2}$, —$R^{C3}$, and —$R^{C4}$
In one embodiment:
each of —$R^{C1}$, —$R^{C2}$, —$R^{C3}$, and —$R^{C4}$, if present, is independently —H or -$Q^C$.
In one embodiment:
—$R^{C1}$, if present, is independently -$Q^C$; and
each of —$R^{C2}$, —$R^{C3}$, and —$R^{C4}$, if present, is independently —H or -$Q^C$.
In one embodiment:
—$R^{C1}$, if present, is independently -$Q^C$; and
each of —$R^{C2}$, —$R^{C3}$, and —$R^{C4}$, if present, is independently —H;
as in, for example:

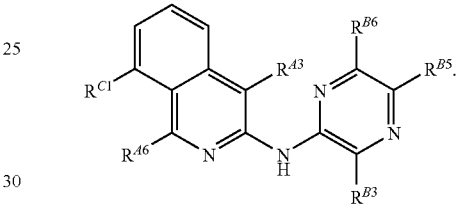

In one embodiment:
—$R^{C3}$, if present, is independently -$Q^C$; and
each of —$R^{C1}$, —$R^{C2}$, and —$R^{C4}$, if present, is independently —H or -$Q^C$.
In one embodiment:
—$R^{C3}$, if present, is independently —H; and
each of —$R^{C1}$, —$R^{C2}$, and —$R^{C4}$, if present, is independently —H or -$Q^C$.
In one embodiment:
—$R^{C3}$, if present, is independently -$Q^C$; and
each of —$R^{C1}$, —$R^{C2}$, and —$R^{C4}$, if present, is independently —H.
In one embodiment:
—$R^{C3}$, if present, is independently —H; and
each of —$R^{C1}$, —$R^{C2}$, and —$R^{C4}$, if present, is independently —H.
In one embodiment:
each of —$R^{C1}$ and —$R^{C3}$, if present, is independently -$Q^C$; and
each of —$R^{C2}$ and —$R^{C4}$, if present, is independently —H or -$Q^C$.
In one embodiment:
each of —$R^{C1}$ and —$R^{C3}$, if present, is independently -$Q^C$; and
each of —$R^{C2}$ and —$R^{C4}$, if present, is independently —H.
In one embodiment:
—$R^{C3}$, if present, is independently —H; and
—$R^{C1}$, if present, is independently -$Q^C$.
each of —$R^{C2}$ and —$R^{C4}$, if present, is independently —H or -$Q^C$.
The Group —$R^{D1}$
In one embodiment, —$R^{D1}$, if present, is independently —H or -$Q^D$.
In one embodiment, —$R^{D1}$, if present, is independently —H.

In one embodiment, —$R^{D1}$, if present, is independently -$Q^D$.

The Groups —$R^{E1}$ and —$R^{E2}$

In one embodiment, each of —$R^{E1}$ and —$R^{E2}$, if present, is independently —H or -$Q^E$.

In one embodiment, —$R^{E1}$, if present, is independently —H or -$Q^E$.

In one embodiment, —$R^{E1}$, if present, is independently —H.

In one embodiment, —$R^{E1}$, if present, is independently -$Q^E$.

In one embodiment, —$R^{E2}$, if present, is independently —H or -$Q^E$.

In one embodiment, —$R^{E2}$, if present, is independently —H.

In one embodiment, —$R^{E2}$, if present, is independently -$Q^E$.

The Group -$Q^{A3}$

In one embodiment, -$Q^{A3}$, if present, is independently:
- —F, —Cl, —Br, —I,
- —$CF_3$, —$OCF_3$,
- —$R^{QA3}$,
- —OH, —$OR^{QA3}$,
- —SH, —$SR^{QA3}$,
- —$NH_2$, —$NHR^{QA3}$, —$NR^{QA3}_2$, or —$NR^{QA3A}R^{QA3B}$;

wherein:
each —$R^{QA3}$ is independently saturated aliphatic $C_{1-6}$alkyl; and
—$NR^{QA3A}R^{QA3B}$ is independently azetidino, pyrrolidino, imidazolidino, pyrazolidino, piperidino, piperazino, morpholino, azepino, or diazepino, and is optionally substituted, for example, with one or more groups selected from saturated aliphatic $C_{1-3}$alkyl, —F, and —$CF_3$.

In one embodiment, -$Q^{A3}$, if present, is independently:
- —F, —Cl, —Br, —I,
- -Me, -Et, -nPr, -iPr,
- —$CF_3$, —$OCF_3$,
- —OH, —OMe, —OEt,
- —SH, —SMe,
- —$NH_2$, —NHMe, or —$NMe_2$.

The Group -$Q^{A6}$

In one embodiment, -$Q^{A6}$; if present, is independently:
- —$CF_3$, —$OCF_3$,
- —$R^{QA6}$,
- —OH, —$OR^{QA6}$,
- —SH, —$SR^{QA6}$,
- —$NH_2$, —$NHR^{QA6}$; —$NR^{QA6}_2$; or —$NR^{QA6A}R^{QA6B}$;

wherein:
each —$R^{QA6}$ is independently saturated aliphatic $C_{1-6}$alkyl; and
—$NR^{QA6A}R^{QA6B}$ is independently azetidino, pyrrolidino, imidazolidino, pyrazolidino, piperidino, piperazino, morpholino, azepino, or diazepino, and is optionally substituted, for example, with one or more groups selected from saturated aliphatic $C_{1-3}$alkyl, —F, and —$CF_3$.

In one embodiment, -$Q^{A6}$, if present, is independently:
- -Me, -Et, -nPr, -iPr,
- —$CF_3$, —$OCF_3$,
- —OH, —OMe, —OEt,
- —SH, —SMe,
- —$NH_2$, —NHMe, or —$NMe_2$.

The Group -$Q^{B3}$

In one embodiment, -$Q^{B3}$, if present, is independently:
- —$CF_3$, —$OCF_3$,
- —$R^{QB3}$,
- —OH, —$OR^{QB3}$,
- —SH, —$SR^{QB3}$,
- —$NH_2$, —$NHR^{QB3}$, —$NR^{QB3}_2$, or —$NR^{QB3A}R^{QB3B}$;

wherein:
each —$R^{QB3}$ is independently saturated aliphatic $C_{1-6}$alkyl; and
—$NR^{QB3A}R^{QB3B}$ is independently azetidino, pyrrolidino, imidazolidino, pyrazolidino, piperidino, piperazino, morpholino, azepino, or diazepino, and is optionally substituted, for example, with one or more groups selected from saturated aliphatic $C_{1-3}$alkyl, —F, and —$CF_3$.

In one embodiment, -$Q^{B3}$, if present, is independently:
- —$OCF_3$,
- -Me, -Et,
- —OH, —OMe, —OEt,
- —SH, —SMe,
- —$NH_2$, —NHMe, or —$NMe_2$.

The Group -$Q^{B5}$

In one embodiment, -$Q^{B5}$, if present, is independently:
- —F, —Cl, —Br, —I,
- —$CF_3$, —$OCF_3$,
- —OH, -$L^{1A}$-OH, —O-$L^{1A}$-OH,
- —$OR^{1A1}$, -$L^{1A}$-$OR^{1A1}$, —O-$L^{1A}$-$OR^{1A1}$,
- —SH, —$SR^{1A1}$,
- —CN,
- —$NO_2$,
- —$NH_2$, —$NHR^{1A1}$, —$NR^{1A1}_2$, —$NR^{1A2}R^{1A3}$,
- -$L^{1A}$-$NH_2$, -$L^{1A}$-$NHR^{1A1}$, -$L^{1A}$-$NR^{1A1}_2$, -$L^{1A}$-$NR^{1A2}R^{1A3}$,
- —O-$L^{1A}$-$NH_2$, —O-$L^{1A}$-$NHR^{1A1}$, —O-$L^{1A}$-$NR^{1A1}_2$, —O-$L^{1A}$-$NR^{1A2}R^{1A3}$,
- —OC(=O)$R^{1A1}$,
- —C(=O)OH, —C(=O)$OR^{1A1}$,
- —C(=O)$R^{1A1}$,
- —C(=O)$NH_2$, —C(=O)$NHR^{1A1}$, —C(=O)$NR^{1A1}_2$, —C(=O)$NR^{1A2}R^{1A3}$,
- —NHC(=O)$R^{1A1}$, —$NR^{1A1}$C(=O)$R^{1A1}$,
- —NHC(=O)$OR^{1A1}$, —$NR^{1A1}$C(=O)$OR^{1A1}$,
- —OC(=O)$NH_2$, —OC(=O)$NHR^{1A1}$, —OC(=O)$NR^{1A1}_2$, —OC(=O)$NR^{1A2}R^{1A3}$,
- —NHC(=O)$NH_2$, —NHC(=O)$NHR^{1A1}$,
- —NHC(=O)$NR^{1A1}_2$, —NHC(=O)$NR^{1A2}R^{1A3}$,
- —$NR^{1A1}$C(=O)$NH_2$, —$NR^{1A1}$C(=O)$NHR^{1A1}$,
- —$NR^{1A1}$C(=O)$NR^{1A1}_2$, —$NR^{1A1}$C(=O)$NR^{1A2}R^{1A3}$,
- —NHS(=O)$_2R^{1A1}$, —$NR^{1A1}$S(=O)$_2R^{1A1}$,
- —S(=O)$_2NH_2$, —S(=O)$_2NHR^{1A1}$, —S(=O)$_2NR^{1A1}_2$, —S(=O)$_2NR^{1A2}R^{1A3}$,
- —S(=O)$R^{1A1}$, —S(=O)$_2R^{1A1}$, —OS(=O)$_2R^{1A1}$, or —S(=O)$_2OR^{1A1}$, wherein:
each -$L^{1A}$- is independently saturated aliphatic $C_{1-5}$alkylene;

in each group —$NR^{1A2}R^{1A3}$, $R^{1A2}$ and $R^{1A3}$, taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O;

each —$R^{1A1}$ is independently:
- —$R^{1B1}$, —$R^{1B2}$, —$R^{1B3}$, —$R^{1B4}$, —$R^{1B5}$, —$R^{1B6}$, —$R^{1B7}$, —$R^{1B8}$,
- -$L^{1B}$-$R^{1B4}$, -$L^{1B}$-$R^{1B5}$, -$L^{1B}$-$R^{1B6}$, -$L^{1B}$-$R^{1B7}$, or -$L^{1B}$-$R^{1B8}$;

each —$R^{1B1}$ is independently saturated aliphatic $C_{1-6}$alkyl;
each —$R^{1B2}$ is independently aliphatic $C_{2-6}$alkenyl;
each —$R^{1B3}$ is independently aliphatic $C_{2-6}$alkynyl;

each —$R^{1B4}$ is independently saturated $C_{3-6}$cycloalkyl;
each —$R^{1B5}$ is independently $C_{3-6}$cycloalkenyl;
each —$R^{1B6}$ is independently non-aromatic $C_{3-8}$heterocyclyl;
each —$R^{1B7}$ is independently $C_{6-10}$-carboaryl;
each —$R^{1B8}$ is independently $C_{5-10}$heteroaryl;
each -$L^{1B}$- is independently saturated aliphatic $C_{1-3}$alkylene;

wherein:
  each —$R^{1B4}$, —$R^{1B5}$, —$R^{1B6}$, —$R^{1B7}$, and —$R^{1B8}$ is optionally substituted, for example, with one or more substituents —$R^{1C1}$ and/or one or more substituents —$R^{1C2}$,
  each —$R^{1B1}$, —$R^{1B2}$, —$R^{1B3}$, and -$L^{1B}$- is optionally substituted, for example, with one or more substituents —$R^{1C2}$, and wherein:
  each —$R^{1C1}$ is independently saturated aliphatic $C_{1-4}$alkyl, phenyl, or benzyl;
  each —$R^{1C2}$ is independently:
    —F, —Cl, —Br, —I,
    —$CF_3$, —$OCF_3$,
    —OH, -$L^{1D}$-OH, —O-$L^{1D}$-OH,
    —$OR^{1D1}$, -$L^{1D}$-$OR^{1D1}$, —O-$L^{1D}$-$OR^{1D1}$,
    —SH, —$SR^{1D1}$,
    —CN,
    —$NO_2$,
    —$NH_2$, —$NHR^{1D1}$, —$NR^{1D1}{}_2$, —$NR^{1D2}R^{1D3}$,
    -$L^{1D}$-$NH_2$, -$L^{1D}$-$NHR^{1D1}$, -$L^{1D}$-$NR^{1D1}{}_2$, -$L^{1D}$-$NR^{1D2}R^{1D3}$,
    —C(=O)OH, —C(=O)$OR^{1D1}$,
    —C(=O)$NH_2$, —C(=O)$NHR^{1D1}$, —C(=O)$NR^{1D1}{}_2$, or —C(=O)$NR^{1D2}R^{1D3}$;

wherein:
  each —$R^{1D1}$ is independently saturated aliphatic $C_{1-4}$alkyl, phenyl, or benzyl;
  each -$L^{1D}$- is independently saturated aliphatic $C_{1-5}$alkylene; and
  in each group —$NR^{1D2}R^{1D3}$, $R^{1D2}$ and $R^{1D3}$, taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O.

In one embodiment, -$Q^{B5}$, if present, is independently:
  —$R^{1A1}$,
  —$CF_3$, —$OCF_3$,
  —OH, -$L^{1A}$-OH, —O-$L^{1A}$-OH,
  —$OR^{1A1}$, -$L^{1A}$-$OR^{1A1}$, —O-$L^{1A}$-$OR^{1A1}$,
  —CN,
  —$NO_2$,
  —$NH_2$, —$NHR^{1A1}$, —$NR^{1A1}{}_2$, —$NR^{1A2}R^{1A3}$,
  -$L^{1A}$-$NH_2$, -$L^{1A}$-$NHR^{1A1}$, -$L^{1A}$-$NR^{1A1}{}_2$, -$L^{1A}$-$NR^{1A2}R^{1A3}$,
  —O-$L^{1A}$-$NH_2$, —O-$L^{1A}$-$NHR^{1A1}$, —O-$L^{1A}$-$NR^{1A1}{}_2$, —O-$L^{1A}$-$NR^{1A2}R^{1A3}$,
  —OC(=O)$R^{1A1}$,
  —C(=O)OH, —C(=O)$OR^{1A1}$,
  —C(=O)$NH_2$, —C(=O)$NHR^{1A1}$, —C(=O)$NR^{1A1}{}_2$, —C(=O)$NR^{1A2}R^{1A3}$,
  —NHC(=O)$R^{1A1}$, or —$NR^{1A1}$C(=O)$R^{1A1}$.

In one embodiment, -$Q^{B5}$, if present, is independently:
  —$R^{1B1}$,
  —$R^{1B8}$,
  —$CF_3$,
  —OH, -$L^{1A}$-OH, —O-$L^{1A}$-OH,
  —$OR^{1A1}$, -$L^{1A}$-$OR^{1A1}$, —O-$L^{1A}$-$OR^{1A1}$,
  —CN,
  —OC(=O)$R^{1A1}$,
  —C(=O)OH, —C(=O)$OR^{1A1}$,
  —C(=O)$NH_2$, —C(=O)$NHR^{1A1}$, —C(=O)$NR^{1A1}{}_2$,
  —C(=O)$NR^{1A2}R^{1A3}$,
  —NHC(=O)$R^{1A1}$, or —$NR^{1A1}$C(=O)$R^{1A1}$.

In one embodiment, -$Q^{B5}$, if present, is independently:
  —$R^{1B1}$,
  —$OR^{1A1}$,
  —CN,
  —C(=O)$NH_2$, —C(=O)$NHR^{1A1}$, —C(=O)$NR^{1A1}{}_2$, or —C(=O)$NR^{1A2}R^{1A3}$.

In one embodiment, -$Q^{B5}$, if present, is independently —CN.

In one embodiment, -$Q^{B5}$, if present, is independently —C(=O)$NH_2$, —C(=O)$NHR^{1A1}$, —C(=O)$NR^{1A1}{}_2$, or —C(=O)$NR^{1A2}R^{1A3}$.

In one embodiment, -$Q^{B5}$, if present, is independently —C(=O)$NH_2$.

In one embodiment, -$Q^{B5}$, if present, is independently —$R^{1B1}$.

In one embodiment, -$Q^{B5}$, if present, is independently -Me.

In one embodiment, -$Q^{B5}$, if present, is independently —$R^{1B8}$.

In one embodiment, -$Q^{B5}$, if present, is independently —$OR^{1A1}$.

In one embodiment, -$Q^{B5}$, if present, is independently —OMe.

In one embodiment, each -$L^{1A}$-, if present, is independently —$(CH_2)_{n1}$—, wherein n1 is independently 1 to 4.

In one embodiment, each -$L^{1A}$-, if present, is independently —$CH_2$— or —$CH_2CH_2$—.

In one embodiment, each —$NR^{1A2}R^{1A3}$, if present, is independently azetidino, pyrrolidino, imidazolidino, pyrazolidino, piperidino, piperazino, morpholino, azepino, or diazepino, and is optionally substituted, for example, with one or more groups selected from $C_{1-3}$alkyl, —$CF_3$, and —F.

In one embodiment, each —$NR^{1A2}R^{1A3}$, if present, is independently pyrrolidino, piperidino, piperazino, or morpholino, and is optionally substituted, for example, with one or more groups selected from $C_{1-3}$alkyl, —$CF_3$, and —F.

In one embodiment, each —$R^{1A1}$, if present, is independently:
  —$R^{1B1}$, —$R^{1B4}$, —$R^{1B6}$, —$R^{1B7}$, —$R^{1B8}$,
  -$L^{1B}$-$R^{1B4}$, -$L^{1B}$-$R^{1B6}$, -$L^{1B}$-$R^{1B7}$, or -$L^{1B}$-$R^{1B8}$.

In one embodiment, each —$R^{1A1}$, if present, is independently:
  —$R^{1B1}$, —$R^{1B7}$, —$R^{1B8}$,
  -$L^{1B}$-$R^{1B7}$, or -$L^{1B}$-$R^{1B8}$.

In one embodiment, each —$R^{1A1}$, if present, is independently:
  —$R^{1B1}$, —$R^{1B7}$, or -$L^{1B}$-$R^{1B7}$.

In one embodiment, each —$R^{1A1}$, if present, is independently:
  —$R^{1B7}$, —$R^{1B8}$, -$L^{1B}$-$R^{1B7}$, or -$L^{1B}$-$R^{1B8}$.

In one embodiment, each —$R^{1B6}$, if present, is independently azetidinyl, pyrrolidinyl, imidazolidinyl, pyrazolidinyl, piperidinyl, piperazinyl, morpholinyl, azepinyl, diazepinyl, tetrahydrofuranyl, tetrahydropyranyl, dioxanyl, and is optionally substituted.

In one embodiment, each —$R^{1B6}$, if present, is independently pyrrolidinyl, piperidinyl, piperazinyl, morpholinyl, tetrahydrofuranyl, or tetrahydropyranyl, and is optionally substituted.

In one embodiment, each —$R^{1B7}$, if present, is independently phenyl, and is optionally substituted.

In one embodiment, each —$R^{1B8}$, if present, is independently $C_{5-6}$heteroaryl, and is optionally substituted.

In one embodiment, each —$R^{1B8}$, if present, is independently furanyl, thienyl, pyrrolyl, imidazolyl, pyrazolyl, triazolyl, oxazolyl, isoxazolyl, thiazolyl, isothiazolyl, pyridyl, pyrimidinyl, or pyridazinyl, and is optionally substituted.

In one embodiment, each —$R^{1B8}$, if present, is independently $C_{9-10}$heteroaryl, and is optionally substituted.

In one embodiment, each —$R^{1B8}$, if present, is independently benzofuranyl, benzothienyl, benzopyrrolyl, benzoimidazolyl, benzopyrazolyl, benzotriazolyl, benzoxazolyl, benzoisoxazolyl, benzothiazolyl, benzoisothiazolyl, benzopyridyl, benzopyrimidinyl, or benzopyridazinyl, and is optionally substituted.

In one embodiment, each -$L^{1B}$-, if present, is independently —$CH_2$— or —$CH_2CH_2$—.

In one embodiment, each -$L^{1B}$-, if present, is independently —$CH_2$—.

In one embodiment, each —$R^{1C1}$, if present, is independently saturated aliphatic $C_{1-4}$alkyl.

In one embodiment, each —$R^{1C2}$ is independently:
—F, —Cl, —Br, —I,
—OH,
—$OR^{1D1}$,
—CN,
—$NO_2$,
—$NH_2$, —$NHR^{1D1}$, —$NR^{1D1}{}_2$, or —$NR^{1D2}R^{1D3}$.

In one embodiment, each —$R^{1D1}$, if present, is independently saturated aliphatic $C_{1-4}$alkyl.

In one embodiment, each -$L^{1D}$-, if present, is independently —$(CH_2)_{m1}$—, wherein m1 is independently 1 to 4.

In one embodiment, each -$L^{1D}$-, if present, is independently —$CH_2$— or —$CH_2CH_2$—.

In one embodiment, each —$NR^{1D2}R^{1D3}$, if present, is independently azetidino, pyrrolidino, imidazolidino, pyrazolidino, piperidino, piperazino, morpholino, azepino, or diazepino, and is optionally substituted, for example, with one or more groups selected from $C_{1-3}$alkyl, —$CF_3$, and —F.

In one embodiment, each —$NR^{1D2}R^{1D3}$, if present, is independently pyrrolidino, piperidino, piperazino, or morpholino, and is optionally substituted, for example, with one or more groups selected from $C_{1-3}$alkyl, —$CF_3$, and —F.

In one embodiment, -$Q^{B5}$, if present, is independently:
—CN, —$OR^{X4}$, —$R^{X4}$, —$C(=O)NH_2$, —$C(=O)NHR^{X4}$, or —$C(=O)NR^{X4}{}_2$;
wherein each $R^{X4}$ is independently saturated aliphatic $C_{1-4}$alkyl.

In one embodiment, -$Q^{B5}$, if present, is independently —CN, —OMe, -Me, or —$C(=O)NH_2$.

The Group -$Q^{B6}$

In one embodiment, -$Q^{B6}$ is independently —O—$R^{QB6}$, —S—$R^{QB6}$, or —$NR^{BN}$—$R^{QB6}$.

In one embodiment, -$Q^{B6}$ is independently —O—$R^{QB6}$.

In one embodiment, -$Q^{B6}$ is independently —S—$R^{QB6}$.

In one embodiment, -$Q^{B6}$ is independently —$NR^{BN}$—$R^{QB6}$.

In one embodiment, —$R^{BN}$, if present, is independently —H or saturated aliphatic $C_{1-4}$alkyl.

In one embodiment, —$R^{BN}$, if present, is independently —H or -Me.

In one embodiment, —$R^{BN}$, if present, is independently —H.

The Group —$R^{QB6}$

In one embodiment, —$R^{QB6}$, if present, is independently:
—$R^{4A1}$,
-$L^{4A}$-OH, -$L^{4A}$-$OR^{4A1}$,
-$L^{4A}$-$NH_2$, -$L^{4A}$-$NHR^{4A1}$, -$L^{4A}$-$NR^{4A1}{}_2$, or -$L^{4A}$-$NR^{4A2}R^{4A3}$, wherein:
each -$L^{4A}$- is independently saturated aliphatic $C_{2-6}$alkylene;

in each group —$NR^{4A2}R^{4A3}$, $R^{4A2}$ and $R^{4A3}$, taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O;

each —$R^{4A1}$ is independently:
—$R^{4B1}$, —$R^{4B2}$, —$R^{4B3}$, —$R^{4B4}$, —$R^{4B5}$, —$R^{4B6}$, —$R^{4B7}$, —$R^{4B8}$,
-$L^{4B}$-$R^{4B4}$, -$L^{4B}$-$R^{4B5}$, -$L^{4B}$-$R^{4B6}$, -$L^{4B}$-$R^{4B7}$, or -$L^{4B}$-$R^{4B8}$;

each —$R^{4B1}$ is independently saturated aliphatic $C_{1-6}$alkyl;
each —$R^{4B2}$ is independently aliphatic $C_{2-6}$alkenyl;
each —$R^{4B3}$ is independently aliphatic $C_{2-6}$alkynyl;
each —$R^{4B4}$ is independently saturated $C_{3-6}$cycloalkyl;
each —$R^{4B5}$ is independently $C_{3-6}$cycloalkenyl;
each —$R^{4B6}$ is independently non-aromatic $C_{3-8}$heterocyclyl;
each —$R^{4B7}$ is independently $C_{6-10}$-carboaryl;
each —$R^{4B8}$ is independently $C_{5-10}$heteroaryl;
each -$L^{4B}$- is independently saturated aliphatic $C_{1-3}$alkylene;

wherein:
each —$R^{4B4}$, —$R^{4B5}$, —$R^{4B6}$, —$R^{4B7}$, and —$R^{4B8}$ is optionally substituted, for example, with one or more substituents —$R^{4C1}$ and/or one or more substituents —$R^{4C2}$;

each —$R^{4B1}$, —$R^{4B2}$, —$R^{4B3}$, and -$L^{4B}$- is optionally substituted, for example, with one or more substituents —$R^{4C2}$, and wherein:
each —$R^{4C1}$ is independently saturated aliphatic $C_{1-4}$alkyl, phenyl, or benzyl;
each —$R^{4C2}$ is independently:
—F, —Cl, —Br, —I,
—$CF_3$, —$OCF_3$,
—OH, -$L^{4D}$-OH, —O-$L^{4D}$-OH,
—$OR^{4D1}$, -$L^{4D}$-$OR^{4D1}$, —O-$L^{4D}$-$OR^{4D1}$,
—SH, —$SR^{4D1}$,
—CN,
—$NO_2$,
—$NH_2$, —$NHR^{4D1}$, —$NR^{4D1}{}_2$, —$NR^{4D2}R^{4D3}$,
-$L^{4D}$-$NH_2$, -$L^{4D}$-$NHR^{4D1}$, -$L^{4D}$-$NR^{4D1}{}_2$, -$L^{4D}$-$NR^{4D2}R^{4D3}$,
—$C(=O)OH$, —$C(=O)OR^{4D1}$,
—$C(=O)NH_2$, —$C(=O)NHR^{4D1}$, —$C(=O)NR^{4D1}{}_2$, or —$C(=O)NR^{4D2}R^{4D3}$;

wherein:
each —$R^{4D1}$ is independently saturated aliphatic $C_{1-4}$alkyl, phenyl, or benzyl;
each -$L^{4D}$- is independently saturated aliphatic $C_{1-3}$alkylene; and
in each group —$NR^{4D2}R^{4D3}$, $R^{4D2}$ and $R^{4D3}$, taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O.

In one embodiment, —$R^{QB6}$, if present, is independently:
-$L^{4A}$-OH, -$L^{4A}$-$OR^{4A1}$, -L$^{4A}$-NH$_2$, -L$^{4A}$-NHR$^{4A1}$, -L$^{4A}$-NR$^{4A1}$$_2$, or -L$^{4A}$-NR$^{4A2}$R$^{4A3}$.

In one embodiment, —R$^{QB6}$, if present, is independently:
-L$^{4A}$-OH or -L$^{4A}$-OR$^{4A1}$.

In one embodiment, —R$^{QB6}$, if present, is independently:
-L$^{4A}$-NH$_2$, -L$^{4A}$-NHR$^{4A1}$, -L$^{4A}$-NR$^{4A1}$$_2$, or -L$^{4A}$-NR$^{4A2}$R$^{4A3}$.

In one embodiment, —R$^{QB6}$, if present, is independently —R$^{4A1}$.

In one embodiment, each -L$^{4A}$-, if present, is independently —(CH$_2$)$_{n4}$—, wherein n4 is independently 2 to 6.

In one embodiment, each -L$^{4A}$-, if present, is independently —CH$_2$CH$_2$—, —CH$_2$CH$_2$CH$_2$—, or —CH$_2$CH$_2$CH$_2$CH$_2$—.

In one embodiment, each —NR$^{4A2}$R$^{4A3}$, if present, is independently azetidino, pyrrolidino, imidazolidino, pyrazolidino, piperidino, piperazino, morpholino, azepino, diazepino, or oxazepino, and is optionally substituted, for example, with one or more groups selected from C$_{1-3}$alkyl, —CF$_3$, and —F.

In one embodiment, each —NR$^{4A2}$R$^{4A3}$, if present, is independently pyrrolidino, piperidino, piperazino, or morpholino, and is optionally substituted, for example, with one or more groups selected from C$_{1-3}$alkyl, —CF$_3$, and —F.

In one embodiment, each —R$^{4A1}$, if present, is independently:
—R$^{4B1}$, —R$^{4B4}$, —R$^{4B6}$, —R$^{4B7}$, —R$^{4B8}$,
-L$^{4B}$-R$^{4B4}$, -L$^{4B}$-R$^{4B6}$, -L$^{4B}$-R$^{4B7}$, or -L$^{4B}$-R$^{4B8}$.

In one embodiment, each —R$^{4A1}$, if present, is independently:
—R$^{4B1}$, —R$^{4B7}$, —R$^{4B8}$,
-L$^{4B}$-R$^{4B7}$, or -L$^{4B}$-R$^{4B8}$.

In one embodiment, each —R$^{4A1}$, if present, is independently:
—R$^{4B1}$, —R$^{4B7}$, or -L$^{4B}$-R$^{4B7}$.

In one embodiment, each —R$^{4A1}$, if present, is independently:
—R$^{4B7}$, —R$^{4B8}$, -L$^{4B}$-R$^{4B7}$, or -L$^{4B}$-R$^{4B8}$.

In one embodiment, each —R$^{4A1}$, if present, is independently —R$^{4B6}$ or -L$^{4B}$-R$^{4B6}$.

For example, in one embodiment, —R$^{QB6}$, if present, is independently —R$^{4A1}$, wherein —R$^{4A1}$ is —R$^{4B6}$ or -L$^{4B}$-R$^{4B6}$.

In one embodiment, each —R$^{4B6}$, if present, is independently a C$_{3-8}$heterocyclyl group that is a 4-, 5-, 6-, or 7-membered non-aromatic monocyclic ring or a 7-, 8-, or 9-membered non-aromatic bicyclic ring, said ring having exactly 1 ring heteroatom or exactly 2 ring heteroatoms, wherein each of said ring heteroatoms is independently N, O, or S; and is optionally substituted.

In one embodiment, each —R$^{4B6}$, if present, is independently azetidinyl, pyrrolidinyl, imidazolidinyl, pyrazolidinyl, piperidinyl, piperazinyl, morpholinyl, azepinyl, diazepinyl, oxetanyl, tetrahydrofuranyl, tetrahydropyranyl, dioxanyl, oxazepanyl, 3-aza-bicyclo[3.2.1]octanyl, 8-aza-bicyclo[3.2.1]octanyl, 3,8-diaza-bicyclo[3.2.1]octanyl, 3-aza-bicyclo[3.1.1]heptanyl, 6-aza-bicyclo[3.1.1]heptanyl, 3,6-diaza-bicyclo[3.1.1]heptanyl, 2-azabicyclo[2.2.2]octanyl, 1-azabicyclo[2.2.1]heptanyl, quinuclidinyl, or 9-azabicyclo[3.3.1]nonanyl; and is optionally substituted.

For convenience, the structures of the following groups are illustrated:

 

8-Aza-bicyclo[3.2.1]octane    6-Aza-bicyclo[3.1.1]heptane

 

2-Aza-bicyclo[2.2.2]octane    3,8-Diaza-bicyclo[3.2.1]octane

 

3,6-Diaza-bicyclo[3.1.1]heptane    1-Aza-bicyclo[2.2.1]heptane

 

3-Aza-bicyclo[3.2.1]octane    3-Aza-bicyclo[3.1.1]heptane

 

Quinuclidine    9-Aza-bicyclo[3.3.1]nonane

In one embodiment, each —R$^{4B6}$, if present, is independently pyrrolidinyl, piperidinyl, piperazinyl, morpholinyl, tetrahydrofuranyl, tetrahydropyranyl, oxazepanyl, 8-aza-bicyclo[3.2.1]octanyl, or quinuclidinyl, and is optionally substituted.

In one embodiment, each —R$^{4B6}$, if present, is independently pyrrolidinyl, piperidinyl, or morpholinyl; and is optionally substituted.

In one embodiment, each —R$^{4B7}$, if present, is independently phenyl, and is optionally substituted.

In one embodiment, each —R$^{4B8}$, if present, is independently C$_{5-6}$heteroaryl, and is optionally substituted.

In one embodiment, each —R$^{4B8}$, if present, is independently furanyl, thienyl, pyrrolyl, imidazolyl, pyrazolyl, triazolyl, oxazolyl, isoxazolyl, thiazolyl, isothiazolyl, pyridyl, pyrimidinyl, or pyridazinyl, and is optionally substituted.

In one embodiment, each —R$^{4B8}$, if present, is independently C$_{9-10}$heteroaryl, and is optionally substituted.

In one embodiment, each —R$^{4B8}$, if present, is independently benzofuranyl, benzothienyl, benzopyrrolyl, benzoimidazolyl, benzopyrazolyl, benzotriazolyl, benzoxazolyl, benzoisoxazolyl, benzothiazolyl, benzoisothiazolyl, benzopyridyl, benzopyrimidinyl, or benzopyridazinyl, and is optionally substituted.

In one embodiment, each -L$^{4B}$-, if present, is independently —CH$_2$— or —CH$_2$CH$_2$—.

In one embodiment, each -L$^{4B}$-, if present, is independently —CH$_2$—.

In one embodiment, each —R$^{4C1}$, if present, is independently saturated aliphatic C$_{1-4}$alkyl.

In one embodiment, each —R$^{4C2}$ is independently:
—F, —Cl, —Br, —I,
—OH,
—OR$^{4D1}$,
—CN,
—NO$_2$,
—NH$_2$, —NHR$^{4D1}$, —NR$^{4D1}$$_2$, or —NR$^{4D2}$R$^{4D3}$.

In one embodiment, each —R$^{4D1}$, if present, is independently saturated aliphatic C$_{1-4}$alkyl.

In one embodiment, each -L$^{4D}$-, if present, is independently —(CH$_2$)$_{m1}$—, wherein m1 is independently 1 to 4.

In one embodiment, each -L$^{4D}$-, if present, is independently —CH$_2$— or —CH$_2$CH$_2$—.

In one embodiment, each —NR$^{4D2}$R$^{4D3}$, if present, is independently azetidino, pyrrolidino, imidazolidino, pyrazolidino, piperidino, piperazino, morpholino, azepino, or diazepino, and is optionally substituted, for example, with one or more groups selected from C$_{1-3}$alkyl, —CF$_3$, and —F.

In one embodiment, each —NR$^{4D2}$R$^{4D3}$, if present, is independently pyrrolidino, piperidino, piperazino, or morpholino, and is optionally substituted, for example, with one or more groups selected from C$_{1-3}$alkyl, —CF$_3$, and —F.

In one embodiment, —R$^{QB6}$, if present, is independently selected from groups of the following formulae, wherein p1 is independently 1, 2, 3, or 4; p2 is independently 1, 2, 3, or 4; p3 is independently 0, 1, or 2; and p4 is independently 1, 2, 3, or 4:

(B6-1)

R$^{NN1}$R$^{NN1}$N—(  )$_{p1}$ (B6-1B)

R$^{NN1}$R$^{NN1}$N—(  )$_{p1}$ (B6-2)

R$^{NN1}$O—(  )$_{p2}$ (B6-3)

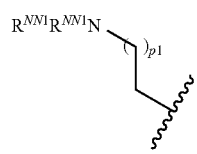

(B6-4)

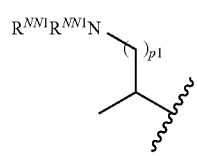

(B6-5)

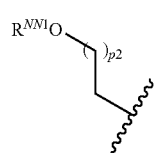

(B6-6)

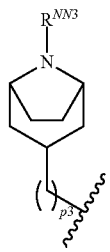

(B6-6)

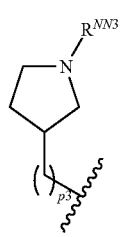

(B6-7)

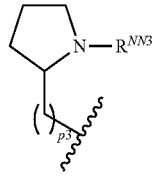

(B6-8)

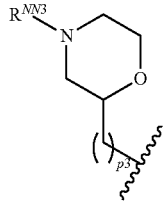

(B6-9)

(B6-10)

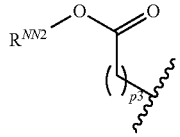

(B6-11)

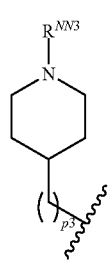

(B6-12)

In one embodiment, —R$^{QB6}$, if present, is independently a group of formula (B6-1).

In one embodiment, —R$^{QB6}$, if present, is independently a group of formula (B6-1B).

In one embodiment, —$R^{QB6}$, if present, is independently a group of formula (B6-2).
In one embodiment, —$R^{QB6}$, if present, is independently a group of formula (B6-3).
In one embodiment, —$R^{QB6}$, if present, is independently a group of formula (B6-4).
In one embodiment, —$R^{QB6}$, if present, is independently a group of formula (B6-5).
In one embodiment, —$R^{QB6}$, if present, is independently a group of formula (B6-6).
In one embodiment, —$R^{QB6}$, if present, is independently a group of formula (B6-7).
In one embodiment, —$R^{QB6}$, if present, is independently a group of formula (B6-8).
In one embodiment, —$R^{QB6}$, if present, is independently a group of formula (B6-9).
In one embodiment, —$R^{QB6}$, if present, is independently a group of formula (B6-10).
In one embodiment, —$R^{QB6}$, if present, is independently a group of formula (B6-11).
In one embodiment, —$R^{QB6}$, if present, is independently a group of formula (B6-12).

In one embodiment, p1, if present, is independently 1.
In one embodiment, p3, if present, is independently 0.
In one embodiment, p3, if present, is independently 1 or 2.
In one embodiment, p4, if present, is independently 1.
In one embodiment, each —$R^{NN1}$, if present, is independently —H, saturated aliphatic $C_{1-4}$alkyl, phenyl, or benzyl; or, the group —$NR^{NN1}R^{NN1}$, if present, is independently azetidino, pyrrolidino, imidazolidino, pyrazolidino, piperidino, piperazino, morpholino, azepino, or diazepino, and is optionally substituted, for example, with one or more groups selected from $C_{1-3}$alkyl, —$CF_3$, and —F.
In one embodiment, each —$R^{NN1}$, if present, is independently —H, saturated aliphatic $C_{1-4}$alkyl, phenyl, or benzyl; or, the group —$NR^{NN1}R^{NN1}$, if present, is independently pyrrolidino, piperidino, piperazino, or morpholino, and is optionally substituted, for example, with one or more groups selected from $C_{1-3}$alkyl, —$CF_3$, and —F.
In one embodiment, each —$R^{NN1}$, if present, is independently —H, saturated aliphatic $C_{1-4}$alkyl, phenyl, or benzyl.
In one embodiment, each —$R^{NN1}$, if present, is independently —H or saturated aliphatic $C_{1-4}$alkyl.
In one embodiment, each —$R^{NN1}$, if present, is independently —H or -Me.
In one embodiment, each —$R^{NN1}$, if present, is independently —H.
In one embodiment, each —$R^{NN2}$, if present, is independently —H or saturated aliphatic $C_{1-4}$alkyl.
In one embodiment, each —$R^{NN2}$, if present, is independently —H or -Me.
In one embodiment, each —$R^{NN2}$, if present, is independently —H.
In one embodiment, each —$R^{NN3}$, if present, is independently —H, saturated aliphatic $C_{1-4}$alkyl, phenyl, or benzyl.
In one embodiment, each —$R^{NN3}$, if present, is independently —H or saturated aliphatic $C_{1-4}$alkyl.
In one embodiment, each —$R^{NN3}$, if present, is independently —H or -Me.
In one embodiment, each —$R^{NN3}$, if present, is independently —H.
In one embodiment, each —$R^{NN3}$, if present, is independently -Me.
In one embodiment, —$R^{NN4}$, if present, is independently saturated aliphatic $C_{1-6}$alkyl.
In one embodiment, —$R^{NN4}$, if present, is independently saturated aliphatic $C_{1-4}$alkyl.

The Groups -$Q^C$ and -$Q^E$

In one embodiment, each -$Q^C$, if present, and each -$Q^E$, if present, is independently selected from:
—$R^{2A1}$,
—F, —Cl, —Br, —I,
—$CF_3$, —$OCF_3$,
—OH, -$L^{2A}$-OH, —O-$L^{2A}$-OH, —NH-$L^{2A}$-OH, —$NR^{2A1}$-$L^{2A}$-OH,
—$OR^{2A1}$, -$L^{2A}$-$OR^{2A1}$, —O-$L^{2A}$-$OR^{2A1}$, —NH-$L^{2A}$-$OR^{2A1}$, —$NR^{2A1}$-$L^{2A}$-$OR^{2A1}$,
—SH, —$SR^{2A1}$,
—CN,
—$NO_2$,
—$NH_2$, —$NHR^{2A1}$, —$NR^{2A1}_2$, —$NR^{2A2}R^{2A3}$,
-$L^{2A}$-$NH_2$, -$L^{2A}$-$NHR^{2A1}$, -$L^{2A}$-$NR^{2A1}_2$, -$L^{2A}$-$NR^{2A2}R^{2A3}$,
—O-$L^{2A}$-$NH_2$, —O-$L^{2A}$-$NHR^{2A1}$, —O-$L^{2A}$-$NR^{2A1}_2$, —O-$L^{2A}$-$NR^{2A2}R^{2A3}$,
—NH-$L^{2A}$-$NH_2$, —$NR^{2A1}$-$L^{2A}$-$NH_2$, —NH-$L^{2A}$-$NHR^{2A1}$, —$NR^{2A1}$-$L^{2A}$-$NHR^{2A1}$,
—NH-$L^{2A}$-$NR^{2A1}_2$, —$NR^{2A1}$-$L^{2A}$-$NR^{2A1}_2$,
—NH-$L^{2A}$-$NR^{2A2}R^{2A3}$, —$NR^{2A1}$-$L^{2A}$-$NR^{2A2}R^{2A3}$,
—OC(=O)$R^{2A1}$,
—C(=O)OH, —C(=O)$OR^{2A1}$,
—C(=O)$R^{2A1}$,
—C(=O)$NH_2$, —C(=O)$NHR^{2A1}$, —C(=O)$NR^{2A1}_2$, —C(=O)$NR^{2A2}R^{2A3}$,
—C(=O)NH-$L^{2A}$-OH, —C(=O)NH-$L^{2A}$-$OR^{2A1}$,
—C(=O)NH-$L^{2A}$-$NH_2$, —C(=O)NH-$L^{2A}$-$NHR^{2A1}$,
—C(=O)NH-$L^{2A}$-$NR^{2A1}_2$, —C(=O)NH-$L^{2A}$-$NR^{2A2}R^{2A3}$,
—NHC(=O)$R^{2A1}$, —$NR^{2A1}$C(=O)$R^{2A1}$,
—NHC(=O)-$L^{2A}$-OH, —NHC(=O)-$L^{2A}$-$OR^{2A1}$,
—NHC(=O)-$L^{2A}$-$NH_2$, —NHC(=O)-$L^{2A}$-$NHR^{2A1}$,
—NHC(=O)-$L^{2A}$-$NR^{2A1}_2$, —NHC(=O)-$L^{2A}$-$NR^{2A2}R^{2A3}$,
—NHC(=O)$OR^{2A1}$, —$NR^{2A1}$C(=O)$OR^{2A1}$,
—OC(=O)$NH_2$, —OC(=O)$NHR^{2A1}$, —OC(=O)$NR^{2A1}_2$, —OC(=O)$NR^{2A2}R^{2A3}$,
—NHC(=O)$NH_2$, —NHC(=O)$NHR^{2A1}$,
—NHC(=O)$NR^{2A1}_2$, —NHC(=O)$NR^{2A2}R^{2A3}$,
—$NR^{2A1}$C(=O)$NH_2$, —$NR^{2A1}$C(=O)$NHR^{2A1}$,
—$NR^{2A1}$C(=O)$NR^{2A1}_2$, —$NR^{2A1}$C(=O)$NR^{2A2}R^{2A3}$,
—NHS(=O)$_2R^{2A1}$, —$NR^{2A1}$S(=O)$_2R^{2A1}$,
—S(=O)$_2NH_2$, —S(=O)$_2NHR^{2A1}$, —S(=O)$_2NR^{2A1}_2$, —S(=O)$_2NR^{2A2}R^{2A3}$,
—S(=O)$R^{2A1}$, —S(=O)$_2R^{2A1}$, —OS(=O)$_2R^{2A1}$, and —S(=O)$_2OR^{2A1}$;

wherein:

each -$L^{2A}$- is independently saturated aliphatic $C_{1-5}$alkylene;
in each group —$NR^{2A2}R^{2A3}$, $R^{2A2}$ and $R^{2A3}$, taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O;
each —$R^{2A1}$ is independently:
—$R^{2B1}$, —$R^{2B2}$, —$R^{2B3}$, —$R^{2B4}$, —$R^{2B5}$, —$R^{2B6}$, —$R^{2B7}$, —$R^{2B8}$,
-$L^{2B}$-$R^{2B4}$, -$L^{2B}$-$R^{2B5}$, -$L^{2B}$-$R^{2B6}$, -$L^{2B}$-$R^{2B7}$, or -$L^{2B}$-$R^{2B8}$;
each —$R^{2B1}$ is independently saturated aliphatic $C_{1-6}$alkyl,
each —$R^{2B2}$ is independently aliphatic $C_{2-6}$alkenyl;
each —$R^{2B3}$ is independently aliphatic $C_{2-6}$alkynyl;
each —$R^{2B4}$ is independently saturated $C_{3-6}$cycloalkyl;
each —$R^{2B5}$ is independently $C_{3-6}$cycloalkenyl;

each —$R^{2B6}$ is independently non-aromatic $C_{3-8}$heterocyclyl;
each —$R^{2B7}$ is independently $C_{6-10}$carboaryl;
each —$R^{2B8}$ is independently $C_{5-10}$heteroaryl;
each -$L^{2B}$- is independently saturated aliphatic $C_{1-3}$alkylene;

wherein:
  each —$R^{2B4}$, —$R^{2B5}$, —$R^{2B6}$, —$R^{2B7}$, and —$R^{2B8}$ is optionally substituted, for example, with one or more substituents —$R^{2C1}$ and/or one or more substituents —$R^{2C2}$,
  each —$R^{2B1}$, —$R^{2B2}$, —$R^{2B3}$, and -$L^{2B}$- is optionally substituted, for example, with one or more substituents —$R^{2C2}$, and wherein:
  each —$R^{2C1}$ is independently saturated aliphatic $C_{1-4}$alkyl, phenyl, or benzyl;
  each —$R^{2C2}$ is independently:
    —F, —Cl, —Br, —I,
    —$CF_3$, —$OCF_3$,
    —OH, -$L^{2D}$-OH, —O-$L^{2D}$-OH,
    —$OR^{2D1}$, -$L^{2D}$-$OR^{2D1}$, —O-$L^{2D}$-$OR^{2D1}$,
    —SH, —$SR^{2D1}$,
    —CN,
    —$NO_2$,
    —$NH_2$, —$NHR^{2D1}$, —$NR^{2D1}_2$, —$NR^{2D2}R^{2D3}$,
    -$L^{2D}$-$NH_2$, -$L^{2D}$-$NHR^{2D1}$, -$L^{2D}$-$NR^{2D1}_2$, -$L^{2D}$-$NR^{2D2}R^{2D3}$,
    —C(=O)OH, —C(=O)$OR^{2D1}$,
    —C(=O)$NH_2$, —C(=O)$NHR^{2D1}$, —C(=O)$NR^{2D1}_2$, or —C(=O)$NR^{2D2}R^{2D3}$;

wherein:
  each —$R^{2D1}$ is independently saturated aliphatic $C_{1-4}$alkyl, phenyl, or benzyl;
  each -$L^{2D}$- is independently saturated aliphatic $C_{1-5}$alkylene; and
  in each group —$NR^{2D2}R^{2D3}$, $R^{2D2}$ and $R^{2D3}$, taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O.

In one embodiment, each -$Q^C$, if present, and each -$Q^E$, if present, is independently selected from:
—$R^{2A1}$,
—F, —Cl, —Br, —I,
—$CF_3$, —$OCF_3$,
—OH, -$L^{2A}$-OH, —O-$L^{2A}$-OH, —NH-$L^{2A}$-OH, —$NR^{2A1}$-$L^{2A}$-OH,
—$OR^{2A1}$, -$L^{2A}$-$OR^{2A1}$, —O-$L^{2A}$-$OR^{2A1}$, —NH-$L^{2A}$-$OR^{2A1}$, —$NR^{2A1}$-$L^{2A}$-$OR^{2A1}$,
—CN,
—$NH_2$, —$NHR^{2A1}$, —$NR^{2A1}_2$, —$NR^{2A2}R^{2A3}$,
-$L^{2A}$-$NH_2$, -$L^{2A}$-$NHR^{2A1}$, -$L^{2A}$-$NR^{2A1}_2$, -$L^{2A}$-$NR^{2A2}R^{2A3}$,
—O-$L^{2A}$-$NH_2$, —O-$L^{2A}$-$NHR^{2A1}$, —O-$L^{2A}$-$NR^{2A1}_2$, —O-$L^{2A}$-$NR^{2A2}R^{2A3}$,
—NH-$L^{2A}$-$NH_2$, —$NR^{2A1}$-$L^{2A}$-$NH_2$, —NH-$L^{2A}$-$NHR^{2A1}$, —$NR^{2A1}$-$L^{2A}$-$NHR^{2A1}$,
—NH-$L^{2A}$-$NR^{2A1}_2$, —$NR^{2A1}$-$L^{2A}$-$NR^{2A1}_2$,
—NH-$L^{2A}$-$NR^{2A2}R^{2A3}$, —$NR^{2A1}$-$L^{2A}$-$NR^{2A2}R^{2A3}$,
—OC(=O)$R^{2A1}$,
—C(=O)OH, —C(=O)$OR^{2A1}$,
—C(=O)$NH_2$, —C(=O)$NHR^{2A1}$, —C(=O)$NR^{2A1}_2$, —C(=O)$NR^{2A2}R^{2A3}$,
—C(=O)NH-$L^{2A}$-OH, —C(=O)NH-$L^{2A}$-$OR^{2A1}$,
—C(=O)NH-$L^{2A}$-$NH_2$, —C(=O)NH-$L^{2A}$-$NHR^{2A1}$,
—C(=O)NH-$L^{2A}$-$NR^{2A1}_2$, —C(=O)NH-$L^{2A}$-$NR^{2A2}R^{2A3}$,
—NHC(=O)$R^{2A1}$, —$NR^{2A1}$C(=O)$R^{2A1}$,
—NHC(=O)-$L^{2A}$-OH, —NHC(=O)-$L^{2A}$-$OR^{2A1}$,
—NHC(=O)-$L^{2A}$-$NH_2$, —NHC(=O)-$L^{2A}$-$NHR^{2A1}$,
—NHC(=O)-$L^{2A}$-$NR^{2A1}_2$, —NHC(=O)-$L^{2A}$-$NR^{2A2}R^{2A3}$,
—NHC(=O)$NH_2$, —NHC(=O)$NHR^{2A1}$,
—NHC(=O)$NR^{2A1}_2$, —NHC(=O)$NR^{2A2}R^{2A3}$,
—$NR^{2A1}$C(=O)$NH_2$, —$NR^{2A1}$C(=O)$NHR^{2A1}$,
—$NR^{2A1}$C(=O)$NR^{2A1}_2$, —$NR^{2A1}$C(=O)$NR^{2A2}R^{2A3}$,
—NHS(=O)$_2R^{2A1}$, —$NR^{2A1}$S(=O)$_2R^{2A1}$,
—S(=O)$_2NH_2$, —S(=O)$_2NHR^{2A1}$, —S(=O)$_2NR^{2A1}_2$,
—S(=O)$_2NR^{2A2}R^{2A3}$,
—S(=O)$R^{2A1}$, —S(=O)$_2R^{2A1}$, —OS(=O)$_2R^{2A1}$, and —S(=O)$_2OR^{2A1}$.

In one embodiment, each -$Q^C$, if present, and each -$Q^E$, if present, is independently selected from:
—$R^{2A1}$,
—F, —Cl, —Br, —I,
—$CF_3$, —$OCF_3$,
—OH, -$L^{2A}$-OH, —O-$L^{2A}$-OH, —NH-$L^{2A}$-OH,
—$OR^{2A1}$, -$L^{2A}$-$OR^{2A1}$, —O-$L^{2A}$-$OR^{2A1}$, —NH-$L^{2A}$-$OR^{2A1}$,
—CN,
—$NH_2$, —$NHR^{2A1}$, —$NR^{2A1}_2$, —$NR^{2A2}R^{2A3}$,
-$L^{2A}$-$NH_2$, -$L^{2A}$-$NHR^{2A1}$, -$L^{2A}$-$NR^{2A1}_2$, -$L^{2A}$-$NR^{2A2}R^{2A3}$,
—O-$L^{2A}$-$NH_2$, —O-$L^{2A}$-$NHR^{2A1}$, —O-$L^{2A}$-$NR^{2A1}_2$,
—O-$L^{2A}$-$NR^{2A2}R^{2A3}$,
—NH-$L^{2A}$-$NH_2$, —NH-$L^{2A}$-$NHR^{2A1}$, —NH-$L^{2A}$-$NR^{2A1}_2$, —NH-$L^{2A}$-$NR^{2A2}R^{2A3}$,
—OC(=O)$R^{2A1}$,
—C(=O)OH, —C(=O)$OR^{2A1}$,
—C(=O)$NH_2$, —C(=O)$NHR^{2A1}$, —C(=O)$NR^{2A1}_2$, —C(=O)$NR^{2A2}R^{2A3}$,
—C(=O)NH-$L^{2A}$-OH, —C(=O)NH-$L^{2A}$-$OR^{2A1}$,
—C(=O)NH-$L^{2A}$-$NH_2$, —C(=O)NH-$L^{2A}$-$NHR^{2A1}$,
—C(=O)NH-$L^{2A}$-$NR^{2A1}_2$, —C(=O)NH-$L^{2A}$-$NR^{2A2}R^{2A3}$,
—NHC(=O)$R^{2A1}$, —$NR^{2A1}$C(=O)$R^{2A1}$,
—NHC(=O)-$L^{2A}$-OH, —NHC(=O)-$L^{2A}$-$OR^{2A1}$,
—NHC(=O)-$L^{2A}$-$NH_2$, —NHC(=O)-$L^{2A}$-$NHR^{2A1}$,
—NHC(=O)-$L^{2A}$-$NR^{2A1}_2$, and —NHC(=O)-$L^{2A}$-$NR^{2A2}R^{2A3}$.

In one embodiment, each -$Q^C$, if present, is independently selected from:
—$R^{2A1}$,
—F, —Cl, —Br, —I,
—$CF_3$, —$OCF_3$,
—OH, -$L^{2A}$-OH, —O-$L^{2A}$-OH, —NH-$L^{2A}$-OH,
—$OR^{2A1}$, -$L^{2A}$-$OR^{2A1}$, —O-$L^{2A}$-$OR^{2A1}$, —NH-$L^{2A}$-$OR^{2A1}$,
—CN,
—$NO_2$,
—$NH_2$, —$NHR^{2A1}$, —$NR^{SA1}_2$, —$NR^{2A2}R^{2A3}$,
-$L^{2A}$-$NH_2$, -$L^{2A}$-$NHR^{2A1}$, -$L^{2A}$-$NR^{2A1}_2$, -$L^{2A}$-$NR^{2A2}R^{2A3}$,
—O-$L^{2A}$-$NH_2$, —O-$L^{2A}$-$NHR^{2A1}$, —O-$L^{2A}$-$NR^{2A1}_2$,
—O-$L^{2A}$-$NR^{2A2}R^{2A3}$,
—NH-$L^{2A}$-$NH_2$, —NH-$L^{2A}$-$NHR^{2A1}$, —NH-$L^{2A}$-$NR^{2A1}_2$, —NH-$L^{2A}$-$NR^{2A2}R^{2A3}$,
—OC(=O)$R^{2A1}$,
—C(=O)OH, —C(=O)$OR^{2A1}$,
—C(=O)$NH_2$, —C(=O)$NHR^{2A1}$, —C(=O)$NR^{2A1}_2$,
—C(=O)$NR^{2A2}R^{2A3}$,
—C(=O)NH-$L^{2A}$-OH, —C(=O)NH-$L^{2A}$-$OR^{2A1}$,
—C(=O)NH-$L^{2A}$-$NH_2$, —C(=O)NH-$L^{2A}$-$NHR^{2A1}$, —C(=O)NH-L$^{2A}$-NR$^{2A1}$$_2$, —C(=O)NH-L$^{2A}$-NR$^{2A2}$R$^{2A3}$,
—NHC(=O)R$^{2A1}$, —NR$^{2A1}$C(=O)R$^{2A1}$,
—NHC(=O)-L$^{2A}$-OH, —NHC(=O)-L$^{2A}$-OR$^{2A1}$,
—NHC(=O)-L$^{2A}$-NH$_2$, —NHC(=O)-L$^{2A}$-NHR$^{2A1}$,
—NHC(=O)-L$^{2A}$-NR$^{2A1}$$_2$, —NHC(=O)-L$^{2A}$-NR$^{2A2}$R$^{2A3}$,
—NHC(=O)NH$_2$, —NHC(=O)NHR$^{2A1}$,
—NHC(=O)NR$^{2A1}$$_2$, —NHC(=O)NR$^{2A2}$R$^{2A3}$,
—NR$^{2A1}$C(=O)NH$_2$, —NR$^{2A1}$C(=O)NHR$^{2A1}$,
—NR$^{2A1}$C(=O)NR$^{2A1}$$_2$, —NR$^{2A1}$C(=O)NR$^{2A2}$R$^{2A3}$,
—NHS(=O)$_2$R$^{2A1}$, —NR$^{2A1}$S(=O)$_2$R$^{2A1}$,
—S(=O)$_2$NH$_2$, —S(=O)$_2$NHR$^{2A1}$, —S(=O)$_2$NR$^{2A1}$$_2$,
—S(=O)$_2$NR$^{2A2}$R$^{2A3}$,
—S(=O)R$^{2A1}$, —S(=O)$_2$R$^{2A1}$, —OS(=O)$_2$R$^{2A1}$, and
—S(=O)$_2$OR$^{2A1}$.

In one embodiment, each -Q$^C$, if present, is independently selected from:
—R$^{2A1}$, —F, —Cl, —Br, —I, —CF$_3$, —OCF$_3$,
—OH, -L$^{2A}$-OH, —O-L$^{2A}$-OH, —NH-L$^{2A}$-OH,
—OR$^{2A1}$, -L$^{2A}$-OR$^{2A1}$, —O-L$^{2A}$-OR$^{2A1}$, —NH-L$^{2A}$-OR$^{2A1}$,
—NH$_2$, —NHR$^{2A1}$, —NR$^{2A1}$$_2$, —NR$^{2A2}$R$^{2A3}$,
-L$^{2A}$-NH$_2$, -L$^{2A}$-NHR$^{2A1}$, -L$^{2A}$-NR$^{2A1}$$_2$, -L$^{2A}$-NR$^{2A2}$R$^{2A3}$,
—O-L$^{2A}$-NH$_2$, —O-L$^{2A}$-NHR$^{2A1}$, —O-L$^{2A}$-NR$^{2A1}$$_2$,
—O-L$^{2A}$-NR$^{2A2}$R$^{2A3}$,
—NH-L$^{2A}$-NH$_2$, —NH-L$^{2A}$-NHR$^{2A1}$, —NH-L$^{2A}$-NR$^{2A1}$$_2$, —NH-L$^{2A}$-NR$^{2A2}$R$^{2A3}$,
—C(=O)NH$_2$, —C(=O)NHR$^{2A1}$, —C(=O)NR$^{2A1}$$_2$,
—C(=O)NR$^{2A2}$R$^{2A3}$,
—C(=O)NH-L$^{2A}$-OH, —C(=O)NH-L$^{2A}$-OR$^{2A1}$,
—C(=O)NH-L$^{2A}$-NH$_2$, —C(=O)NH-L$^{2A}$-NHR$^{2A1}$,
—C(=O)NH-L$^{2A}$-NR$^{2A1}$$_2$, —C(=O)NH-L$^{2A}$-NR$^{2A2}$R$^{2A3}$,
—NHC(=O)R$^{2A1}$, —NR$^{2A1}$C(=O)R$^{2A1}$,
—NHC(=O)-L$^{2A}$-OH, —NHC(=O)-L$^{2A}$-OR$^{2A1}$,
—NHC(=O)-L$^{2A}$-NH$_2$, —NHC(=O)-L$^{2A}$-NHR$^{2A1}$,
—NHC(=O)-L$^{2A}$-NR$^{2A1}$$_2$, and —NHC(=O)-L$^{2A}$-NR$^{2A2}$R$^{2A3}$.

In one embodiment, each -Q$^C$, if present, is independently selected from:
—R$^{2A1}$, —F, —Cl, —Br, —I, —CF$_3$, —OCF$_3$,
—OH, -L$^{2A}$-OH, —O-L$^{2A}$-OH, —NH-L$^{2A}$-OH,
—OR$^{2A1}$, -L$^{2A}$-OR$^{2A1}$, —O-L$^{2A}$-OR$^{2A1}$, —NH-L$^{2A}$-OR$^{2A1}$,
—NH$_2$, —NHR$^{2A1}$, —NR$^{2A1}$$_2$, —NR$^{2A2}$R$^{2A3}$,
-L$^{2A}$-NH$_2$, -L$^{2A}$-NHR$^{2A1}$, -L$^{2A}$-NR$^{2A1}$$_2$, -L$^{2A}$-NR$^{2A2}$R$^{2A3}$,
—O-L$^{2A}$-NH$_2$, —O-L$^{2A}$-NHR$^{2A1}$, —O-L$^{2A}$-NR$^{2A1}$$_2$,
—O-L$^{2A}$-NR$^{2A2}$R$^{2A3}$,
—NH-L$^{2A}$-NH$_2$, —NH-L$^{2A}$-NHR$^{2A1}$, —NH-L$^{2A}$-NR$^{2A1}$$_2$, and —NH-L$^{2A}$-NR$^{2A2}$R$^{2A3}$.

In one embodiment, each -Q$^C$, if present, is independently selected from:
—R$^{2A1}$, —F, —Cl, —Br, —I, —CF$_3$, —OCF$_3$,
—NH-L$^{2A}$-OH, —NH-L$^{2A}$-OR$^{2A1}$,
—NH-L$^{2A}$-NH$_2$, —NH-L$^{2A}$-NHR$^{2A1}$, —NH-L$^{2A}$-NR$^{2A1}$$_2$, and —NH-L$^{2A}$-NR$^{2A2}$R$^{2A3}$.

In one embodiment, each -Q$^E$, if present, is independently selected from:
—R$^{2A1}$,
—CF$_3$,
—OH, -L$^{2A}$-OH, —O-L$^{2A}$-OH,
—OR$^{2A1}$, -L$^{2A}$-OR$^{2A1}$, —O-L$^{2A}$-OR$^{2A1}$,
—CN,
—NH$_2$, —NHR$^{2A1}$, —NR$^{2A1}$$_2$, —NR$^{2A2}$R$^{2A3}$,
-L$^{2A}$-NH$_2$, -L$^{2A}$-NHR$^{2A1}$, -L$^{2A}$-NR$^{2A1}$$_2$, -L$^{2A}$-NR$^{2A2}$R$^{2A3}$,
—C(=O)OH, —C(=O)OR$^{2A1}$,
—C(=O)R$^{2A1}$,
—C(=O)NH$_2$, —C(=O)NHR$^{2A1}$, —C(=O)NR$^{2A1}$$_2$,
—C(=O)NR$^{2A2}$R$^{2A3}$,
—NHC(=O)R$^{2A1}$, —NR$^{2A1}$C(=O)R$^{2A1}$,
—NHC(=O)NH$_2$, —NHC(=O)NHR$^{2A1}$,
—NHC(=O)NR$^{2A1}$$_2$, —NHC(=O)NR$^{2A2}$R$^{2A3}$,
—NR$^{2A1}$C(=O)NH$_2$, —NR$^{2A1}$C(=O)NHR$^{2A1}$,
—NR$^{2A1}$C(=O)NR$^{2A1}$$_2$, —NR$^{2A1}$C(=O)NR$^{2A2}$R$^{2A3}$,
—NHS(=O)$_2$R$^{2A1}$, —NR$^{2A1}$S(=O)$_2$R$^{2A1}$,
—S(=O)$_2$NH$_2$, —S(=O)$_2$NHR$^{2A1}$, —S(=O)$_2$NR$^{2A1}$$_2$,
—S(=O)$_2$NR$^{2A2}$R$^{2A3}$,
—S(=O)R$^{2A1}$, —S(=O)$_2$R$^{2A1}$, —OS(=O)$_2$R$^{2A1}$, and
—S(=O)$_2$OR$^{2A1}$.

In one embodiment, each -Q$^E$, if present, is independently selected from:
—R$^{2A1}$
—CF$_3$,
—OH, -L$^{2A}$-OH, —O-L$^{2A}$-OH,
—OR$^{2A1}$, -L$^{2A}$-OR$^{2A1}$, —O-L$^{2A}$-OR$^{2A1}$,
—CN,
—NH$_2$, —NHR$^{2A1}$, —NR$^{2A1}$$_2$, —NR$^{2A2}$R$^{2A3}$,
-L$^{2A}$-NH$_2$, -L$^{2A}$-NHR$^{2A1}$, -L$^{2A}$-NR$^{2A1}$$_2$, -L$^{2A}$-NR$^{2A2}$R$^{2A3}$,
—C(=O)OH, —C(=O)OR$^{2A1}$,
—C(=O)NH$_2$, —C(=O)NHR$^{2A1}$, —C(=O)NR$^{2A1}$$_2$,
and —C(=O)NR$^{2A2}$R$^{2A3}$.
—NHC(=O)R$^{2A1}$, and —NR$^{2A1}$C(=O)R$^{2A1}$.

In one embodiment, each -Q$^E$, if present, is independently selected from:
—R$^{2A1}$
—CF$_3$,
—OH, -L$^{2A}$-OH, —O-L$^{2A}$-OH,
—OR$^{2A1}$, -L$^{2A}$-OR$^{2A1}$, —O-L$^{2A}$-OR$^{2A1}$,
—CN,
—NH$_2$, —NHR$^{2A1}$, —NR$^{2A1}$$_2$, —NR$^{2A2}$R$^{2A3}$,
-L$^{2A}$-NH$_2$, -L$^{2A}$-NHR$^{2A1}$, -L$^{2A}$-NR$^{2A1}$$_2$, -L$^{2A}$-NR$^{2A2}$R$^{2A3}$,
—C(=O)OH, —C(=O)OR$^{2A1}$,
—C(=O)NH$_2$, —C(=O)NHR$^{2A1}$, —C(=O)NR$^{2A1}$$_2$,
and —C(=O)NR$^{2A2}$R$^{2A3}$.

In one embodiment, each -L$^{2A}$-, if present, is independently —(CH$_2$)$_{n2}$—, wherein n2 is independently 1 to 4.

In one embodiment, each -L$^{2A}$-, if present, is independently —CH$_2$— or —CH$_2$CH$_2$—.

In one embodiment, each —NR$^{2A2}$R$^{2A3}$, if present, is independently azetidino, pyrrolidino, imidazolidino, pyrazolidino, piperidino, piperazino, morpholino, azepino, or diazepino, and is optionally substituted, for example, with one or more groups selected from C$_{1-3}$alkyl, —CF$_3$, and —F.

In one embodiment, each —NR$^{2A2}$R$^{2A3}$, if present, is independently pyrrolidino, piperidino, piperazino, or morpholino, and is optionally substituted, for example, with one or more groups selected from C$_{1-3}$alkyl, —CF$_3$, and —F.

In one embodiment, each —R$^{2A1}$, if present, is independently:
—R$^{2B1}$, —R$^{2B4}$, —R$^{2B6}$, —R$^{2B7}$, —R$^{2B8}$,
-L$^{2B}$-R$^{2B4}$, -L$^{2B}$-R$^{2B6}$, -L$^{2B}$-R$^{2B7}$, or -L$^{2B}$-R$^{2B8}$.

In one embodiment, each —R$^{2A1}$, if present, is independently:
—R$^{2B1}$, —R$^{2B7}$, —R$^{2B8}$,
-L$^{2B}$-R$^{2B7}$, or -L$^{2B}$-R$^{2B8}$.

In one embodiment, each —R$^{2A1}$, if present, is independently:
—R$^{2B1}$, —R$^{2B7}$, or -L$^{2B}$-R$^{2B7}$.

In one embodiment, each —R$^{2A1}$, if present, is independently:
—R$^{2B7}$, —R$^{2B8}$, -L$^{2B}$-R$^{2B7}$, or -L$^{2B}$-R$^{2B8}$.

In one embodiment, each —R$^{2B6}$, if present, is independently azetidinyl, pyrrolidinyl, imidazolidinyl, pyrazolidinyl, piperidinyl, piperazinyl, morpholinyl, azepinyl, diazepinyl, tetrahydrofuranyl, tetrahydropyranyl, dioxanyl, and is optionally substituted.

In one embodiment, each —$R^{2B6}$, if present, is independently pyrrolidinyl, piperidinyl, piperazinyl, morpholinyl, tetrahydrofuranyl, or tetrahydropyranyl, and is optionally substituted.

In one embodiment, each —$R^{2B7}$, if present, is independently phenyl, and is optionally substituted.

In one embodiment, each —$R^{2B8}$, if present, is independently $C_{5-6}$heteroaryl, and is optionally substituted.

In one embodiment, each —$R^{2B8}$, if present, is independently furanyl, thienyl, pyrrolyl, imidazolyl, pyrazolyl, triazolyl, oxazolyl, isoxazolyl, thiazolyl, isothiazolyl, pyridyl, pyrimidinyl, or pyridazinyl, and is optionally substituted.

In one embodiment, each —$R^{2B8}$, if present, is independently $C_{9-10}$heteroaryl, and is optionally substituted.

In one embodiment, each —$R^{2B8}$, if present, is independently benzofuranyl, benzothienyl, benzopyrrolyl, benzoimidazolyl, benzopyrazolyl, benzotriazolyl, benzoxazolyl, benzoisoxazolyl, benzothiazolyl, benzoisothiazolyl, benzopyridyl, benzopyrimidinyl, or benzopyridazinyl, and is optionally substituted.

In one embodiment, each -$L^{2B}$-, if present, is independently —$CH_2$— or —$CH_2CH_2$—.

In one embodiment, each -$L^{2B}$-, if present, is independently —$CH_2$—.

In one embodiment, each —$R^{2C1}$, if present, is independently saturated aliphatic $C_{1-4}$alkyl.

In one embodiment, each —$R^{2C2}$ is independently:
—F, —Cl, —Br, —I,
—OH,
—$OR^{2D1}$,
—CN,
—$NO_2$,
—$NH_2$, —$NHR^{2D1}$, —$NR^{2D1}{}_2$, or —$NR^{2D2}R^{2D3}$.

In one embodiment, each —$R^{2D1}$, if present, is independently saturated aliphatic $C_{1-4}$alkyl.

In one embodiment, each -$L^{2D}$-, if present, is independently —$(CH_2)_{m2}$—, wherein m2 is independently 1 to 4.

In one embodiment, each -$L^{2D}$-, if present, is independently —$CH_2$— or —$CH_2CH_2$—.

In one embodiment, each —$NR^{2D2}R^{2D3}$, if present, is independently azetidino, pyrrolidino, imidazolidino, pyrazolidino, piperidino, piperazino, morpholino, azepino, or diazepino, and is optionally substituted, for example, with one or more groups selected from $C_{1-3}$alkyl, —$CF_3$, and —F.

In one embodiment, each —$NR^{2D2}R^{2D3}$, if present, is independently pyrrolidino, piperidino, piperazino, or morpholino, and is optionally substituted, for example, with one or more groups selected from $C_{1-3}$alkyl, —$CF_3$, and —F.

In one embodiment, each -$Q^C$, if present, is independently selected from:
—$R^{X1}$,
—F, —Cl, —Br, —I,
—$CF_3$, —$OCF_3$,
—OH, —$OR^{X1}$,
—$NH_2$, —$NHR^{X1}$, —$NR^{X1}{}_2$, —$R^{M1}$,
—O—$(CH_2)_z$—OH, —O—$(CH_2)_z$—$OR^{X1}$,
—O—$(CH_2)_z$—$NH_2$, —O—$(CH_2)_z$—$NHR^{X1}$, —O—$(CH_2)_z$—$NR^{X1}{}_2$, —O—$(CH_2)_z$—$R^{M1}$,
—NH—$(CH_2)_z$—OH, —NH—$(CH_2)_z$—$OR^{X1}$,
—NH—$(CH_2)_z$—$NH_2$, —NH—$(CH_2)_z$—$NHR^{X1}$,
—NH—$(CH_2)_z$—$NR^{X1}{}_2$, —NH—$(CH_2)_z$—$R^{M1}$,
—C(=O)NH—$(CH_2)_z$—OH, —C(=O)NH—$(CH_2)_z$—$OR^{X1}$,
—C(=O)NH—$(CH_2)_z$—$NH_2$, —C(=O)NH—$(CH_2)_z$—$NHR^{X1}$,
—C(=O)NH—$(CH_2)_z$—$NR^{X1}{}_2$, —C(=O)NH—$(CH_2)_z$—$R^{M1}$,
—NHC(=O)—$(CH_2)_z$—OH, —NHC(=O)—$(CH_2)_z$—$OR^{X1}$,
—NHC(=O)—$(CH_2)_z$—$NH_2$, —NHC(=O)—$(CH_2)_z$—$NHR^{X1}$,
—NHC(=O)—$(CH_2)_z$—$NR^{X1}{}_2$, and —NHC(=O)—$(CH_2)_z$—$R^{M1}$, wherein:
each z is independently 2 or 3;
each —$R^{X1}$ is independently saturated aliphatic $C_{1-4}$alkyl; and
each —$R^{M1}$ is independently piperidino, piperizino, or morpholino, and is optionally substituted with one or more saturated aliphatic $C_{1-4}$alkyl groups.

In one embodiment, each -$Q^C$, if present, is independently selected from:
—$R^{X1}$,
—F, —Cl, —Br, —I,
—OH, —$OR^{X1}$,
—$NH_2$, —$NHR^{X1}$, —$NR^{X1}{}_2$,
—O—$CH_2CH_2$—OH, —O—$CH_2CH_2$—$OR^{X1}$,
—O—$CH_2CH_2CH_2$—OH, —O—$CH_2CH_2CH_2$—$OR^{X1}$,
—O—$CH_2CH_2$—$NH_2$, —O—$CH_2CH_2$—$NHR^{X1}$,
—O—$CH_2CH_2$—$NR^{X1}{}_2$,
—O—$CH_2CH_2CH_2$—$NH_2$, —O—$CH_2CH_2CH_2$—$NHR^{X1}$, —O—$CH_2CH_2CH_2$—$NR^{X1}{}_2$,
—NH—$CH_2CH_2$—OH, —NH—$CH_2CH_2$—$OR^{X1}$,
—NH—$CH_2CH_2CH_2$—OH, —NH—$CH_2CH_2CH_2$—$OR^{X1}$,
—NH—$CH_2CH_2$—$NH_2$, —NH—$CH_2CH_2$—$NHR^{X1}$,
—NH—$CH_2CH_2$—$NR^{X1}{}_2$,
—NH—$CH_2CH_2CH_2$—$NH_2$, —NH—$CH_2CH_2CH_2$—$NHR^{X1}$, and —NH—$CH_2CH_2CH_2$—$NR^{X1}{}_2$;

wherein each —$R^{X1}$ is independently saturated aliphatic $C_{1-4}$alkyl.

In one embodiment, each -$Q^C$, if present, is independently selected from:
—$R^{X1}$, —F, —Cl, —Br, —I, —$CF_3$, —$OCF_3$,
—NH—$(CH_2)_z$—OH, —NH—$(CH_2)_z$—$OR^{X1}$,
—NH—$(CH_2)_z$—$NH_2$, —NH—$(CH_2)_z$—$NHR^{X1}$,
—NH—$(CH_2)_z$—$NR^{X1}{}_2$, and —NH—$(CH_2)_z$—$R^{M1}$;

wherein:
each —$R^{X1}$ is independently saturated aliphatic $C_{1-4}$alkyl; and
each —$R^{M1}$ is independently piperidino, piperizino, or morpholino, and is optionally substituted with one or more saturated aliphatic $C_{1-4}$alkyl groups.

In one embodiment, each -$Q^C$, if present, is independently selected from:
-Me, —F, —Cl, —Br, —I, and —$CF_3$.

In one embodiment, each -$Q^E$, if present, is independently selected from:
—$R^{X2}$,
—$R^{X2A}$, —$CH_2$—$R^{X2A}$, —$CH_2CH_2$—$R^{X2A}$,
—OH, —$OR^{X2}$,
—$NH_2$, —$NHR^{X2}$, —$NR^{X2}{}_2$, —$R^{M2}$,
—O—$(CH_2)_z$—OH, —O—$(CH_2)_z$—$OR^{X2}$,
—$(CH_2)_z$—OH, —$(CH_2)_z$—$OR^{X2}$,
—$(CH_2)_z$—$NH_2$, —$(CH_2)_z$—$NHR^{X2}$, —$(CH_2)_z$—$NR^{X2}{}_2$,
and —$(CH_2)_z$—$R^{M2}$;

wherein:
each z is independently 2 or 3;
each —$R^{X2A}$ is independently phenyl, pyridyl, thienyl, piperidinyl, or $C_{3-6}$cycloalkyl, and is optionally substituted with one or more groups selected from —$R^{X2}$, —OH, —$OR^{X2}$, —$NH_2$, —$NHR^{X2}$, —$NR^{X2}_2$, or —$R^{M2}$;
each —$R^{X2}$ is independently saturated aliphatic $C_{1-4}$alkyl; and
each —$R^{M2}$ is independently piperidino, piperizino, or morpholino, and is optionally substituted with one or more saturated aliphatic $C_{1-4}$alkyl groups.

In one embodiment, each -$Q^E$, if present, is independently selected from:
- —$R^{X2}$,
- —OH, —$OR^{X2}$,
- —$NH_2$, —$NHR^{X2}$, —$NR^{X2}_2$,
- —O—$CH_2CH_2$—OH, —O—$CH_2CH_2$—$OR^{X2}$,
- —O—$CH_2CH_2CH_2$—OH, —O—$CH_2CH_2CH_2$—$OR^{X2}$,
- —$CH_2CH_2$—OH, —$CH_2CH_2$—$OR^{X2}$,
- —$CH_2CH_2$—$NH_2$, —$CH_2CH_2$—$NHR^{X2}$, and —$CH_2CH_2$—$NR^{X2}_2$;

wherein each —$R^{X2}$ is independently saturated aliphatic $C_{1-4}$alkyl.

The Group -$Q^D$

In one embodiment, -$Q^D$, if present, is independently selected from:
- —$R^{3A1}$
- -$L^{3A}$-OH, -$L^{3A}$-$OR^{3A1}$,
- -$L^{3A}$-$NH_2$, -$L^{3A}$-$NHR^{3A1}$, -$L^{3A}$-$NR^{3A1}_2$, and -$L^{3A}$-$NR^{3A2}R^{3A3}$;

wherein:
each -$L^{3A}$- is independently saturated aliphatic $C_{2-5}$alkylene;
in each group —$NR^{3A2}R^{3A3}$, $R^{3A2}$ and $R^{3A3}$, taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O;
each —$R^{3A1}$ is independently:
—$R^{3B1}$, —$R^{3B2}$, —$R^{3B3}$, —$R^{3B4}$, —$R^{3B5}$, —$R^{3B6}$, —$R^{3B7}$, —$R^{3B8}$,
-$L^{3B}$-$R^{3B4}$, -$L^{3B}$-$R^{3B5}$, -$L^{3B}$-$R^{3B6}$, -$L^{3B}$-$R^{3B7}$, or -$L^{3B}$-$R^{3B8}$;
each —$R^{3B1}$ is independently saturated aliphatic $C_{1-6}$alkyl;
each —$R^{3B2}$ is independently aliphatic $C_{2-6}$alkenyl;
each —$R^{3B3}$ is independently aliphatic $C_{2-6}$alkynyl;
each —$R^{3B4}$ is independently saturated $C_{3-6}$cycloalkyl;
each —$R^{3B5}$ is independently $C_{3-6}$cycloalkenyl;
each —$R^{3B6}$ is independently non-aromatic $C_{3-8}$heterocyclyl;
each —$R^{3B7}$ is independently $C_{6-10}$carboaryl;
each —$R^{3B8}$ is independently $C_{5-10}$heteroaryl;
each -$L^{3B}$- is independently saturated aliphatic $C_{1-3}$alkylene;

wherein:
each —$R^{3B4}$, —$R^{3B5}$, —$R^{3B6}$, —$R^{3B7}$, and —$R^{3B8}$ is optionally substituted, for example, with one or more substituents —$R^{3C1}$ and/or one or more substituents —$R^{3C2}$;
each —$R^{3B1}$, —$R^{3B2}$, —$R^{3B3}$, and -$L^{3B}$- is optionally substituted, for example, with one or more substituents —$R^{3C2}$, and wherein:
each —$R^{3C1}$ is independently saturated aliphatic $C_{1-4}$alkyl, phenyl, or benzyl;
each —$R^{3C2}$ is independently:
- —F, —Cl, —Br, —I,
- —$CF_3$, —$OCF_3$,
- —OH, -$L^{3D}$-OH, —O-$L^{3D}$-OH,
- —$OR^{3D1}$, -$L^{3D}$-$OR^{3D1}$, —O-$L^{3D}$-$OR^{3D1}$,
- —SH, —$SR^{3D1}$,
- —CN,
- —$NO_2$,
- —$NH_2$, —$NHR^{3D1}$, —$NR^{3D1}_2$, —$NR^{3D2}R^{3D3}$,
- -$L^{3D}$-$NH_2$, -$L^{3D}$-$NHR^{3D1}$, -$L^{3D}$-$NR^{3D1}_2$, -$L^{3D}$-$NR^{3D2}R^{3D3}$,
- —C(=O)OH, —C(=O)$OR^{3D1}$,
- —C(=O)$NH_2$, —C(=O)$NHR^{3D1}$, —C(=O)$NR^{3D1}_2$, or —C(=O)$NR^{3D2}R^{3D3}$;

wherein:
each —$R^{3D1}$ is independently saturated aliphatic $C_{1-4}$alkyl, phenyl, or benzyl;
each -$L^{3D}$- is independently saturated aliphatic $C_{1-5}$alkylene; and
in each group —$NR^{3D2}R^{3D3}$, $R^{3D2}$ and $R^{3D3}$, taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O.

In one embodiment, -$Q^D$, if present, is independently selected from:
- —$R^{3A1}$,
- -$L^{3A}$-$NH_2$, -$L^{3A}$-$NHR^{3A1}$, -$L^{3A}$-$NR^{3A1}_2$, and -$L^{3A}$-$NR^{3A2}R^{3A3}$.

In one embodiment, -$Q^D$, if present, is independently selected from:
- -$L^{3A}$-$NH_2$, -$L^{3A}$-$NHR^{3A1}$, -$L^{3A}$-$NR^{3A1}_2$, and -$L^{3A}$-$NR^{3A2}R^{3A3}$.

In one embodiment, -$Q^D$, if present, is independently selected from:
- —$R^{3A1}$,
- -$L^{3A}$-OH, and -$L^{3A}$-$OR^{3A1}$.

In one embodiment, -$Q^D$, if present, is independently selected from:
- -$L^{3A}$-OH and -$L^{3A}$-$OR^{3A1}$.

In one embodiment, each -$L^{3A}$-, if present, is independently —$(CH_2)_{n3}$—, wherein n3 is independently 1 to 4.

In one embodiment, each -$L^{3A}$-, if present, is independently —$CH_2CH_2$— or —$CH_2CH_2CH_2$—.

In one embodiment, each —$NR^{3A2}R^{3A3}$, if present, is independently azetidino, pyrrolidino, imidazolidino, pyrazolidino, piperidino, piperazino, morpholino, azepino, or diazepino, and is optionally substituted, for example, with one or more groups selected from $C_{1-3}$alkyl, —$CF_3$, and —F.

In one embodiment, each —$NR^{3A2}R^{3A3}$, if present, is independently pyrrolidino, piperidino, piperazino, or morpholino, and is optionally substituted, for example, with one or more groups selected from $C_{1-3}$alkyl, —$CF_3$, and —F.

In one embodiment, each —$R^{3A1}$, if present, is independently:
—$R^{3B1}$, —$R^{3B4}$, —$R^{3B6}$, —$R^{3B7}$, —$R^{3B8}$,
-$L^{3B}$-$R^{3B4}$, -$L^{3B}$-$R^{3B6}$, -$L^{3B}$-$R^{3B7}$, or -$L^{3B}$-$R^{3B8}$.

In one embodiment, each —$R^{3A1}$, if present, is independently:
—$R^{3B1}$, —$R^{3B6}$, or -$L^{3B}$-$R^{3B6}$.

In one embodiment, each —$R^{3A1}$, if present, is independently:
—$R^{3B1}$, —$R^{3B7}$, —$R^{3B8}$,
-$L^{3B}$-$R^{3B7}$, or -$L^{3B}$-$R^{3B8}$.

In one embodiment, each —$R^{3A1}$, if present, is independently:
—$R^{3B1}$, —$R^{3B7}$, or -$L^{3B}$-$R^{3B7}$.

In one embodiment, each —$R^{3A1}$, if present, is independently:
—$R^{3B7}$, —$R^{3B8}$, -$L^{3B}$-$R^{3B7}$, or -$L^{3B}$-$R^{3B8}$.

In one embodiment, each —$R^{3B6}$, if present, is independently azetidinyl, pyrrolidinyl, imidazolidinyl, pyrazolidinyl, piperidinyl, piperazinyl, morpholinyl, azepinyl, diazepinyl, tetrahydrofuranyl, tetrahydropyranyl, dioxanyl, and is optionally substituted.

In one embodiment, each —$R^{3B6}$, if present, is independently pyrrolidinyl, piperidinyl, piperazinyl, morpholinyl, tetrahydrofuranyl, or tetrahydropyranyl, and is optionally substituted.

In one embodiment, each —$R^{3B7}$, if present, is independently phenyl, and is optionally substituted.

In one embodiment, each —$R^{3B8}$, if present, is independently $C_{5-6}$heteroaryl, and is optionally substituted.

In one embodiment, each —$R^{3B8}$, if present, is independently furanyl, thienyl, pyrrolyl, imidazolyl, pyrazolyl, triazolyl, oxazolyl, isoxazolyl, thiazolyl, isothiazolyl, pyridyl, pyrimidinyl, or pyridazinyl, and is optionally substituted.

In one embodiment, each —$R^{3B8}$, if present, is independently $C_{9-10}$heteroaryl, and is optionally substituted.

In one embodiment, each —$R^{3B8}$, if present, is independently benzofuranyl, benzothienyl, benzopyrrolyl, benzoimidazolyl, benzopyrazolyl, benzotriazolyl, benzoxazolyl, benzoisoxazolyl, benzothiazolyl, benzoisothiazolyl, benzopyridyl, benzopyrimidinyl, or benzopyridazinyl, and is optionally substituted.

In one embodiment, each -$L^{3B}$-, if present, is independently —$CH_2$— or —$CH_3CH_2$—.

In one embodiment, each -$L^{3B}$-, if present, is independently —$CH_2$—.

In one embodiment, each —$R^{3C1}$, if present, is independently saturated aliphatic $C_{1-4}$alkyl.

In one embodiment, each —$R^{3C2}$ is independently:
—F, —Cl, —Br, —I,
—OH,
—$OR^{3D1}$,
—CN,
—$NO_2$,
—$NH_2$, —$NHR^{3D1}$, —$NR^{3D1}{}_2$, or —$NR^{3D2}R^{3D3}$.

In one embodiment, each —$R^{3D1}$, if present, is independently saturated aliphatic $C_{1-4}$alkyl.

In one embodiment, each -$L^{3D}$-, if present, is independently —$(CH_2)_{m3}$—, wherein m3 is independently 1 to 4.

In one embodiment, each -$L^{3D}$-, if present, is independently —$CH_2$— or —$CH_3CH_2$—.

In one embodiment, each —$NR^{3D2}R^{3D3}$, if present, is independently azetidino, pyrrolidino, imidazolidino, pyrazolidino, piperidino, piperazino, morpholino, azepino, or diazepino, and is optionally substituted, for example, with one or more groups selected from $C_{1-3}$alkyl, —$CF_3$, and —F.

In one embodiment, each —$NR^{3D2}R^{3D3}$, if present, is independently pyrrolidino, piperidino, piperazino, or morpholino, and is optionally substituted, for example, with one or more groups selected from $C_{1-3}$alkyl, —$CF_3$, and —F.

In one embodiment, each -$Q^D$, if present, is independently selected from:
—$R^{X3}$,
—$CH_2CH_2$—OH, —$CH_2CH_2$—$OR^{X3}$,
—$CH_2CH_2CH_2$—OH, —$CH_2CH_2CH_2$—$OR^{X3}$,
—$CH_2CH_2$—$NH_2$, —$CH_2CH_2$—$NHR^{X3}$, —$CH_2CH_2$—$NR^{X3}{}_2$,
—$CH_2CH_2CH_2$—$NH_2$, —$CH_2CH_2CH_2$—$NHR^{X3}$, and —$CH_2CH_2CH_2$—$NR^{X3}{}_2$;

wherein each —$R^{X3}$ is independently saturated aliphatic $C_{1-4}$alkyl.

Molecular Weight

In one embodiment, the BA compound has a molecular weight of from 212 to 1200.

In one embodiment, the bottom of range is 225, 250, 275, 300, or 350.

In one embodiment, the top of range is 1100, 1000, 900, 800, 700, or 600.

In one embodiment, the range is from 225 to 600.

Combinations

Each and every compatible combination and subcombination of the embodiments described above is explicitly disclosed herein, as if each and every combination and subcombination was individually and explicitly recited.

Some Preferred Embodiments

In one preferred embodiment, the compounds are selected from compounds of the following formula and pharmaceutically acceptable salts, hydrates, and solvates thereof:

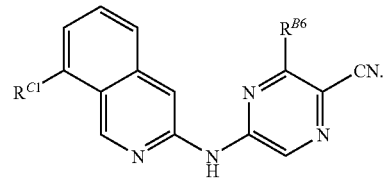

In one preferred embodiment, the compounds are selected from compounds of the following formula and pharmaceutically acceptable salts, hydrates, and solvates thereof:

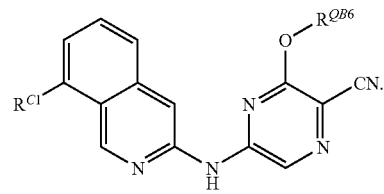

In one preferred embodiment, the compounds are selected from compounds of the following formula and pharmaceutically acceptable salts, hydrates, and solvates thereof:

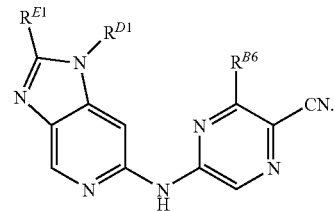

Examples of Specific Embodiments

In one embodiment, the compounds are selected from compounds of the following formulae and pharmaceutically acceptable salts, hydrates, and solvates thereof:

| Cmpd. No. | Synth. No. | Structure |
|---|---|---|
| AA-001 | 4-1-B | 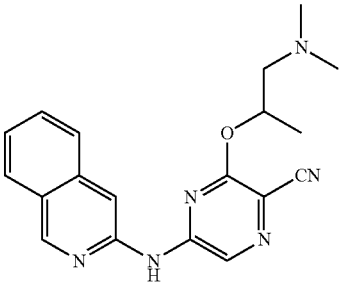 [SMILES: CC(CN(C)C)Oc1nc(Nc2cc3ccccc3cn2)cnc1C#N] |
| AA-002 | 4-2 | 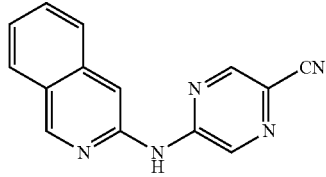 [SMILES: N#Cc1cnc(Nc2cc3ccccc3cn2)cn1] |
| AA-003 | 4-3 | 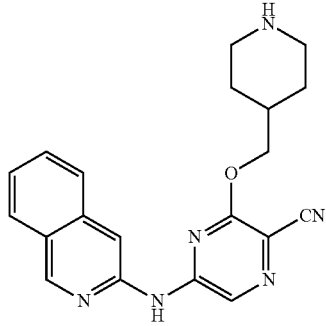 [SMILES: N#Cc1ncc(Nc2cc3ccccc3cn2)nc1OCC1CCNCC1] |
| AA-004 | 4-4 | 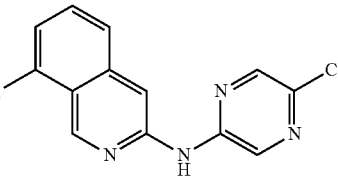 |
| AA-005 | 4-5 | 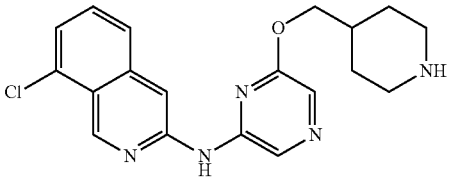 [SMILES: Clc1cccc2cc(Nc3cncc(OCC4CCNCC4)n3)ncc12] |
| AA-006 | 4-6 | 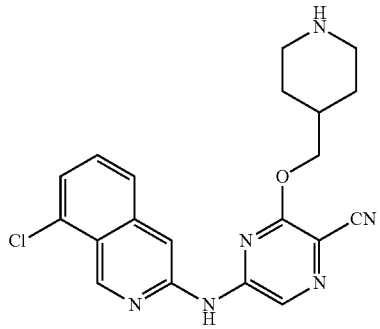 [SMILES: N#Cc1ncc(Nc2cc3cccc(Cl)c3cn2)nc1OCC1CCNCC1] |

-continued
| Cmpd. No. | Synth. No. | Structure |
|---|---|---|
| AA-007 | 4-7 | 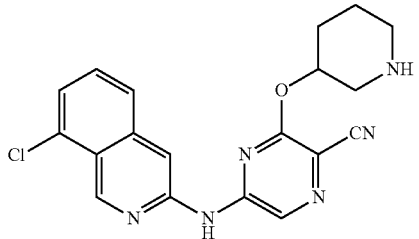 [SMILES: N#Cc1ncc(Nc2cc3cccc(Cl)c3cn2)nc1OC1CCCNC1] |
| AA-008 | 5-1 | 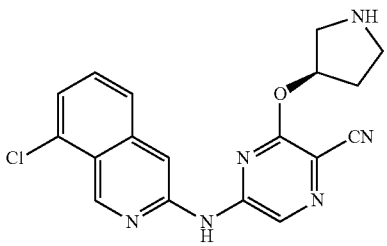 [SMILES: N#Cc1ncc(Nc2cc3cccc(Cl)c3cn2)nc1O[C@@H]1CCNC1] |
| AA-009 | 5-2 | 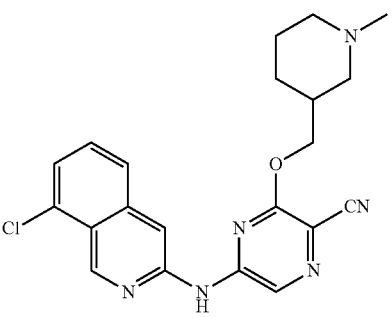 [SMILES: CN1CCCC(COc2nc(Nc3cc4cccc(Cl)c4cn3)cnc2C#N)C1] |
| AA-010 | 5-3 | 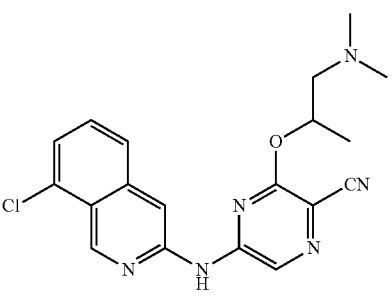 [SMILES: CC(CN(C)C)Oc1nc(Nc2cc3cccc(Cl)c3cn2)cnc1C#N] |
| AA-011 | 6 | 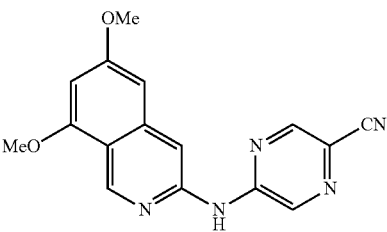 [SMILES: COc1cc(OC)c2cnc(Nc3cnc(C#N)cn3)cc2c1] |
| AA-012 | 5-4 | 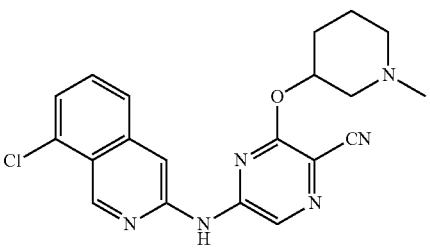 [SMILES: CN1CCCC(Oc2nc(Nc3cc4cccc(Cl)c4cn3)cnc2C#N)C1] |

-continued

| Cmpd. No. | Synth. No. | Structure |
|---|---|---|
| AA-013 | 5-5 | 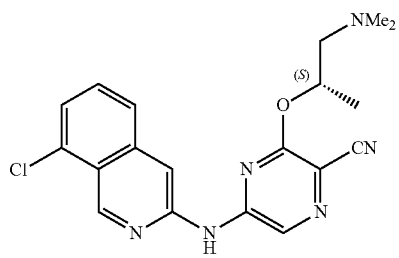 |
| AA-014 | 5-6 | 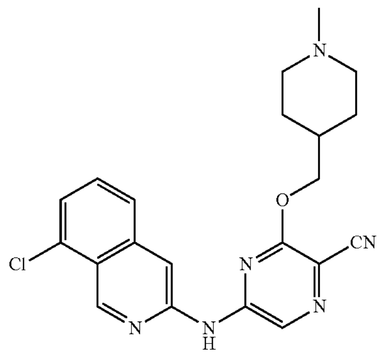 [SMILES: CN1CCC(COc2nc(Nc3cc4cccc(Cl)c4cn3)cnc2C#N)CC1] |
| AA-015 | 5-7 | 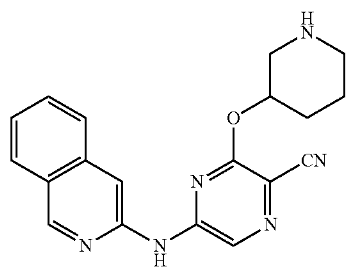 [SMILES: N#Cc1ncc(Nc2cc3ccccc3cn2)nc1OC1CCCNC1] |
| AA-016 | 5-8 | 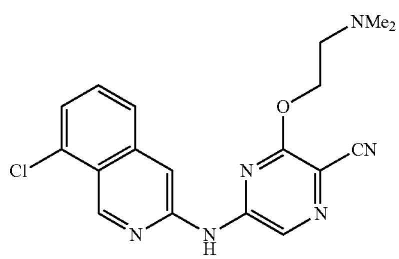 [SMILES: CN(C)CCOc1nc(Nc2cc3cccc(Cl)c3cn2)cnc1C#N] |
| AA-017 | 11-1 | 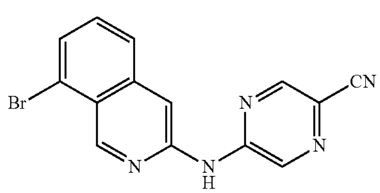 [SMILES: N#Cc1cnc(Nc2cc3cccc(Br)c3cn2)cn1] |
| AA-018 | 11-10 | 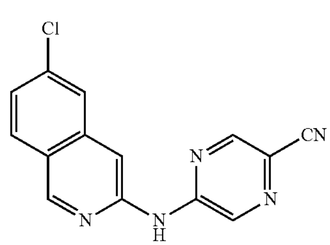 [SMILES: N#Cc1cnc(Nc2cc3cc(Cl)ccc3cn2)cn1] |

-continued

| Cmpd. No. | Synth. No. | Structure |
|---|---|---|
| AA-019 | 12 | 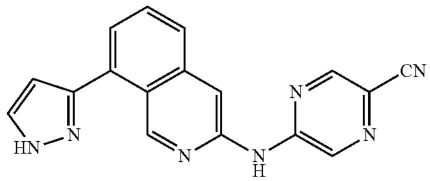 [SMILES: N#Cc1cnc(Nc2cc3cccc(-c4cc[nH]n4)c3cn2)cn1] |
| AA-020 | 13-1 | 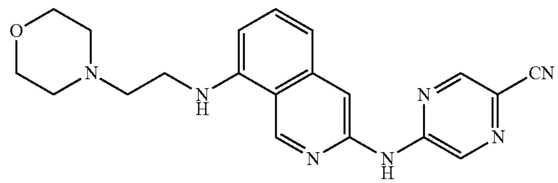 [SMILES: N#Cc1cnc(Nc2cc3cccc(NCCN4CCOCC4)c3cn2)cn1] |
| AA-021 | 14-1 | 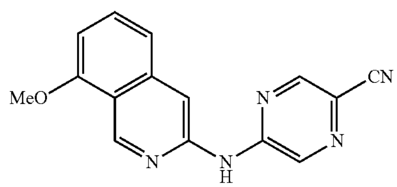 [SMILES: COc1cccc2cc(Nc3cnc(C#N)cn3)ncc12] |
| AA-022 | 5-9 | 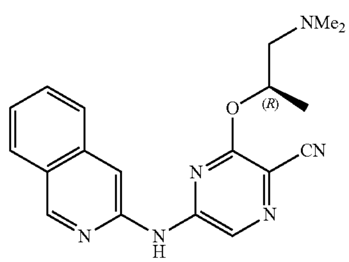 |
| AA-023 | 5-10 | 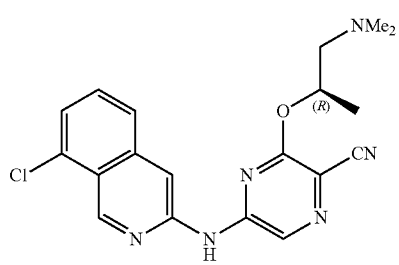 |
| AA-024 | 5-11 | 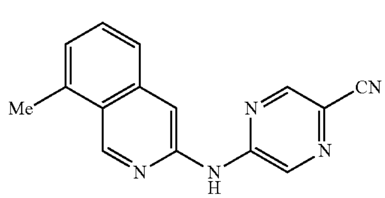 [SMILES: Cc1cccc2cc(Nc3cnc(C#N)cn3)ncc12] |
| AA-025 | 5-12 | 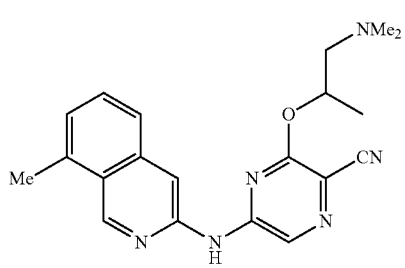 [SMILES: Cc1cccc2cc(Nc3cnc(C#N)c(OC(C)CN(C)C)n3)ncc12] |

-continued
| Cmpd. No. | Synth. No. | Structure |
|---|---|---|
| AA-026 | 11-2 | 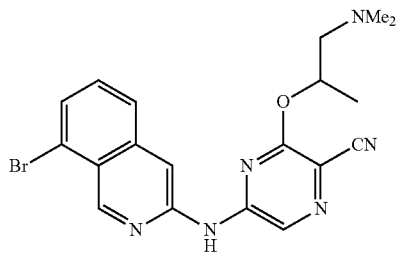 [SMILES: CC(CN(C)C)Oc1nc(Nc2cc3cccc(Br)c3cn2)cnc1C#N] |
| AA-027 | 13-2 | 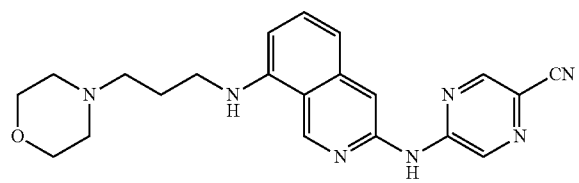 [SMILES: N#Cc1cnc(Nc2cc3cccc(NCCCN4CCOCC4)c3cn2)cn1] |
| AA-028 | 13-3 | 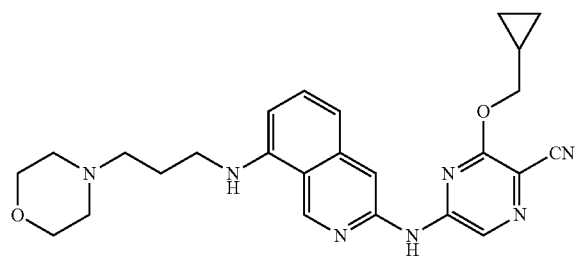 [SMILES: N#Cc1ncc(Nc2cc3cccc(NCCCN4CCOCC4)c3cn2)nc1OCC1CC1] |
| AA-029 | 13-4 | 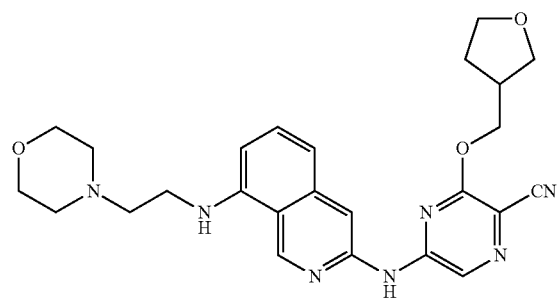 [SMILES: N#Cc1ncc(Nc2cc3cccc(NCCN4CCOCC4)c3cn2)nc1OCC1CCOC1] |
| AA-030 | 13-5 | 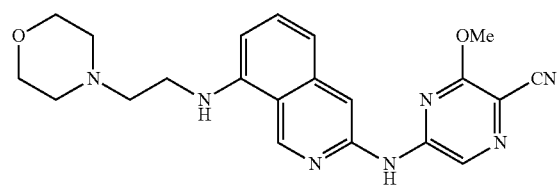 [SMILES: COc1nc(Nc2cc3cccc(NCCN4CCOCC4)c3cn2)cnc1C#N] |
| AA-031 | 15-1 | 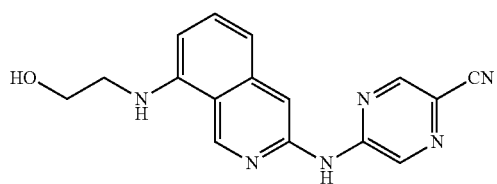 [SMILES: N#Cc1cnc(Nc2cc3cccc(NCCO)c3cn2)cn1] |

-continued
| Cmpd. No. | Synth. No. | Structure |
|---|---|---|
| AA-032 | 15-2 | 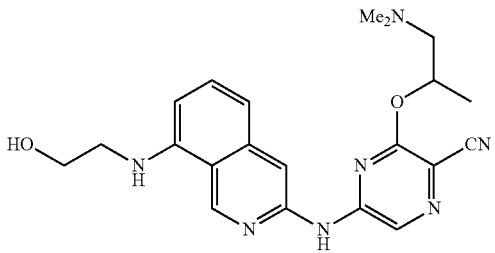 [SMILES: CC(CN(C)C)Oc1nc(Nc2cc3cccc(NCCO)c3cn2)cnc1C#N] |
| AA-033 | 15-3 | 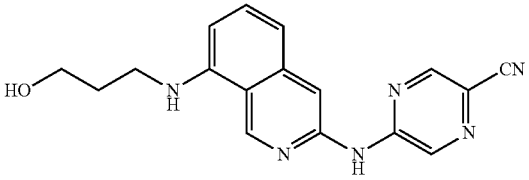 [SMILES: N#Cc1cnc(Nc2cc3cccc(NCCCO)c3cn2)cn1] |
| AA-034 | 15-4 | 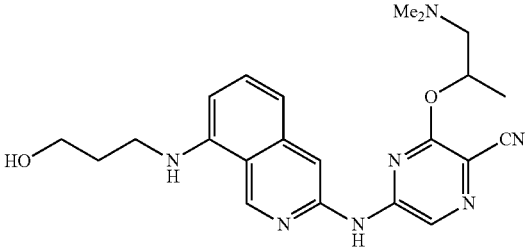 [SMILES: CC(CN(C)C)Oc1nc(Nc2cc3cccc(NCCCO)c3cn2)cnc1C#N] |
| AA-035 | 15-5 | 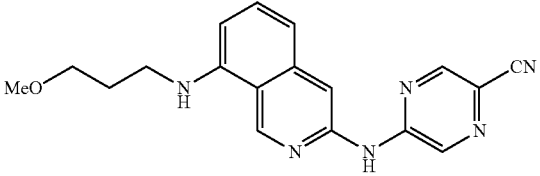 [SMILES: COCCCNc1cccc2cc(Nc3cnc(C#N)cn3)ncc12] |
| AA-036 | 15-6 | 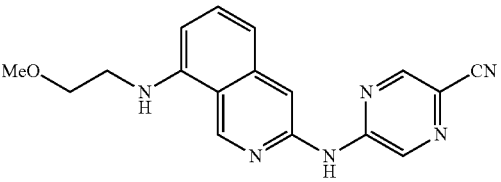 [SMILES: COCCNc1cccc2cc(Nc3cnc(C#N)cn3)ncc12] |
| AA-037 | 15-7 | 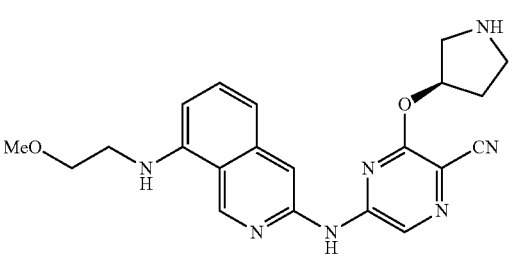 [SMILES: COCCNc1cccc2cc(Nc3cnc(C#N)c(O[C@@H]4CCNC4)n3)ncc12] |
| AA-038 | 15-8 | 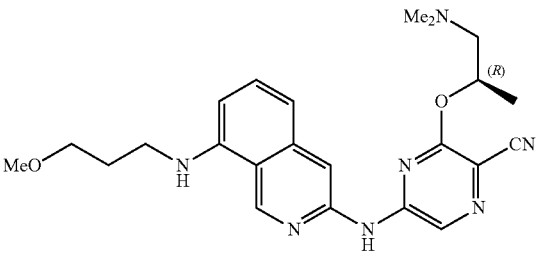 |

-continued

| Cmpd. No. | Synth. No. | Structure |
|---|---|---|
| AA-039 | 15-9 | 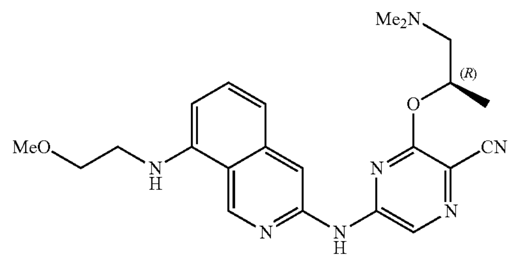 |
| AA-040 | 15-10 | 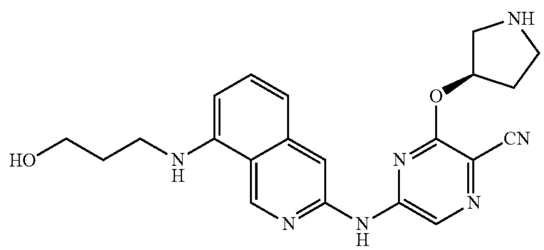 [SMILES: N#Cc1ncc(Nc2cc3cccc(NCCCO)c3cn2)nc1O[C@@H]1CCNC1] |
| AA-041 | 15-11 | 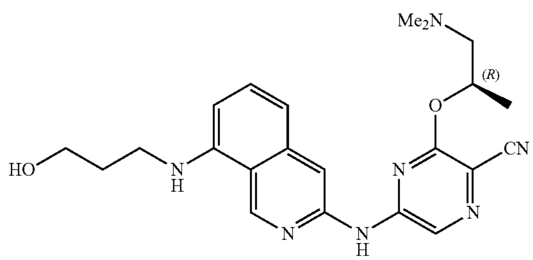 |
| AA-042 | 15-12 | 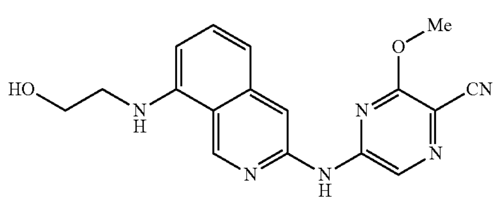 [SMILES: COc1nc(Nc2cc3cccc(NCCO)c3cn2)cnc1C#N] |
| AA-043 | 15-13 | 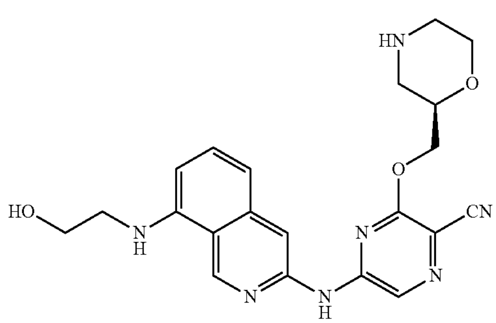 [SMILES: N#Cc1ncc(Nc2cc3cccc(NCCO)c3cn2)nc1OC[C@H]1CNCCO1] |
| AA-044 | 15-14 | 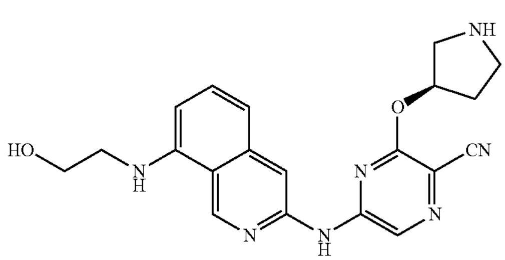 [SMILES: N#Cc1ncc(Nc2cc3cccc(NCCO)c3cn2)nc1O[C@@H]1CCNC1] |

-continued
| Cmpd. No. | Synth. No. | Structure |
|---|---|---|
| AA-045 | 15-15 | 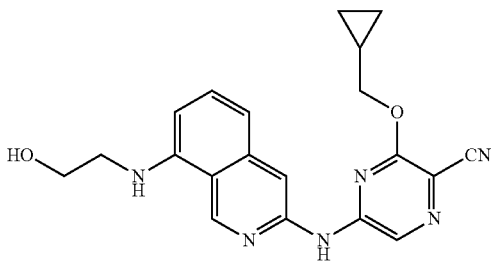 [SMILES: N#Cc1ncc(Nc2cc3cccc(NCCO)c3cn2)nc1OCC1CC1] |
| AA-046 | 15-16 | 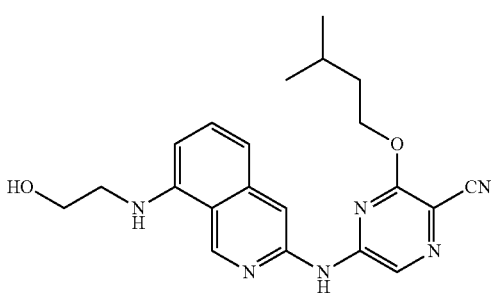 [SMILES: CC(C)CCOc1nc(Nc2cc3cccc(NCCO)c3cn2)cnc1C#N] |
| AA-047 | 15-17 | 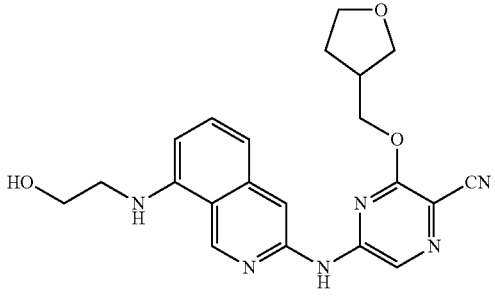 [SMILES: N#Cc1ncc(Nc2cc3cccc(NCCO)c3cn2)nc1OCC1CCOC1] |
| AA-048 | 4-8 | 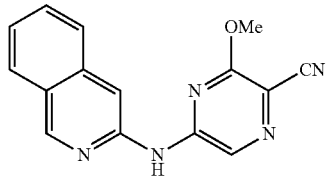 [SMILES: COc1nc(Nc2cc3ccccc3cn2)cnc1C#N] |
| AA-049 | 4-9 | 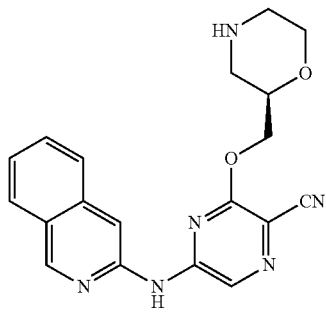 [SMILES: N#Cc1ncc(Nc2cc3ccccc3cn2)nc1OC[C@H]1CNCCO1] |
| AA-050 | 4-10 | 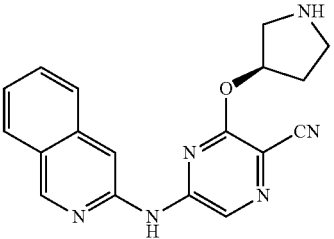 [SMILES: N#Cc1ncc(Nc2cc3ccccc3cn2)nc1O[C@@H]1CCNC1] |

-continued
| Cmpd. No. | Synth. No. | Structure |
|---|---|---|
| AA-051 | 11-3 | 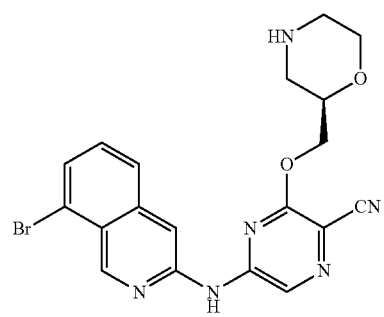 [SMILES: N#Cc1ncc(Nc2cc3cccc(Br)c3cn2)nc1OC[C@H]1CNCCO1] |
| AA-052 | 11-4 | 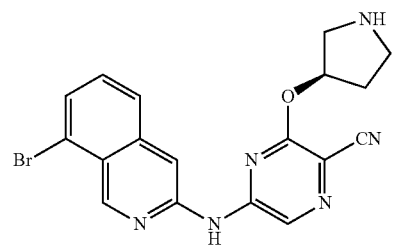 |
| AA-053 | 11-5 | 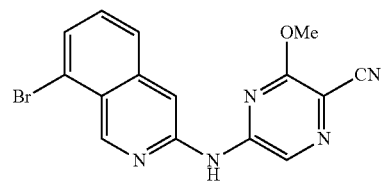 [SMILES: COc1nc(Nc2cc3cccc(Br)c3cn2)cnc1C#N] |
| AA-054 | 11-6 | 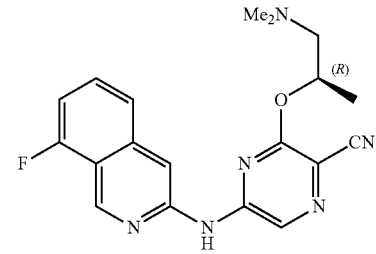 |
| AA-055 | 11-7 | 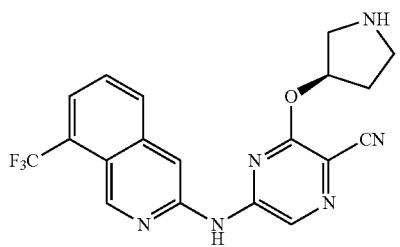 [SMILES: N#Cc1ncc(Nc2cc3cccc(C(F)(F)F)c3cn2)nc1O[C@@H]1CCNC1] |
| AA-056 | 11-8 | 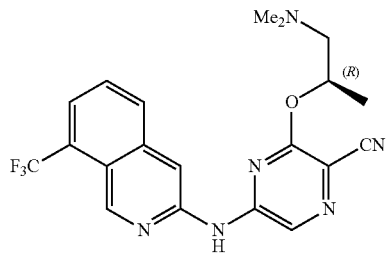 |

-continued

| Cmpd. No. | Synth. No. | Structure |
|---|---|---|
| AA-057 | 5-13 | 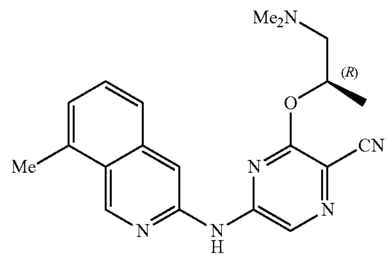 |
| AA-058 | 5-14 | 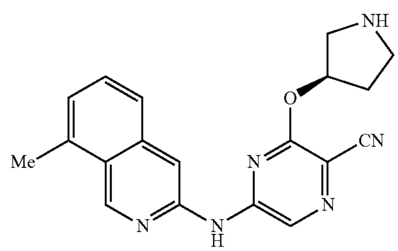 [SMILES: Cc1cccc2cc(Nc3cnc(C#N)c(O[C@@H]4CCNC4)n3)ncc12] |
| AA-059 | 15-18 | 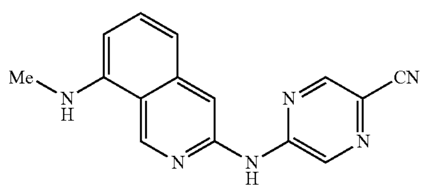 [SMILES: CNc1cccc2cc(Nc3cnc(C#N)cn3)ncc12] |
| AA-060 | 15-19 | 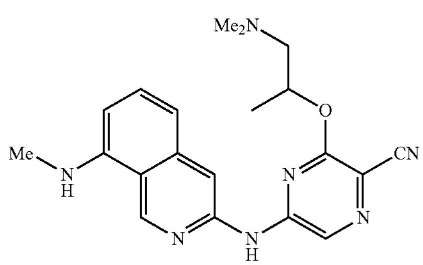 [SMILES: CNc1cccc2cc(Nc3cnc(C#N)c(OC(C)CN(C)C)n3)ncc12] |
| AA-061 | 16-1 | 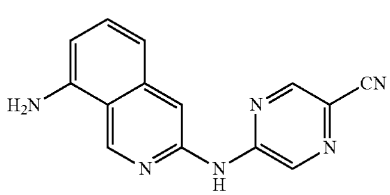 [SMILES: N#Cc1cnc(Nc2cc3cccc(N)c3cn2)cn1] |
| AA-062 | 17-1 | 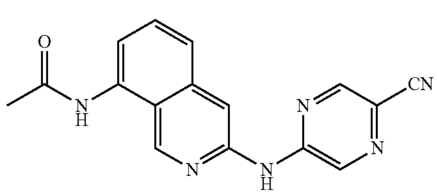 [SMILES: CC(=O)Nc1cccc2cc(Nc3cnc(C#N)cn3)ncc12] |
| AA-063 | 18-1 | 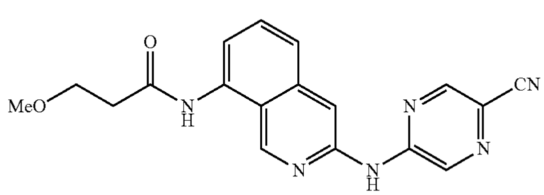 [SMILES: COCCC(=O)Nc1cccc2cc(Nc3cnc(C#N)cn3)ncc12] |

-continued

| Cmpd. No. | Synth. No. | Structure |
|---|---|---|
| AA-064 | 17-2 | 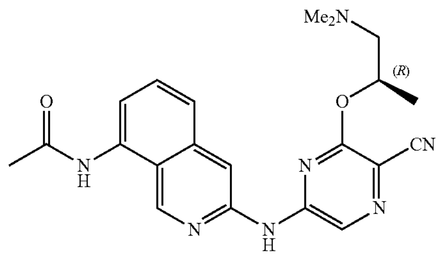 |
| AA-065 | 19-1 | 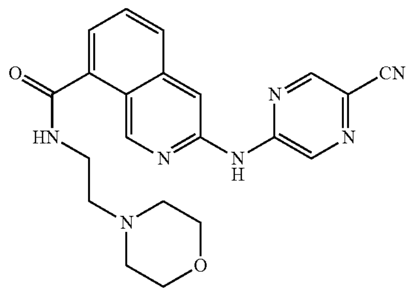 [SMILES: N#Cc1cnc(Nc2cc3cccc(C(=O)NCCN4CCOCC4)c3cn2)cn1] |
| AA-066 | 19-2 | 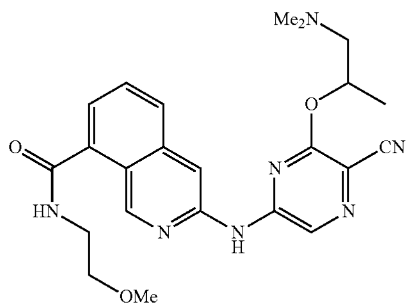 [SMILES: COCCNC(=O)c1cccc2cc(Nc3cnc(C#N)c(OC(C)CN(C)C)n3)ncc12] |
| AA-067 | 20-1-E | 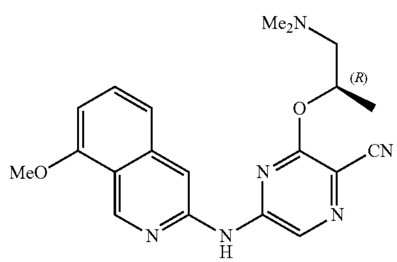 |
| AA-068 | 21-1-A | 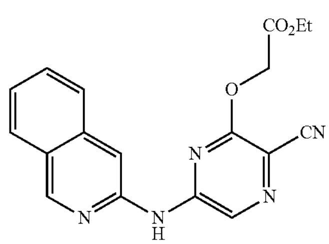 [SMILES: CCOC(=O)COc1nc(Nc2cc3ccccc3cn2)cnc1C#N] |
| AA-069 | 21-1-B | 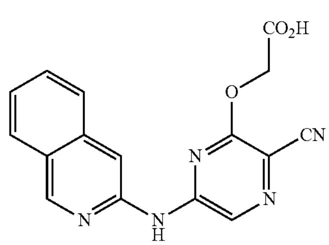 [SMILES: N#Cc1ncc(Nc2cc3ccccc3cn2)nc1OCC(=O)O] |

-continued
| Cmpd. No. | Synth. No. | Structure |
|---|---|---|
| AA-070 | 11-11 | 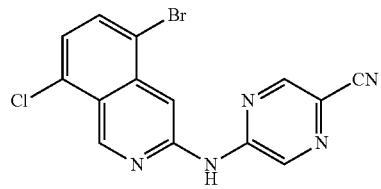 [SMILES: N#Cc1cnc(Nc2cc3c(Br)ccc(Cl)c3cn2)cn1] |
| AA-071 | 22-1 | 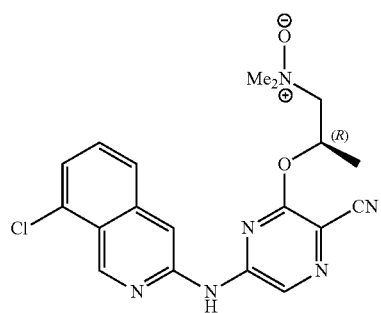 |
| AA-072 | 11-9 | 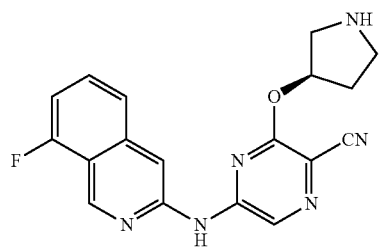 [SMILES: N#Cc1ncc(Nc2cc3cccc(F)c3cn2)nc1O[C@@H]1CCNC1] |
In one embodiment, the compounds are selected from compounds of the following formulae and pharmaceutically acceptable salts, hydrates, and solvates thereof:
| Cmpd. No. | Synth. No. | Structure |
|---|---|---|
| BB-001 | 1-1-D | 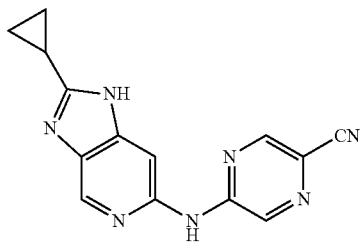 [SMILES: N#Cc1cnc(Nc2cc3[nH]c(C4CC4)nc3cn2)cn1] |
| BB-002 | 1-2 | 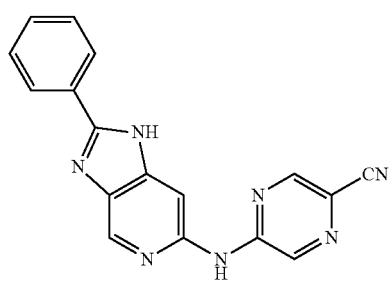 [SMILES: N#Cc1cnc(Nc2cc3[nH]c(-c4ccccc4)nc3cn2)cn1] |
-continued
| Cmpd. No. | Synth. No. | Structure |
|---|---|---|
| BB-003 | 1-3 | 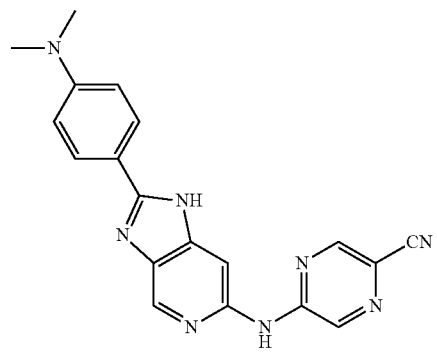 [SMILES: CN(C)c1ccc(-c2nc3cnc(Nc4cnc(C#N)cn4)cc3[nH]2)cc1] |
| BB-004 | 1-4 | 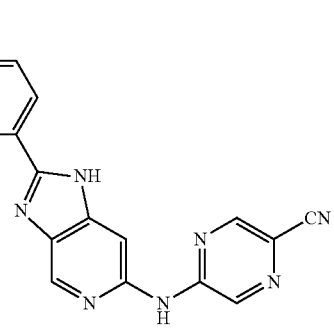 |

-continued
| Cmpd. No. | Synth. No. | Structure |
|---|---|---|
| BB-005 | 1-5 | 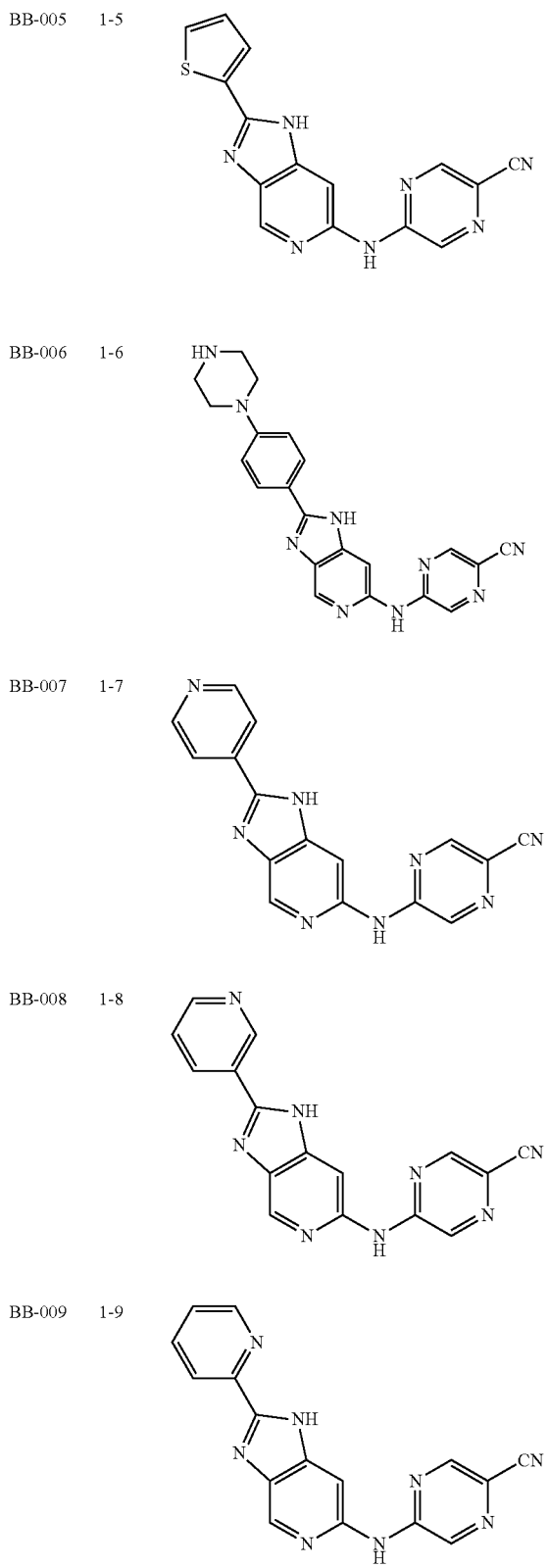 |
| BB-006 | 1-6 | 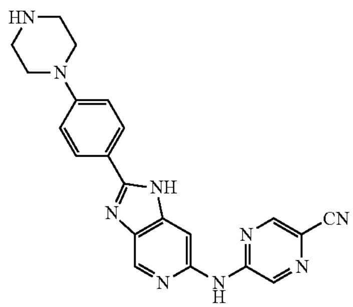 [SMILES: N#Cc1cnc(Nc2cc3[nH]c(-c4ccc(N5CCNCC5)cc4)nc3cn2)cn1] |
| BB-007 | 1-7 | 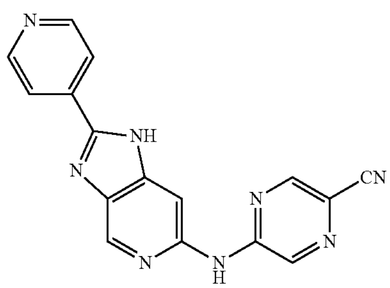 [SMILES: N#Cc1cnc(Nc2cc3[nH]c(-c4ccncc4)nc3cn2)cn1] |
| BB-008 | 1-8 | 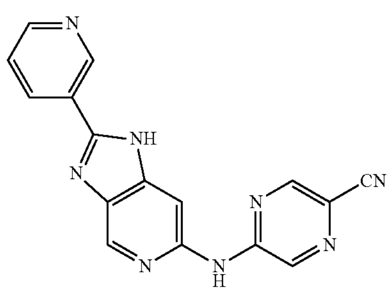 [SMILES: N#Cc1cnc(Nc2cc3[nH]c(-c4cccnc4)nc3cn2)cn1] |
| BB-009 | 1-9 | 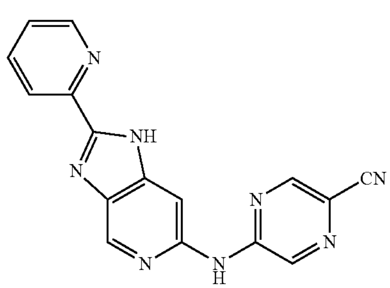 |
-continued
| Cmpd. No. | Synth. No. | Structure |
|---|---|---|
| BB-010 | 1-10 | 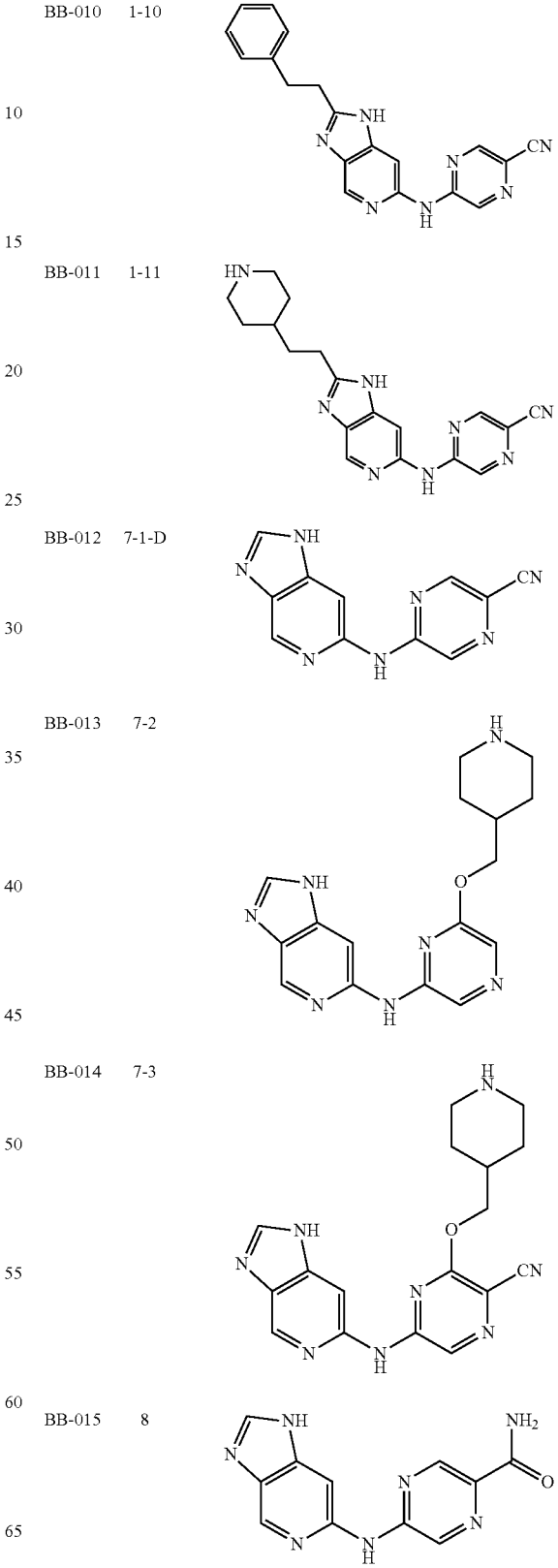 |
| BB-011 | 1-11 | 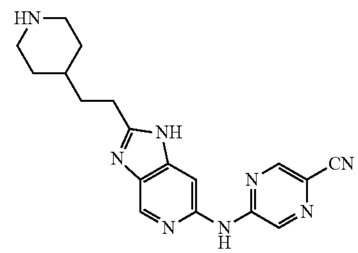 [SMILES: N#Cc1cnc(Nc2cc3[nH]c(CCC4CCNCC4)nc3cn2)cn1] |
| BB-012 | 7-1-D | 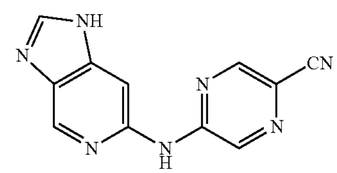 [SMILES: N#Cc1cnc(Nc2cc3[nH]cnc3cn2)cn1] |
| BB-013 | 7-2 | 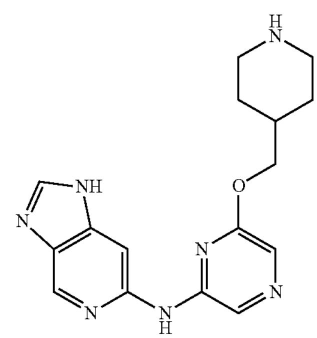 [SMILES: c1nc2cnc(Nc3cncc(OCC4CCNCC4)n3)cc2[nH]1] |
| BB-014 | 7-3 | 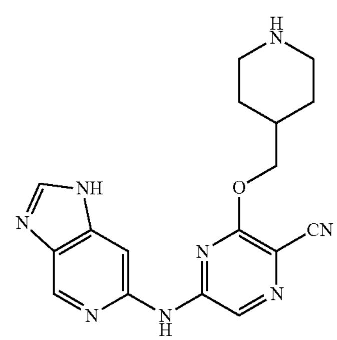 [SMILES: N#Cc1ncc(Nc2cc3[nH]cnc3cn2)nc1OCC1CCNCC1] |
| BB-015 | 8 | 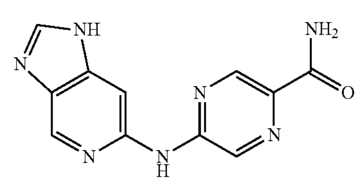 [SMILES: NC(=O)c1cnc(Nc2cc3[nH]cnc3cn2)cn1] |

US 8,530,468 B2
| Cmpd. No. | Synth. No. | Structure |
|---|---|---|
| BB-016 | 9-1-B | 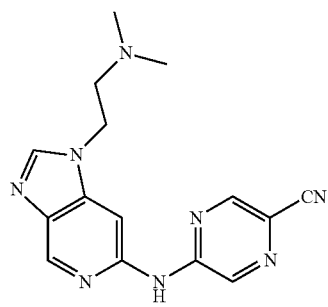 [SMILES: CN(C)CCn1cnc2cnc(Nc3cnc(C#N)cn3)cc21] |
| BB-017 | 9-2-B | 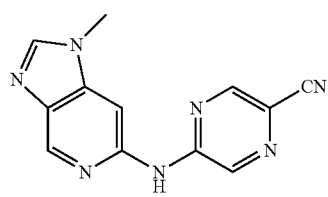 [SMILES: Cn1cnc2cnc(Nc3cnc(C#N)cn3)cc21] |
| BB-018 | 9-3-B | 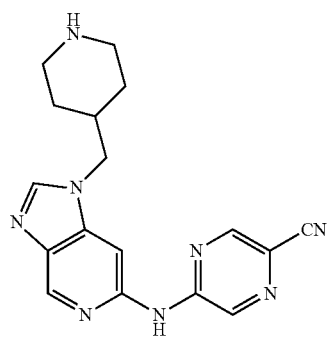 [SMILES: N#Cc1cnc(Nc2cc3c(cn2)ncn3CC2CCNCC2)cn1] |
| BB-019 | 9-4-B | 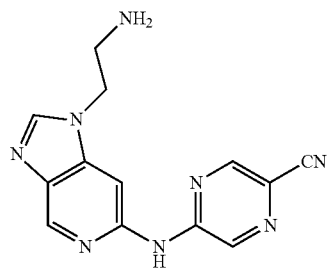 [SMILES: N#Cc1cnc(Nc2cc3c(cn2)ncn3CCN)cn1] |
| BB-020 | 9-5-B | 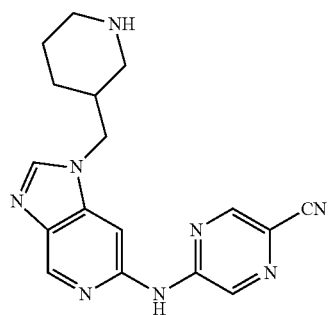 [SMILES: N#Cc1cnc(Nc2cc3c(cn2)ncn3CC2CCCNC2)cn1] |
| BB-021 | 9-6-B | 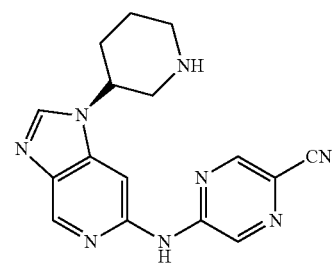 |
| BB-022 | 9-7-B | 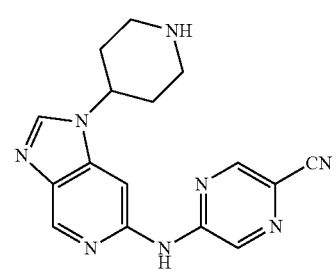 [SMILES: N#Cc1cnc(Nc2cc3c(cn2)ncn3C2CCNCC2)cn1] |
| BB-023 | 9-8-B | 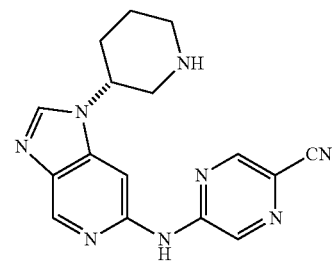 |
| BB-024 | 10-1 | 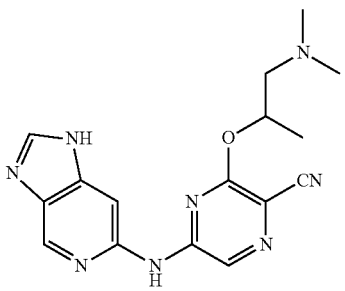 [SMILES: CC(CN(C)C)Oc1nc(Nc2cc3[nH]cnc3cn2)cnc1C#N] |
| BB-025 | 10-2 | 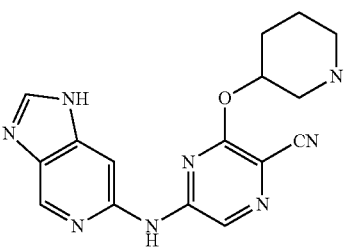 |

61

-continued

| Cmpd. No. | Synth. No. | Structure |
|---|---|---|
| BB-026 | 10-3 | 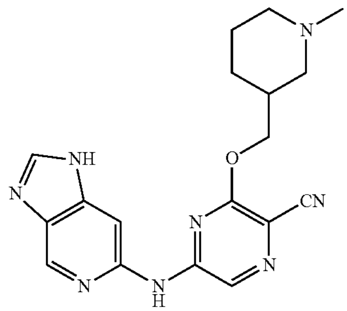 [SMILES: CN1CCCC(COc2nc(Nc3cc4[nH]cnc4cn3)cnc2C#N)C1] |
| BB-027 | 10-4 | 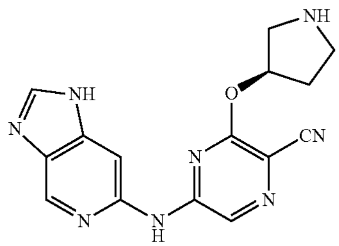 [SMILES: N#Cc1ncc(Nc2cc3[nH]cnc3cn2)nc1O[C@@H]1CCNC1] |
| BB-028 | 10-5 | 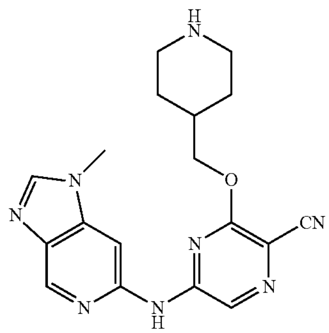 [SMILES: Cn1cnc2cnc(Nc3cnc(C#N)c(OCC4CCNCC4)n3)cc21] |

In one embodiment, the compounds are selected from compounds of the following formulae and pharmaceutically acceptable salts, hydrates, and solvates thereof:

| Cmpd. No. | Synth. No. | Structure |
|---|---|---|
| CC-001 | 23-1-A | 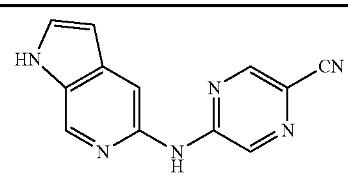 |

Substantially Purified Forms

One aspect of the present invention pertains to BCAA compounds, as described herein, in substantially purified form and/or in a form substantially free from contaminants.

In one embodiment, the substantially purified form is at least 50% by weight, e.g., at least 60% by weight, e.g., at least 70% by weight, e.g., at least 80% by weight, e.g., at least 90% by weight, e.g., at least 95% by weight, e.g., at least 97% by weight, e.g., at least 98% by weight, e.g., at least 99% by weight.

Unless specified, the substantially purified form refers to the compound in any stereoisomeric or enantiomeric form.

62

For example, in one embodiment, the substantially purified form refers to a mixture of stereoisomers, i.e., purified with respect to other compounds. In one embodiment, the substantially purified form refers to one stereoisomer, e.g., optically pure stereoisomer. In one embodiment, the substantially purified form refers to a mixture of enantiomers. In one embodiment, the substantially purified form refers to a equimolar mixture of enantiomers (i.e., a racemic mixture, a racemate). In one embodiment, the substantially purified form refers to one enantiomer, e.g., optically pure enantiomer.

In one embodiment, the contaminants represent no more than 50% by weight, e.g., no more than 40% by weight, e.g., no more than 30% by weight, e.g., no more than 20% by weight, e.g., no more than 10% by weight, e.g., no more than 5% by weight, e.g., no more than 3% by weight, e.g., no more than 2% by weight, e.g., no more than 1% by weight.

Unless specified, the contaminants refer to other compounds, that is, other than stereoisomers or enantiomers. In one embodiment, the contaminants refer to other compounds and other stereoisomers. In one embodiment, the contaminants refer to other compounds and the other enantiomer.

In one embodiment, the substantially purified form is at least 60% optically pure (i.e., 60% of the compound, on a molar basis, is the desired stereoisomer or enantiomer, and 40% is the undesired stereoisomer or enantiomer), e.g., at least 70% optically pure, e.g., at least 80% optically pure, e.g., at least 90% optically pure, e.g., at least 95% optically pure, e.g., at least 97% optically pure, e.g., at least 98% optically pure, e.g., at least 99% optically pure.

Isomers

Certain compounds may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g., C$_{1-7}$alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hydroxyazo, and nitro/aci-nitro.

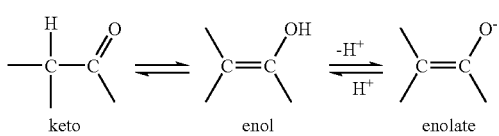

keto ⇌ enol ⇌ enolate

Note that specifically included in the term "isomer" are compounds with one or more isotopic substitutions. For example, H may be in any isotopic form, including $^1H$, $^2H$ (D), and $^3H$ (T); C may be in any isotopic form, including $^{12}C$, $^{13}C$, and $^{14}C$; O may be in any isotopic form, including $^{16}O$ and $^{18}O$; and the like.

Unless otherwise specified, a reference to a particular compound includes all such isomeric forms, including mixtures (e.g., racemic mixtures) thereof. Methods for the preparation (e.g., asymmetric synthesis) and separation (e.g., fractional crystallisation and chromatographic means) of such isomeric forms are either known in the art or are readily obtained by adapting the methods taught herein, or known methods, in a known manner.

Salts

It may be convenient or desirable to prepare, purify, and/or handle a corresponding salt of the compound, for example, a pharmaceutically-acceptable salt. Examples of pharmaceutically acceptable salts are discussed in Berge et al., 1977, "Pharmaceutically Acceptable Salts," *J. Pharm. Sci.*, Vol. 66, pp. 1-19.

For example, if the compound is anionic, or has a functional group which may be anionic (e.g., —COOH may be —COO$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{+3}$. Examples of suitable organic cations include, but are not limited to, ammonium ion (i.e., NH$_4^+$) and substituted ammonium ions (e.g., NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group which may be cationic (e.g., —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Unless otherwise specified, a reference to a particular compound also includes salt forms thereof.

Solvates and Hydrates

It may be convenient or desirable to prepare, purify, and/or handle a corresponding solvate of the compound. The term "solvate" is used herein in the conventional sense to refer to a complex of solute (e.g., compound, salt of compound) and solvent. If the solvent is water, the solvate may be conveniently referred to as a hydrate, for example, a mono-hydrate, a di-hydrate, a tri-hydrate, etc.

Unless otherwise specified, a reference to a particular compound also includes solvate and hydrate forms thereof.

Chemically Protected Forms

It may be convenient or desirable to prepare, purify, and/or handle the compound in a chemically protected form. The term "chemically protected form" is used herein in the conventional chemical sense and pertains to a compound in which one or more reactive functional groups are protected from undesirable chemical reactions under specified conditions (e.g., pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Green and P. Wuts; 4th Edition; John Wiley and Sons, 2006).

Unless otherwise specified, a reference to a particular compound also includes chemically protected forms thereof.

A wide variety of such "protecting," "blocking," or "masking" methods are widely used and well known in organic synthesis. For example, a compound which has two non-equivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

For example, a hydroxy group may be protected as an ether (—OR) or an ester (—OC(=O)R), for example, as: a t-butyl ether; a benzyl, benzhydryl(diphenylmethyl), or trityl(triphenylmethyl)ether; a trimethylsilyl or t-butyldimethylsilyl ether; or an acetyl ester (—OC(=O)CH$_3$, —OAc).

For example, an aldehyde or ketone group may be protected as an acetal (R—CH(OR)$_2$) or ketal (R$_2$C(OR)$_2$), respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid.

For example, an amine group may be protected, for example, as an amide (—NRCO—R) or a urethane (—NRCO—OR), for example, as: a methyl amide (—NHCO—CH$_3$); a benzyloxy amide (—NHCO—OCH$_2$C$_6$H$_5$, —NH-Cbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulfonyl)ethyloxy amide (—NH-Psec); or, in suitable cases (e.g., cyclic amines), as a nitroxide radical (>N—O.).

For example, a carboxylic acid group may be protected as an ester for example, as: an $C_{1-7}$alkyl ester (e.g., a methyl ester; a t-butyl ester); a $C_{1-7}$haloalkyl ester (e.g., a $C_{1-7}$trihaloalkyl ester); a tri$C_{1-7}$alkylsilyl-$C_{1-7}$alkyl ester; or a $C_{5-20}$aryl-$C_{1-7}$alkyl ester (e.g., a benzyl ester; a nitrobenzyl ester); or as an amide, for example, as a methyl amide.

For example, a thiol group may be protected as a thioether (—SR), for example, as: a benzyl thioether; an acetamidomethyl ether (—S—CH$_2$NHC(=O)CH$_3$).

Prodrugs

It may be convenient or desirable to prepare, purify, and/or handle the compound in the form of a prodrug. The term "prodrug," as used herein, pertains to a compound which, when metabolised (e.g., in vivo), yields the desired active compound. Typically, the prodrug is inactive, or less active than the desired active compound, but may provide advantageous handling, administration, or metabolic properties.

Unless otherwise specified, a reference to a particular compound also includes prodrugs thereof.

For example, some prodrugs are esters of the active compound (e.g., a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Also, some prodrugs are activated enzymatically to yield the active compound, or a compound which, upon further chemical reaction, yields the active compound (for example, as in ADEPT, GDEPT, LIDEPT, etc.). For example, the prodrug may be a sugar derivative or other glycoside conjugate, or may be an amino acid ester derivative.

Chemical Synthesis

Several methods for the chemical synthesis of fused bicyclic diarylamine compounds of the present invention are described herein. These and/or other well known methods may be modified and/or adapted in known ways in order to facilitate the synthesis of additional compounds within the scope of the present invention.

In one approach, compounds of type (vi) and (vii) are prepared as shown in the following scheme. 2-Bromo-4-chloro-5-nitropyridine (i) is treated with 4-methoxybenzylamine (PMB-NH$_2$), typically in acetonitrile and in the presence of a tertiary base to afford the intermediate (ii). Reduction of the nitro group using tin (II) chloride or a metal/acid mixture followed by treatment with formamide or a mixture of acetic anhydride and triethylorthoformate gives the fused bicyclic intermediate (iv). Palladium-mediated amination of (iv) with 2-amino-5-cyanopyrazine, typically with heating and in the presence of a base and a suitable phosphine ligand, gives intermediate (v). Removal of the 4-methoxybenzyl group is effected by treatment with trifluoroacetic acid (TFA) or by hydrogenolysis to give intermediate (vi). Alternatively, prolonged treatment with TFA gives the target compound (vii).

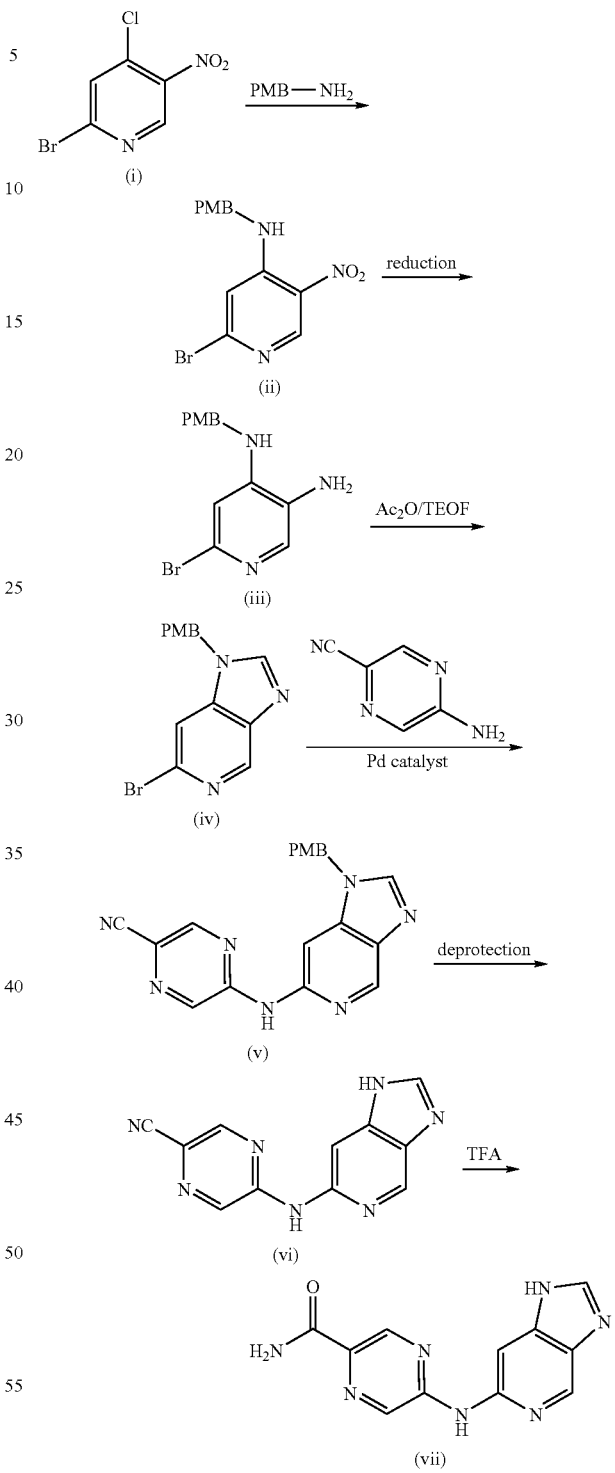

In another approach, 2-alkoxy-5-amino pyrazines (x) are prepared as shown in the following scheme. 2,6-Dichloropyrazine (viii) is treated with ammonia to give 2-chloro-6-aminopyrazine (ix) which is then treated with suitable alcohols (ROH), typically with heating in acetonitrile and in the presence of a base such as sodium hydride, to give the required intermediates (x).

Scheme 2

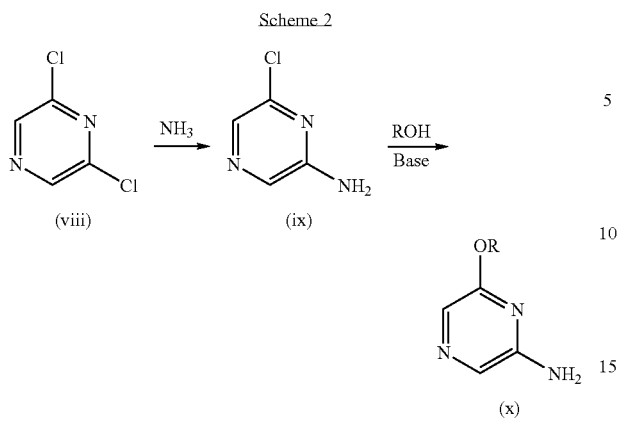

Scheme 4

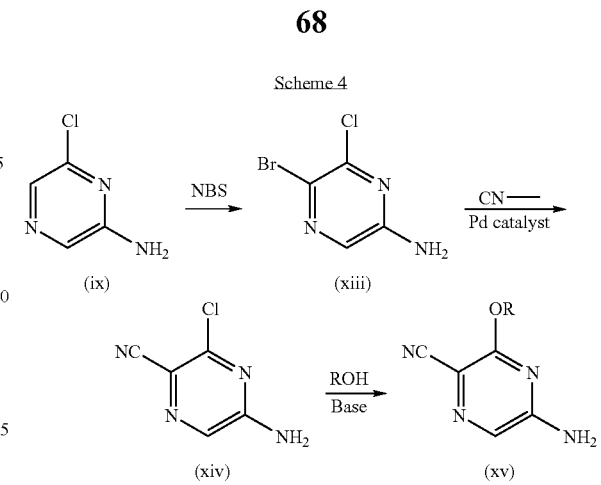

Compounds of type (xii) are prepared as shown in the following scheme. Intermediate (iv) is subjected to palladium-mediated amination with aminopyrazines (x), typically with heating and in the presence of a base and a suitable phosphine ligand, to give intermediates (xi). Removal of the 4-methoxybenzyl group and any protecting groups on the pyrazine component then gives the target compounds (xii).

Compounds of type (xvii) are prepared as shown in the following scheme. Intermediate (iv) is subjected to palladium-mediated amination with aminopyrazines (xv), typically with heating and in the presence of a base and a suitable phosphine ligand to give (xvi). Removal of the 4-methoxybenzyl group and any protecting groups on the pyrazine component then gives the target compounds (xvii).

Scheme 3

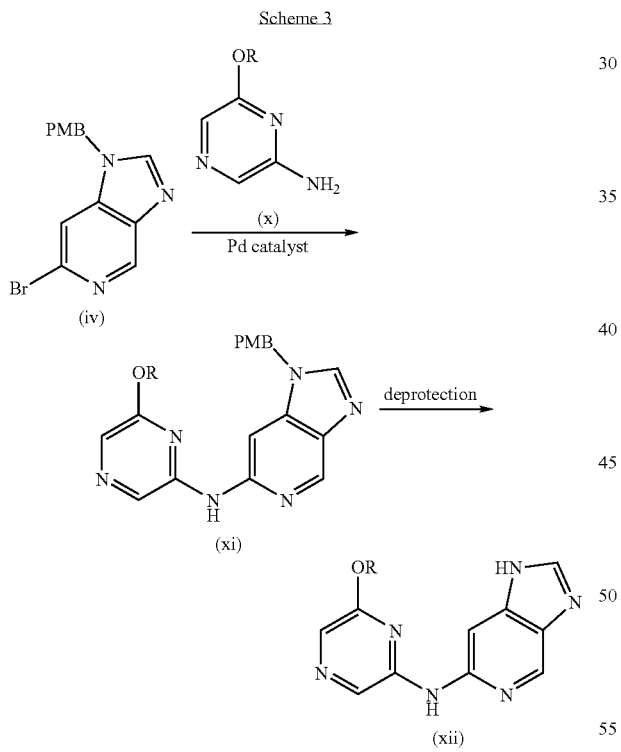

Scheme 5

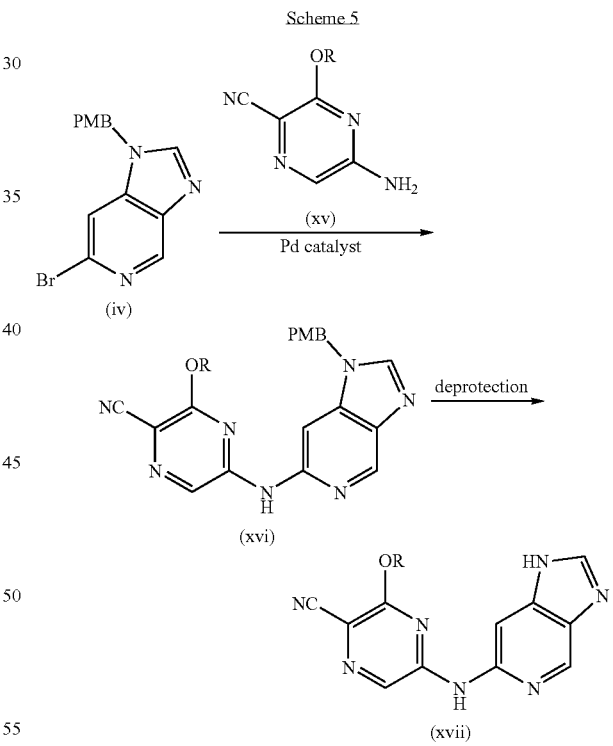

In another approach, 2-alkoxy-3-cyano-5-amino pyrazines (xv) are prepared as shown in the following scheme. 2-Chloro-6-aminopyrazine (ix) is brominated, typically with NBS, to give intermediate (xiii). Treatment of this intermediate with a cyanide source such as potassium cyanide under palladium-mediated reaction conditions then gives intermediate (xiv) which upon treatment with suitable alcohols (ROH), usually with heating in acetonitrile and in the presence of a base such as sodium hydride, gives the required intermediates (xv).

In another approach, compounds of type (xxi) are prepared according to the following scheme. Intermediate (ii) is subjected to palladium-mediated amination with 2-amino-5-cyanopyrazine, typically with heating and in the presence of a base and a suitable phosphine ligand to give intermediate (xviii). Reduction of the nitro group using tin (II) chloride or a metal/acid mixture gives intermediate (xix) which is treated with a suitable aldehyde (RCHO) under oxidative cyclisation conditions, typically sodium metabisulphite in DMF with heating, to give the fused bicyclic diarylamines (xx).

Removal of the 4-methoxybenzyl group and any protecting groups on the aldehyde component then gives the target compounds (xxi).

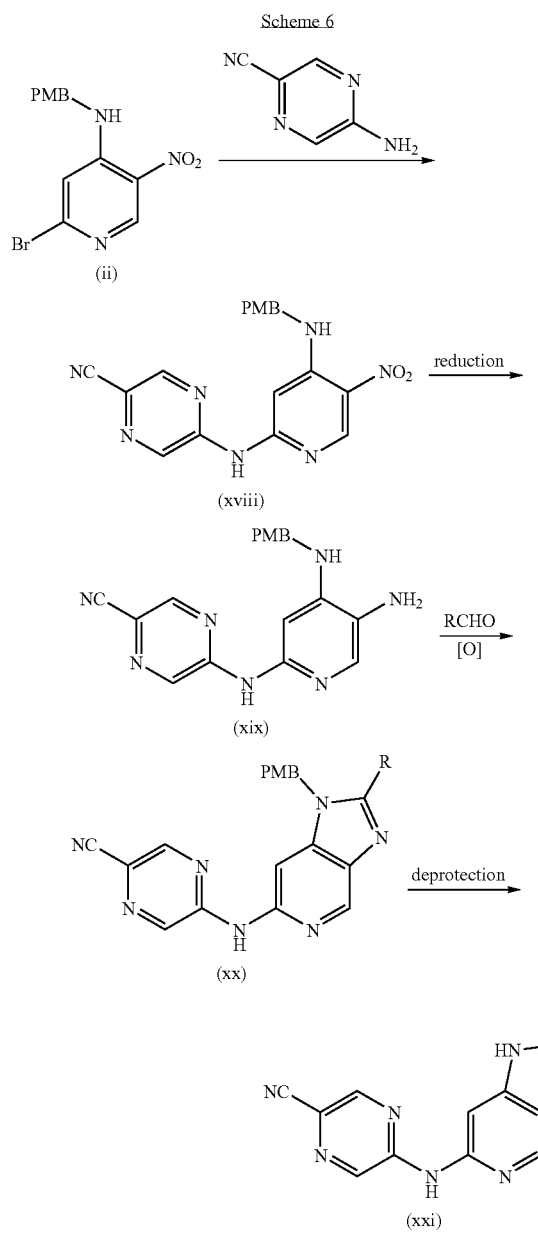

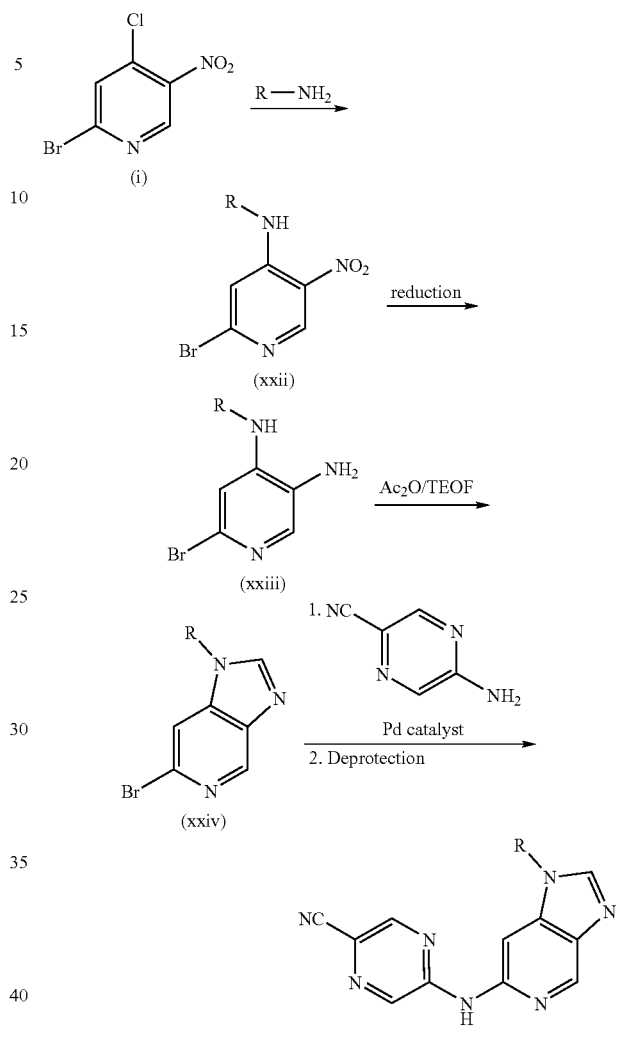

In another approach, compounds of type (xxv) are prepared according to the following scheme. 2-Bromo-4-chloro-5-nitropyridine (i) is treated with an appropriate amine (R—NH$_2$), typically in acetonitrile and in the presence of a tertiary base to afford intermediate (xxii). Reduction of the nitro group using tin (II) chloride or a metal/acid mixture followed by treatment with formamide or a mixture of acetic anhydride and triethylorthoformate gives the fused bicyclic intermediate (xxiv). Palladium-mediated amination of intermediate (iv) with 2-amino-5-cyanopyrazine, typically with heating and in the presence of a base and a suitable phosphine ligand, followed by removal of any protecting groups on the amine component gives the target compounds (xxv).

In another approach, compounds of type (xxvii) are prepared according to the following scheme. 2-Amino-5-cyanopyrazine and an appropriate 3-chloro, or 3-bromo, or 3-(trifluoromethansulfonyloxy)isoquinoline (xxvi) are coupled under palladium-mediated amination conditions typically with heating and in the presence of a base and a suitable phosphine ligand, followed by removal of any protecting groups, to give the target compounds (xxvii).

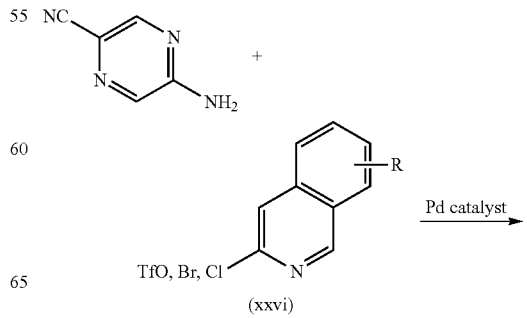

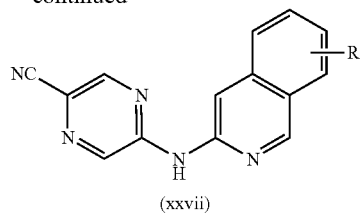

(xxvii)

In another approach, compounds of type (xxviii) are prepared according to the following scheme. A 2-amino-6-alkoxypyrazine (x) and an appropriate 3-chloro, or 3-bromo, or 3-(trifluoromethansulfonyloxy)isoquinoline (xxvi) are coupled under palladium-mediated amination conditions typically with heating and in the presence of a base and a suitable phosphine ligand, followed by removal of any protecting groups, to give the target compounds (xxvii).

Scheme 9

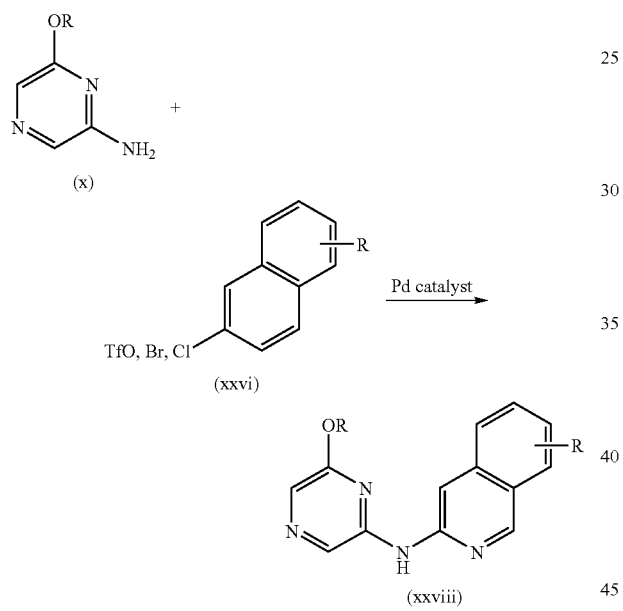

(xxviii)

In another approach, compounds of type (xxix) are prepared according to the following scheme. A 2-amino-5-cyano-6-alkoxypyrazine (xv) and an appropriate 3-chloro, or 3-bromo, or 3-(trifluoromethansulfonyloxy)isoquinoline (xxvi) are coupled under palladium-mediated amination conditions typically with heating and in the presence of base of a suitable phosphine ligand, followed by removal of any protecting groups, to give the target compounds (xxix).

Scheme 10

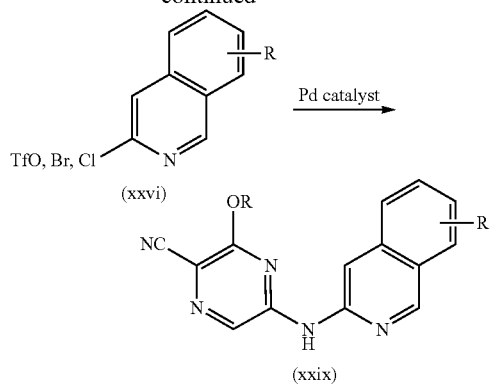

(xxix)

In another approach, compounds of type (xxxii) are prepared according to the following scheme. A 2-amino-5-cyano-6-alkoxypyrazine (xv) and 5-chloro- or 5-bromo-3-(trifluoromethanesulfonyloxy)isoquinoline (xxx) are selectively coupled under palladium-mediated amination conditions, typically with heating and in the presence of base of a suitable phosphine ligand, to give the corresponding 5-haloisoquinoline compounds (xxxi). The 5-haloisoquinolines (xxxi) are further reacted under palladium catalysis with either a boronic acid, typically in the presence of a suitable base and phosphine ligand and with heating, or with an amine, typically in the presence of a suitable base and phosphine ligand and with heating. Alternatively, the 5-haloisoquinolines (xxxi) are reacted with an alkoxide in the presence of a suitable copper (I) compound, typically with heating. The removal of any protecting groups gives the target compounds (xxxii).

Scheme 11

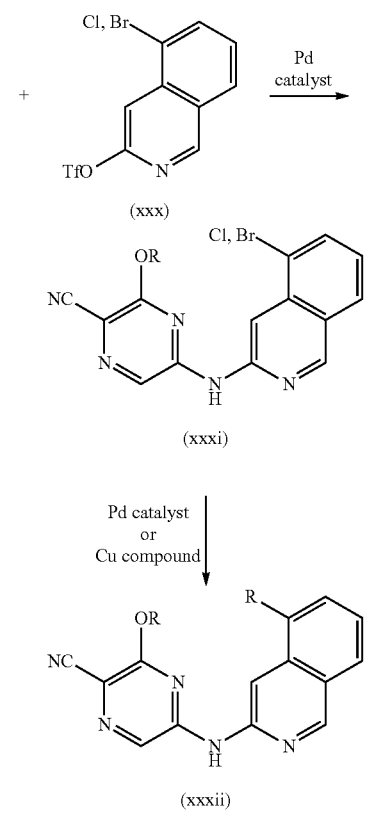

(xxxii)

In another approach, compounds of type (xxxiii) are prepared according to the following scheme. 2-Amino-5-cyanopyrazine and an appropriate tert-butyl 5-chloro-1H-pyrrolo[2,3-c]pyridine-1-carboxylate (xxxiv) are coupled under palladium-mediated amination conditions typically with heating and in the presence of a base and a suitable phosphine ligand, with concomitant removal of the nitrogen protecting group, to give the target compounds (xxxiii).

Scheme 12

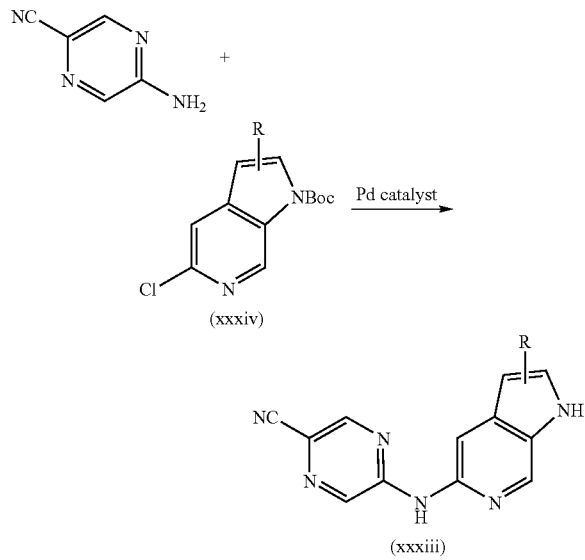

Compositions

One aspect of the present invention pertains to a composition (e.g., a pharmaceutical composition) comprising a BCAA compound, as described herein, and a pharmaceutically acceptable carrier, diluent, or excipient.

Another aspect of the present invention pertains to a method of preparing a composition (e.g., a pharmaceutical composition) comprising admixing a BCAA compound, as described herein, and a pharmaceutically acceptable carrier, diluent, or excipient.

Uses

The compounds described herein are useful, for example, in the treatment of diseases and conditions that are ameliorated by the inhibition of CHK1 kinase function, such as, for example, proliferative conditions, cancer, etc.

Use in Methods of Inhibiting CHK1

One aspect of the present invention pertains to a method of inhibiting CHK1 kinase function, in vitro or in vivo, comprising contacting a CHK1 kinase with an effective amount of a BCAA compound, as described herein.

One aspect of the present invention pertains to a method of inhibiting CHK1 kinase function in a cell, in vitro or in vivo, comprising contacting the cell with an effective amount of a BCAA compound, as described herein.

In one embodiment, the method further comprises contacting the cell with one or more other agents selected from: (a) a DNA topoisomerase I or II inhibitor; (b) a DNA damaging agent; (c) an antimetabolite or TS inhibitor; (d) a microtubule targeted agent; and (e) ionising radiation.

Suitable assays for determining CHK1 kinase function inhibition are described herein and/or are known in the art.

Use in Methods of Inhibiting Cell Proliferation, Etc.

The BCAA compounds described herein, e.g., (a) regulate (e.g., inhibit) cell proliferation; (b) inhibit cell cycle progression; (c) promote apoptosis; or (d) a combination of one or more of these.

One aspect of the present invention pertains to a method of regulating (e.g., inhibiting) cell proliferation (e.g., proliferation of a cell), inhibiting cell cycle progression, promoting apoptosis, or a combination of one or more these, in vitro or in vivo, comprising contacting a cell with an effective amount of a BCAA compound, as described herein.

In one embodiment, the method is a method of regulating (e.g., inhibiting) cell proliferation (e.g., proliferation of a cell), in vitro or in vivo, comprising contacting a cell with an effective amount of a BCAA compound, as described herein.

In one embodiment, the method further comprises contacting the cell with one or more other agents selected from: (a) a DNA topoisomerase I or II inhibitor; (b) a DNA damaging agent; (c) an antimetabolite or TS inhibitor; (d) a microtubule targeted agent; and (e) ionising radiation.

In one embodiment, the method is performed in vitro.
In one embodiment, the method is performed in vivo.
In one embodiment, the BCAA compound is provided in the form of a pharmaceutically acceptable composition.

Any type of cell may be treated, including but not limited to, lung, gastrointestinal (including, e.g., bowel, colon), breast (mammary), ovarian, prostate, liver (hepatic), kidney (renal), bladder, pancreas, brain, and skin.

One of ordinary skill in the art is readily able to determine whether or not a candidate compound regulates (e.g., inhibits) cell proliferation, etc. For example, assays which may conveniently be used to assess the activity offered by a particular compound are described herein.

For example, a sample of cells (e.g., from a tumour) may be grown in vitro and a compound brought into contact with said cells, and the effect of the compound on those cells observed. As an example of "effect," the morphological status of the cells (e.g., alive or dead, etc.) may be determined. Where the compound is found to exert an influence on the cells, this may be used as a prognostic or diagnostic marker of the efficacy of the compound in methods of treating a patient carrying cells of the same cellular type.

Use in Methods of Therapy

Another aspect of the present invention pertains to a BCAA compound, as described herein, for use in a method of treatment of the human or animal body by therapy.

In one embodiment, the method of treatment comprises treatment with both (i) a BCAA compound, as described herein, and (ii) one or more other agents selected from: (a) a DNA topoisomerase I or II inhibitor; (b) a DNA damaging agent; (c) an antimetabolite or TS inhibitor; (d) a microtubule targeted agent; and (e) ionising radiation.

Another aspect of the present invention pertains to (a) a DNA topoisomerase I or II inhibitor, (b) a DNA damaging agent, (c) an antimetabolite or TS inhibitor, or (d) a microtubule targeted agent, as described herein, for use in a method of treatment of the human or animal body by therapy, wherein the method of treatment comprises treatment with both (i) a BCAA compound, as described herein, and (a) the DNA topoisomerase I or II inhibitor, (b) the DNA damaging agent, (c) the antimetabolite or TS inhibitor, or (d) the microtubule targeted agent.

Use in the Manufacture of Medicaments

Another aspect of the present invention pertains to use of a BCAA compound, as described herein, in the manufacture of a medicament for use in treatment.

In one embodiment, the medicament comprises the BCAA compound.

In one embodiment, the treatment comprises treatment with both (i) a medicament comprising a BCAA compound, as described herein, and (ii) one or more other agents selected from: (a) a DNA topoisomerase I or II inhibitor; (b) a DNA damaging agent; (c) an antimetabolite or TS inhibitor; (d) a microtubule targeted agent; and (e) ionising radiation.

Another aspect of the present invention pertains to use of (a) a DNA topoisomerase I or II inhibitor, (b) a DNA damaging agent, (c) an antimetabolite or TS inhibitor, or (d) a microtubule targeted agent, as described herein, in the manufacture of a medicament for use in a treatment, wherein the treatment comprises treatment with both (i) a BCAA compound, as described herein, and (a) the DNA topoisomerase I or II inhibitor, (b) the DNA damaging agent, (c) the antimetabolite or TS inhibitor, or (d) the microtubule targeted agent.

Methods of Treatment

Another aspect of the present invention pertains to a method of treatment comprising administering to a patient in need of treatment a therapeutically effective amount of a BCAA compound, as described herein, preferably in the form of a pharmaceutical composition.

In one embodiment, the method further comprises administering to the subject one or more other agents selected from: (a) a DNA topoisomerase I or II inhibitor; (b) a DNA damaging agent; (c) an antimetabolite or TS inhibitor; (d) a microtubule targeted agent; and (e) ionising radiation.

Conditions Treated—Conditions Mediated by CHK1

In one embodiment (e.g., of use in methods of therapy, of use in the manufacture of medicaments, of methods of treatment), the treatment is treatment of a disease or condition that is mediated by CHK1.

Conditions Treated—Conditions Ameliorated by the Inhibition of CHK1 Kinase Function In one embodiment (e.g., of use in methods of therapy, of use in the manufacture of medicaments, of methods of treatment), the treatment is treatment of: a disease or condition that is ameliorated by the inhibition of CHK1 kinase function.

Conditions Treated—Proliferative Conditions and Cancer

In one embodiment (e.g., of use in methods of therapy, of use in the manufacture of medicaments, of methods of treatment), the treatment is treatment of: a proliferative condition.

The term "proliferative condition," as used herein, pertains to an unwanted or uncontrolled cellular proliferation of excessive or abnormal cells which is undesired, such as, neoplastic or hyperplastic growth.

In one embodiment, the treatment is treatment of: a proliferative condition characterised by benign, pre-malignant, or malignant cellular proliferation, including but not limited to, neoplasms, hyperplasias, and tumours (e.g., histocytoma, glioma, astrocyoma, osteoma), cancers (see below), psoriasis, bone diseases, fibroproliferative disorders (e.g., of connective tissues), pulmonary fibrosis, atherosclerosis, smooth muscle cell proliferation in the blood vessels, such as stenosis or restenosis following angioplasty.

In one embodiment, the treatment is treatment of: cancer.

In one embodiment, the treatment is treatment of: cancer characterised by, or further characterised by, cancer cells which overexpress Checkpoint Kinase 1 (CHK1).

In one embodiment, the treatment is treatment of: p53 negative cancer.

In one embodiment, the treatment is treatment of: lung cancer, small cell lung cancer, non-small cell lung cancer, gastrointestinal cancer, stomach cancer, bowel cancer, colon cancer, rectal cancer, colorectal cancer, thyroid cancer, breast cancer, ovarian cancer, endometrial cancer, prostate cancer, testicular cancer, liver cancer, kidney cancer, renal cell carcinoma, bladder cancer, pancreatic cancer, brain cancer, glioma, sarcoma, osteosarcoma, bone cancer, nasopharyngeal cancer (e.g., head cancer, neck cancer), skin cancer, squamous cancer, Kaposi's sarcoma, melanoma, malignant melanoma, lymphoma, or leukemia.

In one embodiment, the treatment is treatment of:

a carcinoma, for example a carcinoma of the bladder, breast, colon (e.g., colorectal carcinomas such as colon adenocarcinoma and colon adenoma), kidney, epidermal, liver, lung (e.g., adenocarcinoma, small cell lung cancer and non-small cell lung carcinomas), oesophagus, gall bladder, ovary, pancreas (e.g., exocrine pancreatic carcinoma), stomach, cervix, thyroid, prostate, skin (e.g., squamous cell carcinoma);

a hematopoietic tumour of lymphoid lineage, for example leukemia, acute lymphocytic leukemia, B-cell lymphoma, T-cell lymphoma, Hodgkin's lymphoma, non-Hodgkin's lymphoma, hairy cell lymphoma, or Burkett's lymphoma;

a hematopoietic tumor of myeloid lineage, for example acute and chronic myelogenous leukemias, myelodysplastic syndrome, or promyelocytic leukemia;

a tumour of mesenchymal origin, for example fibrosarcoma or habdomyosarcoma;

a tumor of the central or peripheral nervous system, for example astrocytoma, neuroblastoma, glioma or schwannoma;

melanoma; seminoma; teratocarcinoma; osteosarcoma; xenoderoma pigmentoum; keratoctanthoma; thyroid follicular cancer; or Kaposi's sarcoma.

In one embodiment, the treatment is treatment of solid tumour cancer.

In one embodiment, the treatment is treatment of: lung cancer, breast cancer, ovarian cancer, colorectal cancer, melanoma, or glioma.

In one embodiment, the cancer is characterised by, or further characterised by, cancer stem cells.

The anti-cancer effect may arise through one or more mechanisms, including but not limited to, the regulation of cell proliferation, the inhibition of cell cycle progression, the inhibition of angiogenesis (the formation of new blood vessels), the inhibition of metastasis (the spread of a tumour from its origin), the inhibition of invasion (the spread of tumour cells into neighbouring normal structures), or the promotion of apoptosis (programmed cell death). The compounds of the present invention may be used in the treatment of the cancers described herein, independent of the mechanisms discussed herein.

Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, alleviatiation of symptoms of the condition, amelioration of the condition, and cure of the condition. Treatment as a prophylactic measure (i.e., prophylaxis) is also included. For example, use with patients who have not yet developed the condition, but who are at risk of developing the condition, is encompassed by the term "treatment."

For example, treatment includes the prophylaxis of cancer, reducing the incidence of cancer, alleviating the symptoms of cancer, etc.

The term "therapeutically-effective amount," as used herein, pertains to that amount of a compound, or a material, composition or dosage form comprising a compound, which is effective for producing some desired therapeutic effect, commensurate with a reasonable benefit/risk ratio, when administered in accordance with a desired treatment regimen.

Combination Therapies

The term "treatment" includes combination treatments and therapies, in which two or more treatments or therapies are combined, for example, sequentially or simultaneously. For example, the compounds described herein may also be used in combination therapies, e.g., in conjunction with other agents, for example, cytotoxic agents, anticancer agents, etc. Examples of treatments and therapies include, but are not limited to, chemotherapy (the administration of active agents, including, e.g., drugs, antibodies (e.g., as in immunotherapy), prodrugs (e.g., as in photodynamic therapy, GDEPT, ADEPT, etc.); surgery; radiation therapy; photodynamic therapy; gene therapy; and controlled diets.

For example, it may be beneficial to combine treatment with a compound as described herein with one or more other (e.g., 1, 2, 3, 4) agents or therapies that regulates cell growth or survival or differentiation via a different mechanism, thus treating several characteristic features of cancer development.

One aspect of the present invention pertains to a compound as described herein, in combination with one or more additional therapeutic agents, as described below.

The particular combination would be at the discretion of the physician who would select dosages using his common general knowledge and dosing regimens known to a skilled practitioner.

The agents (i.e., the compound described herein, plus one or more other agents) may be administered simultaneously or sequentially, and may be administered in individually varying dose schedules and via different routes. For example, when administered sequentially, the agents can be administered at closely spaced intervals (e.g., over a period of 5-10 minutes) or at longer intervals (e.g., 1, 2, 3, 4 or more hours apart, or even longer periods apart where required), the precise dosage regimen being commensurate with the properties of the therapeutic agent(s).

The agents (i.e., the compound described here, plus one or more other agents) may be formulated together in a single dosage form, or alternatively, the individual agents may be formulated separately and presented together in the form of a kit, optionally with instructions for their use.

Combination Therapies Employing DNA Damaging Agents

As discussed herein, in some embodiments, the BCAA compound is employed in combination with (e.g., in conjunction with) with one or more other agents selected from: (a) a DNA topoisomerase I or II inhibitor; (b) a DNA damaging agent; (c) an antimetabolite or TS inhibitor; (d) a microtubule targeted agent; and (e) ionising radiation.

When both a BCAA compound and one or more other agents are employed, they may be used (e.g., contacted, administered, etc.) in any order. Furthermore, they may be used (e.g., contacted, administered, etc.) together, as part of a single formulation, or separately, as separate formulations.

For example, in regard to methods of treatment employing both a BCAA compound and one or more other agents, treatment with (e.g., administration of) the BCAA compound may be prior to, concurrent with, or may follow, treatment with (e.g., administration of) the one or more other agents, or a combination thereof.

In one embodiment, treatment with (e.g., administration of) a BCAA compound is concurrent with, or follows, treatment with (e.g., administration of) the one or more other agents.

In one embodiment, the one or more other agents is a DNA topoisomerase I or II inhibitor; for example, Etoposide, Toptecan, Camptothecin, Irinotecan, SN-38, Doxorubicin, Daunorubicin.

In one embodiment, the one or more other agents is a DNA damaging agent; for example, alkylating agents, platinating agents, or compounds that generate free radicals; for example, Temozolomide, Cisplatin, Carboplatin, Mitomycin C, Cyclophosphamide, BCNU, CCNU, Bleomycin.

In one embodiment, the one or more other agents is an antimetabolite or TS inhibitor; for example, 5-fluorouracil, hydroxyurea, Gemcitabine, Arabinosylcytosine, Fludarabine, Tomudex, ZD9331.

In one embodiment, the one or more other agents is a microtubule targeted agent; for example, Paclitaxel, Docetaxel, Vincristine, Vinblastine.

In one embodiment, the one or more other agents is ionising radiation (e.g., as part of radiotherapy).

Other Uses

The BCAA compounds described herein may also be used as cell culture additives to inhibit CHK1 kinase function, e.g., to inhibit cell proliferation, etc.

The BCAA compounds described herein may also be used as part of an in vitro assay, for example, in order to determine whether a candidate host is likely to benefit from treatment with the compound in question.

The BCAA compounds described herein may also be used as a standard, for example, in an assay, in order to identify other compounds, other CHK1 kinase function inhibitors, other anti-proliferative agents, other anti-cancer agents, etc.

Kits

One aspect of the invention pertains to a kit comprising (a) a BCAA compound as described herein, or a composition comprising a BCAA compound as described herein, e.g., preferably provided in a suitable container and/or with suitable packaging; and (b) instructions for use, e.g., written instructions on how to administer the compound or composition.

In one embodiment, the kit further comprises one or more other agents selected from: (a) a DNA topoisomerase I or II inhibitor; (b) a DNA damaging agent; (c) an antimetabolite or TS inhibitor; and (d) a microtubule targeted agent.

The written instructions may also include a list of indications for which the active ingredient is a suitable treatment.

Routes of Administration

The BCAA compound or pharmaceutical composition comprising the BCAA compound may be administered to a subject by any convenient route of administration, whether systemically/peripherally or topically (i.e., at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

The Subject/Patient

The subject/patient may be a chordate, a vertebrate, a mammal, a placental mammal, a marsupial (e.g., kangaroo, wombat), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

Furthermore, the subject/patient may be any of its forms of development, for example, a foetus.

In one preferred embodiment, the subject/patient is a human.

Formulations

While it is possible for the BCAA compound to be administered alone, it is preferable to present it as a pharmaceutical formulation (e.g., composition, preparation, medicament) comprising at least one BCAA compound, as described herein, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents. The formulation may further comprise other active agents, for example, other therapeutic or prophylactic agents.

Thus, the present invention further provides pharmaceutical compositions, as defined above, and methods of making a pharmaceutical composition comprising admixing at least one BCAA compound, as described herein, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the compound.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

Suitable carriers, diluents, excipients, etc. can be found in standard pharmaceutical texts, for example, *Remington's Pharmaceutical Sciences,* 18th edition, Mack Publishing Company, Easton, Pa., 1990; and *Handbook of Pharmaceutical Excipients,* 5th edition, 2005.

The formulations may be prepared by any methods well known in the art of pharmacy. Such methods include the step of bringing into association the compound with a carrier which constitutes one or more accessory ingredients. In general, the formulations are prepared by uniformly and intimately bringing into association the compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations may suitably be in the form of liquids, solutions (e.g., aqueous, non-aqueous), suspensions (e.g., aqueous, non-aqueous), emulsions (e.g., oil-in-water, water-in-oil), elixirs, syrups, electuaries, mouthwashes, drops, tablets (including, e.g., coated tablets), granules, powders, losenges, pastilles, capsules (including, e.g., hard and soft gelatin capsules), cachets, pills, ampoules, boluses, suppositories, pessaries, tinctures, gels, pastes, ointments, creams, lotions, oils, foams, sprays, mists, or aerosols.

Formulations may suitably be provided as a patch, adhesive plaster, bandage, dressing, or the like which is impregnated with one or more compounds and optionally one or more other pharmaceutically acceptable ingredients, including, for example, penetration, permeation, and absorption enhancers. Formulations may also suitably be provided in the form of a depot or reservoir.

The compound may be dissolved in, suspended in, or admixed with one or more other pharmaceutically acceptable ingredients. The compound may be presented in a liposome or other microparticulate which is designed to target the compound, for example, to blood components or one or more organs.

Formulations suitable for oral administration (e.g., by ingestion) include liquids, solutions (e.g., aqueous, non-aqueous), suspensions (e.g., aqueous, non-aqueous), emulsions (e.g., oil-in-water, water-in-oil), elixirs, syrups, electuaries, tablets, granules, powders, capsules, cachets, pills, ampoules, boluses.

Formulations suitable for buccal administration include mouthwashes, losenges, pastilles, as well as patches, adhesive plasters, depots, and reservoirs. Losenges typically comprise the compound in a flavored basis, usually sucrose and acacia or tragacanth. Pastilles typically comprise the compound in an inert matrix, such as gelatin and glycerin, or sucrose and acacia. Mouthwashes typically comprise the compound in a suitable liquid carrier.

Formulations suitable for sublingual administration include tablets, losenges, pastilles, capsules, and pills.

Formulations suitable for oral transmucosal administration include liquids, solutions (e.g., aqueous, non-aqueous), suspensions (e.g., aqueous, non-aqueous), emulsions (e.g., oil-in-water, water-in-oil), mouthwashes, losenges, pastilles, as well as patches, adhesive plasters, depots, and reservoirs.

Formulations suitable for non-oral transmucosal administration include liquids, solutions (e.g., aqueous, non-aqueous), suspensions (e.g., aqueous, non-aqueous), emulsions (e.g., oil-in-water, water-in-oil), suppositories, pessaries, gels, pastes, ointments, creams, lotions, oils, as well as patches, adhesive plasters, depots, and reservoirs.

Formulations suitable for transdermal administration include gels, pastes, ointments, creams, lotions, and oils, as well as patches, adhesive plasters, bandages, dressings, depots, and reservoirs.

Tablets may be made by conventional means, e.g., compression or moulding, optionally with one or more accessory ingredients. Compressed tablets may be prepared by compressing in a suitable machine the compound in a free-flowing form such as a powder or granules, optionally mixed with one or more binders (e.g., povidone, gelatin, acacia, sorbitol, tragacanth, hydroxypropylmethyl cellulose); fillers or diluents (e.g., lactose, microcrystalline cellulose, calcium hydrogen phosphate); lubricants (e.g., magnesium stearate, talc, silica); disintegrants (e.g., sodium starch glycolate, cross-linked povidone, cross-linked sodium carboxymethyl cellulose); surface-active or dispersing or wetting agents (e.g., sodium lauryl sulfate); preservatives (e.g., methyl p-hydroxybenzoate, propyl p-hydroxybenzoate, sorbic acid); flavours, flavour enhancing agents, and sweeteners. Moulded tablets may be made by moulding in a suitable machine a mixture of the powdered compound moistened with an inert liquid diluent. The tablets may optionally be coated or scored and may be formulated so as to provide slow or controlled release of the compound therein using, for example, hydroxypropylmethyl cellulose in varying proportions to provide the desired release profile. Tablets may optionally be provided with a coating, for example, to affect release, for example an enteric coating, to provide release in parts of the gut other than the stomach.

Ointments are typically prepared from the compound and a paraffinic or a water-miscible ointment base.

Creams are typically prepared from the compound and an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the compound through the skin or other affected areas. Examples of such dermal penetration enhancers include dimethylsulfoxide and related analogues.

Emulsions are typically prepared from the compound and an oily phase, which may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulfate. The choice of suitable oils or fats for the formulation is based on achieving the desired cosmetic properties, since the solubility of the compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for intranasal administration, where the carrier is a liquid, include, for example, nasal spray, nasal drops, or by aerosol administration by nebuliser, include aqueous or oily solutions of the compound.

Formulations suitable for intranasal administration, where the carrier is a solid, include, for example, those presented as a coarse powder having a particle size, for example, in the range of about 20 to about 500 microns which is administered in the manner in which snuff is taken, i.e., by rapid inhalation through the nasal passage from a container of the powder held close up to the nose.

Formulations suitable for pulmonary administration (e.g., by inhalation or insufflation therapy) include those presented as an aerosol spray from a pressurised pack, with the use of a suitable propellant, such as dichlorodifluoromethane, trichlorofluoromethane, dichoro-tetrafluoroethane, carbon dioxide, or other suitable gases.

Formulations suitable for ocular administration include eye drops wherein the compound is dissolved or suspended in a suitable carrier, especially an aqueous solvent for the compound.

Formulations suitable for rectal administration may be presented as a suppository with a suitable base comprising, for example, natural or hardened oils, waxes, fats, semi-liquid or liquid polyols, for example, cocoa butter or a salicylate; or as a solution or suspension for treatment by enema.

Formulations suitable for vaginal administration may be presented as pessaries, tampons, creams, gels, pastes, foams or spray formulations containing in addition to the compound, such carriers as are known in the art to be appropriate.

Formulations suitable for parenteral administration (e.g., by injection), include aqueous or non-aqueous, isotonic, pyrogen-free, sterile liquids (e.g., solutions, suspensions), in which the compound is dissolved, suspended, or otherwise provided (e.g., in a liposome or other microparticulate). Such liquids may additional contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the compound in the liquid is from about 1 ng/ml to about 10 µg/ml, for example from about 10 ng/ml to about 1 µg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Dosage

It will be appreciated by one of skill in the art that appropriate dosages of the BCAA compounds, and compositions comprising the BCAA compounds, can vary from patient to patient. Determining the optimal dosage will generally involve the balancing of the level of therapeutic benefit against any risk or deleterious side effects. The selected dosage level will depend on a variety of factors including, but not limited to, the activity of the particular BCAA compound, the route of administration, the time of administration, the rate of excretion of the BCAA compound, the duration of the treatment, other drugs, compounds, and/or materials used in combination, the severity of the condition, and the species, sex, age, weight, condition, general health, and prior medical history of the patient. The amount of BCAA compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the BCAA compound is in the range of about 10 µg to about 250 mg (more typically about 100 µg to about 25 mg) per kilogram body weight of the subject per day. Where the compound is a salt, an ester, an amide, a prodrug, or the like, the amount administered is calculated on the basis of the parent compound and so the actual weight to be used is increased proportionately.

EXAMPLES

The following examples are provided solely to illustrate the present invention and are not intended to limit the scope of the invention, as described herein.
Chemical Synthesis
General Conditions for LC-MS Analyses
Solvent A (Aqueous):
0.02% Ammonia and 0.063% ammonium formate in water.
Solvent B (Organic):
0.02% Ammonia and 5% Buffer A in acetonitrile.
Method: LCMS (1)
Column: Phenomenex Gemini C18, 3 μm, 3.0×30 mm.
Injection Volume: 5 μL.
UV detection: 220 to 400 nm.
Column Temperature: 35° C.
0.00 to 2.50 min: 95% A to 5% A (1.2 mL/min).
2.50 to 2.75 min: 5% A (1.2 mL/min).
2.75 to 3.50 min: 5% A (2.0 mL/min).
3.50 to 3.65 min: 5% A to 95% A (2.0 mL/min).
3.65 to 4.00 min: 95% A (1.2 mL/min).
Method: LCMS (2)
Column: Phenomenex Gemini C18, 5 μm, 4.6×30 mm.
Injection Volume: 5 μL.
UV detection: 220 to 400 nm.
Column Temperature: 35° C.
0.00 to 4.25 min: 95% A to 5% A (2.0 mL/min).
4.25 to 5.80 min: 5% A (2.0 mL/min).
5.80 to 5.90 min: 5% A to 95% A (2.0 mL/min).
5.90 to 7.00 min: 95% A (2.0 mL/min).
Method: LCMS (3)
Column: Waters X-Bridge C18, 2.5 μM, 3.0×30 mm.
Injection Volume: 5 μL.
UV detection: 220 to 400 nm.
Column Temperature: 35° C.
0.00 to 2.50 min 95% A to 5% A (1.0 mL/min).
2.50 to 2.75 min 5% A (1.0 mL/min).
2.75 to 3.55 min 5% A (1.66 mL/min).
3.55 to 3.65 min 5% A to 95% A (1.66 mL/min).
3.65 to 4.00 min 95% A (1.0 mL/min).

Synthesis 1-1-A

N-(4-Methoxybenzyl)-2-bromo-5-nitropyridin-4-amine

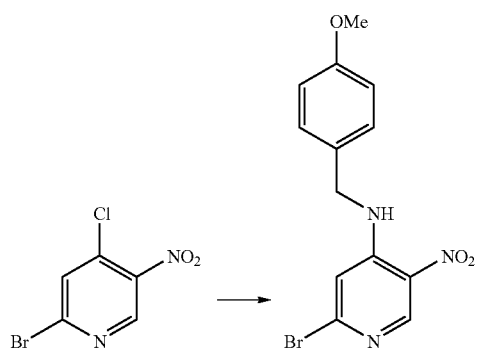 [SMILES: O=[N+]([O-])c1cnc(Br)cc1Cl ; COc1ccc(CNc2cc(Br)ncc2[N+](=O)[O-])cc1]

A solution of 4-methoxybenzylamine (0.756 g, 5.51 mmol) in acetonitrile (2 mL) was added to a mixture of 2-bromo-4-chloro-5-nitropyridine (1.19 g, 5.01 mmol) and triethylamine (0.768 mL, 5.51 mmol) in acetonitrile (8 mL). After stirring for 1.5 hours, the solution was diluted with ethyl acetate (100 mL) which was then washed successively with water and brine before being concentrated in vacuo to a light brown oil which solidified on standing to give the title compound (1.31 g, 3.87 mmol, 77%). $^1$H NMR (d$_6$-DMSO, 400 MHz) δ 9.00 (br t, 1H, J=6.3 Hz), 8.80 (s, 1H), 7.35 (d, 2H, J=8.7 Hz), 7.10 (s, 1H), 6.95 (d, 2H, J=8.8 Hz), 4.60 (d, 2H, J=6.0 Hz), 3.70 (s, 3H). LCMS (1) Rt=2.13 min; m/z (ESI−) 336, 338 (M−H).

Synthesis 1-1-B 5-(4-(4-Methoxybenzylamino)-5-nitropyridin-2-ylamino)pyrazine-2-carbonitrile

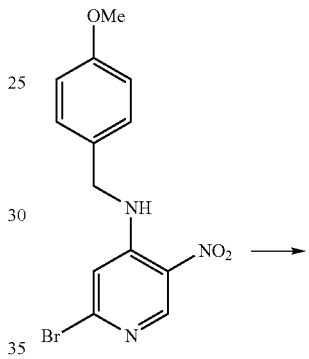

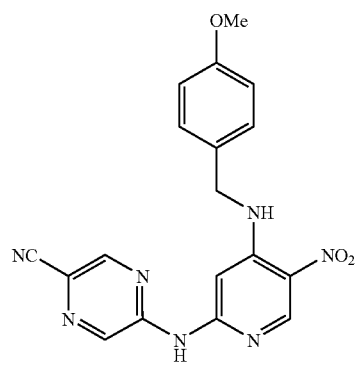

A mixture of palladium (II) acetate (38 mg, 0.17 mmol) and (±)-2,2"-bis(diphenylphosphino)-1,1"-binaphthalene (318 mg, 0.51 mmol) a mixture of toluene and DMF (1:1, 10 mL) was degassed under a stream of nitrogen gas with stirring for 30 minutes. After addition of 2-amino-5-cyanopyrazine (245 mg, 2.04 mmol), sodium tert-butoxide (196 mg, 2.04 mmol) and N-(4-methoxybenzyl)-2-bromo-5-nitropyridin-4-amine (575 mg, 1.70 mmol), the mixture was degassed for a further 5 minutes and then heated at 140° C. for 30 minutes in a microwave reactor. Upon cooling, the mixture was diluted with methanol and isolated by SPE using 3×2.5 g MP-TsOH cartridges, washing with methanol and then eluting with 2 M ammonia in methanol. The basic fractions were concentrated in vacuo to give the title compound (470 mg, 1.25 mmol, 73%) which was used without further purification. LCMS (2) Rt=2.18 min; m/z (ESI−) 376 (M−H); (ESI+) 378 (MH$^+$).

Synthesis 1-1-C

5-(4-(4-Methoxybenzylamino)-5-aminopyridin-2-ylamino)pyrazine-2-carbonitrile

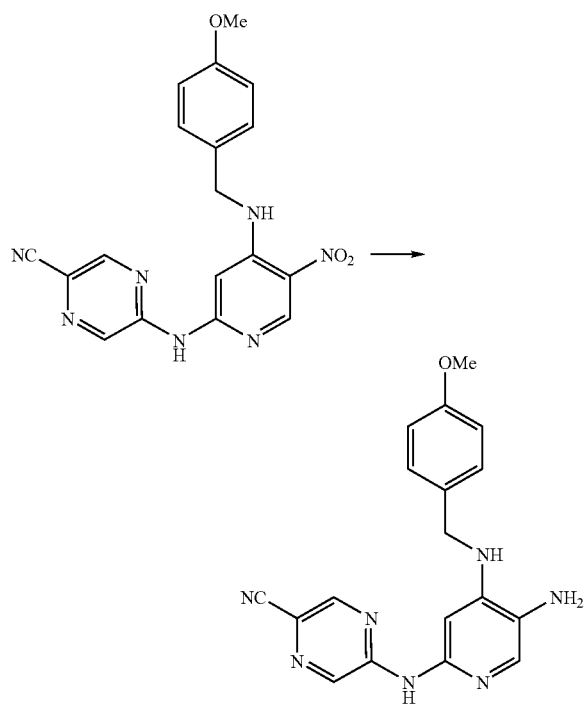

Tin(II)chloride dihydrate (1.59 g, 7.04 mmol) was added portionwise to 5-(4-(4-methoxybenzylamino)-5-nitropyridin-2-ylamino)pyrazine-2-carbonitrile (531 mg, 1.41 mmol) in absolute EtOH (10 mL) at room temperature. The mixture was heated at 70° C. for 2 hours before being concentrated in vacuo. The residue was suspended in a mixture of ethyl acetate and saturated sodium bicarbonate solution, then filtered to remove insoluble material. The solids were then washed with EtOAc. The aqueous phase was re-extracted with ethyl acetate and the combined organic extracts were washed with brine, dried (Na$_2$SO$_4$) and concentrated to give crude title compound (415 mg) as a brown solid. The product was 50% pure by LCMS analysis and was used without further purification. LCMS (2) Rt=1.73 min; m/z (ESI−) 346 (M−H); (ESI+) 348 (MH$^+$).

Synthesis 1-1-D

5-(2-Cyclopropyl-1H-imidazo[4,5-c]pyridin-6-ylamino)pyrazine-2-carbonitrile (BB-001)

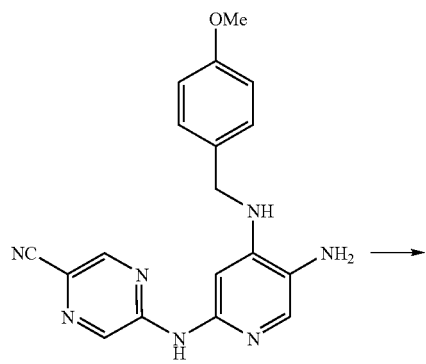

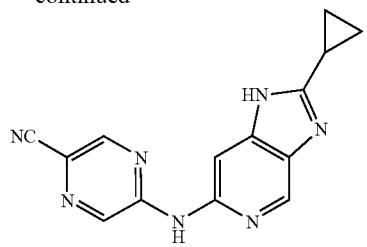

A mixture of crude 5-(4-(4-methoxybenzylamino)-5-aminopyridin-2-ylamino)pyrazine-2-carbonitrile (0.083 mmol), cyclopropane carboxaldehyde (5.9 mg, 0.083 mmol) and sodium metabisulfite (16 mg, 0.083 mmol) in DMF (1 mL) was heated at 100° C. for 4 hours. Upon cooling, the mixture was partitioned between ethyl acetate and water. The organic layer was washed with brine, dried (Na$_2$SO$_4$) and concentrated to a light brown solid. The solid was stirred at 65° C. with trifluoroacetic acid. Upon completion of the reaction, the mixture was concentrated. Preparative HPLC gave the title compound (3.7 mg, 16%). $^1$H NMR (d$_6$-DMSO, 400 MHz) δ 12.60 (br s, 1H), 10.75 (br s, 1H), 8.80 (s, 1H), 8.75 (s, 1H), 8.50 (s, 1H), 8.10 (s, 1H), 2.10-2.20 (m, 1H), 1.00-1.20 (m, 4H). LCMS (2) Rt=1.68 min; m/z (ESI−) 276 (M−H); (ESI+) 278 (MH$^+$).

The following compounds were prepared using methods analogous to those described in Synthesis 1-1, using the appropriate aldehydes in place of cyclopropane carboxaldehyde in Synthesis 1-1-D.

| Synthesis | 1-2 |
|---|---|
| Compound | BB-002 |
| Structure | |
| NMR | $^1$H NMR (d$_6$-DMSO, 400 MHz) δ 13.30 (br s, 1H), 10.90 (br s, 1H), 8.80 (s, 2H), 8.75 (s, 1H), 8.30 (s, 1H), 8.20 (d, 2H, J = 6.5 Hz), 7.55-7.65 (m, 3H). |
| LCMS | LCMS (2) Rt = 2.20 min; m/z (ESI−) 312 (M − H); (ESI+) 314 (MH$^+$). |
| Synthesis | 1-3 |
| Compound | BB-003 |
| Structure | |

| | |
|---|---|
| NMR | ¹H NMR (d₆-DMSO, 400 MHz) δ 12.90 (s, 1H), 10.85 (s, 1H), 8.80 (s, 1H), 8.75 (s, 1H), 8.65 (s, 1H), 8.20 (s, 1H), 8.00 (d, 2H, J = 9.2 Hz), 6.85 (d, 2H, J = 9.2 Hz), 3.00 (s, 6H). |
| LCMS | LCMS (2) Rt = 2.20 min; m/z (ESI−) 355 (M − H); (ESI+) 357 (MH⁺). |
| Synthesis | 1-4 |
| Compound | BB-004 |
| Structure | |

| | |
|---|---|
| NMR | ¹H NMR (d₆-DMSO, 400 MHz) δ 13.13 (br s, 1H), 10.87 (br s, 1H), 8.79 (s, 1H), 8.78 (s, 2H), 8.71 (s, 1H), 8.27 (s, 1H), 8.12 (d, 2H, J = 8.0 Hz), 7.15 (d, 2H, J = 8.0 Hz), 3.86 (s, 3H). |
| LCMS | LCMS (2) Rt = 2.24 min; m/z (ESI−) 342 (M − H); (ESI+) 344 (MH⁺). |
| Synthesis | 1-5 |
| Compound | BB-005 |
| Structure | |

| | |
|---|---|
| NMR | ¹H NMR (d₆-DMSO, 400 MHz) δ 8.65 (br s, 1H), 8.62 (d, 1H, J = 1.4 Hz), 8.54 (d, 1H J = 1.4 Hz), 8.07 (br s, 1H), 7.77 (dd, 1H, J = 1.3, 3.8 Hz), 7.65 (dd, 1H, J = 1.3, 5.0 Hz), 7.11 (dd, 1H, J = 3.8, 5.0 Hz). |
| LCMS | LCMS (2) Rt = 2.04 min; m/z (ESI−) 318 (M − H); (ESI+) 320 (MH⁺). |
| Synthesis | 1-6 |
| Compound | BB-006 |
| Structure | |

| | |
|---|---|
| NMR | ¹H NMR (d₆-DMSO, 400 MHz) δ 8.80 (s, 1H), 8.76 (s, 1H), 8.65 (s, 1H), 8.21 (s, 1H), 8.02 (d, 2H, J = 9.0 Hz), 7.08 (d, 2H, J = 9.0 Hz), 3.20-3.25 (m, 4H), 2.85-2.90 (m, 4H). |

| | |
|---|---|
| LCMS | LCMS (2) Rt = 1.88 min; m/z (ESI−) 396 (M − H); (ESI+) 398 (MH⁺). |
| Synthesis | 1-7 |
| Compound | BB-007 |
| Structure | |

| | |
|---|---|
| NMR | ¹H NMR (d₆-DMSO, 400 MHz) δ 8.84 (d, 1H, J = 1.0 Hz), 8.79-8.81 (m, 3H), 8.78 (s, 1H), 8.36 (s, 1H), 8.08-8.11 (m, 2H). |
| LCMS | LCMS (2) Rt = 1.54 min; m/z (ESI−) 313 (M − H); (ESI+) 315 (MH⁺). |
| Synthesis | 1-8 |
| Compound | BB-008 |
| Structure | |

| | |
|---|---|
| NMR | ¹H NMR (d₆-DMSO, 400 MHz) δ 13.50 (br s, 1H), 10.92 (br s, 1H), 9.35 (d, 1H, J = 1.5 Hz), 8.78-8.82 (m 3H), 8.72-8.75 (dd, 1H, J = 1.5, 4.8 Hz), 8.50 (d, 1H, J = 8.3 Hz), 8.35 (s, 1H), 7.62-7.66 (dd, 1H, J = 4.8, 8.0 Hz). |
| LCMS | LCMS (2) Rt = 1.62 min; m/z (ESI−) 313 (M − H); (ESI+) 315 (MH⁺). |
| Synthesis | 1-9 |
| Compound | BB-009 |
| Structure | |

| | |
|---|---|
| NMR | |
| LCMS | LCMS (2) Rt = 2.20 min; m/z (ESI−) 313 (M − H); (ESI+) 315 (MH⁺). |

-continued

| | |
|---|---|
| Synthesis | 1-10 |
| Compound | BB-010 |
| Structure | 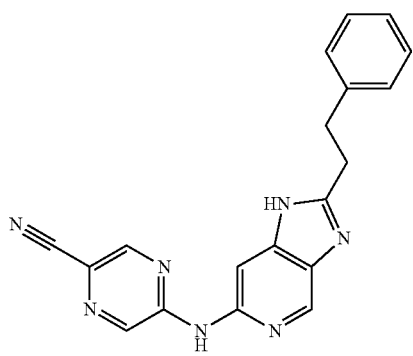 [SMILES: N#Cc1cnc(Nc2cc3[nH]c(CCc4ccccc4)nc3cn2)cn1] |
| NMR | ¹H NMR (d₆-DMSO, 400 MHz) δ 12.62 (s, 1H), 10.81 (s, 1H), 8.78 (s, 1H), 8.76, (s, 1H), 8.62 (s, 1H), 8.14 (s, 1H), 7.24-7.31 (m, 4H), 7.17-7.21 (m, 1H), 3.13-3.18 (m, 4H). |
| LCMS | LCMS (2) Rt = 2.32 min; m/z (ESI−) 340 (M − H); (ESI+) 342 (MH⁺). |
| Synthesis | 1-11 |
| Compound | BB-011 |
| Structure | 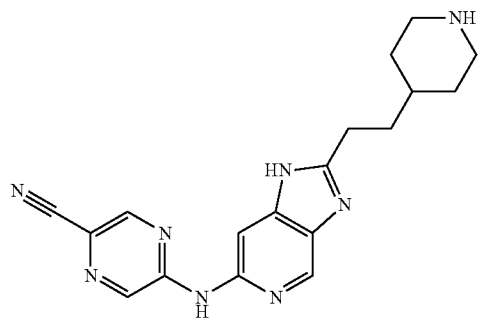 [SMILES: N#Cc1cnc(Nc2cc3[nH]c(CCC4CCNCC4)nc3cn2)cn1] |
| NMR | ¹H NMR (d₆-DMSO, 400 MHz) δ 10.90 (s, 1H), 8.77 (s, 2H), 8.68 (s, 1H), 8.52 (br s, 1H), 8.24 (br s, 1H), 3.27 (br d, 2H, J = 12.4 Hz), 2.93 (dd, 2H, J = 7.8, 7.8 Hz), 2.78-2.89 (m, 2H), 1.86 (br d, 2H, J = 12.8 Hz), 1.74-1.81 (m, 2H), 1.54-1.62 (m, 1H), 1.21-1.38 (m, 2H). |
| LCMS | LCMS (2) Rt = 1.58 min; m/z (ESI−) 347 (M − H); (ESI+) 349 (MH⁺). |

Synthesis 2-1-A

6-Chloropyrazin-2-amine

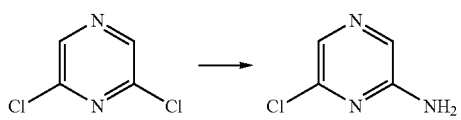 [SMILES: Clc1cncc(Cl)n1 ; Nc1cncc(Cl)n1]

2,6-Dichloropyrazine (2.89 g, 19.4 mmol) was stirred in aqueous ammonia (28%, 10 mL) and heated to 100° C. overnight in a sealed tube. The reaction mixture was cooled and the resultant precipitate was filtered. Trituration with water and then ether gave the title compound as a white solid (2.28 g, 17.6 mmol, 91%). ¹H NMR (d₆-DMSO, 400 MHz) δ 7.80 (d, 1H, J=0.4 Hz), 7.70 (d, 1H, J=0.4 Hz), 6.9 (br s, 2H). LC-MS (2) rt 1.05 min; m/z (ESI+) 130/132.

Synthesis 2-1-B 5-bromo-6-chloropyrazin-2-amine

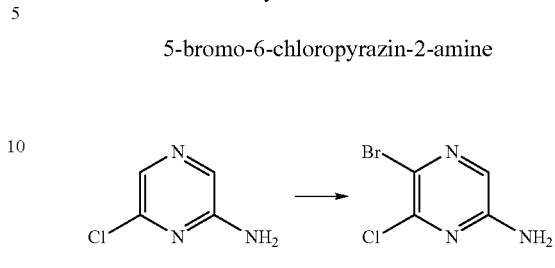

6-Chloropyrazin-2-amine (2.50 g, 19.3 mmol) was stirred in dichloromethane (60 mL) and cooled to 0° C. N-Bromosuccinimide (2.92 g, 16.4 mmol) was added slowly and the reaction mixture was stirred at 0° C. for 60 minutes. The reaction mixture was filtered through celite and concentrated to give a brown oil. Purification by flash chromatography, eluting with 0-25% ethyl acetate-hexane, gave the title compound as a yellow solid (1.69 g, 8.16 mmol, 42%). ¹HMR (d₆-DMSO, 400 MHz) δ 7.65 (s, 1H), 7.1 (br s, 2H). LC-MS (1) rt 1.46 min; m/z (ESI−) 205 (M−H).

Synthesis 2-1-C 5-amino-3-chloropyrazine-2-carbonitrile

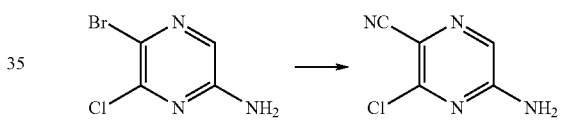

A mixture of 5-bromo-6-chloropyrazin-2-amine (1.00 g, 4.8 mmol), copper (I) iodide (914 mg, 4.8 mmol), 18-crown-6 (95 mg, 0.36 mmol) and tetrakis(triphenylphosphine)palladium (0) (83 mg, 0.072 mmol) was suspended in dry DMF (20 mL) and a stream of nitrogen was passed through it for 5 minutes. Potassium cyanide (312 mg, 4.8 mmol) was added and the mixture was stirred at room temperature for 30 minutes, then refluxed at 200° C. for 3 hours. The mixture was cooled and diluted with EtOAc and absorbed onto silica gel (10 g). DMF was removed by evaporation in a Genevac evaporator. The product was purified by flash chromatography, eluting with 1:1 ethyl acetate-hexane, to yield the title compound as a yellow solid (607 mg, 3.93 mmol, 82%). ¹H NMR (d₆-DMSO, 400 MHz) δ 8.1 (br s, 2H), 7.87 (s, 1H). LC-MS (1) Rt=1.20 min; m/z (ESI−) 153 (M−H).

Synthesis 2-1-D 5-amino-3-(1-(dimethylamino)propan-2-yloxy)pyrazine-2-carbonitrile

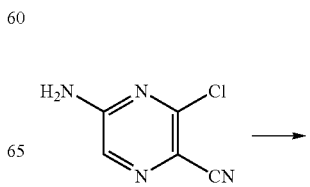

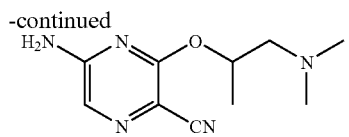

1-(Dimethylamino)propan-2-ol (187 mg, 1.81 mmol) was added to a stirred suspension of sodium hydride (123 mg, 60% in mineral oil, 1.81 mmol) in 1,4-dioxane. After 30 minutes, 5-amino-3-chloropyrazine-2-carbonitrile (140 mg, 0.906 mmol) was added. The vial was capped and the reaction mixture was heated to 100° C. overnight. The reaction mixture was concentrated, diluted with methanol and adsorbed onto an SPE (TsOH) cartridge (pre-conditioned with methanol). The cartridge was rinsed with methanol and the product was eluted with 2 M $NH_3$ in methanol. The basic fractions were concentrated to give the title compound as an orange oil which was used without further purification (79.2 mg, 0.358 mmol, 40%). LC-MS (1) Rt=1.33 m/z (ESI+) 222 ($MH^+$).

The following intermediates were prepared using methods analogous to those described in Synthesis 2-1, replacing 1-(dimethylamino)propan-2-ol with the appropriate alcohols in Synthesis 2-1-D. For the N-Boc protected compounds, the SPE step was replaced by an aqueous workup, extracting into ethyl acetate.

| Synthesis | Structure | LCMS |
|---|---|---|
| 2-2 | 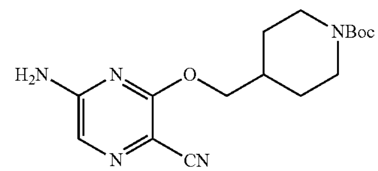 [SMILES: CC(C)(C)OC(=O)N1CCC(COc2nc(N)cnc2C#N)CC1] | LC-MS (1) Rt = 1.94 min; m/z (ESI−) 332 (M − H) |
| 2-3 | 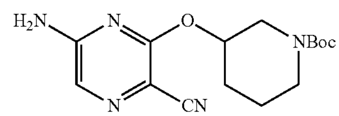 [SMILES: CC(C)(C)OC(=O)N1CCCC(Oc2nc(N)cnc2C#N)C1] | LC-MS (3) Rt = 2.06 min; m/z (ESI−) 318 (M − H). |
| 2-4 | 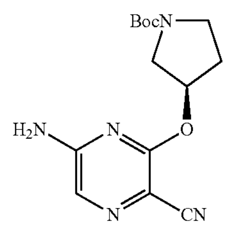 [SMILES: CC(C)(C)OC(=O)N1CC[C@@H](Oc2nc(N)cnc2C#N)C1] | LC-MS (1) Rt = 1.82 min; m/z (ESI−) 304 (M − H). |
| 2-5 | 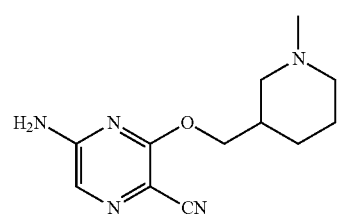 [SMILES: CN1CCCC(COc2nc(N)cnc2C#N)C1] | LC-MS (1) Rt = 1.43 min; m/z (ESI−) 246 (M − H). |
| 2-6 | 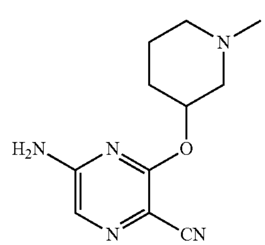 [SMILES: CN1CCCC(Oc2nc(N)cnc2C#N)C1] | LC-MS (1) Rt = 1.58 min; m/z (ESI+) 234 (M + $H^+$). |
| 2-7 | 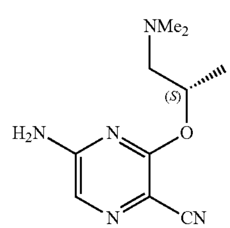 | LC-MS (1) Rt = 1.58 min; m/z (ESI+) 222 (M + $H^+$). |

-continued

| Synthesis | Structure | LCMS |
|---|---|---|
| 2-8 | 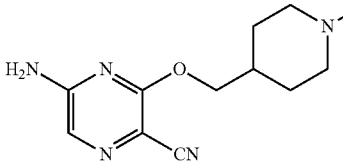 | LC-MS (1) Rt = 1.53 min; m/z (ESI+) 248 (M + H+). |
| 2-9 | 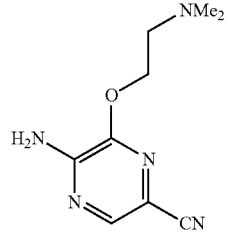 [SMILES: CN(C)CCOc1nc(C#N)cnc1N] | LC-MS (1) Rt = 1.43 min; m/z (ESI−) 206 (M − H). |
| 2-10 | 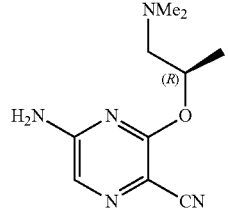 | LC-MS (1) Rt = 1.60 min; m/z (ESI+) 222 (M + H+). |
| 2-11 | 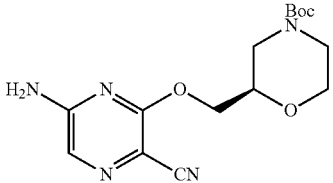 [SMILES: CC(C)(C)OC(=O)N1CCO[C@@H](COc2nc(N)cnc2C#N)C1] | LC-MS (3) Rt = 1.64 min; m/z (ESI+) 336 (M + H+). |

The following intermediate was prepared using a method analogous to that described in Synthesis 2-1-D, replacing 5-amino-3-chloropyrazine-2-carbonitrile with 2-amino-6-chloropyrazine and replacing 1-(dimethylamino)propan-2-ol with tert-butyl 4-(hydroxymethyl)piperidine-1-carboxylate.

| Synthesis | Structure | LCMS |
|---|---|---|
| 2-12 | 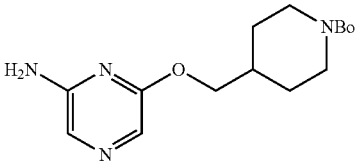 | LC-MS (1) Rt = 1.89 min; m/z (ESI+) 309 (M + H+). |

Synthesis 2-13

5-Amino-3-methoxypyrazine-2-carbonitrile

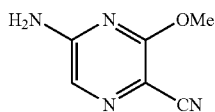

Sodium methoxide (70 mg, 1.29 mmol) was added to a stirred solution of 5-amino-3-chloropyrazine-2-carbonitrile (100 mg, 0.647 mmol) in dioxane (1 mL). The reaction mixture was heated in a sealed tube at 90° C. overnight. The solvent was removed in vacuo, and the residue was partitioned between water and ethyl acetate. The aqueous layer was re-extracted with ethyl acetate. The combined organic layers were washed with brine, dried ($Na_2SO_4$) and concentrated to give the title compound (32 mg, 0.213 mmol, 33%). LC-MS (3) Rt=0.96 min; m/z (ESI+) 151 (M+H$^+$).

Synthesis 2-14

5-Amino-3-(cyclopropylmethoxy)pyrazine-2-carbonitrile

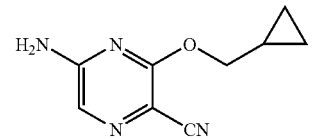 [SMILES: N#Cc1ncc(N)nc1OCC1CC1]

To a solution of sodium hydride (93 mg, 3.882 mmol) in dioxane (4 mL) was added cyclopropylmethanol (280 mg, 3.882 mmol) dropwise. The solution was stirred for 30 minutes and then 5-amino-3-chloropyrazine-2-carbonitrile (300 mg, 1.941 mmol) was added and the reaction mixture heated at 90° C. for 14 hours. The reaction mixture was poured into aqueous HCl (1 M) and extracted with ethyl acetate. The aqueous layer was re-extracted with ethyl acetate. The combined organic layers were washed with brine, dried ($Na_2SO_4$) and concentrated to dryness to give the title compound (305 mg, 1.605 mmol, 83%) which was used in subsequent steps without further purification. LC-MS (3) Rt=1.49 min; m/z (ESI+) 191 (M+H$^+$).

The following intermediates were prepared using a method analogous to that described in Synthesis 2-14, replacing cyclopropylmethanol with the appropriate alcohol.

| Synthesis | Structure | LCMS |
|---|---|---|
| 2-15 | ![structure] | LC-MS (3) Rt = 1.80 min; m/z (ESI+) 207 (M + H$^+$). |
| 2-16 | ![structure] | LC-MS (3) Rt = 1.17 min; m/z (ESI+) 221 (M + H$^+$). |
| 2-17 | ![structure] | LC-MS (3) Rt = 1.67 min; m/z (ESI+) 223 (M + H$^+$). |

Synthesis 3-A

2-Chloro-6-(cyanomethyl)benzonitrile

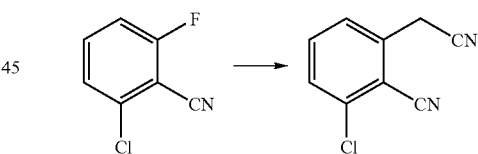

Sodium hydride (60% in mineral oil, 5.00 g, 129 mmol) was stirred in DMF (30 mL) and cooled to 0° C. Methyl cyanoacetate (12.7 g, 129 mmol) in DMF (10 mL) was added dropwise and the reaction mixture was allowed to warm to room temperature for 1 hour. 2-Chloro-6-fluorobenzonitrile (10.00 g, 64.3 mmol) was added portionwise. The reaction mixture was heated to 50° C. for 4 hours. The mixture was diluted with 2 M HCl and extracted with ethyl acetate (×3). The organic extracts were combined, washed with brine, dried ($Na_2SO_4$) and concentrated to give an orange oil. LC-MS (1) Rt=1.29 min; m/z (ESI−) 233 (M−H).

The intermediate was immediately stirred in DMSO (18 mL) and water (2 mL) and heated to reflux for 6 hours. Water was added to the cooled reaction mixture and the resulting yellow solid was collected. The solid was triturated in ether and filtered to give the title compound as an off-white solid (6.46 g, 36.6 mmol, 60%). $^1$H NMR (d$_6$-DMSO, 400 MHz) δ

7.81-7.75 (m, 2H), 7.65-7.62 (m, 1H), 4.35 (s, 2H). LC-MS (1) Rt=1.74 min; m/z (ESI−) 175 (M−H).

Synthesis 3-B

N-(1-Bromo-8-chloroisoquinolin-3-yl)acetamide

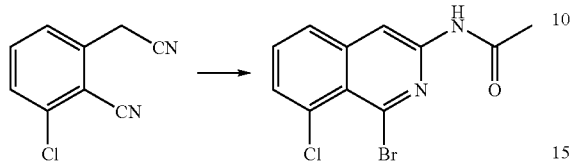

2-Chloro-6-(cyanomethyl)benzonitrile (3.12 g, 17.7 mmol) was added to a solution of HBr in acetic acid (20 mL) and stirred at room temperature overnight. The reaction mixture was added drop wise to a saturated solution of $NaHCO_3$. The resulting precipitate was collected by filtration to give a yellow solid, which was stirred in dichloromethane (100 mL). Triethylamine (3.7 mL, 26.5 mmol) and acetyl chloride (1.9 mL, 26.7 mmol) were added and the reaction mixture was stirred overnight at room temperature. Solvents were evaporated and residue was triturated with water, then ether, to the title compound as a pale yellow solid (2.67 g, 8.91 mmol, 51%). $^1$H NMR ($d_6$-DMSO, 400 MHz) δ 8.47 (s, 1H), 8.00 (dd, 1H, J=8.6, 1.3 Hz), 7.74-7.72 (m, 1H), 7.67-7.64 (m, 1H), 2.14 (s, 3H). LC-MS (1) Rt=2.05 min; m/z (ESI+) 299 (MH$^+$).

Synthesis 3-C

8-Chloroisoquinolin-3-amine

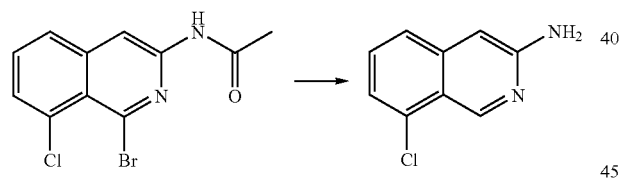

N-(1-Bromo-8-chloroisoquinolin-3-yl)acetamide (1.00 g, 3.33 mmol), potassium carbonate (0.508 mg, 3.67 mmol), triphenylphosphine (35 mg, 0.134 mmol) and palladium acetate (7.49 mg, 0.033 mmol) were stirred in 1-butanol (10 mL) with nitrogen bubbling through it for 10 minutes. Butanol (5 mL) was added to the reaction mixture, which was then heated overnight at 100° C. in a sealed vial. The reaction mixture was cooled, diluted with water and extracted twice with ethyl acetate. The combined organic layers were washed with brine, dried ($Na_2SO_4$) and concentrated to give an orange solid. Flash chromatography on silica (20 g), eluting with 15-60% ethyl acetate-hexane, gave the title compound as a yellow solid (333 mg, 1.51 mmol, 45%). LC-MS (1) Rt=1.68 min; m/z (ES+) 221/223.

The intermediate was suspended in 2 M HCl and heated at 100° C. for 2 hours. The reaction mixture was neutralised with saturated sodium bicarbonate solution and the aqueous solution was extracted twice with ethyl acetate. The organic extracts were dried and concentrated to give 8-chloroisoquinolin-3-amine (247 mg, 1.38 mmol, 92%) as a yellow solid. $^1$H NMR ($d_6$-DMSO, 400 MHz) δ 9.02 (br s, 1H), 7.51 (d, 1H, J=8.4 Hz), 7.39 (dd, 1H, J=8.3, 7.2 Hz), 7.23 (dd, 1H, J=7.1, 1.0 Hz), 6.65 (s, 1H), 6.22 (br s, 2H). LC-MS (1) Rt=1.63 min; m/z (ESI−) 179 (M−H).

Synthesis 3-D 3,8-Dichloroisoquinoline

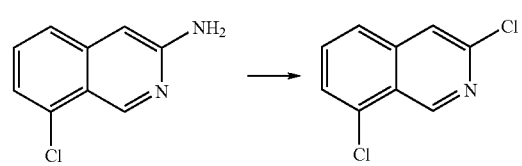 [SMILES: Nc1cc2cccc(Cl)c2cn1 ; Clc1cc2cccc(Cl)c2cn1]

8-Chloroisoquinolin-3-amine (724 mg, 4.05 mmol) was suspended in 10 M HCl and cooled to 0° C. Sodium nitrite (336 mg, 4.86 mmol) was added in portions over 10 minutes. The reaction mixture was stirred for 2 hours, slowly warming to room temperature over an additional 1 hour. After 3 hours, the mixture was poured cautiously into saturated sodium bicarbonate solution, and extracted into ethyl acetate. The organic extract was washed with brine, dried ($Na_2SO_4$) and concentrated. Flash chromatography on silica, eluting with dichloromethane, gave the title compound as a white solid (362 mg, 1.83 mmol, 45%). $^1$H NMR ($d_6$-DMSO, 400 MHz) δ 9.40 (br t, 1H, J=0.8 Hz), 8.20 (br s, 1H), 8.00-7.98 (m, 1H), 7.88-7.81 (m, 2H). LCMS (3) Rt=2.49 min; m/z (ESI+) 198 (MH$^+$).

Synthesis 4-1-A

3-Chloroisoquinoline

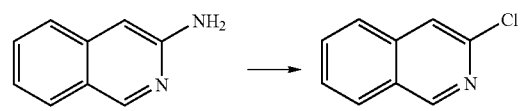 [SMILES: Nc1cc2ccccc2cn1 ; Clc1cc2ccccc2cn1]

3-Aminoisoquinoline (1.44 g, 10 mmol) was suspended in 10M HCl (5 mL) and cooled to 0° C. Sodium nitrite (689 mg, 10 mmol) was added in portions over 5 minutes. The reaction mixture was stirred at 0° C. for 2 hours and allowed to warm to room temperature over 1 hour. The reaction mixture was added carefully to saturated $NaHCO_3$ solution (200 mL) and extracted into ethyl acetate. The insoluble byproduct was removed by filtration and the aqueous layer was re-extracted into ethyl acetate. The combined organics were washed with water and brine, dried ($Na_2SO_4$) and concentrated to a brown oil which solidified on standing. Flash chromatography on silica, eluting with dichloromethane, gave the title compound as a white solid (827 mg, 5.05 mmol, 51%). $^1$H NMR ($d_6$-DMSO, 400 MHz) δ 9.12 (s, 1H), 8.41 (s, 1H), 8.12 (dd, 1H, J=7.5, 1.0 Hz), 7.93-7.90 (m, 1H), 7.84-7.80 (m, 1H), 7.74-7.70 (m, 1H). LCMS (1) Rt=1.79 min; m/z (ESI+) 164 (MH$^+$).

Synthesis 4-1-B 3-(1-(Dimethylamino)propan-2-yloxy)-5-(isoquinolin-3-ylamino)pyrazine-2-carbonitrile (AA-001)

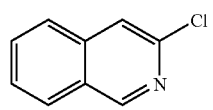

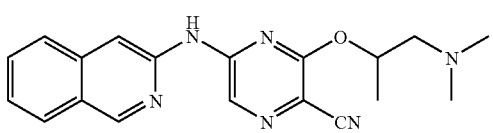

A mixture of palladium (II) acetate (24 mg, 0.11 mmol) and (±)-2,2"-bis(diphenylphosphino)-1,1"-binaphthalene (140 mg, 0.22 mmol) in toluene (2 mL) was degassed under a stream of nitrogen gas with stirring for 10 minutes. After addition of 3-chloroisoquinoline (59 mg, 0.36 mmol), 5-amino-3-(1-(dimethylamino)propan-2-yloxy)pyrazine-2-carbonitrile (80 mg, 0.36 mmol) in DMF (0.5 mL), and sodium tert-butoxide (42 mg, 0.43 mmol), the mixture was degassed for a further 5 minutes and then heated at 140° C. for 30 minutes in a microwave reactor. Upon cooling, the mixture was diluted with methanol and isolated by SPE using a MP-TsOH cartridge, washing with methanol and then eluting with 2 M ammonia in methanol. The basic fractions were combined and concentrated in vacuo. Preparative HPLC gave the title compound (8.9 mg, 0.026 mmol, 7%). $^1$H NMR ($d_6$-DMSO, 400 MHz) δ 9.22 (s, 1H), 8.45 (s, 1H), 8.23 (s, 1H), 8.09 (d, 1H, J=9.1 Hz), 7.84 (d, 1H, J=8.1 Hz), 7.77-7.73 (m, 1H), 7.58-7.54 (m, 1H), 5.53-5.49 (m, 1H), 2.67-2.63 (m, 1H), 2.34-2.32 (m, 1H), 2.21 (s, 6H), 1.46 (d, 3H, J=6.3 Hz). LC-MS (2) Rt=2.93 min m/z (ESI−) 347 (M−H).

The following compounds were prepared using methods analogous to those described in Synthesis 4-1-B replacing 3-chloroisoquinoline with the appropriate aryl halide, and replacing 5-amino-3-(1-(dimethylamino)propan-2-yloxy)pyrazine-2-carbonitrile with the appropriate aminopyrazine.

| Synthesis | 4-2 |
|---|---|
| Compound | AA-002 |
| Structure | 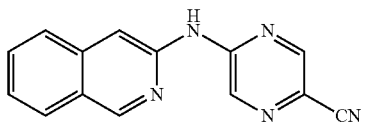 [SMILES: N#Cc1cnc(Nc2cc3ccccc3cn2)cn1] |
| NMR | 1H NMR ($d_6$-DMSO, 400 MHz) δ 11.03 (s, 1H), 9.21 (s, 1H), 8.82 (d, 1H, J = 1.3 Hz), 8.72 (d, 1H, J = 1.3 Hz), 8.50 (s, 1H), 8.08 (d, 1H, J = 8.1 Hz), 7.91 (d, 1H, J = 8.3 Hz), 7.75-7.71 (m, 1H), 7.56-7.52 (m, 1H) |
| LCMS | LC-MS (2) Rt = 2.77 min; m/z (ESI+) 248 (MH$^+$) |

| Synthesis | 4-3 |
|---|---|
| Compound | AA-003 |
| Structure | 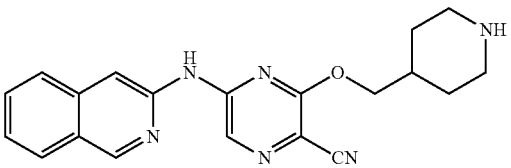 [SMILES: N#Cc1ncc(Nc2cc3ccccc3cn2)nc1OCC1CCNCC1] |
| NMR | 1H NMR ($d_6$-DMSO, 400 MHz) δ 9.22 (s, 1H), 8.48 (s, 1H), 8.24 (s, 1H), 8.09 (d, 1H, J = 8.6 Hz), 7.84 (d, 1H, J = 7.6 Hz), 7.78-7.74 (m, 1H), 7.58-7.54 (m, 1H), 4.83 (d, 2H J = 6.6 Hz), 2.99 (br d, 2H, J = 12.1 Hz), 2.53-2.47 (m, 2H, obscured by DMSO), 2.03-1.93 (m, 1H), 1.75 (br d, 2H, J = 12.9 Hz), 1.32-1.22 (m, 2H). |
| LCMS | LC-MS (2) Rt = 2.38 min; m/z (ESI+) 361 (MH$^+$). |

| Synthesis | 4-4 |
|---|---|
| Compound | AA-004 |
| Structure | 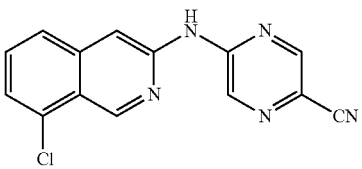 [SMILES: N#Cc1cnc(Nc2cc3cccc(Cl)c3cn2)cn1] |
| NMR | 1H NMR ($d_6$-DMSO, 400 MHz) δ 11.20 (br s, 1H), 9.40 (s, 1H), 8.84 (d, 1H, J = 1.5 Hz), 8.72 (d, 1H, J = 1.5 Hz), 8.57 (s, 1H), 7.92 (d, 1H, J = 8.1 Hz), 7.71-7.64 (m, 2H). |
| LCMS | LC-MS (2) Rt = 3.04 min; m/z (ESI+) 282 (MH$^+$). |

| | |
|---|---|
| Synthesis | 4-5 |
| Compound | AA-005 |
| Structure | 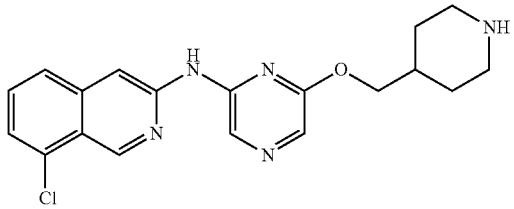 [SMILES: Clc1cccc2cc(Nc3cncc(OCC4CCNCC4)n3)ncc12] |
| NMR | 1H NMR (d$_6$-DMSO, 400 MHz) δ 9.75 (br s, 1H), 9.42 (s, 1H), 8.42 (s, 1H), 8.05 (dd, 1H, J = 7.7, 0.8 Hz), 8.03 (s, 1H), 8.01 (s, 1H), 7.80-7.76 (m, 1H), 7.66-7.64 (m, 2H), 3.96 (d, 2H, J = 6.6 Hz), 3.04-2.99 (m, 2H), 2.57-2.53 (m, 2H), 1.87-1.77 (m, 1H), 1.63-1.59 (m, 2H), 1.18-1.14 (m, 2H). |
| LCMS | LC-MS (2) Rt = 2.95 min; m/z (ESI−) 368 (M − H). |

| | |
|---|---|
| Synthesis | 4-6 |
| Compound | AA-006 |
| Structure | 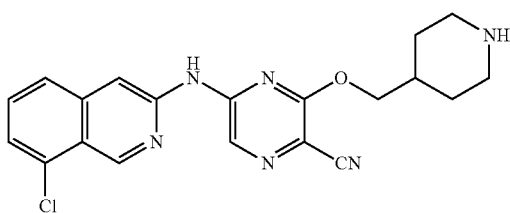 [SMILES: N#Cc1ncc(Nc2cc3cccc(Cl)c3cn2)nc1OCC1CCNCC1] |
| NMR | $^1$H NMR (d$_6$-DMSO, 400 MHz) δ 9.44 (br s, 1H), 8.50 (s, 1H), 8.46 (s, 2H), 8.31 (s, 1H), 7.85 (m, 1H), 7.76-7.71 (m, 1H), 7.68-7.65 (m, 1H), 4.44 (d, 2H, J = 6.4 Hz), 3.05-2.99 (m, 2H), 2.07-1.95 (m, 2H), 1.80-1.73 (m, 2H), 1.36-1.25 (m, 3H). |
| LCMS | LCMS (2) Rt = 3.23 min; m/z (ESI$^+$) 395 (MH$^+$), (ESI$^−$) 393 (M − H) |

| | |
|---|---|
| Synthesis | 4-7 |
| Compound | AA-007 |
| Structure | 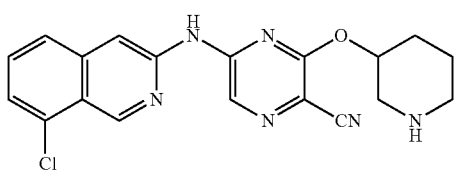 [SMILES: N#Cc1ncc(Nc2cc3cccc(Cl)c3cn2)nc1OC1CCCNC1] |
| NMR | $^1$H NMR (d$_6$-DMSO, 400 MHz) δ 11.30 (br s, 1H), 9.41 (s, 1H), 8.57 (s, 1H), 8.36 (s, 1H), 8.23 (m, 1H), 7.96 (m, 1H), 7.77-7.72 (m, 1H), 7.70-7.67 (m, 1H), 5.12 (m, 2H), 2.92-2.83 (m, 1H), 2.76-2.69 (m, 1H), 2.27-2.19 (m, 1H), 1.84-1.75 (m, 1H), 1.62-1.53 (m, 1H), 1.38 (m, 1H), 1.24 (m, 1H). |
| LCMS | LCMS (2) Rt = 2.91 min; m/z (ESI$^+$) 381 (MH$^+$), (ESI$^−$) 379 (M − H). |

| | |
|---|---|
| Synthesis | 4-8 |
| Compound | AA-048 |
| Structure | 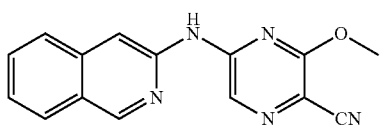 [SMILES: COc1nc(Nc2cc3ccccc3cn2)cnc1C#N] |
| NMR | $^1$H NMR (d$_6$-DMSO, 400 MHz) δ 9.21 (S, 1H), 8.55 (S, 1H), 8.24 (S, 1H), 8.08 (d, 1H, J = 7.3 Hz), 7.95 (d, 1H, J = 7.8 Hz), 7.76-7.71 (m, 1H), 7.57-7.53 (m, 1H), 4.17 (S, 3H). |
| LCMS | LCMS (2) Rt = 2.91 min; m/z (ESI$^+$) 278 (MH$^+$). |

| | |
|---|---|
| Synthesis | 4-9 |
| Compound | AA-049 |
| Structure | 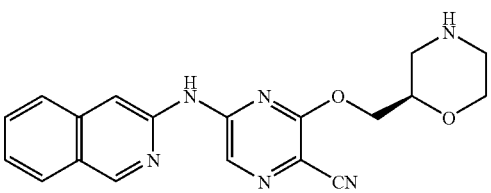 [SMILES: N#Cc1ncc(Nc2cc3ccccc3cn2)nc1OC[C@H]1CNCCO1] |
| NMR | $^1$H NMR (d$_6$-DMSO, 400 MHz) δ 11.14 (s, 1H), 9.21 (s, 1H), 8.48 (s, 1H), 8.24 (s, 1H), 8.09 (d, 1H, J = 8.3 Hz), 7.89 (d, 1H, J = 7.8 Hz), 7.78-7.74 (m, 1H), 7.58-7.54 (m, 1H), 4.59-4.51 (m, 2H), 3.93-3.87 (m, 1H), 3.85-3.81 (m, 1H), 3.55-3.49 (m, 2H), 3.01-2.98 (m, 1H), 2.78-2.64 (m, 3H) |
| LCMS | LCMS (2) Rt = 2.29 min; m/z (ESI$^+$) 363 (MH$^+$). |

Synthesis 4-10
Compound AA-050

Structure

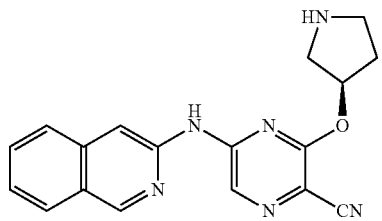 [SMILES: N#Cc1ncc(Nc2cc3ccccc3cn2)nc1O[C@@H]1CCNC1]

NMR  ¹H NMR (d₆-DMSO, 400 MHz) δ 9.21 (s, 1H), 8.51 (br s, 1H), 8.33 (br s, 1H), 8.21 (br s, 1H), 8.09 (d, 1H, J = 8.1 Hz), 7.93 (d, 1H, J = 7.8 Hz), 7.77-7.72 (m, 1H), 7.58-7.54 (m, 1H), 5.69-5.65 (m, 1H), 3.44-3.39 (m, 1H), 3.23-3.20 (m, 1H), 3.08-3.04 (m, 2H), 2.33-2.24 (m, 1H), 2.12-2.06 (m, 1H).
LCMS  LCMS (2) Rt = 2.45 min; m/z (ESI⁻) 331 (MH⁻).

Synthesis 5-1

(R)-5-(8-Chloroisoquinolin-3-ylamino)-3-(pyrrolidin-3-yloxy)pyrazine-2-carbonitrile (AA-008)

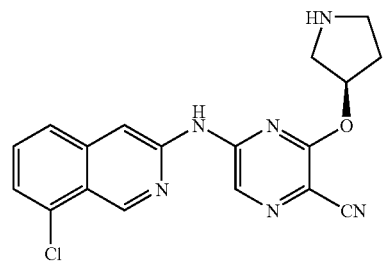 [SMILES: N#Cc1ncc(Nc2cc3cccc(Cl)c3cn2)nc1O[C@@H]1CCNC1]

A mixture of tris(dibenzylideneacetone)dipalladium(0) (23 mg, 0.025 mmol) and 9,9-dimethyl-4,5-bis(diphenylphosphino)xanthene (29 mg, 0.05 mmol) in toluene (1.5 mL) was degassed under a stream of nitrogen gas with stirring for 10 minutes. 3,8-Dichloroisoquinoline (50 mg, 0.252 mmol), (R)-5-amino-3-(pyrrolidin-3-yloxy)pyrazine-2-carbonitrile (85 mg, 0.278 mmol) in DMF (0.5 mL) and caesium carbonate (165 mg, 0.505 mmol) were added and the mixture was degassed for a further 5 minutes, then heated at 130° C. for 30 minutes in a microwave reactor. Upon cooling, the mixture was diluted with methanol and isolated by SPE using a MP-TsOH cartridge, washing with methanol and then eluting with 2 M ammonia in methanol. The combined basic fractions were concentrated in vacuo. Preparative HPLC gave (R)-5-(8-chloroisoquinolin-3-ylamino)-3-(pyrrolidin-3-yloxy)pyrazine-2-carbonitrile (3.8 mg, 0.01 mmol, 4%). ¹H NMR (d₄-MeOD) δ 9.42 (d, 1H, J=0.9 Hz), 8.52 (s, 1H), 8.32 (d, 1H, J=5.3 Hz), 7.85 (d, 1H, J=8.3 Hz), 7.66-7.62 (m, 1H), 7.59-7.57 (m, 1H), 5.89-5.86 (m, 1H), 3.67-3.65 (m, 2H), 3.50-3.46 (m, 2H), 2.52-2.47 (m, 2H). LC-MS (2) Rt=2.65 min; m/z (ESI–) 365 (M–H).

The following compounds were prepared using methods analogous to those described in Synthesis 5-1, replacing 3,8-dichloroisoquinoline with the appropriate aryl halide and replacing (R)-5-amino-3-(pyrrolidin-3-yloxy)pyrazine-2-carbonitrile with the appropriate aminopyrazine.

Synthesis 5-2
Compound AA-009

Structure

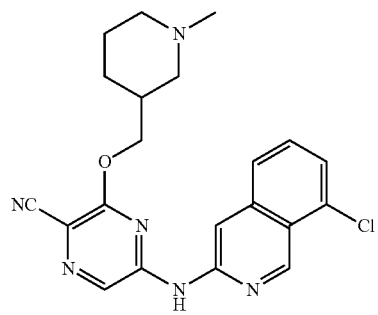 [SMILES: CN1CCCC(COc2nc(Nc3cc4cccc(Cl)c4cn3)cnc2C#N)C1]

NMR  ¹H NMR (d₆-DMSO, 400 MHz) δ 11.10 (br s, 1H), 9.41 (s, 1H), 8.50 (s, 1H), 8.31 (s, 1H), 7.86 (d, 1H, J = 8.3 Hz), 7.73 (dd, 1H, J = 7.6 Hz, 8.1 Hz), 7.66 (dd, 1H, J = 1.0, 7.6 Hz).
LCMS  LCMS (2) Rt = 3.44 min; m/z (ESI–) 407 (M – H); (ESI+) 409 (MH⁺).

Synthesis 5-3
Compound AA-010

Structure

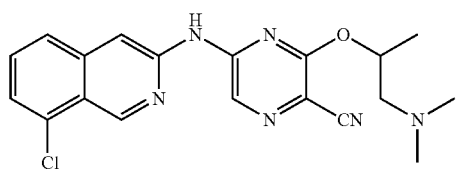 [SMILES: CC(CN(C)C)Oc1nc(Nc2cc3cccc(Cl)c3cn2)cnc1C#N]

NMR  ¹H NMR (d₆-DMSO, 400 MHz) δ 9.40 (s, 1H), 8.50 (s, 1H), 8.25 (s, 1H), 7.84 (d, 1H, 8.3), 7.74-7.70 (m, 1H), 7.68-7.66 (m, 1H), 5.51-5.47 (m, 1H), 2.68-2.63 (m, 1H), 2.56-2.52 (m, 1H), 2.20 (s, 6H), 1.46 (d, 3H, J = 6.3 Hz).
LCMS  LC-MS (2) Rt = 3.34 min; m/z (ESI+) 381 (MH⁺).

Synthesis 5-4
Compound AA-012

Structure

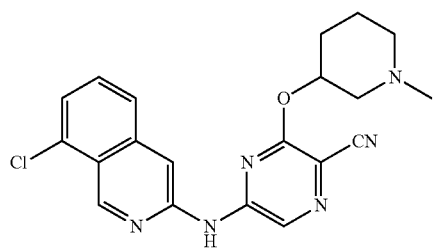 [SMILES: CN1CCCC(Oc2nc(Nc3cc4cccc(Cl)c4cn3)cnc2C#N)C1]

NMR  ¹H NMR (d₆-DMSO, 400 MHz) δ 10.62 (br s, 1H), 9.33 (s, 1H), 8.11 (s, 1H), 8.03 (s, 1H), 7.92 (m, 1H), 7.85 (m, 2H), 4.68-4.59 (m, 1H), 2.68 (m, 1H), 2.45-2.39 (m, 1H), 2.10 (s, 3H), 2.06-1.93 (m, 2H), 1.80-1.72 (m, 1H), 1.67-1.58 (m, 1H), 1.36-1.20 (m, 2H).
LCMS  LCMS (2) Rt = 2.90 min; m/z (ESI+) 395 (MH⁺).

| Synthesis | 5-5 |
|---|---|
| Compound | AA-013 |
| Structure | 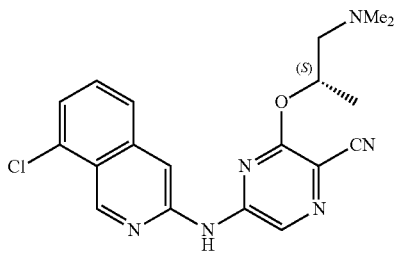 |
| NMR | ¹H NMR (d₆-DMSO, 400 MHz) δ 9.41 (s, 1H), 8.50 (s, 1H), 8.24 (s, 1H), 7.85 (d, 1H, J = 8.1 Hz), 7.75-7.71 (m, 1H), 7.68-7.66 (m, 1H), 5.52-5.47 (m, 1H), 2.68-2.63 (m, 1H), 2.56-2.50 (m, 1H, partly obscured by DSMO), 2.20 (s, 6H), 1.46 (d, 3H, J = 6.3 Hz). |
| LCMS | LCMS (2) Rt = 3.28 min; m/z (ESI−) 381 & 383 (M − H). |

| Synthesis | 5-6 |
|---|---|
| Compound | AA-014 |
| Structure | 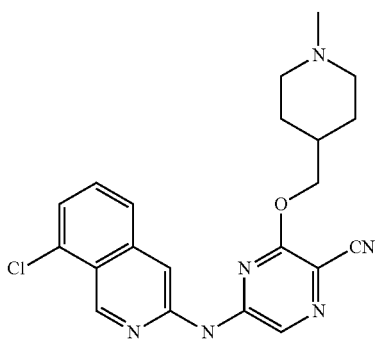 |
| NMR | |
| LCMS | LCMS (2) Rt = 3.25 min; m/z (ESI+) 409 & 411 (MH⁺). |

| Synthesis | 5-7 |
|---|---|
| Compound | AA-015 |
| Structure | 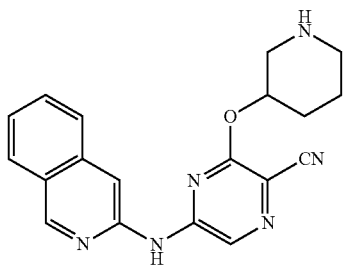 [SMILES: N#Cc1ncc(Nc2cc3ccccc3cn2)nc1OC1CCCNC1] |
| NMR | |
| LCMS | LCMS (2) Rt = 2.55 min; m/z (ESI−) 345 (M − H); (ESI+) 347 (MH⁺). |

| Synthesis | 5-8 |
|---|---|
| Compound | AA-016 |
| Structure | 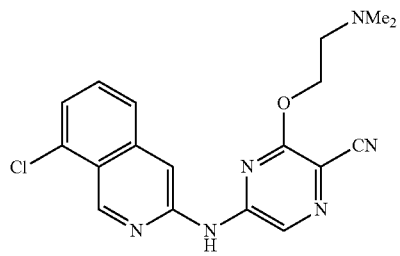 [SMILES: CN(C)CCOc1nc(Nc2cc3cccc(Cl)c3cn2)cnc1C#N] |
| NMR | ¹H NMR (DMSO, 400 MHz) δ 11.25 (br s, 1H), 9.40 (s, 1H), 8.55 (s, 1H), 8.25 (s, 1H), 7.91 (d, 1H, J = 8.1 Hz), 7.75-7.66 (m, 2H), 4.68 (t, 2H, J = 5.8 Hz), 2.78 (t, 2H, J = 5.8 Hz), 2.27 (s, 6H). |
| LCMS | LCMS (2) Rt = 3.09 min, m/z (ESI⁺) 369 (MH⁺). |

| Synthesis | 5-9 |
|---|---|
| Compound | AA-022 |
| Structure | 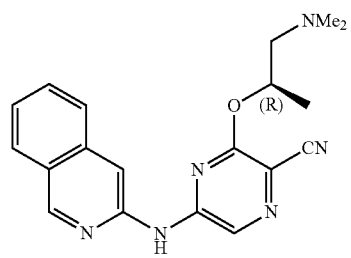 |
| NMR | ¹H NMR (DMSO, 400 MHz) δ 11.06 (br s, 1H), 9.23 (s, 1H), 8.45 (s, 1H), 8.24 (s, 1H), 8.10 (d, 1H, J = 8.3 Hz), 7.85 (d, 1H, J = 8.1 Hz), 7.70-7.75 (m, 1H), 7.50-7.55 (m, 1H), 5.50-5.55 (m, 1H), 2.64-2.69 (m, 1H), 2.50-2.60 (m, 1H, partially obscured by DMSO), 2.22 (s, 6H), 1.47 (d, 3H, 5.9Hz). |
| LCMS | LCMS (2) Rt = 2.91 min, m/z (ESI⁺) 349 (MH⁺) |

| Synthesis | 5-10 |
|---|---|
| Compound | AA-023 |
| Structure | 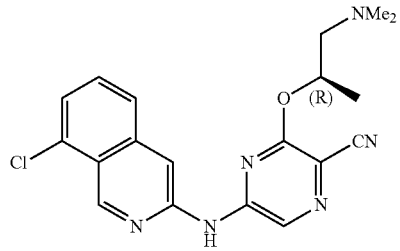 |
| NMR | ¹H NMR (DMSO, 400 MHz) δ 11.20 (br s, 1H), 9.41 (s, 1H), 8.51 (s, 1H), 8.25 (s, 1H), 7.85 (d, 1H, J = 7.8 Hz), 7.73 (dd, 1H, J = 7.5, 7.8 Hz), 7.67 (d, 1H, J = 7.5 Hz), 5.48-5.53 (m, 1H), 2.65-2.70 (m, 1H), 2.50-2.60 (m, 1H, partially obscured by DMSO), 2.21 (s, 6H), 1.47 (d, 3H, J = 6.3 Hz). |
| LCMS | LCMS (2) Rt = 3.32 min, m/z (ESI⁺) 383 (MH⁺) |

Synthesis 5-11
Compound AA-024

Structure

NMR  ¹H NMR (DMSO, 400 MHz) δ 11.10 (br s, 1H),
9.32 (s, 1H), 8.81 (s, 1H), 8.74 (s, 1H), 8.46 (s, 1H), 7.73
(d, 1H, J = 8.0 Hz), 7.60 (dd, 1H, J = 7.0, 8.0 Hz), 7.33
(d, 1H, J = 7.0 Hz), 2.75 (s, 3H).

LCMS  LCMS (2) Rt = 2.93 min, m/z (ESI⁺) 262 (MH⁺)

Synthesis 5-12
Compound AA-025

Structure

NMR  ¹H NMR (DMSO, 400 MHz) δ 11.05
(br s, 1H), 9.31 (s, 1H), 8.41 (s, 1H), 8.23 (s, 1H), 7.59-
7.66 (m, 2H), 7.33 (d, 1H, J = 6.6 Hz),
5.46-5.53 (m, 1H), 2.74 (s, 3H), 2.65-2.70
(m, 1H), 2.50-2.60 (m, 1H, partially obscured by DMSO),
2.22 (s, 6H), 1.46 (d, 3H, J = 6.0 Hz).

LCMS  LCMS (2) Rt = 3.10 min, m/z (ESI⁺) 363 (MH⁺)

Synthesis 5-13
Compound AA-057

Structure

NMR  ¹H NMR (DMSO, 400 MHz) δ 11.01 (s, 1H), 9.14
(s, 1H), 8.33 (s, 1H), 8.24 (s, 1H), 7.98 (d, 1H, J = 8.3 Hz),
7.57-7.62 (m, 1H), 7.38-7.41 (m, 1H), 5.45-5.55 (m, 1H),
3.35 (s, 1H), 2.62-2.70 (m, 1H), 2.52-2.59 (m, 1H),
2.22 (s, 6H), 1.47 (d, 3H, J = 6.3Hz).

LCMS  LCMS (2) Rt = 3.09 min, m/z (ESI⁺) 363 (MH⁺)

Synthesis 5-14
Compound AA-058

Structure

NMR  ¹H NMR (DMSO, 400 MHz) δ 9.15 (s, 1H),
8.40 (s, 1H), 8.27 (s, 1H), 8.00 (d, 1H, J = 8.7 Hz),
7.66-7.70 (m, 1H), 7.40-7.44 (m, 1H), 5.61-5.70 (m, 1H),
3.35-3.42 (m, 1H), 3.13-3.21 (m, 1H), 2.96-3.10 (m, 2H),
2.55 (s, 3H), 2.22-2.34 (m, 1H), 2.02-2.12 (m, 1H).

LCMS  LCMS (2) Rt = 2.65 min, m/z (ESI⁺) 347 (MH⁺)

Synthesis 6

5-(6,8-Dimethoxyisoquinolin-3-ylamino)pyrazine-2-carbonitrile (AA-011)

The title compound was prepared according to the method described in Synthesis 4-1-B from 2-amino-5-cyanopyrazine and 3-bromo-6,8-dimethoxyisoquinoline. The 3-bromo-6,8-dimethoxyisoquinoline was prepared as described in White et al., 1967. ¹H NMR (d₆-DMSO, 400 MHz) δ 10.98 (s, 1H), 9.12 (s, 1H), 8.80 (s, 1H), 8.72 (s, 1H), 8.34 (s, 1H), 6.86 (s, 1H), 6.57 (s, 1H), 3.98 (s, 3H), 3.92 (s, 3H). LCMS (2) Rt=2.88 min; m/z (ESI−) 306 (M−H); (ESI+) 308 (MH⁺).

Synthesis 7-1-A

N⁴-(4-methoxybenzyl)-6-bromopyridine-3,4-diamine

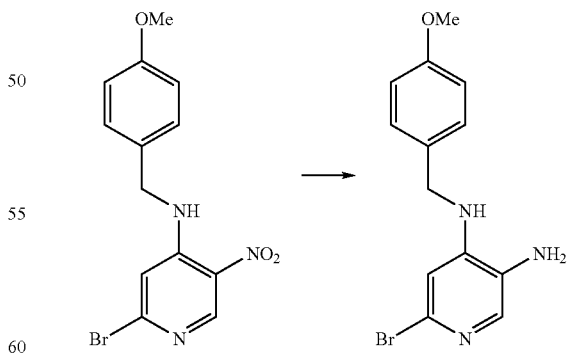

Tin (II) chloride dihydrate (4.37 g, 19.4 mmol) was added portionwise to N-(4-methoxybenzyl)-2-bromo-5-nitropyridin-4-amine (1.31 g, 3.87 mmol) in absolute EtOH (10 mL) at room temperature. The mixture was then heated at 70° C. for 2 hours before being concentrated in vacuo. The residue was suspended in a mixture of ethyl acetate and saturated sodium bicarbonate solution and filtered. The insoluble solids were washed with EtOAc. The aqueous phase was re-extracted with ethyl acetate and the combined organic layers were washed with brine, dried (Na$_2$SO$_4$) and concentrated to give the title compound as a brown solid (1.05 g, 3.41 mmol, 88%). $^1$H NMR (d$_6$-DMSO, 400 MHz) δ 7.40 (s, 1H), 7.30 (d, 2H, 8.6 Hz), 6.90 (d, 2H, 8.6 Hz), 6.45 (s, 1H), 6.3 (br t, 1H, 5.5 Hz), 4.85 (br s, 2H), 4.3 (d, 2H, 5.5 Hz), 3.75 (s, 3H). LCMS (1) Rt=1.77 min; m/z (ESI−) 306, 308; (ESI+) 308, 310.

Synthesis 7-1-B 1-(4-methoxybenzyl)-6-bromo-1H-imidazo[4,5-c]pyridine

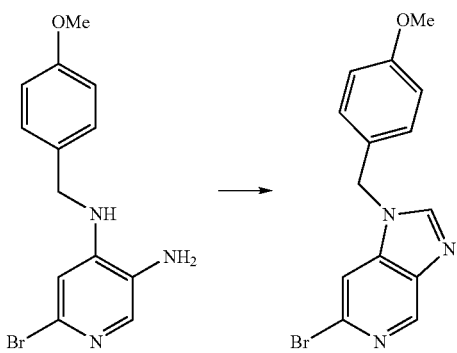 [SMILES: COc1ccc(CNc2cc(Br)ncc2N)cc1 ; COc1ccc(Cn2cnc3cnc(Br)cc32)cc1]

Acetic anhydride (1.28 mL, 13.6 mmol) was added to a solution of N$^4$-(4-methoxybenzyl)-6-bromopyridine-3,4-diamine (1.05 g, 3.41 mmol) in triethylorthoformate (13 mL). The mixture was heated at 100° C. for 18 hours and then concentrated to give the title compound as a brown oil (1.18 g, quantitative). $^1$H NMR (d$_6$-DMSO, 400 MHz) δ 8.75 (s, 1H), 8.60 (s, 1H), 8.00 (s, 1H), 7.35 (d, 2H, J=8.8 Hz), 6.90 (d, 2H, J=8.8 Hz), 5.45 (s, 2H), 3.70 (s, 3H). LCMS (2) Rt=2.27 min; m/z (ESI+) 318, 320 (MH+).

Synthesis 7-1-C 5-(1-(4-methoxybenzyl)-1H-imidazo[4,5-c]pyridin-6-ylamino)pyrazine-2-carbonitrile

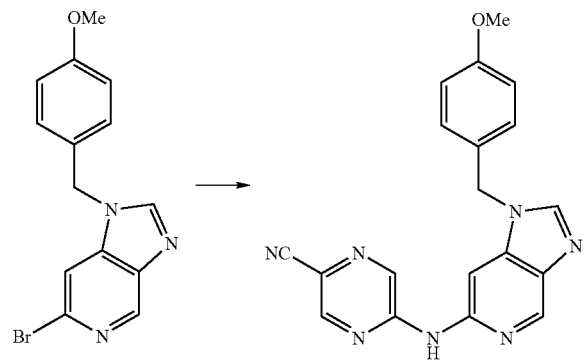

Palladium (II) acetate (3.5 mg, 16 μmol) was added to (±)-2,2″-bis(diphenylphosphino)-1,1″-binaphthalene (59 mg, 94 μmol) in DMF/toluene (1:2) and the resulting mixture was degassed under a stream of nitrogen gas for 10 minutes. 2-Amino-5-cyanopyrazine (19 mg, 0.16 mmol), sodium tert-butoxide (45 mg, 0.47 mmol) and 1-(4-methoxybenzyl)-6-bromo-1H-imidazo[4,5-c]pyridine (50 mg, 0.16 mmol) were added and the mixture was degassed for a further 5 minutes before heating at 150° C. for 30 minutes using microwave irradiation. The reaction mixture was partitioned between water and dichloromethane. The aqueous phase extracted with dichloromethane. The combined organic layers were dried (Na$_2$SO$_4$) and concentrated. The residue was dissolved in methanol, passed through a PS-Thiol column and concentrated. The product was purified using preparative HPLC to give the title compound (22.4 mg, 40%). $^1$H NMR (d$_6$-DMSO, 400 MHz) δ 10.84 (br s, 1H), 8.77 (d, 1H, J=1.3 Hz), 8.74 (m, 2H), 8.49 (s, 1H), 8.17 (s, 1H), 7.34 (m, 2H), 5.41 (s, 2H), 3.72 (s, 3H). LCMS (2) Rt=2.32 min; m/z (ESI+) 358 (MH+), (ESI−) 356 (M−H).

Synthesis 7-1-D 5-(1H-imidazo[4,5-c]pyridin-6-ylamino)pyrazine-2-carbonitrile (BB-012)

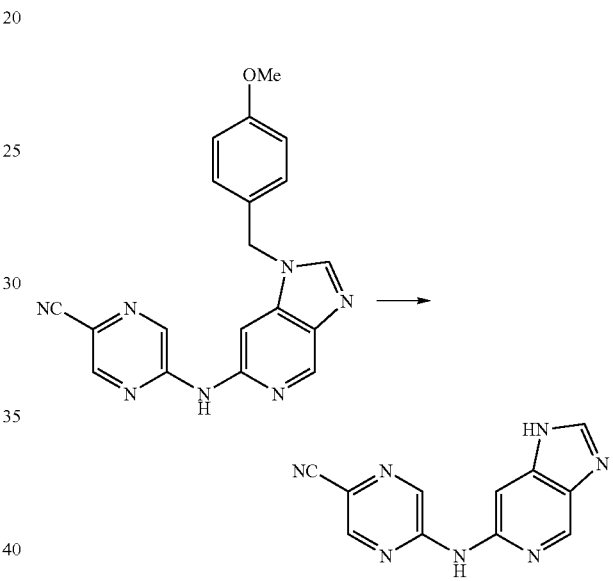

5-(1-(4-Methoxybenzyl)-1H-imidazo[4,5-c]pyridin-6-ylamino)pyrazine-2-carbonitrile (10.6 mg, 30 μmol) was treated with TFA at 80° C. over 30 minutes. Isolation by SPE on a MP-TsOH cartridge, eluting with 2N ammonia in methanol, followed by concentration, gave the title compound as a white solid (7.02 mg, 100%). $^1$H NMR (d$_6$-DMSO, 400 MHz) δ 12.79 (br s, 1H), 10.85 (br s, 1H), 8.76 (s, 2H), 8.75 (s, 1H), 8.35 (s, 1H), 8.26 (s, 1H). LCMS (2) Rt=1.36 min; m/z (ESI+) 238 (MH+), (ESI−) 236 (M−H).

The following compounds were prepared using methods analogous to those described in Synthesis 7-1-C and 7-1-D, replacing 2-amino-5-cyanopyrazine with the appropriate 2-aminopyrazine in Synthesis 7-1-C.

| Synthesis | 7-2 |
|---|---|
| Compound | BB-013 |
| Structure | 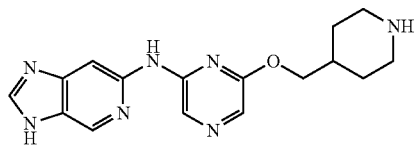 [SMILES: c1nc2cc(Nc3cncc(OCC4CCNCC4)n3)ncc2[nH]1] |

| | |
|---|---|
| NMR | 1H NMR (MeOD, 400 MHz) δ 8.82 (d, 1H, J = 1.0 Hz), 8.26 (s, 1H), 8.18 (s, 1H), 8.06 (br s, 1H), 7.57 (s, 1H), 4.35 (d, 2H, J = 5.8 Hz), 3.44 (d, 2H, J = 12.8 Hz), 3.07-2.99 (m, 2H), 2.09 (d, 2H, J = 14.4 Hz), 1.70-1.59 (m, 2H), 0.92-0.84 (m, 1H). |
| LCMS | LC-MS (2) Rt = 1.59 min; m/z (ESI-) 324 (M − H). |

| | |
|---|---|
| Synthesis | 7-3 |
| Compound | BB-014 |
| Structure | 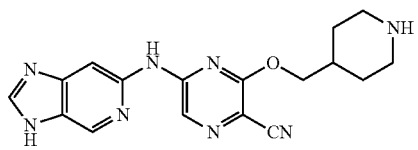 [SMILES: N#Cc1ncc(Nc2cc3nc[nH]c3cn2)nc1OCC1CCNCC1] |
| NMR | 1H NMR (d6-DMSO, 400 MHz) δ 10.85 (br s, 1H), 8.75 (d, 1H, J = 1.0 Hz), 8.36 (s, 1H), 8.31 (br s, 1H), 8.19 (br s, 1H), 4.37 (d, 2H, J = 6.3 Hz), 3.13 (d, 2H, J = 11.6 Hz), 2.70-2.64 (m, 2H), 2.08-1.98 (m, 1H), 1.82 (d, 2H, J = 11.8 Hz), 1.44-1.35 (m, 2H). |
| LCMS | LC-MS (2) Rt = 1.50 min; m/z (ESI+) 351 (M − H). |

Synthesis 8

5-(1H-imidazo[4,5-c]pyridin-6-ylamino)pyrazine-2-carboxamide (BB-015)

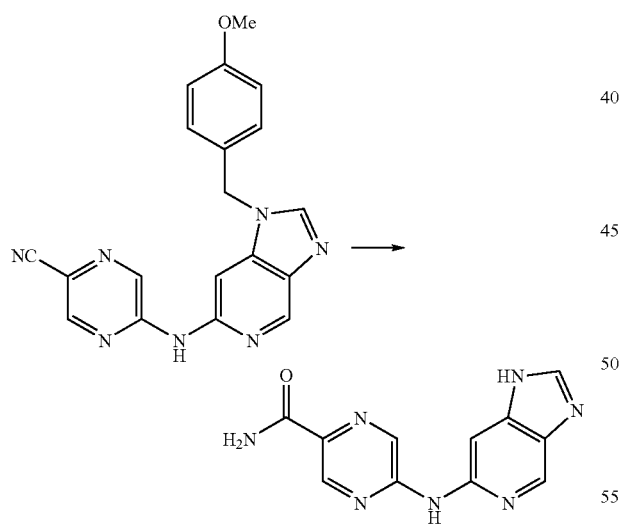

5-(1-(4-Methoxybenzyl)-1H-imidazo[4,5-c]pyridin-6-ylamino)pyrazine-2-carbo-nitrile (0.16 mmol) was treated overnight with trifluoroacetic acid at 80° C. The solution was evaporated to dryness and the residue was purified using preparative HPLC to give the title compound (3.23 mg, 8%). 1H NMR (d6-DMSO, 400 MHz) δ 12.68 (br s, 1H), 10.46 (br s, 1H), 8.76 (d, 1H, J=1.2 Hz), 8.72 (d, 2H, =1.2 Hz), 8.28 (br s, 2H), 7.90 (s, 1H), 7.51 (s, 1H). LCMS (2) Rt=1.02 min; m/z (ESI+) 256 (MH+), (ESI−) 254 (M−H).

Synthesis 9-1-A 2-(6-bromo-1H-imidazo[4,5-c]pyridin-1-yl)-N,N-dimethylethanamine

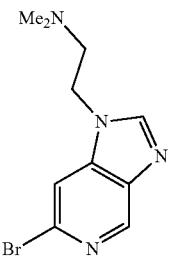 [SMILES: CN(C)CCn1cnc2cnc(Br)cc21]

The title compound was prepared using methods analogous to those described in Synthesis 1-1-A, 7-1-A, and 7-1-B, replacing 4-methoxybenzylamine with $N^1,N^1$-dimethylethane-1,2-diamine in Synthesis 1-1-A. 1H NMR (d6-DMSO, 400 MHz) δ 8.75 (s, 1H), 8.40 (s, 1H), 8.05 (s, 1H), 4.35 (t, 2H, J=6.0 Hz), 2.60 (t, 2H, J=6.0 Hz), 2.15 (s, 6H). LC-MS (1) Rt=1.24 min; m/z (ESI+) 269 & 271 (MH+).

Synthesis 9-1-B

5(1-(2-(dimethylamino)ethyl)-1H-imidazo[4,5-c]pyridin-6-ylamino)pyrazine-2-carbonitrile (BB-016)

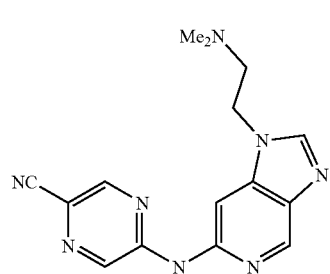

The title compound was prepared using the methods analogous to those described in Synthesis 7-1-C. 1H NMR (d6-DMSO, 400 MHz) δ 10.88 (br s, 1H), 8.78 (s, 1H), 8.73-8.75 (m, 2H), 8.31 (s, 1H), 8.21 (s, 1H), 8.16 (s, 1H), 4.31 (t, 2H, J=6.1 Hz), 2.65 (t, 2H, J=6.1 Hz), 2.19 (s, 6H). LCMS (2) Rt=1.71 min; m/z (ESI−) 307 (M−H); (ESI+) 309 (MH+).

Synthesis 9-2-A

6-Bromo-1-methyl-1H-imidazo[4,5-c]pyridine

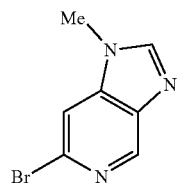

The title compound was prepared using methods analogous to those described in Synthesis 1-1-A, 7-1-A, and 7-1-B, replacing 4-methoxybenzylamine with methylamine in Synthesis 1-1-A. LC-MS (1) Rt=1.08 min; m/z (ESI+) 212 & 214 (MH+).

Synthesis 9-2-B 5-(1-Methyl-1H-imidazo[4,5-c]pyridin-6-ylamino)pyrazine-2-carbonitrile (BB-017)

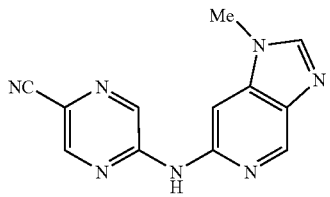

The title compound was prepared using methods analogous to those described in Synthesis 7-1-C. $^1$H NMR (d$_6$-DMSO, 400 MHz) δ 10.83 (br s, 1H), 8.70 (m, 2H), 8.69 (s, 1H), 8.22 (s, 1H), 8.11 (s, 1H), 3.77 (s, 3H). LCMS (2) Rt=1.53 min; m/z (ESI$^+$) 252 (MH$^+$), (ESI$^-$) 250 (M−H).

Synthesis 9-3-A tert-Butyl 4-((6-bromo-1H-imidazo[4,5-c]pyridin-1-yl)methyl)piperidine-1-carboxylate

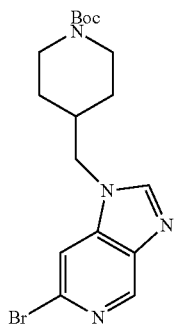 [SMILES: CC(C)(C)OC(=O)N1CCC(Cn2cnc3cnc(Br)cc32)CC1]

The title compound was prepared using methods analogous to those described in Synthesis 1-1-A, 7-1-A, and 7-1-B, replacing 4-methoxybenzylamine with tert-butyl 4-(aminomethyl)piperidine-1-carboxylate in Synthesis 1-1-A. LC-MS (1) Rt=1.91 min; m/z (ESI+) 395 & 397 (MH$^+$).

Synthesis 9-3-B 5-(1-(piperidin-4-ylmethyl)-1H-imidazo[4,5-c]pyridin-6-ylamino)pyrazine-2-carbonitrile (BB-018)

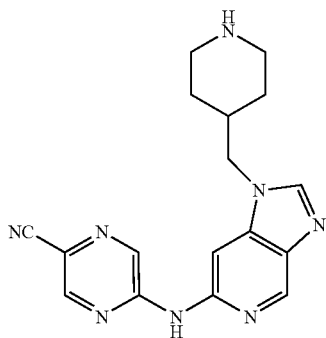

The title compound was prepared using methods analogous to those described in Synthesis 7-1-C and 7-1-D. $^1$H NMR (d$_6$-DMSO, 400 MHz) δ 10.87 (br s, 1H), 8.80 (d, 1H, J=1.2 Hz), 8.77 (d, 1H, =1.2 Hz), 8.40 (s, 1H), 8.34 (s, 1H), 8.16 (s, 1H), 4.16 (m, 1H), 3.11-3.04 (m, 2H), 2.61-2.54 (m, 3H), 2.02 (m, 1H), 1.59-1.52 (m, 2H), 1.41-1.21 (m, 2H). LCMS (2) Rt=1.47 min; m/z (ESI$^+$) 335 (MH$^+$), (ESI$^-$) 333 (M−H).

Synthesis 9-4-A tert-Butyl 2-(6-bromo-1H-imidazo[4,5-c]pyridin-1-yl)ethylcarbamate

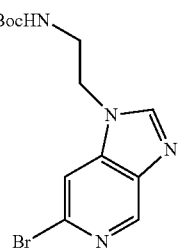

The title compound was prepared using methods analogous to those described in Synthesis 1-1-A, 7-1-A and 7-1-B, replacing 4-methoxybenzylamine with tert-butyl 2-aminoethylcarbamate in Synthesis 1-1-A. LC-MS (1) Rt=1.55 min; m/z (ESI+) 341 & 343 (MH$^+$).

Synthesis 9-4-B 5-(1-(2-Aminoethyl)-1H-imidazo[4,5-c]pyridin-6-ylamino)pyrazine-2-carbonitrile (BB-019)

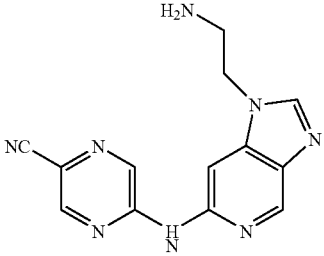

The title compound was prepared using methods analogous to those described in Synthesis 7-1-C and 7-1-D. $^1$H NMR (d$_6$-DMSO, 400 MHz) δ 10.87 (br s, 1H), 8.79 (d, 1H, 1.2 Hz), 8.76 (d, 1H, J=1.2 Hz), 8.31 (s, 1H), 8.30 (s, 1H), 8.17 (s, 1H), 4.21 (t, 2H, J=6 Hz), 2.99 (t, 2H, J=6 Hz). LCMS (2) Rt=1.29 min; m/z (ESI$^+$) 281 (MH$^+$), (ESI$^-$) 279 (M−H).

Synthesis 9-5-A tert-Butyl 3-((6-bromo-1H-imidazo[4,5-c]pyridin-1-yl)methyl)piperidine-1-carboxylate

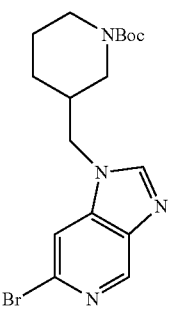 [SMILES: CC(C)(C)OC(=O)N1CCCC(Cn2cnc3cnc(Br)cc32)C1]

The title compound was prepared using methods analogous to those described in Synthesis 1-1-A, 7-1-A and 7-1-B, replacing 4-methoxybenzylamine with tert-butyl 3-(aminomethyl)piperidine-1-carboxylate in Synthesis 1-1-A. LC-MS (1) Rt=2.57 min; m/z (ESI+) 395 & 397 (MH⁺).

Synthesis 9-5-B 5-(1-(Piperidin-3-ylmethyl)-1H-imidazo[4,5-c]pyridin-6-ylamino)pyrazine-2-carbonitrile (BB-020)

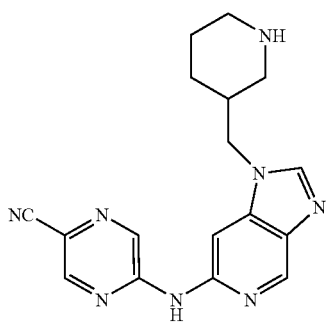

The title compound was prepared using methods analogous to those described in Synthesis 7-1-C and 7-1-D. $^1$H NMR (d$_6$-DMSO, 400 MHz) δ 10.88 (br s, 1H), 8.80-8.77 (m, 3H), 8.34 (s, 1H), 8.32 (s, 1H), 8.17 (s, 1H), 4.20-4.16 (m, 2H), 2.99-2.86 (m, 3H), 2.61-2.42 (m, 2H), 2.10 9 s, 1H), 1.66 (m, 2H), 1.48-1.36 (m, 1H), 1.41-1.26 (m, 1H). LCMS (2) Rt=1.73 min; m/z (ESI⁺) 335 (MH⁺), (ESI⁻) 333 (M−H).

Synthesis 9-6-A (S)-tert-Butyl 3-(6-bromo-1H-imidazo[4,5-c]pyridin-1-yl)piperidine-1-carboxylate

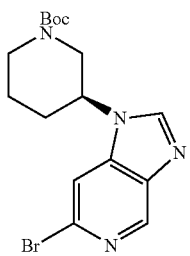 [SMILES: CC(C)(C)OC(=O)N1CCC[C@H](n2cnc3cnc(Br)cc32)C1]

The title compound was prepared using methods analogous to those described in Synthesis 1-1-A, 7-1-A and 7-1-B, replacing 4-methoxybenzylamine with (S)-tert-butyl 3-aminopiperidine-1-carboxylate in Synthesis 1-1-A. LC-MS (1) Rt=1.88 min; m/z (ESI+) 381 & 383 (MH⁺).

Synthesis 9-6-B (S)-5-(1-(Piperidin-3-yl)-1H-imidazo[4,5-c]pyridin-6-ylamino)pyrazine-2-carbonitrile (BB-021)

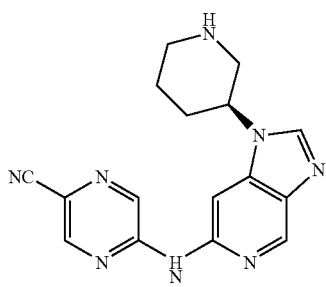

The title compound was prepared using methods analogous to those described in Synthesis 7-1-C and 7-1-D. $^1$H NMR (d$_6$-DMSO, 400 MHz) δ 10.86 (br s, 1H), 8.81-8.76 (m, 3H), 8.52 (s, 1H), 8.21 (m, 2H), 4.38-4.30 (m, 1H), 3.22-3.16 (m, 1H), 2.98-2.86 (m, 2H), 2.63-2.54 (m, 1H), 2.17-1.98 (m, 2H), 1.81-1.74 (m, 1H), 1.67-1.56 (m, 1H). LCMS (2) Rt=1.62 min; m/z (ESI⁺) 321 (MH⁺), (ESI⁻) 319 (M−H).

Synthesis 9-7-A tert-Butyl 4-(6-bromo-1H-imidazo[4,5-c]pyridin-1-yl)piperidine-1-carboxylate

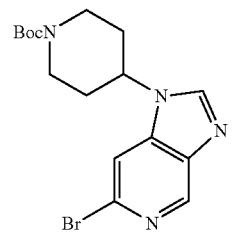 [SMILES: CC(C)(C)OC(=O)N1CCC(n2cnc3cnc(Br)cc32)CC1]

The title compound was prepared using methods analogous to those described in Synthesis 1-1-A, 7-1-A and 7-1-B, replacing 4-methoxybenzylamine with tert-butyl 4-aminopiperidine-1-carboxylate in Synthesis 1-1-A. LC-MS (1) Rt=1.87 min; m/z (ESI+) 381 & 383 (MH⁺).

Synthesis 9-7-B 5-(1-(Piperidin-4-yl)-1H-imidazo[4,5-c]pyridin-6-ylamino)pyrazine-2-carbonitrile (BB-022)

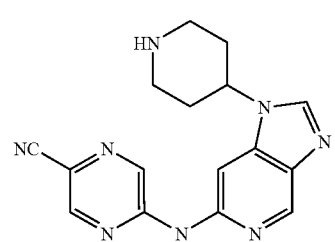

The title compound was prepared using methods analogous to those described in Synthesis 7-1-C and 7-1-D. $^1$H NMR (d$_6$-DMSO, 400 MHz) δ 10.84 (br s, 1H), 8.81 (m, 1H), 8.78-8.76 (m, 2H), 8.45 (s, 1H), 8.25 (s, 1H), 8.22 (s, 1H), 4.48-4.39 (m, 1H), 3.20-3.13 (m, 2H), 2.79-2.70 (m, 2H), 2.06-1.93 (m, 4H). LCMS (2) Rt=1.65 min; m/z (ESI⁺) 321 (MH⁺), (ESI⁻) 319 (M−H).

Synthesis 9-8-A (R)-tert-Butyl 3-(6-bromo-1H-imidazo[4,5-c]pyridin-1-yl)piperidine-1-carboxylate

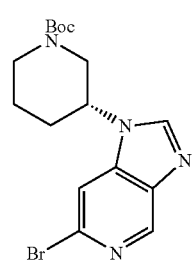 [SMILES: CC(C)(C)OC(=O)N1CCC[C@@H](n2cnc3cnc(Br)cc32)C1]

The title compound was prepared using methods analogous to those described in Synthesis 1-1-A, 7-1-A and 7-1-B, replacing 4-methoxybenzylamine with (R)-tert-butyl 3-aminopiperidine-1-carboxylate in Synthesis 1-1-A. LC-MS (1) Rt=1.92 min; m/z (ESI+) 381 & 383 (MH⁺).

Synthesis 9-8-B (R)-5-(1-(Piperidin-3-yl)-1H-imidazo[4,5-c]pyridin-6-ylamino)pyrazine-2-carbonitrile (BB-023)

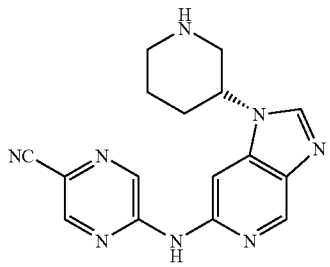

The title compound was prepared using methods analogous to those described in Synthesis 7-1-C and 7-1-D. ¹H NMR (d₆-DMSO, 400 MHz) δ 10.86 (br s, 1H), 8.81 (m, 1H), 8.78-8.76 (m, 2H), 8.51 (s, 1H), 8.26 (s, 1H), 8.21 (br s, 1H), 4.37-4.30 (m, 1H), 3.20-3.15 (m, 2H), 2.98-2.88 (m, 2H), 2.16-2.00 (m, 2H), 1.80-1.73 (m, 1H), 1.65-1.55 (m, 1H). LCMS (2) Rt=1.57 min; m/z (ESI⁺) 321 (MH⁺), (ESI⁻) 319 (M−H).

Synthesis 10-1

5-(3H-Imidazo[4,5-c]pyridin-6-ylamino)-3-(1-(dimethylamino)propan-2-yloxy)pyrazine-2-carbonitrile (BB-024)

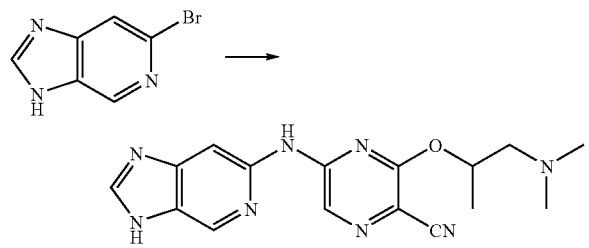

A mixture of tris(dibenzylideneacetone)dipalladium(0) (14 mg, 0.016 mmol) and 9,9-dimethyl-4,5-bis(diphenylphosphino)xanthene (18 mg, 0.031 mmol) in toluene (1.5 mL) was degassed under a stream of nitrogen gas with stirring for 10 minutes. After addition of 1-(4-methoxybenzyl)-6-bromo-1H-imidazo[4,5-c]pyridine (50 mg, 0.157 mmol), 5-amino-3-(1-(dimethylamino)propan-2-yloxy)pyrazine-2-carbonitrile in DMF (0.5 mL) (38 mg, 0.173 mmol) and caesium carbonate (102 mg, 0.314 mmol), the mixture was degassed for a further 5 minutes and then heated at 120° C. for 30 minutes in a microwave reactor. Upon cooling, the mixture was diluted with methanol and isolated by SPE using a MP-TsOH cartridge, washing with methanol and then eluting with 2 M ammonia in methanol. The combined basic fractions were concentrated in vacuo. Preparative HPLC gave the title compound (10.8 mg, 0.032 mmol, 20%). ¹H NMR (d₆-DMSO, 400 MHz) δ 10.82 (br s, 1H), 8.75 (d, 1H, J=1.0 Hz), 8.36 (br s, 1H), 8.28 (br s, 1H), 8.21 (s, 1H), 8.15 (br s, 1H), 5.48-5.41 (m, 1H), 2.62 (dd, 1H, J=13.1, 7.1 Hz), 2.5-2.46 (m, partly obscured by DMSO, 1H), 2.19 (s, 6H), 1.41 (d, 3H, J=6.3 Hz). LC-MS (2) Rt=1.78 min; m/z (ESI−) 337 (M−H).

The following compounds were prepared using methods analogous to those described in Synthesis 10-1, replacing 5-amino-3-(1-(dimethylamino)propan-2-yloxy)pyrazine-2-carbonitrile with the appropriate 2-aminopyrazine.

| Synthesis | 10-2 |
|---|---|
| Compound | BB-025 |
| Structure | 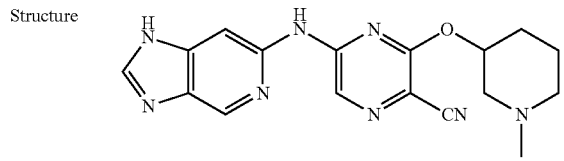 |
| NMR | 1H NMR (d₆-DMSO, 400 MHz) δ 12.84 (br s, 1H), 10.80 (s, 1H), 8.75 (s, 1H), 8.33 (s, 1H), 8.02 (br s, 1H), 5.22-5.18 (m, 1H), 3.17-3.16 (m, 1H), 2.90-2.80 (m, 1H), 2.46-2.38 (m, 1H), 2.28-2.22 (m, 1H), 2.20 (s, 3H), 2.08-1.98 (m, 1H), 1.83-1.72 (m, 1H), 1.70-1.62 (m, 1H), 1.60-1.45 (m, 1H). |
| LCMS | LC-MS (2) Rt = 2.07 min; m/z (ESI-) 349 (M − H). |

| Synthesis | 10-3 |
|---|---|
| Compound | BB-026 |
| Structure | 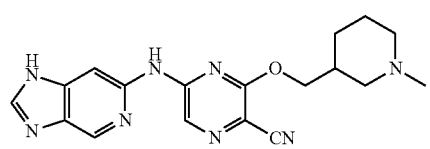 [SMILES: CN1CCCC(COc2nc(Nc3cc4[nH]cnc4cn3)cnc2C#N)C1] |
| NMR | 1H NMR (d₆-DMSO, 400 MHz) δ 10.69 (br s, 1H), 8.73 (s, 1H), 8.35 (br s, 1H), 8.33 (s, 1H), 8.11 (br s, 1H), 4.39-4.36 (m, 2H), 2.85-2.82 (m, 1H), 2.67-2.64 (m, 1H), 2.18 (s, 3H), 2.15-2.06 (m, 1H), 1.98-1.88 (m, 1H), 1.79-1.74 (m, 1H), 1.69-1.64 (m, 1H), 1.55-1.45 (m, 1H), 1.19-1.10 (m, 1H). |
| LCMS | LC-MS (2) Rt = 2.03 min; m/z (ESI-) 363 (M − H). |

| Synthesis | 10-4 |
|---|---|
| Compound | BB-027 |
| Structure | 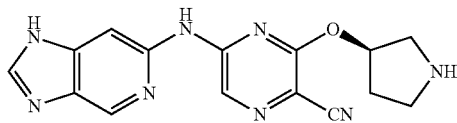 [SMILES: N#Cc1ncc(Nc2cc3[nH]cnc3cn2)nc1O[C@@H]1CCNC1] |
| NMR | 1H NMR (d₆-DMSO, 400 MHz) δ 10.90 (br s, 1H), 8.75 (s, 1H), 8.36 (s, 1H), 8.28 (brs, 1H), 8.23 (brs, 1H), 5.57-5.54 (m, 1H), 3.38-3.33 (m, 1H), 3.11 (br d, 1H, J = 13.3 Hz), 3.07-3.02 (m, 1H), 2.98-2.92 (m, 1H), 2.27-2.20 (m, 1H), 2.04-1.97 (m, 1H). |
| LCMS | LC-MS (2) Rt = 1.67 min; m/z (ESI-) 321 (M − H⁻). |

Synthesis 10-5

5-(3H-Imidazo[4,5-c]pyridin-6-ylamino)-3-(1-(dimethylamino)propan-2-yloxy)pyrazine-2-carbonitrile (BB-028)

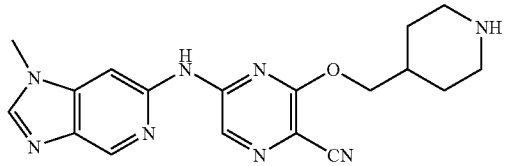 [SMILES: Cn1cnc2cnc(Nc3cnc(C#N)c(OCC4CCNCC4)n3)cc21]

The title compound was prepared using methods analogous to those described in Synthesis 10-1, replacing 5-amino-3-(1-(dimethylamino)propan-2-yloxy)pyrazine-2-carbonitrile with tert-butyl 4-(((6-amino-3-cyanopyrazin-2-yloxy)methyl)piperidine-1-carboxylate and replacing 1-(4-methoxybenzyl)-6-bromo-1H-imidazo[4,5-c]pyridine with 6-bromo-1-methyl-1H-imidazo[4,5-c]pyridine. 1H NMR (d$_6$-DMSO, 400 MHz) δ 8.76 (d, 1H, J=0.8 Hz), 8.35 (br s, 1H), 8.29 (br s, 1H), 4.39 (d, 2H, J=6.8), 3.84 (s, 3H), 3.01 (d, 2H, J=12.9 Hz), 2.58-2.52 (m, 2H), 1.96-1.94 (m, 1H), 1.75 (d, 2H, J=12.6 Hz), 1.26-1.22 (m, 2H). LC-MS (2) Rt=1.79 min; m/z (ESI+) 365 (MH$^+$).

Synthesis 11-1-A

N-(2-Bromobenzyl)-2,2-diethoxyacetamide

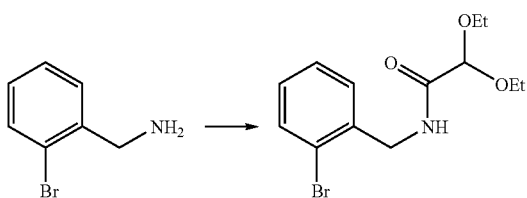 [SMILES: NCc1ccccc1Br ; CCOC(OCC)C(=O)NCc1ccccc1Br]

1-[3-(Dimethylamino)propyl]-3-ethylcarbodiimide (1.15 g, 6.00 mmol) was added to a mixture of 2-bromobenzylamine (0.744 g, 4.00 mmol), sodium 2,2-diethoxyacetate (0.816 g, 4.80 mmol), 1-hydroxybenzotriazole hydrate (0.919 g, 6.00 mmol) and Hunig's base (1.53 mL, 8.80 mmol) in DMF (10 mL) with stirring. After 18 hours at room temperature, the mixture was partitioned between water and ethyl acetate. The organic layer was washed successively with 2 M HCl, saturated sodium bicarbonate solution and brine, then dried (Na$_2$SO$_4$) and concentrated to a viscous colourless oil (1.02 g, 81%). LC-MS (1) Rt==2.23 min; m/z (ESI+) 316 & 318 (M+H$^+$).

Synthesis 11-1-B

8-Bromoisoquinolin-3-yl trifluoromethanesulfonate

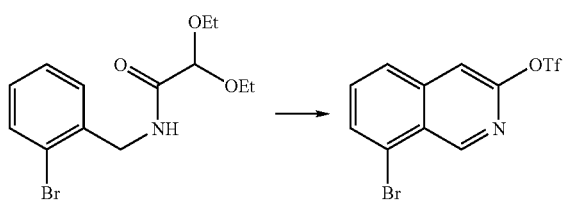 [SMILES: CCOC(OCC)C(=O)NCc1ccccc1Br ; O=S(=O)(Oc1cc2cccc(Br)c2cn1)C(F)(F)F]

The title compound was prepared using a method analogous to that described in Durola et al., 2007.

Synthesis 11-1-C 5-(8-Bromoisoquinolin-3-ylamino)pyrazine-2-carbonitrile (AA-017)

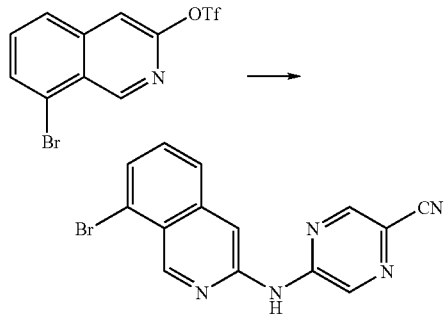

The title compound was prepared using methods analogous to those described in Synthesis 5-1 using 2-amino-5-cyanopyrazine in place of (R)-5-amino-3-(pyrrolidin-3-yloxy)pyrazine-2-carbonitrile and 8-bromoisoquinolin-3-yl trifluoromethanesulfonate in place of 3,8-dichloroisoquinoline. $^1$H NMR (DMSO, 400 MHz) δ 11.30 (br s, 1H), 9.40 (s, H), 8.95 (s, H), 8.80 (s, H), 8.60 (s, H), 8.05 (d, 1H, J=8.5 Hz), 7.95 (d, 1H, J=7.5 Hz), 7.75 (dd, 1H, J=8.5 Hz, 7.5 Hz). LC-MS (2) Rt=3.21 min, m/z (ESI$^+$) 326 & 328 (MH$^+$).

The following compounds were prepared using methods analogous to those described in Synthesis 11-1-C, replacing 2-amino-5-cyanopyrazine with the appropriate 3-alkoxy substituted 5-aminopyrazine-2-carbonitrile and reacting with the appropriate 8-substituted isoquinolin-3-yl trifluoromethanesulfonate.

| Synthesis | 11-2 |
|---|---|
| Compound | AA-026 |
| Structure | 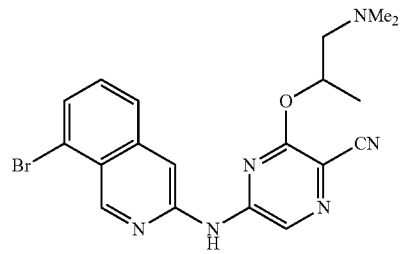 |
| NMR | 1H NMR (d$_6$-DMSO, 400 MHz) δ 11.24 (br s, 1H), 9.33 (s, 1H), 8.48 (s, 1H), 8.26 (s, 1H), 7.85-7.90 (m, 2H), 7.66 (dd, 1H, J = 7.6, 8.1 Hz), 5.48-5.53 (m, 1H), 2.65-2.70 (m, 1H), 2.50-2.60 (m, 1H, partially obscured by DMSO), 2.22 (s, 6H), 1.47 (d, 3H, J = 6.1 Hz). |
| LCMS | LCMS (2) Rt = 3.38 min, m/z (ESI$^+$) 427 & 429 (MH$^+$). |

| Synthesis | 11-3 |
|---|---|
| Compound | AA-051 |
| Structure | 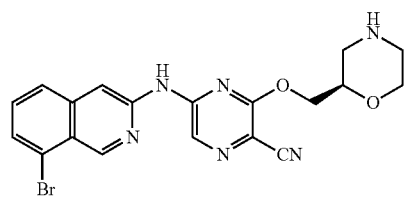 [SMILES: N#Cc1ncc(Nc2cc3cccc(Br)c3cn2)nc1OC[C@H]1CNCCO1] |

-continued

| | |
|---|---|
| NMR | 1H NMR (d6-DMSO, 400 MHz) δ 9.31 (s, 1H), 8.50 (s, 1H), 8.25 (s, 1H), 7.91 (d, 1H, J = 8.6 Hz), 7.85 (d, 1H, J = 8.4 Hz), 7.67-7.63 (m, 1H), 4.59-4.48 (m, 2H), 3.87-3.82 (m, 1H), 3.80-3.77 (m, 1H), 3.51-3.44 (m, 1H), 2.94-2.90 (m, 1H), 2.67-2.66 (m, 2H), 2.64-2.58 (m, 1H). |
| LCMS | LC-MS (2) Rt = 2.98 min; m/z (ESI+) 441/443 (M + H). |

| | |
|---|---|
| Synthesis | 11-4 |
| Compound | AA-052 |
| Structure | 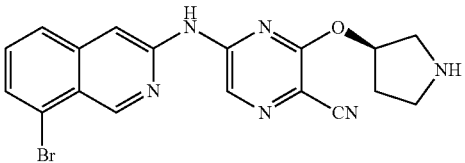 [SMILES: N#Cc1ncc(Nc2cc3cccc(Br)c3cn2)nc1O[C@@H]1CCNC1] |
| NMR | 1H NMR (d6-DMSO, 400 MHz) δ 9.33 (s, 1H), 8.58 (s, 1H), 8.23 (s, 1H), 7.95 (d, 1H, J = 8.4 Hz), 7.86 (d, 1H, J = 7.3 Hz), 7.66 (dd, 1H, J = 7.6, 8.1 Hz), 5.59-5.65 (m, 1H), 3.23-3.30 (m, 1H), 3.01-3.08 (m, 1H), 2.92-3.01 (m, 1H), 2.84-2.92 (m, 1H) 2.14-2.26 (m, 1H), 1.93-2.03 (m, 1H). |
| LCMS | LC-MS (2) Rt = 2.84 min; m/z (ESI+) 409/411 (M+H). |

| | |
|---|---|
| Synthesis | 11-5 |
| Compound | AA-053 |
| Structure | 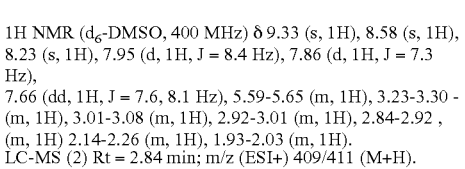 |
| NMR | 1H NMR (d6-DMSO, 400 MHZ) δ 9.31 (s, 1H), 8.58 (s,1H), 8.26 (s, 1H), 8.00 (d, 1H, J = 8.6 Hz), 7.84 (d, 1H, J = 7.6 Hz), 7.65-7.61 (m, 1H), 4.18 (s, 3H). |
| LCMS | LC-MS (2) Rt = 3.63 min; m/z (ESI+) 356/358 (M+H). |

| | |
|---|---|
| Synthesis | 11-6 |
| Compound | AA-054 |
| Structure | 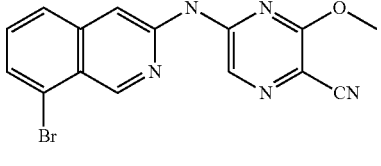 |

| | |
|---|---|
| NMR | 1H NMR (d6-DMSO, 400 MHz) δ 11.15 (s br, 1H), 9.35 (s, 1H), 8.49 (s, 1H), 8.26 (s, 1H), 7.71-7.72 (m, 1H), 7.68 (d, 1H, J = 8.6 Hz), 7.35-7.31 (m, 1H), 5.52-5.47 (m, 1H), 2.68-2.63 (m, 1H), 2.57-2.52 (m, 1H), 2.21 (s, 6H), 1.46 (d, 1H, J = 6.3 Hz). |
| LCMS | LC-MS (2) Rt = 3.06 min; m/z (ESI+) 367 (M + H). |

| | |
|---|---|
| Synthesis | 11-7 |
| Compound | AA-055 |
| Structure | 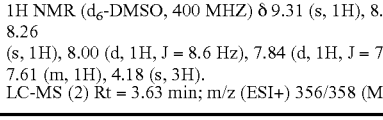 |
| NMR | 1H NMR (MeOD-d4, 500 MHz) δ 9.32 (s, 1H), 8.44 (s, 1H), 8.28 (s, 1H), 7.72-7.67 (m, 2H), 7.23-7.19 (m, 1H), 5.80-5.78 (m, 1H), 3.48-3.41 (m, 2H), 3.32-3.28 (m, 1H), 3.22-3.18 (m, 1H), 2.44-2.37 (m, 1H), 2.34-2.30 (m, 1H). |
| LCMS | LC-MS (2) Rt =2.01 min; m/z (ESI+) 351 (M + H). |

| | |
|---|---|
| Synthesis | 11-8 |
| Compound | AA-056 |
| Structure | 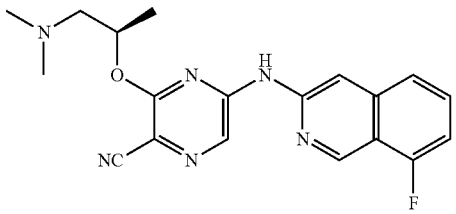 [SMILES: C[C@H](CN(C)C)Oc1nc(Nc2cc3cccc(F)c3cn2)cnc1C#N] |
| NMR | 1H NMR (MeOD-d4, 500 MHz) δ 9.35 (s, 1H), 8.50 (s, 1H), 8.27 (s, 1H), 8.11 (d, 1H, J = 8.4 Hz), 7.91 (d, 1H, J = 7.2 Hz), 7.80 (t, 1H, J = 8.0 Hz), 5.65-5.61 (m, 1H), 2.87 (dd, 1H, J = 13.6, 8.2 Hz), 2.69 (dd, 1H, J = 13.6, 3.2 Hz), 2.37 (s, 6H), 1.53 (d, 3H, J = 6.2 Hz). |
| LCMS | LC-MS (3) Rt = 2.12 min; m/z (ESI+) 417 (M + H) |

| | |
|---|---|
| Synthesis | 11-9 |
| Compound | AA-072 |
| Structure |  |

| | |
|---|---|
| NMR | ¹H NMR (DMSO-d₆, 500 MHz) δ 9.30 (s, 1H), 8.65 (s, 1H), 8.26 (d, 1H, J = 7.9 Hz), 8.24 (s, 1H), 7.98 (d, 1H, J = 7.2 Hz), 7.87 (t, 1H, J = 7.8 Hz), 5.70-5.68 (m, 1H), 3.19 (d, 1H, J = 12.8 Hz), 3.07-2.99 (m, 2H), 2.30-2.23 (m, 1H), 2.09-2.06 (m, 1H). |
| LCMS | LC-MS (3) Rt =2.08 min; m/z (ESI⁺) 401 (M + H). |

Synthesis 11-10

5-(6-Chloroisoquinolin-3-ylamino)pyrazine-2-carbonitrile (AA-018)

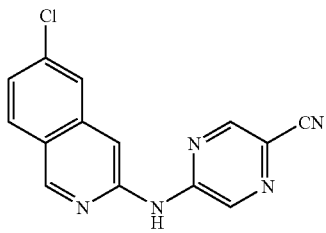 [SMILES: N#Cc1cnc(Nc2cc3cc(Cl)ccc3cn2)cn1]

The title compound was prepared using methods analogous to those described in Synthesis 5-1 using 2-amino-5-cyanopyrazine in place of (R)-5-amino-3-(pyrrolidin-3-yloxy)pyrazine-2-carbonitrile and 6-chloroisoquinolin-3-yl trifluoromethanesulfonate in place of 3,8-dichloroisoquinoline. 6-Chloroisoquinolin-3-yl trifluoromethanesulfonate was prepared using methods analogous to those described in Synthesis 11-1 for 8-bromoisoquinolin-3-yl trifluoromethanesulfonate. ¹H NMR (DMSO, 400 MHz) δ 11.11 (s, 1H), 9.24 (s, 1H), 8.82 (d, 1H, J=1.3 Hz), 8.74 (d, 1H, J=1.3 Hz), 8.47 (s, 1H), 8.13 (d, 1H, J=8.6 Hz), 8.09 (d, 1H, J=1.8 Hz), 7.55 (dd, 1H, J=8.8, 2.0 Hz). LCMS (2) Rt=3.04 min, m/z (ESI⁺) 282 & 284 (MH⁺).

Synthesis 11-11

5-(5-Bromo-8-chloroisoquinolin-3-ylamino)pyrazine-2-carbonitrile (AA-070)

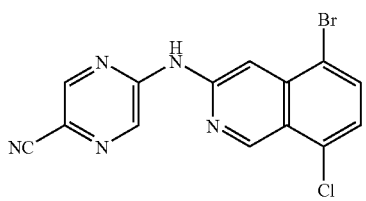

The title compound was prepared using methods analogous to those described in Synthesis 5-1 using 2-amino-5-cyanopyrazine in place of (R)-5-amino-3-(pyrrolidin-3-yloxy)pyrazine-2-carbonitrile, and using 5-bromo-8-chloroisoquinolin-3-yl trifluoromethanesulfonate in place of 3,8-dichloroisoquinoline. 5-Bromo-8-chloroisoquinolin-3-yl trifluoromethanesulfonate was prepared using methods analogous to those described in Synthesis 11-1 for 8-bromoisoquinolin-3-yl trifluoromethanesulfonate. ¹H NMR (DMSO, 400 MHz) δ 11.3 (br s, 1H), 9.42 (s, 1H, J=0.8 Hz), 8.85 (d, 1H, J=1.3 Hz), 8.81 (d, 1H, J=1.3 Hz), 8.79 (d, 1H, J=0.8 Hz), 8.07 (d, 1H, J=8.1 Hz), 7.58 (d, 1H, J=8.1 Hz). LCMS (2) Rt=3.58 min; m/z (ESI+) 360 & 362 (M+H).

Synthesis 12

5-(8-(1H-pyrazol-3-yl)isoquinolin-3-ylamino)pyrazine-2-carbonitrile (AA-019)

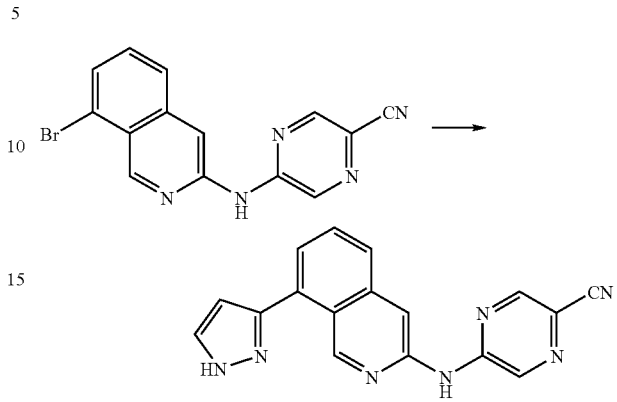

A mixture of 5-(8-bromoisoquinolin-3-ylamino)pyrazine-2-carbonitrile (65 mg, 0.20 mmol), 1H-pyrazol-3-yl boronic acid (33 mg, 0.30 mmol) and aqueous sodium carbonate (0.5M, 0.60 mL, 0.30 mmol) in DMF (2 mL) was degassed for 15 minutes before the addition of tetrakis(triphenylphosphine)palladium(0) (12 mg, 0.10 mmol). The mixture was further degassed for 5 minutes and then heated to 140° C. for 20 minutes in a microwave reactor. The cooled mixture was partitioned between ethyl acetate and water. The aqueous layer was further extracted with ethyl acetate and the combined organics were washed with water and brine, dried (Na₂SO₄), and passed sequentially through two PS-Thiol cartridges. The eluent was concentrated to a yellow solid which was dissolved in methanol and purified by SPE on a MP-TsOH cartridge, eluting with 2 M ammonia in methanol. Concentration of the eluent gave the required product as a light yellow solid (18 mg, 0.06 mmol, 29%). ¹H NMR (DMSO, 400 MHz) δ 13.25 (br s, 1H), 11.10 (br s, 1H), 10.00 (s, 1H), 8.84 (s, 1H), 8.72 (s, 1H), 8.55 (s, 1H), 7.80-8.00 (m, 2H), 7.70-7.80 (m, 2H), 6.80 (s, 1H). LCMS (2) Rt=2.46 min, m/z (ESI⁺) 314 (MH⁺).

Synthesis 13-1

5-(8-(2-morpholinoethylamino)isoquinolin-3-ylamino)pyrazine-2-carbonitrile (AA-020)

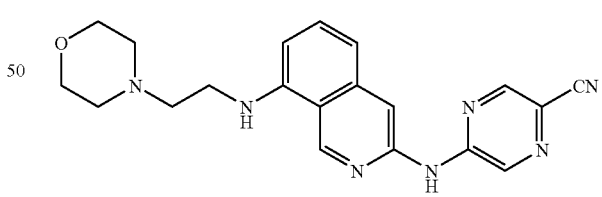

The title compound was prepared using methods analogous to those described in Synthesis 5-1, replacing 3,8-dichloroisoquinoline with 5-(8-bromoisoquinolin-3-ylamino)pyrazine-2-carbonitrile and replacing (R)-5-amino-3-(pyrrolidin-3-yloxy)pyrazine-2-carbonitrile with N-(2-aminoethyl)morpholine, and conducting the reaction at 140° C.

¹H NMR (DMSO, 400 MHz) δ 10.93 (br s, 1H), 9.38 (s, 1H), 8.80 (s, 1H), 8.71 (s, 1H), 8.28 (s, 1H), 7.48-7.43 (m, 1H), 7.00 (d, 1H, J=8.1 Hz), 6.71-6.67 (m, 1H), 6.51 (d, 1H, J=7.8 Hz), 3.63-3.59 (m, 3H), 3.39-3.24 (m, 2H), 2.67-2.62 (m, partially obscured by residual water peak), 2.52-2.46 (m, partially obscured by residual solvent peak). LCMS (2) Rt=2.62 min; m/z (ESI+) 376 (MH+).

The following compounds were prepared using methods analogous to those described in Synthesis 13, using the appropriately substituted 5-(8-bromoisoquinolin-3-ylamino)pyrazine-2-carbonitrile prepared using methods analogous to those described in Synthesis 11-3 and the appropriate N-aminoalkylmorpholine.

| Synthesis | 13-2 |
|---|---|
| Compound | AA-027 |
| Structure | 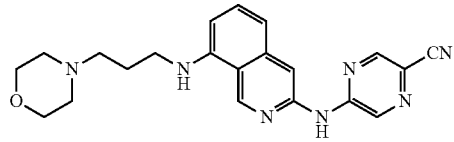 [SMILES: N#Cc1cnc(Nc2cc3cccc(NCCCN4CCOCC4)c3cn2)cn1] |
| NMR | $^1$H NMR (d$_6$-DMSO, 400MHz) δ 10.95, (br s, 1H), 9.40 (s, 1H), 8.80 (s, 1H), 8.70 (s, 1H), 8.30 (s, 1H), 7.45-7.50 (m, 1H), 6.98 (d, 1H, J = 8.2 Hz), 6.92 (br t, 1H), 6.47 (d, 1H, J = 7.3 Hz), 3.60-3.63 (m, 3H), 3.25-3.30 (m, 2H), 2.40-2.48 (m, 5H), 1.80-1.90 (m, 2H). |
| LCMS | LC-MS (2) Rt = 2.72 min; m/z (ESI+) 390 (M + H). |

| Synthesis | 13-3 |
|---|---|
| Compound | AA-028 |
| Structure | 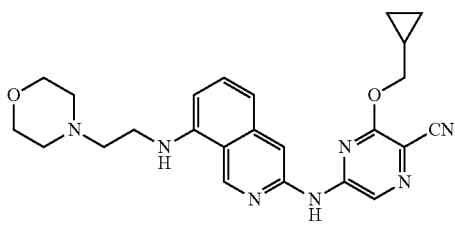 [SMILES: N#Cc1ncc(Nc2cc3cccc(NCCN4CCOCC4)c3cn2)nc1OCC1CC1] |
| NMR | $^1$H NMR (d$_6$-DMSO, 400 MHz) δ 10.85 (br s, 1H), 9.37 (s, 1H), 8.29 (s, 1H), 8.24 (s, 1H), 7.50-7.46 (m, 1H), 6.97-6.92 (m, 1H), 6.70-6.66 (m, 1H), 6.55-6.48 (m, 1H), 4.41 (d, 2H, J = 7.3 Hz), 3.64-3.58 (m, 4H), 3.41-3.28 (m, 4H), 2.69-2.62 (m, 2H), 1.46-1.35 (m, 1H), 0.68-0.60 (m, 2H), 0.48-0.43 (m, 2H). |
| LCMS | LC-MS (2) Rt = 3.13 min; m/z (ESI+) 446 (M + H). |

| Synthesis | 13-4 |
|---|---|
| Compound | AA-029 |
| Structure | 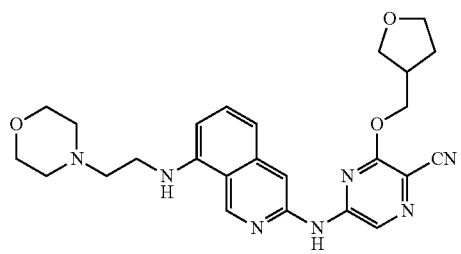 [SMILES: N#Cc1ncc(Nc2cc3cccc(NCCN4CCOCC4)c3cn2)nc1OCC1CCOC1] |
| NMR | — |
| LCMS | LC-MS (2) Rt = 2.71 min; m/z (ESI+) 476 (M + H). |

| Synthesis | 13-5 |
|---|---|
| Compound | AA-030 |
| Structure | 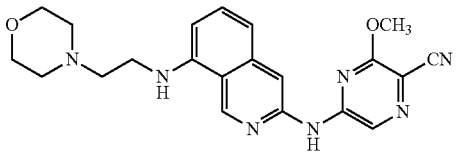 [SMILES: COc1nc(Nc2cc3cccc(NCCN4CCOCC4)c3cn2)cnc1C#N] |
| NMR | $^1$H NMR (d$_6$-DMSO, 400 MHz) δ 9.38 (s, 1H), 8.36 (s, 1H), 8.24 (s, 1H), 7.84-7.44 (m, 1H), 7.03 (d, 1H, J = 8.1 Hz), 6.70 (t, 1H, J = 5.5 Hz), 6.51 (d, 1H, J = 7.6 Hz), 4.15 (s, 3H), 3.62-3.60 (m, 4H), 2.66-2.63 (m, 2H). |
| LCMS | LC-MS (2) Rt = 2.75 min; m/z (ESI+) 406 (M + H). |

Synthesis 14-1

5-(8-methoxyisoquinolin-3-ylamino)pyrazine-2-carbonitrile (AA-021)

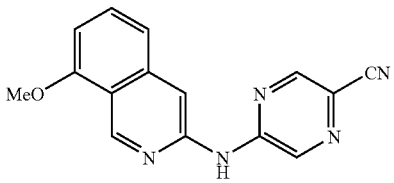 [SMILES: COc1cccc2cc(Nc3cnc(C#N)cn3)ncc12]

Sodium methoxide (55 mg, 0.10 mmol) was added to a pre-stirred mixture of 5-(8-bromoisoquinolin-3-ylamino) pyrazine-2-carbonitrile (33 mg, 0.10 mmol) and copper iodide (19 mg, 0.10 mmol) in DMF in triplicate. The three reaction mixtures were heated at 140° C. for 30 minutes, 110° C. for 18 hours, and 120° C. for 10 minutes, respectively. The combined reaction mixtures were partitioned between ethyl acetate and water and the aqueous layer re-extracted with more ethyl acetate. The combined organic phases were washed with brine, dried (Na$_2$SO$_4$), and concentrated in vacuo. Purification by preparative HPLC gave the title compound (1.7 mg, 0.006 mmol, 2%). $^1$H NMR (DMSO, 400 MHz) δ 9.33 (s, 1H), 8.81 (d, 1H, J=1.3 Hz), 8.71 (d, 1H, J=1.3 Hz), 8.43 (s, 1H), 7.64 (t, 1H, J=8.1 Hz), 7.43 (d, 1H, J=8.3 Hz), 6.97 (d, 1H, J=7.6 Hz), 4.01 (s, 3H). LCMS (2) Rt=2.87 min, m/z (ESI+) 278 (MH+).

Synthesis 15-1

5-(8-(2-Hydroxyethylamino)isoquinolin-3-ylamino)pyrazine-2-carbonitrile (AA-031)

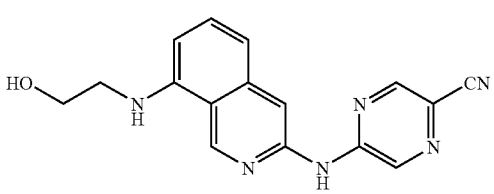 [SMILES: N#Cc1cnc(Nc2cc3cccc(NCCO)c3cn2)cn1]

A mixture of tris(dibenzylideneacetone)dipalladium (0) (18 mg, 0.020 mmol) and 9,9-dimethyl-4,5-bis(diphenylphosphino)xanthene (23 mg, 0.040 mmol) in toluene (1 mL) and DMF (1 mL) was degassed under a stream of nitrogen gas with stirring for 15 minutes. 5-(8-Bromoisoquinolin- 3-ylamino)pyrazine-2-carbonitrile (65 mg, 0.20 mmol), ethanolamine (61 mg, 1.00 mmol) and caesium carbonate (130 mg, 0.40 mmol) were added and the mixture was degassed for a further 5 minutes, then heated at 140° C. for 40 minutes in a microwave reactor. Upon cooling the reaction mixture was partitioned between ethyl acetate and aqueous sodium hydrogen carbonate (2.5%) and filtered through celite. The aqueous phase was re-extracted with ethyl acetate and then the combined organic phases were washed sequentially with aqueous sodium hydrogencarbonate and brine. The organic phase was dried ($Na_2SO_4$) and passed sequentially through two PS-Thiol cartridges and concentrated to dryness. Preparative HPLC gave the title compound (8.14 mg, 0.034 mmol, 17%). $^1$H NMR ($d_6$-DMSO, 400 MHz) δ 10.94 (br s, 1H), 9.41 (s, 1H), 8.80 (s, 1H), 8.70 (s, 1H), 8.29 (s, 1H), 7.43-7.46 (m, 1H), 6.98 (d, 1H, J=8.4 Hz), 6.70 (br t, 1H), 6.50 (d, 1H, J=7.6 Hz), 4.82 (t, 1H, J=5.8 Hz), 3.65-3.70 (m, 2H), 3.25-3.30 (m, 2H, partially obscured by water signal). LC-MS (2) Rt=2.27 min; m/z (ESI+) 308 (M+H).

The following compounds were prepared using methods analogous to those described in Synthesis 15-1, using the appropriately substituted 5-(8-bromoisoquinolin-3-ylamino)pyrazine-2-carbonitrile prepared using methods analogous to those described in Synthesis 11-3, and the appropriate hydroxy or alkoxy substituted alkyl amine.

| | |
|---|---|
| Synthesis | 15-2 |
| Compound | AA-032 |
| Structure | 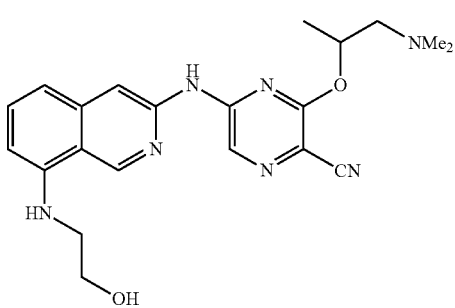 [SMILES: CC(CN(C)C)Oc1nc(Nc2cc3cccc(NCCO)c3cn2)cnc1C#N] |
| NMR | $^1$H NMR ($d_6$-DMSO, 400 MHz) δ 10.95 (br s, 1H), 9.42 (s, 1H), 8.27 (s, 1H), 8.21 (s, 1H), 7.45-7.50 (m, 1H), 6.92 (d, 1H, J = 8.1 Hz), 6.74 (br t, 1H), 6.51 (d, 1H, J = 7.6 Hz), 5.46-5.53 (m, 1H), 4.82 (br s, 1H), 3.67-3.71 (m, 2H), 3.25-3.35 (m, 2H, partially obscured by water signal), 2.60-2.70 (m, 1H), 2.50-2.60 (m, 1H), 2.22 (s, 6H), 1.45 (d, 3H, J = 6.3 Hz). |
| LCMS | LC-MS (2) Rt = 2.49 min; m/z (ESI+) 408 (M + H). |

| | |
|---|---|
| Synthesis | 15-3 |
| Compound | AA-033 |
| Structure | 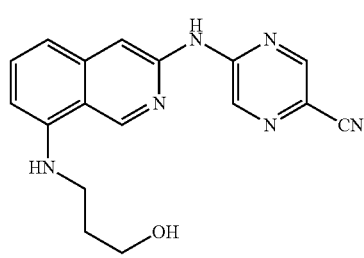 [SMILES: N#Cc1cnc(Nc2cc3cccc(NCCCO)c3cn2)cn1] |
| NMR | $^1$H NMR ($d_6$-DMSO, 400 MHz) δ 10.95 (br s, 1H), 9.40 (s, 1H), 8.80 (s, 1H), 8.71 (s, 1H), 8.28 (s, 1H), 7.43-7.47 (m, 1H), 6.97 (d, 1H, J = 8.3 Hz), 6.76 (br t, 1H), 6.47 (d, 1H, J = 7.9 Hz), 4.58 (t, 1H, J = 5.0 Hz), 3.55-3.60 (m, 2H), 3.25-3.30 (m, 2H, partially obscured by water signal), 1.82-1.88 (m, 2H). |
| LCMS | LC-MS (2) Rt = 2.39 min; m/z (ESI+) 321 (M + H). |

| | |
|---|---|
| Synthesis | 15-4 |
| Compound | AA-034 |
| Structure | 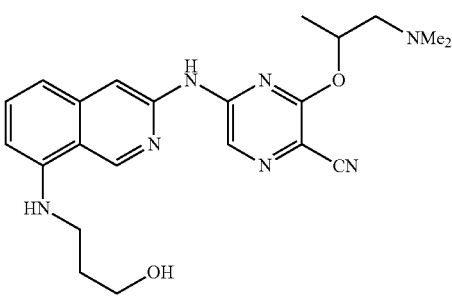 [SMILES: CC(CN(C)C)Oc1nc(Nc2cc3cccc(NCCCO)c3cn2)cnc1C#N] |
| NMR | $^1$H NMR ($d_6$-DMSO, 400 MHz) δ 10.95 (br s, 1H), 9.41 (s, 1H), 8.26 (s, 1H), 8.21 (s, 1H), 7.45-7.49 (m, 1H), 6.91 (d, 1H, J = 7.8 Hz), 6.75 (br t, 1H), 6.48 (d, 1H, J = 8.2 Hz), 5.44-5.52 (m, 1H), 4.60 (br s, 1H), 3.56-3.59 (m, 2H), 3.25-3.30 (m, 2H, partially obscured by water signal), 2.60-2.70 (m, 1H), 2.50-2.60 (m, 1H), 2.22 (s, 6H), 1.80-1.90 (m, 2H), 1.45 (d, 3H, J = 6.4 Hz). |
| LCMS | LC-MS (2) Rt = 2.57 min; m/z (ESI+) 422 (M+H). |

| | |
|---|---|
| Synthesis | 15-5 |
| Compound | AA-035 |
| Structure | |
| NMR | $^1$H NMR ($d_6$-DMSO, 400 MHz) δ 10.89 (br s, 1H), 9.41 (s, 1H), 8.79 (s, 1H), 8.72 (s, 1H), 8.27 (s, 1H), 7.49-7.43 (m, 1H), 6.98 (d, 1H, J = 8.1 Hz), 6.75 (br t, 1H), 6.47 (d, 1H, J = 7.6 Hz), 3.51-3.46 (m, 2H), 3.30-3.25 (m, 2H), 3.28 (s, 3H), 1.96-1.89 (m, 2H). |
| LCMS | LC-MS (2) Rt = 2.95 min; m/z (ESI+) 335 (M + H). |

| | |
|---|---|
| Synthesis | 15-6 |
| Compound | AA-036 |
| Structure | 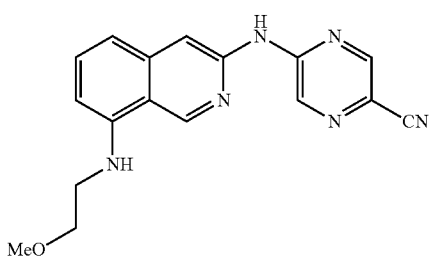 [SMILES: COCCNc1cccc2cc(Nc3cnc(C#N)cn3)ncc12] |
| NMR | $^1$H NMR (d$_6$-DMSO, 400 MHz) δ 10.91 (br s, 1H), 9.42 (s, 1H), 8.79 (s, 1H), 8.71 (s, 1H), 8.27 (s, 1H), 7.48-7.43 (m, 1H), 6.99 (d, 1H, J = 8.3 Hz), 6.78 (br t, 1H, J = 5.2 Hz), 6.51 (d, 1H, J = 7.7 Hz), 3.65-3.61 (m, 2H), 3.45-3.39 (m, 2H), 3.32 (s, 3H). |
| LCMS | LC-MS (2) Rt = 2.76 min; m/z (ESI+) 321 (M + H). |

| | |
|---|---|
| Synthesis | 15-7 |
| Compound | AA-037 |
| Structure | 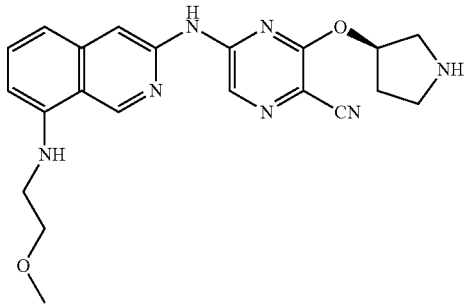 [SMILES: COCCNc1cccc2cc(Nc3cnc(C#N)c(O[C@@H]4CCNC4)n3)ncc12] |
| NMR | $^1$H NMR (d$_6$-DMSO, 400 MHz) δ 9.41 (s, 1H), 8.36 (s, 1H), 8.17 (s, 1H), 7.48-7.44 (m, 1H), 6.98 (d, 1H, J = 8.1 Hz), 6.80 (t, 1H, J = 5.3 Hz), 6.52 (d, 1H, J = 7.8 Hz), 5.58-5.54 (m, 1H), 3.62 (d, 2H, J = 5.8 Hz), 3.44-3.39 (m, 2H), 3.32 (s, 3H), 3.28-3.23 (m, 1H), 3.04-3.01 (m, 1H), 2.97-2.92 (m, 1H), 2.87-2.84 (m, 1H), 2.23-2.14 (m, 1H), 1.99-1.91 (m, 1H). |
| LCMS | LC-MS (2) Rt = 2.45 min; m/z (ESI+) 406 (M + H). |

| | |
|---|---|
| Synthesis | 15-8 |
| Compound | AA-038 |
| Structure | 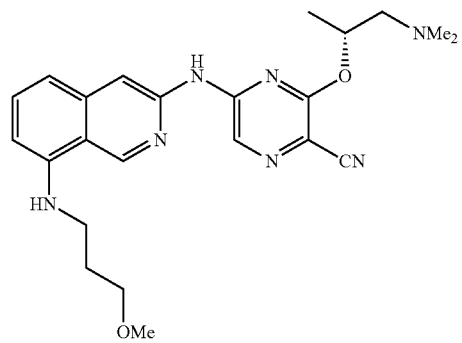 [SMILES: COCCCNc1cccc2cc(Nc3cnc(C#N)c(O[C@H](C)CN(C)C)n3)ncc12] |
| NMR | $^1$H NMR (d$_6$-DMSO, 400 MHz) δ 10.96 (s, 1H), 9.42 (s, 1H), 8.26 (s, 1H), 8.21 (s, 1H), 7.47 (dd, 1H, J = 7.8, 8.2 Hz), 6.92 (d, 1H, J = 8.1 Hz), 6.79 (br t, 1H, J = 5.2 Hz), 6.47 (d, 1H, J = 7.8 Hz), 5.44-5.52 (m, 1H), 3.46-3.51 (m, 2H), 3.25-3.31 (m, 2H), 3.28 (s, 3H), 2.61-2.69 (m, 1H), 2.50-2.57 (m, 1H), 2.21 (s, 6H), 1.89-1.97 (m, 2H), 1.45 (d, 3H, J = 6.4 Hz). |
| LCMS | LC-MS (2) Rt = 3.11 min; m/z (ESI+) 436 (M + H). |

| | |
|---|---|
| Synthesis | 15-9 |
| Compound | AA-039 |
| Structure | (structure) |
| NMR | $^1$H NMR (d$_6$-DMSO, 400 MHz) δ 10.97 (s, 1H), 9.43 (s, 1H), 8.27 (s, 1H), 8.21 (s, 1H), 7.47 (dd, 1H, J = 8.2, 7.7 Hz), 6.93 (d, 1H, J = 8.1 Hz), 6.83 (br t, 1H, J = 5.6 Hz), 6.52 (d, 1H, J = 7.6 Hz), 5.44-5.52 (m, 1H), 3.61-3.65 (m, 2H), 3.39-3.45 (m, 2H), 3.32 (s, 3H), 2.62-2.69 (m, 1H), 2.50-2.57 (m, 1H), 2.21 (s, 6H), 1.45 (d, 3H, J = 6.3 Hz). |
| LCMS | LC-MS (2) Rt = 2.93 min; m/z (ESI+) 422 (M + H). |

| | |
|---|---|
| Synthesis | 15-10 |
| Compound | AA-040 |
| Structure | (structure) |
| NMR | $^1$H NMR (d$_6$-DMSO, 400 MHz) δ 9.40 (s, 1H), 8.34 (br s, 1H), 8.17 (br s, 1H) 7.48-7.44 (m, 1H), 6.96 (d, 1H, J = 8.1 Hz), 6.78-6.75 (m, 1H), 6.48 (d, 1H, J = 8.1 Hz), 5.58-5.54 (m, 1H), 4.6 (br s, 1H), 3.59-3.56 (m, 2H), 3.30-3.25 (m, 3H), 3.08-3.04 (m, 1H), 3.00-2.86 (m, 2H), 2.24-2.15 (m, 1H), 2.02-1.95 (m, 1H), 1.88-1.82 (m, 2H). |
| LCMS | LC-MS (2) Rt = 2.11 min; m/z (ESI+) 406 (M + H). |

| | |
|---|---|
| Synthesis | 15-11 |
| Compound | AA-041 |
| Structure | 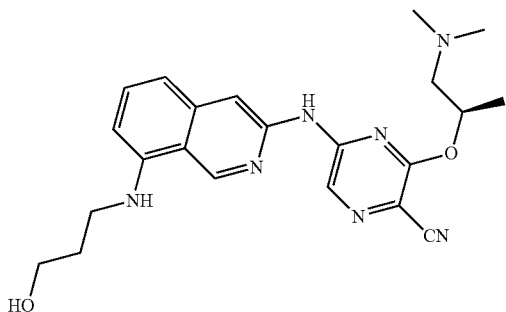 [SMILES: C[C@H](CN(C)C)Oc1nc(Nc2cc3cccc(NCCCO)c3cn2)cnc1C#N] |
| NMR | $^1$H NMR (d$_6$-DMSO, 400 MHz) δ 10.97 (s, 1H), 9.40 (s, 1H), 8.26 (br s, 1H), 8.20 (br s, 1H), 7.48-7.44 (m, 1H), 6.91 (d, 1H, J = 7.8 Hz), 6.80-6.77 (m, 1H), 6.48 (d, 1H, J = 7.8 Hz), 5.50-5.45 (m, 1H), 3.58-3.55 (m, 2H), 3.48-3.45 (m, 1H), 3.30-3.25 (m, 2H), 2.67-2.62 (m, 1H), 2.56-2.53 (m, 1H), 2.21 (s, 6H), 1.88-1.81 (m, 2H), 1.44 (d, 3H, J = 6.1 Hz) |
| LCMS | LC-MS (2) Rt = 2.57 min; m/z (ESI+) 422 (M + H). |

| | |
|---|---|
| Synthesis | 15-12 |
| Compound | AA-042 |
| Structure | 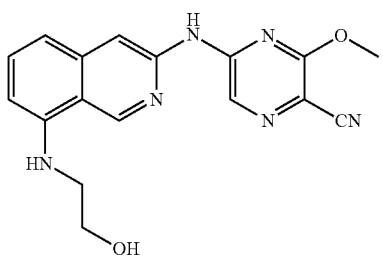 [SMILES: COc1nc(Nc2cc3cccc(NCCO)c3cn2)cnc1C#N] |

-continued

| | |
|---|---|
| NMR | $^1$H NMR (d$_6$-DMSO, 400 MHz) δ 9.41 (s, 1H), 8.34 (s, 1H), 8.23 (s, 1H), 7.47-7.43 (m, 1H), 7.01 (d, 1H, J = 8.3 Hz), 6.70 (t, 1H, J = 5.6 Hz), 6.50 (d, 1H, J = 7.8 Hz), 4.8 (br s, 1H), 4.14 (s, 3H), 3.71-3.68 (m, 2H). |
| LCMS | LC-MS (2) Rt = 2.43 min; m/z (ESI+) 337 (M + H). |

| | |
|---|---|
| Synthesis | 15-13 |
| Compound | AA-043 |
| Structure | 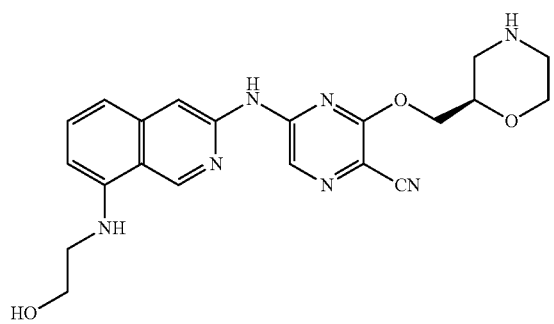 [SMILES: N#Cc1ncc(Nc2cc3cccc(NCCO)c3cn2)nc1OC[C@H]1CNCCO1] |
| NMR | $^1$H NMR (d$_6$-DMSO, 400 MHz) δ 11.03 (s, 1H), 9.39 (s, 1H), 8.9 (s, br, 1H), 8.25 (s, 1H), 8.21 (s, 1H), 7.44-7.41 (m, 1H), 6.99 (d, 1H, J = 8.3 Hz), 6.71 (t, 1H, J = 5.3 Hz), 6.47 (d, 1H, J = 7.3 Hz), 4.79 (t, 1H, J = 5.8 Hz), 4.60-4.58 (m, 2H), 4.18-4.13 (m, 1H), 4.03-3.99 (m, 1H), 3.75-3.68 (m, 1H), 3.68-3.63 (m, 2H), 3.17 (br d, J = 14.1 Hz) 3.02-2.93 (m, 2H). |
| LCMS | LC-MS (2) Rt = 1.96 min; m/z (ESI+) 422 (M + H). |

| | |
|---|---|
| Synthesis | 15-14 |
| Compound | AA-044 |
| Structure | 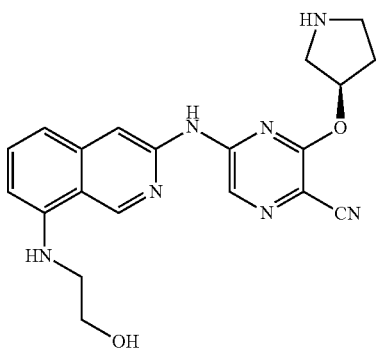 [SMILES: N#Cc1ncc(Nc2cc3cccc(NCCO)c3cn2)nc1O[C@@H]1CCNC1] |

| | |
|---|---|
| NMR | ¹H NMR (d₆-DMSO, 400 MHz) δ 9.41 (s, 1H), 8.36 (s, 1H), 8.18 (s, 1H), 7.47 (dd, 1H, J = 7.9, 8.0 Hz), 6.99 (d, 1H, J = 8.0 Hz), 6.71 (t, 1H, J = 5.5 Hz), 6.51 (d, 1H, J = 7.9 Hz), 5.54-5.60 (m, 1H), 4.77-4.82 (m, 1H), 3.67-3.74 (m, 2H), 3.24-3.35 (m, 3H, partially obscured by water signal), 3.01-3.08 (m, 1H), 2.91-3.00 (m, 1H), 2.83-2.92 (m, 1H), 2.14-2.24 (m, 1H), 1.92-2.03 (m, 1H). |
| LCMS | LC-MS (2) Rt = 1.99 min; m/z (ESI+) 392 (M + H). |

| | |
|---|---|
| Synthesis | 15-15 |
| Compound | AA-045 |
| Structure | 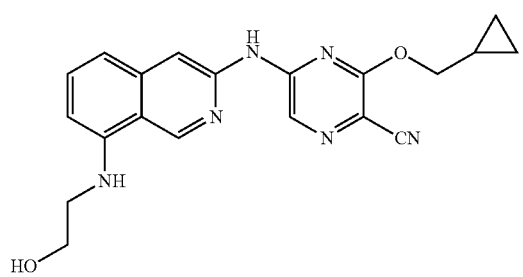 [SMILES: N#Cc1ncc(Nc2cc3cccc(NCCO)c3cn2)nc1OCC1CC1] |
| NMR | ¹H NMR (d₆-DMSO, 400 MHz) δ 10.95 (br s, 1H), 9.41 (s, 1H), 8.30 (s, 1H), 8.23 (s, 1H), 7.51-7.45 (m, 1H), 6.94 (d, 1H, J = 8.1 Hz), 6.71 (br t, 1H), 6.51 (d, 1H, 8.1 Hz), 4.81 (br s, 1H), 4.44-4.41 (m, 2H), 3.74-3.67 (m, 2H), 1.44-1.37 (m, 1H), 0.67-0.61 (m, 2H), 0.49-0.43 (m, 2H). |
| LCMS | LC-MS (2) Rt = 2.80 min; m/z (ESI+) 377 (M + H). |

| | |
|---|---|
| Synthesis | 15-16 |
| Compound | AA-046 |
| Structure | 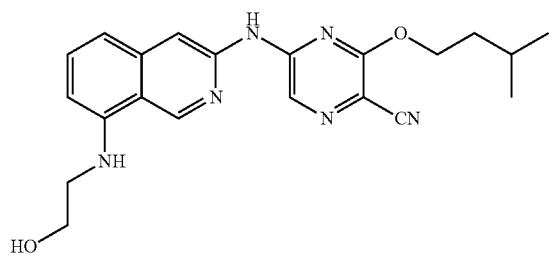 [SMILES: CC(C)CCOc1nc(Nc2cc3cccc(NCCO)c3cn2)cnc1C#N] |
| NMR | ¹H NMR (d₆-DMSO, 400 MHz) δ 10.94 (br s, 1H), 9.41 (s, 1H), 8.30 (s, 1H), 8.21 (s, 1H), 7.49-7.45 (m, 1H), 6.95 (d, 1H, 8.1 Hz), 6.71 (br t, 1H), 6.51 (d, 1H, 7.6 Hz), 4.83-4.78 (m, 1H), 4.62-4.57 (m, 2H), 3.73-3.67 (m, 1H), 3.35-3.29 (m, 2H), 1.88-1.79 (m, 1H), 1.79-1.73 (m, 2H), 0.99 (s, 3H), 0.97 (s, 3H). |
| LCMS | LC-MS (2) Rt = 3.17 min; m/z (ESI+) 393 (M + H). |

| | |
|---|---|
| Synthesis | 15-17 |
| Compound | AA-047 |
| Structure | 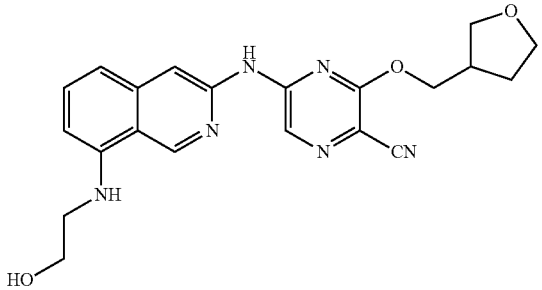 [SMILES: N#Cc1ncc(Nc2cc3cccc(NCCO)c3cn2)nc1OCC1CCOC1] |
| NMR | $^1$H NMR (d$_6$-DMSO, 400 MHz) δ 10.96 (br s, 1H), 9.42 (s, 1H), 8.28 (s, 1H), 8.23 (s, 1H), 7.49-7.45 (m, 1H), 6.95 (d, 1H, J = 8.1 Hz), 6.75-6.71 (m, 1H), 6.51 (d, 1H, J = 7.6 Hz), 4.85 (br s, 1H), 4.57-4.44 (m, 2H), 3.86-3.79 (m, 2H), 3.73-3.61 (m, 4H), 3.55-3.28 (m, 2H), 2.87-2.76 (m, 1H), 2.13-2.03 (m, 1H), 1.81-1.72 (m, 1H). |
| LCMS | LC-MS (2) Rt = 2.40 min; m/z (ESI+) 407 (M + H). |

| | |
|---|---|
| Synthesis | 15-18 |
| Compound | AA-059 |
| Structure | 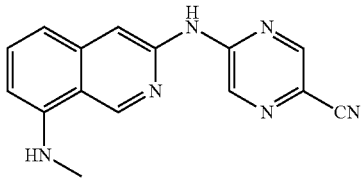 [SMILES: CNc1cccc2cc(Nc3cnc(C#N)cn3)ncc12] |
| NMR | $^1$H NMR (d$_6$-DMSO, 400 MHz) δ 10.9 (s, 1H, br), 9.35 (s, 1H), 8.79 (d, 1H, J = 1.5 Hz), 8.70 (d, 1H, J = 1.3 Hz), 8.27 (s, 1H), 747 (t, 1H, J = 7.8 Hz), 6.98 (d, 1H, J = 8.3 Hz), 6.96-6.92 (m, 1H), 6.40 (d, 1H, J = 7.3 Hz), 2.86 (d, 1H, J = 4.5 Hz). |
| LCMS | LC-MS (2) Rt = 2.78 min; m/z (ESI+) 277 (M + H). |

| | |
|---|---|
| Synthesis | 15-19 |
| Compound | AA-060 |
| Structure | 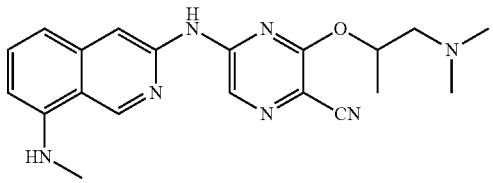 [SMILES: CNc1cccc2cc(Nc3cnc(C#N)c(OC(C)CN(C)C)n3)ncc12] |
| NMR | $^1$H NMR (d$_6$-DMSO, 400 MHz) δ 10.94 (br s, 1H), 9.35 (s, 1H), 8.25 (s, 1H), 8.20 (s, 1H), 7.50-7.46 (m, 1H), 6.97-6.94 (m, 1H), 6.92 (d, 1H, J = 8.1 Hz), 6.41 (d, 1H, J = 7.8 Hz), 5.52-5.44 (m, 1H), 2.86 (d, 3H, J = 4.5 Hz), 2.67-2.62 (m, 1H), 2.56-2.52 (m, 1H), 2.21 (s, 6H), 1.45 (d, 3H, J = 6.3 Hz). |
| LCMS | LC-MS (2) Rt = 2.97 min; m/z (ESI+) 378 (M + H). |

Synthesis 16-1

5-(8-Aminoisoquinolin-3-ylamino)pyrazine-2-carbonitrile (AA-061)

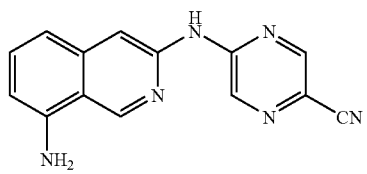 [SMILES: N#Cc1cnc(Nc2cc3cccc(N)c3cn2)cn1]

A mixture of tris(dibenzylideneacetone)dipalladium (0) (18 mg, 0.020 mmol) and 9,9-dimethyl-4,5-bis(diphenylphosphino)xanthene (23 mg, 0.040 mmol) in toluene (1 mL) and DMF (1 mL) was degassed under a stream of nitrogen gas with stirring for 15 minutes. 5-(8-Bromoisoquinolin-3-ylamino)pyrazine-2-carbonitrile (65 mg, 0.20 mmol), benzophenone imine (36 mg, 0.20 mmol) and caesium carbonate (130 mg, 0.40 mmol) were added and the mixture was degassed for a further 5 minutes, then heated at 140° C. for 40 minutes in a microwave reactor. Upon cooling the reaction mixture was diluted with ethyl acetate and filtered through celite, washed sequentially with water and brine then dried (Na$_2$SO$_4$) and concentrated to dryness to afford a brown oil. The residue was dissolved in THF (2 mL) and treated with aqueous hydrogen chloride (2 mL, 2M) for 30 minutes and then concentrated to dryness. Preparative HPLC gave the title compound (5.64 mg, 0.022 mmol, 11%). $^1$H NMR (d$_6$-DMSO, 400 MHz) δ 10.90 (br s, 1H), 9.35 (s, 1H), 8.80 (s, 1H), 8.70 (s, 1H), 8.25 (s, 1H), 7.40 (t, 1H, J=7.8, 6.8 Hz), 6.95 (d, 1H, J=7.8 Hz), 6.60 (d, 1H, J=6.8 Hz), 6.25 (s, 1H). LC-MS (2) Rt=2.32 min; m/z (ESI$^+$) 263 (M+H).

Synthesis 17-1

N-(3-(5-Cyanopyrazin-2-ylamino)isoquinolin-8-yl)acetamide (AA-062)

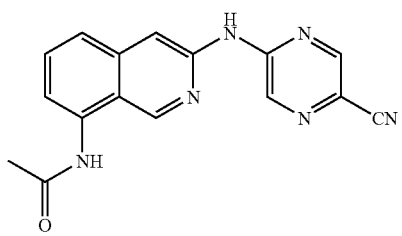 [SMILES: CC(=O)Nc1cccc2cc(Nc3cnc(C#N)cn3)ncc12]

Acetyl chloride (13 mg, 0.16 mmol) was added to a solution of 5-(8-aminoisoquinolin-3-ylamino)pyrazine-2-carbonitrile (36 mg, 0.14 mmol) and diisopropylethylamine (39 mg, 0.30 mmol) in DCE (1.5 mL). The reaction mixture stirred at room temperature for 16 hours and another portion of acetyl chloride (6.5 mg, 0.08 mmol) was added. Stirring was continued for a further 24 hours. The reaction mixture was washed once with water and the organic phase was dried (Na$_2$SO$_4$) and concentrated to dryness. Preparative HPLC gave N-(3-(5-cyanopyrazin-2-ylamino)isoquinolin-8-yl)acetamide (13.4 mg, 0.044 mmol, 32%). $^1$H NMR (d$_6$-DMSO, 400 MHz) δ 11.05 (br s, 1H), 10.20 (s, 1H), 9.36 (s, 1H), 8.82 (d, 1H, J=1.2 Hz), 8.72 (d, 1H, J=1.2 Hz), 8.48 (s, 1H), 7.65-7.75 (m, 3H), 2.22 (s, 3H). LC-MS (2) Rt=1.96 min; m/z (ESI+) 305 (M+H).

The following compound was prepared using methods analogous to those described in Synthesis 17-1, using the appropriately substituted 5-(8-aminoisoquinolin-3-ylamino)pyrazine-2-carbonitrile prepared using methods analogous to those described in Synthesis 16-1.

| Synthesis | 17-002 |
|---|---|
| Compound | AA-064 |
| Structure | 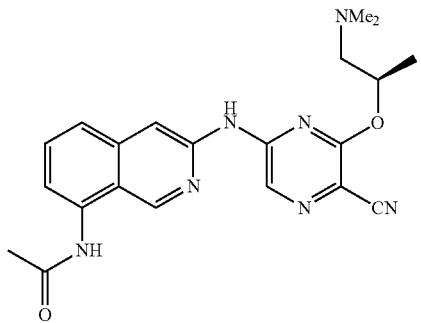 [SMILES: CC(=O)Nc1cccc2cc(Nc3cnc(C#N)c(O[C@H](C)CN(C)C)n3)ncc12] |
| NMR | $^1$H NMR (d$_6$-DMSO, 400 MHz) δ 10.2 (s, 1H), 9.37 (s, 1H), 8.43 (s, (1H), 8.24 (s, 1H), 7.69-7.75 (m, 2H), 7.62 (d, 1H, J = 8.5 Hz), 5.45-5.55 (m, 1H), 2.64-2.69 (m, 1H), 2.55-2.60 (m, 1H), 2.22 (s, 6H), 1.47 (d, 3H, J = 6.3 Hz). |
| LCMS | LC-MS (2) Rt = 2.22 min; m/z (ESI+) 406 (M + H). |

Synthesis 18-1

N-(3-(5-Cyanopyrazin-2-ylamino)isoquinolin-8-yl)-3-methoxypropanamide (AA-063)

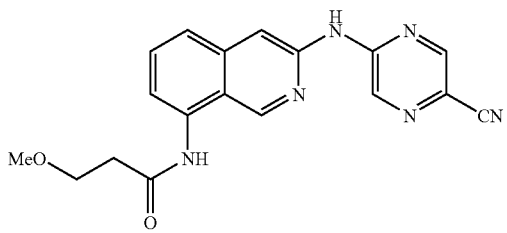 [SMILES: COCCC(=O)Nc1cccc2cc(Nc3cnc(C#N)cn3)ncc12]

To a solution of 5-(8-aminoisoquinolin-3-ylamino)pyrazine-2-carbonitrile (36 mg, 0.14 mmol), 3-methoxypropionic acid (34 mg, 0.32 mmol), N-hydroxybenzotriazole hydrate (64 mg, 0.42 mmol) and diisopropylethylamine (78 mg, 0.60 mmol) in DMF (1 mL), was added 1-ethyl-3-(3-dimethylaminopropyl)carbodiimide hydrochloride (78 mg, 0.42 mmol). The reaction mixture was stirred at 40° C. for 48 hours and then concentrated to dryness. Preparative HPLC gave the title compound (5.7 mg, 0.016 mmol, 12%). $^1$H NMR (d$_6$-DMSO, 400 MHz) δ 11.05 (br s, 1H), 10.20 (s, 1H), 9.32 (s, 1H), 8.82 (d, 1H, J=1.2 Hz), 8.71 (d, 1H, J=1.2 Hz), 8.49 (s, 1H), 7.65-7.75 (m, 3H), 3.71 (t, 2H, J=6.1 Hz), 3.32 (s, 3H, obscured by water signal), 2.75 (t, 2H, J=6.1 Hz). LC-MS (2) Rt=2.10 min; m/z (ESI+) 349 (M+H).

Synthesis 19-1

3-(5-Cyanopyrazin-2-ylamino)-N-(2-morpholinoethyl)isoquinoline-8-carboxamide (AA-065)

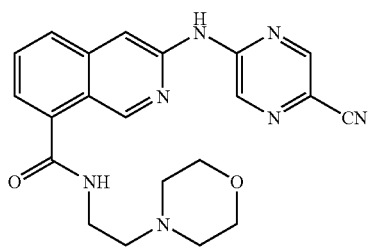 [SMILES: N#Cc1cnc(Nc2cc3cccc(C(=O)NCCN4CCOCC4)c3cn2)cn1]

A mixture of 5-(8-bromoisoquinolin-3-ylamino)pyrazine-2-carbonitrile (33 mg, 0.10 mmol), N-(2-aminoethyl)morpholine (26 mg, 0.20 mmol), triphenylphosphine (8 mg, 0.030 mmol), and sodium acetate (3.3 mg, 0.040 mmol) in DMF (1 mL) was degassed by bubbling N$_2$ through the solution for 5 mins. Palladium (II) acetate (6.8 mg, 0.030 mmol) was added and the mixture degassed for a further 5 minutes. Carbon monoxide was then bubbled through the solution for 5 minutes, before the reaction vessel was sealed. The solution was stirred at 80° C. under a balloon of carbon monoxide for 90 minutes and then partitioned between ethyl acetate and aqueous sodium hydrogen carbonate (2.5%). The phases were separated and the aqueous phase washed with ethyl acetate. The combined organic phases were washed with aqueous sodium hydrogen carbonate (2.5%) before being dried (Na$_2$SO$_4$) and then passed sequentially through two PS-Thiol cartridges and concentrated to dryness. Preparative HPLC gave the title compound (5.1 mg, 0.013 mmol, 12%). $^1$H NMR (d$_6$-DMSO, 400 MHz) δ 11.05 (s, 1H), 9.58 (s, 1H), 8.83 (d, 1H, J=1.2 Hz), 8.73 (d, 1H, J=1.2 Hz), 8.63 (br t, 1H, J=5.8 Hz), 8.56 (s, 1H), 8.00 (d, 1H, J=8.4 Hz), 7.75 (dd, 1H, J=7.1, 8.3 Hz), 7.57 (d, 1H, J=6.8 Hz), 3.62-3.68 (m, 4H), 3.46-3.52 (m, 2H), 2.52-2.58 (m, 2H), 2.46-2.52 (m, 4H, partially obscured by DMSO). LC-MS (2) Rt=1.95 min; m/z (ESI+) 404 (M+H).

The following compound was prepared using methods analogous to those described in Synthesis 19-1, using the appropriately substituted 5-(8-bromoisoquinolin-3-ylamino)pyrazine-2-carbonitrile prepared using methods analogous to those described in Synthesis 11.

| Synthesis | 19-2 |
|---|---|
| Compound | AA-066 |
| Structure | 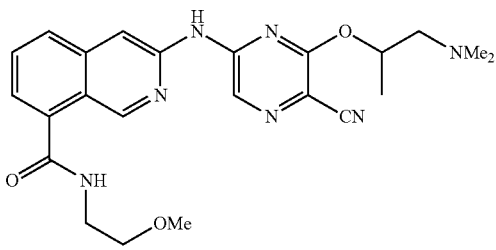 [SMILES: COCCNC(=O)c1cccc2cc(Nc3cnc(C#N)c(OC(C)CN(C)C)n3)ncc12] |
| NMR | $^1$H NMR (d$_6$-DMSO, 400 MHz) δ 9.45 (s, 1H), 8.75 (br t, 1H), 8.49 (s, 1H), 8.23 (s, 1H), 7.92 (d, 1H, J = 8.3 Hz), 7.76 (dd, 1H, J = 7.1, 8.3 Hz), 7.60 (d, 1H, J = 7.1 Hz), 5.49 (m, 1H), 3.50-3.60 (m, 4H), 2.62-2.70 (m, 1H), 2.52-2.58 (m, 1H), 2.21 (s, 6H), 1.47 (d, 3H, J = 6.3 Hz). |
| LCMS | LC-MS (2) Rt = 2.27 min; m/z (ESI+) 450 (M + H). |

Synthesis 20-1-A 2,2-Diethoxy-N-(2-fluorobenzyl)acetamide

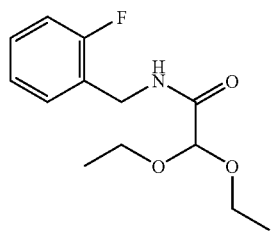 [SMILES: CCOC(OCC)C(=O)NCc1ccccc1F]

2-Fluorobenzylamine (2.00 g, 16.0 mmol), sodium 2,2-diethoxyacetate (3.26 g, 19.2 mmol), N-hydroxybenzotriazole hydrate (3.67 g, 24.0 mmol) and diisopropylethylamine (4.18 mL, 24.0 mmol) were stirred in DMF (20 mL) at room temperature. 1-Ethyl-3-(3-dimethylaminopropyl)carbodiimide hydrochloride (4.6 g, 24.0 mmol) was added and the reaction mixture was allowed to stir at room temperature overnight. The reaction mixture was diluted water and ethyl acetate. The organic phase was washed sequentially with HCl (aq) (1 M), saturated sodium bicarbonate, water and brine, dried over sodium sulfate and concentrated to dryness. The crude material was used directly in the following reaction.

Synthesis 20-1-B

8-Fluoroisoquinolin-3-ol

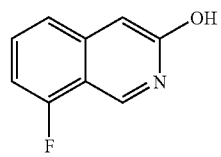

2,2-Diethoxy-N-(2-fluorobenzyl)acetamide (4.1 g, 16.0 mmol) was stirred in concentrated sulfuric acid (10 mL) for 16 hours. The reaction mixture was poured onto ice and neutralized by the addition of ammonium hydroxide forming a precipitate which was removed by filtration. The filtrate was extracted with ethyl acetate three times, and the combined organic phases were rinsed with brine then dried (Na$_2$SO$_4$) and concentrated to dryness affording an oily solid. Trituration with ether afforded the title compound (1.56 g, 9.6 mmol, 60% over 2 steps). LC-MS (3) Rt=1.00 min; m/z (ESI+) 164 (M+H).

Synthesis 20-1-C

8-Methoxyisoquinolin-3-ol

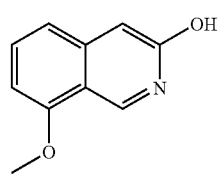

8-Fluoroisoquinolin-3-ol (561 mg, 3.43 mmol) was dissolved in DMF (3 mL) and sodium methoxide (828 mg, 15.33 mmol) added. The reaction mixture was heated at 90° C. for 14 hours, then diluted with methanol and absorbed onto an SPE (TsOH) cartridge. The column was rinsed with methanol and the compound was then eluted with 7 M ammonia in methanol to afford the title compound (140 mg, 0.798 mmol, 23.2%). LC-MS (2) Rt=1.23 min; m/z (ESI+) 176 (M+H).

Synthesis 20-1-D

8-Methoxyisoquinolin-3-yl trifluoromethanesulfonate

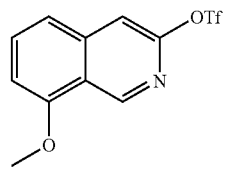

8-Methoxyisoquinolin-3-ol (140 mg, 0.798 mmol) was dissolved in DCM (5 mL) and N,N-diisopropylethylamine (309 mg, 2.394 mmol) and cooled to 0° C. Triflic anhydride (293 mg, 1.037 mmol) was added dropwise and the reaction was warmed to room temperature and stirred for an additional 16 hours. The reaction mixture was quenched with saturated aqueous ammonium chloride and extracted into DCM. The aqueous layer was re-extracted with DCM and the combined organic phases washed with brine, dried (Na₂SO₄) and concentrated to dryness. The product was purified by flash chromatography to afford the title compound (26.6 mg, 0.087 mmol, 11%). LC-MS (3) Rt=2.23 min; m/z (ESI+) 308 (M+H).

Synthesis 20-1-E (R)-3-(1-(Dimethylamino)propan-2-yloxy)-5-(8-methoxyisoquinolin-3-ylamino)pyrazine-2-carbonitrile (AA-067)

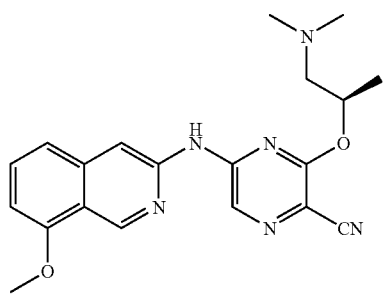 [SMILES: COc1cccc2cc(Nc3cnc(C#N)c(O[C@H](C)CN(C)C)n3)ncc12]

A mixture of tris(dibenzylideneacetone)dipalladium (0) (7.9 mg, 0.009 mmol) and 9,9-dimethyl-4,5-bis(diphenylphosphino)xanthene (10 mg, 0.017 mmol) in toluene (1 mL) and DMF (1 mL) was degassed under a stream of nitrogen gas with stirring for 15 minutes. 8-Methoxyisoquinolin-3-yl trifluoromethanesulfonate (26.6 mg, 0.087 mmol), cesium carbonate (28 mg, 0.087 mmol) and (R)-5-amino-3-(1-(dimethylamino)propan-2-yloxy)pyrazine-2-carbonitrile (19 mg, 0.087 mmol) were added and the mixture degassed for a further 5 minutes. The mixture was heated at 130° C. for 30 minutes in a microwave reactor and then partitioned between ethyl acetate and aqueous sodium hydrogen carbonate (2.5%). The aqueous phase was extracted with ethyl acetate and the combined organic phases were washed with aqueous sodium hydrogen carbonate (2.5%) and brine, then dried (Na₂SO₄) and passed sequentially through 2 PS-Thiol cartridges and concentrated to dryness. Preparative HPLC afforded the title compound (0.62 mg, 0.00016 mmol, 2%). ¹H NMR (d₆-DMSO, 400 MHz) δ 9.34 (s, 1H), 8.40 (s, 1H), 8.23 (s, 1H), 7.69-7.65 (m, 1H), 7.37 (d, 1H, J=8.3 Hz), 6.99 (d, 1H, J=7.6 Hz), 5.53-5.47 (m, 1H), 4.02 (s, 3H), 2.68-2.63 (m, 1H), 2.57-2.53 (m, 1H), 2.21 (s, 6H), 1.46 (d, 3H, J=6.3 Hz). LC-MS (2) Rt=3.18 min; m/z (ESI+) 379 (M+H).

Synthesis 21-1-A

Ethyl 2-(3-cyano-6-(isoquinolin-3-ylamino)pyrazin-2-yloxy)acetate (AA-068)

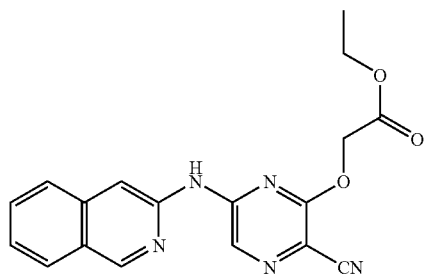 [SMILES: CCOC(=O)COc1nc(Nc2cc3ccccc3cn2)cnc1C#N]

A mixture of tris(dibenzylideneacetone)dipalladium (0) (39 mg, 0.043 mmol) and 9,9-dimethyl-4,5-bis(diphenylphosphino)xanthene (50 mg, 0.086 mmol) in toluene (1.5 mL) and DMF (1.5 mL) was degassed under a stream of nitrogen gas with stirring for 15 minutes. 3-Chloroisoquinoline (70 mg, 0.428 mmol), caesium carbonate (279 mg, 0.856 mmol) and ethyl 2-(6-amino-3-cyanopyrazin-2-yloxy)acetate (105 mg, 0.471 mmol) were added and the mixture was degassed for a further 5 minutes. The mixture was then heated at 100° C. for 20 minutes, then at 130° C. for 20 minutes in a microwave reactor. The reaction mixture was partitioned between aqueous Na₂HCO₃ solution (2.5%) and ethyl acetate. The aqueous phase was re-extracted with ethyl acetate and the combined organic layers were washed with brine, dried (Na₂SO₄), passed sequentially through two PS-Thiol cartridges and concentrated to dryness. The residue was triturated with methanol and then ether affording ethyl 2-(3-cyano-6-(isoquinolin-3-ylamino)pyrazin-2-yloxy)acetate (37 mg, 0.107 mmol, 25%). LC-MS (2) Rt 2.89 min; m/z (ESI+) 350 (M+H).

Synthesis 21-1-B 2-(3-Cyano-6-(isoquinolin-3-ylamino)pyrazin-2-yloxy)acetic acid (AA-069)

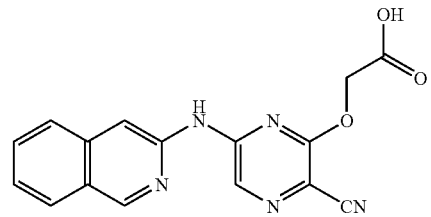 [SMILES: N#Cc1ncc(Nc2cc3ccccc3cn2)nc1OCC(=O)O]

Ethyl 2-(3-cyano-6-(isoquinolin-3-ylamino)pyrazin-2-yloxy)acetate (35 mg, 0.099 mmol) was dissolved in THF (1 mL) and lithium hydroxide (2.4 mg, 0.099 mmol) added. The reaction was stirred at room temperature for 15 hours. Methanol (1 mL) was added and the reaction mixture was stirred for a further 24 hours and then concentrated to dryness. Purification by preparative HPLC afforded the title compound (10.8 mg, 0.0336 mmol, 34%). ¹H NMR (MeOD, 400 MHz) δ 9.04 (s, 1H), 8.53 (s, 1H), 8.14-8.10 (m, 2H), 7.97 (d, 1H, J=8.0 Hz), 7.72-7.67 (m, 1H), 7.53-7.48 (m, 1H), 4.96 (br s, 2H), 2.67 (s, 1H). LC-MS (2) Rt=1.46 min; No ionization.

Synthesis 22-1

(R)-2-(6-(8-Chloroisoquinolin-3-ylamino)-3-cyanopyrazin-2-yloxy)-N,N-dimethylpropan-1-amine oxide (AA-071)

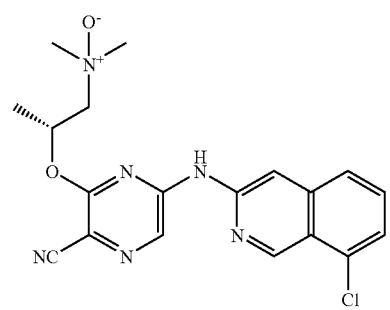

(R)-5-(8-Chloroisoquinolin-3-ylamino)-3-(1-(dimethylamino)propan-2-yloxy)pyrazine-2-carbonitrile (30 mg, 0.078 mmol) was dissolved in DCM (1 mL) and cooled to −10° C. 3-Chloroperoxybenzoic acid (77% wt., 12 mg, 0.086 mmol) dissolved in DCM (1 mL) was added dropwise to the solution. The reaction mixture was stirred at −10° C. for 15 minutes, and was then warmed to room temperature. The reaction mixture was diluted with water, the layers partitioned and the aqueous phase extracted with DCM. The combined organic phases were washed with brine, dried (Na$_2$SO$_4$) and concentrated to dryness. The residue was dissolved in methanol and absorbed on to an SPE (TsOH) cartridge. The cartridge was washed with methanol and the compound eluted with 2 M and 7 M ammonia in methanol. Preparative HPLC afforded the title compound (23 mg, 0.057 mmol, 73%). $^1$H NMR (d$_6$-DMSO, 400 MHz) δ 9.25 (s, 1H), 8.39 (s, 1H), 8.30 (s, 1H), 8.12 (s, 1H), 7.73-7.71 (m, 1H), 7.57-7.56 (m, 1H), 6.10-6.07 (m, 1H), 4.16-4.10 (m, 1H), 3.77 (br d, 1H, J=14 Hz), 3.43 (s, 3H), 3.28 (s, 3H), 1.44 (d, 3H, J=6.6 Hz). LC-MS (2) Rt=2.20 min; m/z (ESI+) 399 & 401 (M+H).

Synthesis 23-1-A tert-Butyl 5-chloro-1H-pyrrolo[2,3-c]pyridine-1-carboxylate

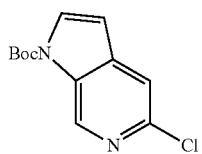

Triethylamine (0.147 mL, 1.05 mmol) was added to a solution of 5-chloro-1H-pyrrolo[2,3-c]pyridine (0.100 g, 0.655 mmol) and di-tert-butyl dicarbonate (0.215 g, 0.983 mmol) in dichloromethane (3 mL) and the mixture was stirred at room temperature for 16 hours. The solution was washed with aqueous 0.2 M HCl and the aqueous layer was extracted with dichloromethane. The combined organic layers were dried (Na$_2$SO$_4$) and concentrated. Purification by column chromatography gave tert-butyl 5-chloro-1H-pyrrolo[2,3-c]pyridine-1-carboxylate (0.164 g, 0.649 mmol, 99%). LC-MS (3) Rt=2.70 min; m/z (ESI+) 197 & 199 ((M+H-$^t$Bu)+H).

Synthesis 23-1-B 5-(1H-Pyrrolo[2,3-c]pyridin-5-ylamino)pyrazine-2-carbonitrile (CC-001)

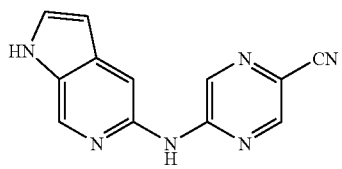 [SMILES: N#Cc1cnc(Nc2cc3cc[nH]c3cn2)cn1]

A mixture of tert-butyl 5-chloro-1H-pyrrolo[2,3-c]pyridine-1-carboxylate (0.030 g, 0.119 mmol), 5-aminopyrazine-2-carbonitrile (0.017 g, 0.142 mmol), cesium carbonate (0.077 g, 0.237 mmol), Xantphos (0.011 g, 0.019 mmol) and tris(benzylideneacetone)dipalladium (0) (0.009 g, 0.010 mmol) in dioxane (0.8 mL) was degassed by bubbling argon through the mixture for 10 minutes. The sealed reaction vessel was heated to 150° C. for 1 hour in a microwave reactor. The crude mixture was filtered through an SCX-2 acidic resin cartridge, eluting with 2 M ammonia in methanol. The basic filtrate was concentrated and purified by column chromatography to give the title compound (0.018 g, 0.054 mmol, 45%). LC-MS (3) Rt=1.30 min; m/z (ESI+) 237 (M+H).

Biological Methods

Measurement of Inhibition of CHK1 Kinase Function

CHK1 kinase function was measured in a DELFIA® assay in order to monitor phosphorylation of a CDC25C peptide using a specific phospho antibody.

The enzyme reaction was carried out in polypropylene plates (Greiner) using a reaction mix (25 μL) containing enzyme and peptide mix (CHK1, 1 nM; Biotin-KKKVSRS-GLYRSPSMPENLNRPR, 1 μM or 15 μL), ATP (30 μM or 5 μL) and either DMSO (2.5%) or test compound (5 μL) diluted to a give a range of concentrations (from 0 to 100 μM in 2.5% DMSO, final concentrations) in assay buffer (40 mM Tris, 40 mM NaCl, 2 mM MgCl$_2$, 1 mM DTT and 0.1% Tween 20). The reaction mixture was incubated for 30 minutes at room temperature and then stopped by the addition of buffer (125 μL) containing 40 mM EDTA, 0.05% Tween 20, 0.1% BSA in TBS (10× concentrate, Sigma). An aliquot (100 μL) of the stopped reaction mixture was transferred to a black neutravidin-coated plate (Perbio) and incubated for 1 hour on a shaker (Titertek, Flow Laboratories) at room temperature. The plates were washed four times with wash buffer (25 mM Tris (pH 8), 150 mM NaCl, and 0.1% Tween 20) (WellWash4, Thermo Life Sciences) and incubated for 1 hour as before with an antibody mixture (100 μL) consisting of anti-phospho CDC25C (1.25 nM, #9528, Cell Signalling Technology) and europium-labelled anti-rabbit IgG (0.3 μg/mL, AD0105, PerkinElmer Life Sciences) diluted in DELFIA assay buffer (PerkinElmer Life Sciences). The plates were washed a further four times with wash buffer before the addition of enhancement solution (100 μL/well, PerkinElmer Life Sciences). The plate was read on a Victor$^2$ 1420 multilabel counter (Perkin Elmer Life Sciences) using a time-resolved measurement mode reading fluorescence at 615 nm.

Cytotoxicity Assay

HT29 colon carcinoma cells were obtained from ATCC (Rockville, Md., USA). Cells were grown in DMEM supplemented with 10% foetal calf serum and containing L-glutamine 5 mM, glucose, penicillin, and streptomycin. Cells were grown at 37° C. in a dry 5% CO$_2$ atmosphere. Cytotoxicity assays were carried out in 96-well plates using quadruplicate wells for each dose. Cells were seeded at 1.6× 10$^3$ per well in 160 μL medium and were allowed to attach for 36 hours prior to treatment. Test compounds were dissolved in DMSO at 10 mM and serially diluted in culture medium to 5× final concentration prior to addition in a volume of 40 μl per well. Cells were left for 4 doublings (96 hours) in the presence of the test compounds and then fixed in 10% TCA for 30 minutes, washed in water, and dried. The fixed cells were stained with Sulfurhodamine B (SRB, 0.4% in 1% acetic acid, Sigma, Dorset, UK) for 30 minutes, washed in 1% acetic acid, and dried. SRB was resolubilised in 10 mM Tris base and the OD was measured at 490 nm. Results were expressed relative to untreated controls and the concentration of compound required to inhibit growth by 50% (SRB IC$_{50}$) was calculated.

Mitosis Inhibition Assay (MIA)

Checkpoint abrogation by CHK1 kinase function inhibitors in combination with genotoxic agents was assessed using a europium based ELISA assay designed to quantify the number of cells trapped in mitosis after treatment with a genotoxic agent (to induce G2 arrest) followed by a test compound in combination with nocodazole to abrogate this arrest.

HT29 cells were seeded at $10^4$ cells per well into 96 well plates in a volume of 160 μL and left to attach for 36 hours. Etoposide (10 mM stock in DMSO) was diluted in medium to 250 μM and then 40 μL was added to appropriate wells to give a final concentration of 50 μM and incubated for 1 hour. This treatment had previously been optimised to induce a G2 arrest in 80% of cells 16 hours following treatment. After genotoxic drug exposure, the medium was removed and replaced with fresh medium (160 μL). Cells were either untreated (untreated control or etoposide pre-treatment alone), exposed to nocodazole following etoposide pre-treatment or nocodazole alone (100 ng/mL final concentration), or exposed to increasing concentrations of test compound (200 μM-0.01 nM final concentration) in combination with nocodazole (100 ng/mL final concentration). Test compounds were added in 40 μL using quadruplicate wells for each dose. After 21 hours exposure, the medium was removed and cells were fixed in 4% formaldehyde in phosphate buffered saline (PBS, pH 7.4, pre-cooled to 4° C.) for 30 minutes at 4° C., followed by 100% methanol (pre-cooled to −20° C.) for 10 minutes at ambient temperature. Wells were washed with PBS and blocked with 5% dried milk (Marvel) in Tris-buffered saline (TBS, pH 7.4) at 37° C. for 30 minutes. Each well was washed three times with water containing 0.1% tween 20. Primary antibody (MPM-2, Upstate cat#05-368, 1 μg/mL in 5% milk in TBS) was added to each well and incubated overnight with shaking at 4° C. Primary antibody was removed and wells were washed with water containing 0.1% Tween 20. The secondary antibody (europium labelled anti-mouse, Perkin-Elmer cat#AD0124, 333 ng/mL in assay buffer Perkin-Elmer cat#1244-111) was added to each well and incubated at 37° C. for 1 hour. Each well was washed with water 0.1% containing tween 20 and treated with enhancement solution (Perkin-Elmer cat#1244-105). Europium emissions were counted on a Wallac, Victor$^2$ counter (Perkin-Elmer, Bucks UK). Appropriate controls were included and results were expressed as the concentration of test compound required to allow 50% of cells to enter mitosis (MIA $IC_{50}$).

Biological Data

Biological data were obtained using the CHK1 kinase function inhibition assay described above for the following compounds: AA-001 through AA-072, BB-001 through BB-028, and CC-001.

For the CHK1 kinase function inhibition assay, the following compounds had $IC_{50}$ values of 1 μM or less: AA-001, AA-003, AA-004, AA-006, AA-007, AA-008, AA-009, AA-010, AA-013, AA-014, AA-015, AA-016, AA-020, AA-022, AA-023, AA-025, AA-026, BB-011, BB-014, BB-021, BB-024, BB-025, BB-026, BB-027, BB-028.

For the CHK1 kinase function inhibition assay, the following compounds had IC50 values of 1 μM or less: AA-001, AA-003, AA-004, AA-006, AA-007, AA-008, AA-009, AA-010, AA-013, AA-014, AA-015, AA-016, AA-020, M-022, AA-023, AA-025, AA-026, AA-027, AA-028, AA-029, AA-030, AA-031, AA-032, AA-033, AA-034, AA-035, AA-036, AA-037, AA-038, M-039, AA-040, AA-041, AA-042, AA-043, AA-044, AA-045, AA-048, AA-049, AA-050, AA-051, AA-052, AA-054, AA-055, M-056, AA-057, AA-058, AA-059, AA-060, AA-061, AA-062, AA-064, AA-067, AA-071, AA-072, BB-011, BB-014, BB-021, BB-024, BB-025, BB-026, BB-027, BB-028.

For the CHK1 kinase function inhibition assay, the following compounds had IC50 values of more than 1 μM and less than 10 μM: AA-002, AA-005, AA-011, AA-017, AA-018, AA-021, AA-024, BB-001, BB-006, BB-012, BB-013, BB-018, BB-019, BB-020, BB-022, BB-023.

For the CHK1 kinase function inhibition assay, the following compounds had IC50 values of more than 1 μM and less than 10 μM: AA-002, AA-005, AA-011, AA-017, AA-018, AA-019, AA-021, AA-024, AA-046, AA-047, M-053, AA-063, AA-066, AA-068, AA-069, AA-070, BB-001, BB-006, BB-012, BB-013, BB-018, BB-019, BB-020, BB-022, BB-023, CC-001.

For the CHK1 kinase function inhibition assay, all of the compounds had IC50 values of less than 100 μM.

One compound, compound AA-002, had an IC50 value of 1.8 μM.

One compound, compound BB-012, had an IC50 value of 1.9 μM.

One compound, compound CC-012, had 34% inhibition at 1 μM.

Biological data were obtained using the mitosis inhibition assay (MIA) described above.

For the mitosis inhibition assay (MIA), the following compounds had IC50 values of 10 μM or less: AA-001, AA-003, AA-004, AA-006, AA-007, AA-008, AA-010, AA-014, AA-020, AA-022, AA-023, AA-025, AA-026, AA-027, AA-029, AA-030, AA-031, AA-032, AA-033, AA-034, AA-035, AA-036, AA-037, AA-038, AA-039, AA-040, AA-041, AA-043, AA-044, AA-049, AA-050, AA-051, AA-052, AA-054, AA-055, AA-057, AA-058, AA-059, AA-060, AA-061, AA-066, AA-067, AA-071, AA-072.

One compound, compound AA-001, had an IC50 value of 0.16 μM.

One compound, compound BB-012, had an IC50 value of 33 μM.

Biological data were obtained using the cytotoxicity assay described above.

For the cytotoxicity assay, the following compounds had IC50 values of 10 μM or less: AA-001, AA-003, AA-006, AA-007, AA-008, AA-010, AA-014, AA-015, AA-020, AA-022, AA-023, AA-025, AA-026, AA-027, AA-031, AA-032, AA-033, AA-034, AA-037, AA-038, AA-039, AA-040, AA-041, AA-043, AA-044, AA-049, AA-050, AA-051, AA-052, AA-054, AA-055, AA-057, AA-058, AA-059, AA-060, AA-061, AA-067.

One compound, compound AA-001, had an IC50 value of 1.4 μM.

One compound, compound BB-012, had an IC50 value of 61 μM.

The foregoing has described the principles, preferred embodiments, and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of the present invention.

REFERENCES

A number of patents and publications are cited above in order to more fully describe and disclose the invention and the state of the art to which the invention pertains. Full citations for these references are provided below. Each of these references is incorporated herein by reference in its entirety into the present disclosure, to the same extent as if each individual reference was specifically and individually indicated to be incorporated by reference.

Balaint and Vousden, 2001, "Activation and activities of the p53 tumour suppressor protein," *Br. J. Cancer*, Vol. 85, pp. 1813-1823.

Bartek and Lukas, 2003, "Chk1 and Chk2 kinases in checkpoint control and cancer," *Cancer Cell*, Vol. 3, pp. 421-429.

Carson and Lois, 1995, "Cancer progression and p53," *Lancet*, Vol. 346, pp. 1009-1011.

Dixon and Norbury, 2002, "Therapeutic exploitation of checkpoint defects in cancer cells lacking p53 function," *Cell Cycle*, Vol. 1, pp. 362-368.

Durola et al., 2007, "A New Family of Biisoquinoline Chelates", *Eur. J. Org. Chem.*, Issue 1, pp. 125-135.

Greenblatt et al., 1994, "Mutations in the p53 tumor suppressor gene: clues to cancer etiology and molecular pathogenesis," *Cancer Res.*, Vol. 54, pp. 4855-4878.

Liu et al., 2000, "Chk1 is an essential kinase that is regulated by Atr and required for the G(2)/M DNA damage checkpoint," *Genes Dev.*, Vol. 14, pp. 1448-1459.

Plettenburg et al., 2007, "Isoquinoline Derivatives as Inhibitors of Rho-Kinase", international patent application publication number WO 2007/000240 A1, published 4 Jan. 2007.

Sanchez et al., 1997, "Conservation of the Chk1 checkpoint pathway in mammals: linkage of DNA damage to Cdk regulation through Cdc25," *Science*, Vol. 277, pp. 1497-1501. Sorensen at al., 2005, "Cell-cycle checkpoint kinase Chk1 is required for mammalian homologous recombination repair," *Nat. Cell Biol.*, Vol 7, pp. 195-201.

Tao and Lin, 2006, "Chk1 inhibitors for novel cancer treatment," *Anti-Cancer Agents in Medicinal Chemistry*, Vol. 6, pp. 377-388.

Wang et al., 1996, "UCN-01: a potent abrogator of G2 checkpoint function in cancer cells with disrupted p53," *J. Natl. Cancer Inst.*, Vol. 8, pp. 956-965.

Weinert and Hartwell, 1989, "Control of G2 delay by the rad9 gene of *Saccharomyces cerevisiae*," *J. Cell Sci. Suppl.*, Vol. 12, pp. 145-148.

White et al., 1967, "Gattermann reaction of 3,5-dimethoxyphenylacetonitrile. Synthesis of 6,8-dioxyisoquinolines" *J. Org. Chem.*, Vol. 32, pp. 2689-2692.

Xiao et al., 2006, "Differential roles of checkpoint kinase 1, checkpoint kinase 2, and mitogen-activated protein kinase-activated protein kinase 2 in mediating DNA damage-induced cell cycle arrest: implications for cancer therapy," *Mol. Cancer. Ther.*, Vol. 5, pp. 1935-1943.

Zachos et al., 2003, "Chk1-deficient tumour cells are viable but exhibit multiple checkpoint and survival defects," *EMBO J.*, Vol. 22, pp. 713-723.

Zhao et al., 2002, "Disruption of the checkpoint kinase 1/cell division cycle 25A pathway abrogates ionizing radiation-induced S and G2 checkpoints," *Proc. Natl. Acad. Sci. USA*, Vol. 99, pp. 14795-14800.

The invention claimed is:

1. A compound of the following formula, or a pharmaceutically acceptable salt thereof:

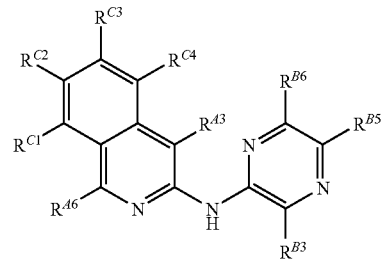

wherein:
each of $-R^{C1}$, $-R^{C2}$, $-R^{C3}$, and $-R^{C4}$ is independently $-H$ or $-Q^C$;
$-R^{A3}$ is $-H$;
$-R^{A6}$ is $-H$;
$-R^{B3}$ is $-H$;
$-R^{B5}$ is $-Q^{B5}$;
$-R^{B6}$ is $-O-R^{QB6}$;
$-Q^{B5}$ is $-CN$;
$-Q^{B6}$ is $-O-R^{QB6}$;
wherein:
$-R^{QB6}$ is independently:
$-R^{AA1}$,
$-L^{AA}-OH$, $-L^{AA}-OR^{AA1}$,
$-L^{AA}-NH_2$, $-L^{AA}-NHR^{AA1}$, $-L^{AA}-NR^{AA1}{}_2$, or $-L^{AA}-NR^{AA2}R^{AA3}$;
wherein:
each $-L^{AA}-$ is saturated aliphatic $C_{2-6}$alkylene;
each $-NR^{AA2}R^{AA3}$ is independently azetidino, pyrrolidino, imidazolidino, pyrazolidino, piperidino, piperazino, morpholino, azepino, diazepino, or oxazepino, and is optionally substituted with one or more groups selected from $C_{1-3}$alkyl, $-CF_3$, and $-F$;
each $-R^{AA1}$ is independently:
$-R^{AB1}$, $-R^{AB4}$, $-R^{AB6}$, $-R^{AB7}$, $-R^{AB8}$, $-L^{AB}-R^{AB4}$, $-L^{AB}-R^{AB6}$, $-L^{AB}-R^{AB7}$, or $-L^{AB}-R^{AB8}$;
each $-R^{AB1}$ is saturated aliphatic $C_{1-6}$alkyl;
each $-R^{AB4}$ is saturated $C_{3-6}$cycloalkyl;
each $-R^{AB6}$ is non-aromatic $C_{3-8}$heterocyclyl;
each $-R^{AB7}$ is phenyl;

---

SEQUENCE LISTING

<160> NUMBER OF SEQ ID NOS: 1

<210> SEQ ID NO 1
<211> LENGTH: 23
<212> TYPE: PRT
<213> ORGANISM: Artificial sequence
<220> FEATURE:
<223> OTHER INFORMATION: Synthetic peptide

<400> SEQUENCE: 1

Lys Lys Lys Val Ser Arg Ser Gly Leu Tyr Arg Ser Pro Ser Met Pro
1               5                   10                  15

Glu Asn Leu Asn Arg Pro Arg
            20 each —$R^{4B8}$ is $C_{5-6}$heteroaryl;
each -$L^{4B}$- is saturated aliphatic $C_{1-3}$alkylene;
wherein:
  each —$R^{4B4}$, —$R^{4B6}$, —$R^{4B7}$, and —$R^{4B8}$ is optionally substituted with one or more substituents —$R^{4C1}$ and/or one or more substituents —$R^{4C2}$;
  each —$R^{4B1}$ and -$L^{4B}$- is optionally substituted with one or more substituents —$R^{4C2}$;
wherein:
  each —$R^{4C1}$ is independently saturated aliphatic $C_{1-4}$alkyl, phenyl, or benzyl;
  each —$R^{4C2}$ is independently:
    —F, —Cl, —Br, —I,
    —$CF_3$, —$OCF_3$,
    —OH, -$L^{4D}$-OH, —O-$L^{4D}$-OH,
    —$OR^{4D1}$, -$L^{4D}$-$OR^{4D1}$, —O-$L^{4D}$-$OR^{4D1}$,
    —SH, —$SR^{4D1}$,
    —CN,
    —$NO_2$,
    —$NH_2$, —$NHR^{4D1}$, —$NR^{4D1}{}_2$, —$NR^{4D2}R^{4D3}$,
    -$L^{4D}$-$NH_2$, -$L^{4D}$-$NHR^{4D1}$, -$L^{4D}$-$NR^{4D1}{}_2$, -$L^{4D}$-$NR^{4D2}R^{4D3}$;
    —C(=O)OH, —C(=O)$OR^{4D1}$,
    —C(=O)$NH_2$, —C(=O)$NHR^{4D1}$, —C(=O)$NR^{4D1}{}_2$, or —C(=O)$NR^{4D2}R^{4D3}$;
wherein:
  each —$R^{4D1}$ is independently saturated aliphatic $C_{1-4}$alkyl, phenyl, or benzyl;
  each -$L^{4D}$- is saturated aliphatic $C_{1-5}$alkylene; and
  each —$NR^{4D2}R^{4D3}$ is independently pyrrolidino, piperidino, piperazino, or morpholino, and is optionally substituted with one or more groups selected from $C_{1-3}$alkyl, —$CF_3$, and —F;
and wherein:
each -$Q^C$ is independently selected from:
  —$R^{2A1}$, —F, —Cl, —Br, —I, —$CF_3$, —$OCF_3$,
  —OH, -$L^{2A}$-OH, —O-$L^{2A}$-OH, —NH-$L^{2A}$-OH,
  —$OR^{2A1}$, $L^{2A}$-OH, —O-$L^{2A}$-OH, —NH-$L^{2A}$-OH,
  —$NH_2$, —$NHR^{2A}$, —$NR^{2A1}{}_3$, —$NR^{2A2}R^{2A3}$,
  —$NH_2$, —$NHR^{2A1}$, $NR^{2A1}{}_2$, -$L^{2A}$-$NR^{2A1}{}_2$, -$L^{2A}$-$NR^{2A2}R^{2A3}$,
  -$L^{2A}$-$NH_2$, -$L^{2A}$-$NHR^{2A1}$, -$L^{2A}$-$NR^{2A1}{}_2$, -$L^{2A}$-$NR^{2A2}R^{2A3}$,
  —O-$L^{2A}$-$NH_2$, —O-$L^{2A}$-$NHR^{2A1}$, —O-$L^{2A}$-$NR^{2A1}{}_2$, —O-$L^{2A}$-$NR^{2A2}R^{2A3}$,
  —NH-$L^{2A}$-$NH_2$, —NH-$L^{2A}$-$NHR^{2A1}$, —NH-$L^{2A}$-$NR^{2A1}{}_2$, —NH-$L^{2A}$-$NR^{2A2}R^{2A3}$,
  —C(=O)$NH_2$, —C(=O)$NHR^{2A1}$, —C(=O)$NR^{2A1}{}_2$, —C(=O)$NR^{2A2}R^{2A3}$,
  —C(=O)NH-$L^{2A}$-OH, —C(=O)NH-$L^{2A}$-$OR^{2A1}$,
  —C(=O)NH-$L^{2A}$-$NH_2$, —C(=O)NH-$L^{2A}$-$NHR^{2A1}$,
  —C(=O)NH-$L^{2A}$-$NR^{2A1}{}_2$, —C(=O)NH-$L^{2A}$-$NR^{2A2}R^{2A3}$,
  —NHC(=O)$R^{2A1}$, —$NR^{2A1}$C(=O)$R^{2A1}$,
  —NHC(=O)-$L^{2A}$-OH, —NHC(=O)-$L^{2A}$-$OR^{2A1}$,
  —NHC(=O)-$L^{2A}$-$NH_2$, —NHC(=O)-$L^{2A}$-$NHR^{2A1}$,
  —NHC(=O)-$L^{2A}$-$NR^{2A1}{}_2$, and —NHC(=O)-$L^{2A}$-$NR^{2A2}R^{2A3}$;
wherein:
  each -$L^{2A}$- is saturated aliphatic $C_{1-5}$alkylene;
  each —$NR^{2A2}R^{2A3}$ is independently pyrrolidino, piperidino, piperazino, or morpholino, and is optionally substituted with one or more groups selected from $C_{1-3}$alkyl, —$CF_3$, and —F;
  each —$R^{2A1}$ is independently —$R^{2B1}$, —$R^{2B7}$, or -$L^{2B}$-$R^{2B7}$;
  each —$R^{2B1}$ is saturated aliphatic $C_{1-6}$alkyl;

each —$R^{2B7}$ is phenyl;
each -$L^{2B}$- is saturated aliphatic $C_{1-3}$alkylene;
wherein:
  each —$R^{2B7}$ is optionally substituted with one or more substituents —$R^{2C1}$ and/or one or more substituents —$R^{2C2}$;
  each —$R^{2B1}$ and -$L^{2B}$- is optionally substituted with one or more substituents —$R^{2C2}$;
wherein:
  each —$R^{2C1}$ is independently saturated aliphatic $C_{1-4}$alkyl, phenyl, or benzyl;
  each —$R^{2C2}$ is independently:
    —F, —Cl, —Br, —I,
    —$CF_3$, —$OCF_3$,
    —OH, -$L^{2D}$-OH, —O-$L^{2D}$-OH,
    —$OR^{2D1}$, -$L^{2D}$-$OR^{2D1}$, —O-$L^{2D}$-$OR^{2D1}$,
    —SH, —$SR^{2D1}$,
    —CN,
    —$NO_2$,
    —$NH_2$, —$NHR^{2D1}$, —$NR^{2D1}{}_2$, —$NR^{2D2}R^{2D3}$,
    -$L^{2D}$-$NH_2$, -$L^{2D}$-$NHR^{2D1}$, -$L^{2D}$-$NR^{2D1}{}_2$, -$L^{2D}$-$NR^{2D2}R^{2D3}$,
    —C(=O)OH, —C(=O)$OR^{2D1}$,
    —C(=O)$NH_2$, —C(=O)$NHR^{2D1}$, —C(=O)$NR^{2D1}{}_2$, or —C(=O)$NR^{2D2}R^{2D3}$;
wherein:
  each —$R^{2D1}$ is independently saturated aliphatic $C_{1-4}$alkyl, phenyl, or benzyl;
  each -$L^{2D}$- is saturated aliphatic $C_{1-5}$alkylene; and
  each —$NR^{2D2}R^{2D3}$ is independently pyrrolidino, piperidino, piperazino, or morpholino, and is optionally substituted with one or more groups selected from $C_{1-3}$alkyl, —$CF_3$, and —F.

2. A compound according to claim 1, wherein —$R^{C1}$ is -$Q^C$; and each of —$R^{C2}$, —$R^{C3}$, and —$R^{C4}$ is —H.

3. A compound according to claim 2, wherein —$R^{QB6}$ is independently -$L^{4A}$-$NH_2$, -$L^{4A}$-$NHR^{4A1}$, -$L^{4A}$-$NR^{4A1}{}_2$, or -$L^{4A}$-$NR^{4A2}R^{4A3}$.

4. A compound according to claim 2, wherein —$R^{QB6}$ is —$R^{4A1}$.

5. A compound according to claim 3, wherein each —$NR^{4A2}R^{4A3}$, if present, is independently pyrrolidino, piperidino, piperazino, or, morpholino, and is optionally substituted with one or more groups selected from $C_{1-3}$alkyl, —$CF_3$, and —F.

6. A compound according to claim 4, wherein —$R^{4A1}$ is independently —$R^{4B6}$ or -$L^{4B}$-$R^{4B6}$.

7. A compound according to claim 6, wherein each —$R^{4B6}$ is independently pyrrolidinyl, piperidinyl, piperazinyl, morpholinyl, tetrahydrofuranyl, tetrahydropyranyl, oxazepanyl, 8-aza-bicyclo[3.2.1]octanyl, or quinuclidinyl, and is optionally substituted with one or more substituents —$R^{4C1}$ and/or one or more substituents —$R^{4C2}$.

8. A compound according to claim 2, wherein each -$Q^C$ is independently selected from:
  —$R^{2A1}$, —F, —Cl, —Br, —I, —$CF_3$, —$OCF_3$,
  —OH, -$L^{2A}$-OH, —O-$L^{2A}$-OH, —NH-$L^{2A}$-OH,
  —$OR^{2A1}$, -$L^{2A}$-$OR^{2A1}$, —O-$L^{2A}$-$OR^{2A1}$, —NH-$L^{2A}$-$OR^{2A1}$,
  —$NH_2$, —$NHR^{2A1}$, —$NR^{2A1}{}_2$, —$NR^{2A2}R^{2A3}$
  -$L^{2A}$-$NH_2$, -$L^{2A}$-$NHR^{2A1}$, -$L^{2A}$-$NR^{2A1}{}_2$, -$L^{2A}$-$NR^{2A2}R^{2A3}$,
  —O-$L^{2A}$-$NH_2$, —O-$L^{2A}$-$NHR^{2A1}$, —O-$L^{2A}$-$NR^{2A1}{}_2$,
  —O-$L^{2A}$-$NR^{2A2}R^{2A3}$,
  —NH-$L^{2A}$-$NH_2$, —NH-$L^{2A}$-$NHR^{2A1}$, —NH-$L^{2A}$-$NR^{2A1}{}_2$, and —NH-$L^{2A}$-$NR^{2A2}R^{2A3}$.

9. A compound according to claim 2, wherein each -$Q^C$ is independently selected from:

—$R^{2A1}$, —F, —Cl, —Br, —I, —$CF_3$, —$OCF_3$, —NH-$L^{2A}$-OH, —NH-$L^{2A}$-$OR^{2A1}$, —NH-$L^{2A}$-$NH_2$, —NH-$L^{2A}$-$NHR^{2A1}$, —NH-$L^{2A}$-$NR^{2A1}{}_2$, and —NH-$L^{2A}$-$NR^{2A2}R^{2A3}$.

10. A compound according to claim 3, wherein each -$Q^C$ is independently selected from:

—$R^{2A1}$, —F, —Cl, —Br, —I, —$CF_3$, —$OCF_3$, —NH-$L^{2A}$-OH, —NH-$L^{2A}$-$OR^{2A1}$, —NH-$L^{2A}$-$NH_2$, —NH-$L^{2A}$-$NHR^{2A1}$, —NH-$L^{2A}$-$NR^{2A1}{}_2$, and —NH-$L^{2A}$-$NR^{2A2}R^{2A3}$.

11. A compound according to claim 4, wherein each -$Q^C$ is independently selected from:

—$R^{2A1}$, —F, —Cl, —Br, —I, —$CF_3$, —$OCF_3$, —NH-$L^{2A}$-OH, —NH-$L^{2A}$-$OR^{2A1}$, —NH-$L^{2A}$-$NH_2$, —NH-$L^{2A}$-$NHR^{2A1}$, —NH-$L^{2A}$-$NR^{2A2}$, and —NH-$L^{2A}$-$NR^{2A2}R^{2A3}$.

12. A compound according to claim 5, wherein each -$Q^C$ is independently selected from:

—$R^{2A1}$, —F, —Cl, —Br, —I, —$CF_3$, —$OCF_3$, —NH-$L^{2A}$-OH, —NH-$L^{2A}$-$OR^{2A1}$, —NH-$L^{2A}$-$NH_2$, —NH-$L^{2A}$-$NHR^{2A1}$, —NH-$L^{2A}$-$NR^{2A1}{}_2$, and —NH-$L^{2A}$-$NR^{2A2}R^{2A3}$.

13. A compound according to claim 6, wherein each -$Q^C$ is independently selected from:

—$R^{2A1}$, —F, —Cl, —Br, —I, —$CF_3$, —$OCF_3$, —NH-$L^{2A}$-OH, —NH-$L^{2A}$-$OR^{2A1}$, —NH-$L^{2A}$-$NH_2$, —NH-$L^{2A}$-$NHR^{2A1}$, —NH-$L^{2A}$-$NR^{2A1}{}_2$, and —NH-$L^{2A}$-$NR^{2A2}R^{2A3}$.

14. A compound of the following formula, or a pharmaceutically acceptable salt thereof:

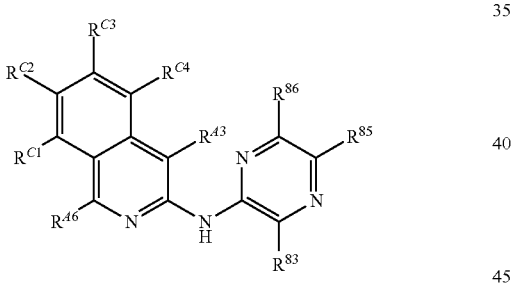

wherein:
—$R^{C1}$ is -$Q^C$;
each of —$R^{C2}$, —$R^{C3}$, and —$R^{C4}$ is —H;
—$R^{A3}$ is —H;
—$R^{A6}$ is —H;
—$R^{B3}$ is —H;
—$R^{B5}$ is -$Q^{B5}$;
—$R^{B6}$ is -$Q^{B6}$;
-$Q^{B5}$ is —CN;
-$Q^{B6}$ is —O—$R^{QB6}$;
and wherein —$R^{QB6}$ is independently selected from groups of the following formulae:

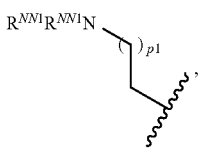
(B6-1)

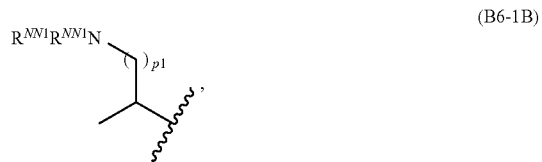
(B6-1B)

(B6-2)

(B6-3)

(B6-4)

(B6-5)

(B6-6)

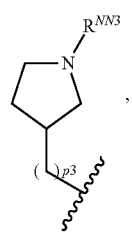
(B6-6)

-continued

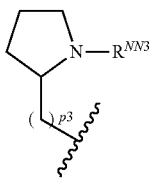
(B6-7)

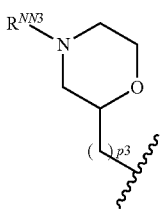
(B6-8)

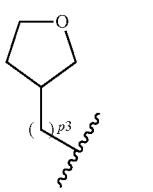
(B6-9)

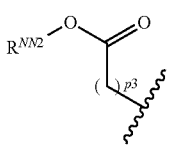
(B6-10)

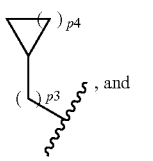
(B6-11)

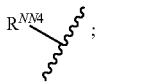
(B6-12)

wherein:
p1 is independently 1, 2, 3, or 4;
p2 is independently 1, 2, 3, or 4;
p3 is independently 0, 1, or 2;
p4 is independently 1, 2, 3, or 4;
either: each —$R^{NN1}$ is independently —H, saturated aliphatic $C_{1-4}$alkyl, phenyl, or benzyl;
or: the group —$NR^{NN1}R^{NN1}$ is independently azetidino, pyrrolidino, imidazolidino, pyrazolidino, piperidino, piperazino, morpholino, azepino, or diazepino, and is optionally substituted with one or more groups selected from $C_{1-3}$alkyl, —$CF_3$, and —F;
each —$R^{NN2}$ is independently —H or saturated aliphatic $C_{1-4}$alkyl;
each —$R^{NN3}$ is independently —H, saturated aliphatic $C_{1-4}$alkyl, phenyl, or benzyl; and
—$R^{NN4}$ is -saturated aliphatic $C_{1-6}$alkyl;
and wherein -$Q^C$ is independently selected from:
—$R^{2A1}$, —F, —Cl, —Br, —I, —$CF_3$, —$OCF_3$,
—OH, -$L^{2A}$-OH, —O-$L^{2A}$-OH, —NH-$L^{2A}$-OH,
—$OR^{2A1}$, $L^{2A}$-$OR^{2A1}$, —O-$L^{2A}$-$OR^{2A1}$, —NH-$L^{2A}$-$OR^{2A1}$,
—$NH_2$, —$NHR^{2A1}$; —$NR^{2A1}{}_2$, —$NR^{2A2}R^{2A3}$,
-$L^{2A}NH_2$, -$L^{2A}$-$NHR^{2A1}$, -$L^{2A}$-$NR^{2A1}{}_2$; -$L^{2A}$-$NR^{2A2}R^{2A3}$,
—O-$L^{2A}$-$NH_2$, —O-$L^{2A}$-$NHR^{2A1}$, —O-$L^{2A}$-$NR^{2A1}{}_2$, —O-$L^{2A}$-$NR^{2A2}R^{2A3}$,
—NH-$L^{2A}$-$NH_2$, —NH-$L^{2A}$-$NHR^{2A1}$, —NH-$L^{2A}$-$NR^{2A1}{}_2$, —NH-$L^{2A}$-$NR^{2A2}R^{2A3}$,
—C(=O)$NH_2$, —C(=O)$NHR^{2A1}$, —C(=O)$NR^{2A1}{}_2$, —C(=O)$NR^{2A2}R^{2A3}$,
—C(=O)NH-$L^{2A}$-OH, —C(=O)NH-$L^{2A}$-$OR^{2A1}$,
—C(=O)NH-$L^{2A}$-$NH_2$, —C(=O)NH-$L^{2A}$-$NHR^{2A1}$,
—C(=O)NH-$L^{2A}$-C(=O)NH-$L^{2A}$- $NR^{2A2}R^{2A3}$,
—NHC(=O)$R^{2A1}$, —$NR^{2A1}$C(=O)$R^{2A1}$,
—NHC(=O)-$L^{2A}$-OH, —NHC(=O)-$L^{2A}$-$OR^{2A1}$,
—NHC(=O)-$L^{2A}$-$NH_2$, —NHC(=O)-$L^{2A}$-$NHR^{2A1}$,
—NHC(=O)-$L^{2A}$-$NR^{2A1}{}_2$, and —NHC(=O)-$L^{2A}$-$NR^{2A2}R^{2A3}$;
wherein:
each -$L^{2A}$- is saturated aliphatic $C_{1-5}$alkylene;
each —$NR^{2A2}R^{2A3}$ is independently pyrrolidino, piperidino, piperazino, or morpholino, and is optionally substituted with one or more groups selected from $C_{1-3}$alkyl, —$CF_3$, and —F;
each —$R^{2A1}$ is independently —$R^{2B1}$, —$R^{2B7}$, or -$L^{2B}$-$R^{2B7}$;
each —$R^{2B1}$ is saturated aliphatic $C_{1-6}$alkyl;
each —$R^{2B7}$ is phenyl;
each -$L^{2B}$- is saturated aliphatic $C_{1-3}$alkylene;
wherein:
each —$R^{2B7}$ is optionally substituted with one or more substituents —$R^{2C1}$ and/or one or more substituents —$R^{2C2}$;
each —$R^{2B1}$ and -$L^{2B}$- is optionally substituted with one or more substituents —$R^{2C2}$;
wherein:
each —$R^{2C1}$ is independently saturated aliphatic $C_{1-4}$alkyl, phenyl, or benzyl;
each —$R^{2c2}$ is independently:
—F, —Cl, —Br, —I,
—$CF_3$, —$OCF_3$,
—OH, -$L^{2D}$-OH, —O-$L^{2D}$-OH,
—$OR^{2D1}$, $L^{2D}$-$OR^{2D1}$, —O-$L^{2D}$-$OR^{2D1}$,
—SH, —$SR^{2D1}$,
—CN,
—$NO_2$,
—$NH_2$, —$NHR^{2D1}$, —$NR^{2D1}{}_2$, —$NR^{2D2}R^{2D3}$,
-$L^{2D}$-$NH_2$, -$L^{2D}$-$NHR^{2D1}$, -$L^{2D}$-$NR^{2D1}{}_2$, -$L^{2D}$-$NR^{2D2}R^{2D3}$,
—C(=O)OH, —C(=O)$OR^{2D1}$,
—C(=O)$NH_2$, —C(=O)$NHR^{2D1}$, —C(=O)$NR^{2D1}{}_2$, or —C(=O)$NR^{2D2}R^{2D3}$;
wherein:
each —$R^{2D1}$ is independently saturated aliphatic $C_{1-4}$alkyl, phenyl, or benzyl;
each -$L^{2D}$- is saturated aliphatic $C_{1-5}$alkylene; and
each —$NR^{2D2}R^{2D3}$ is independently pyrrolidino, piperidino, piperazino, or morpholino, and is optionally substituted with one or more groups selected from $C_{1-3}$alkyl, —$CF_3$, and —F.

15. A compound according to claim 14, wherein:
—$R^{QB6}$ is a group of formula (B6-1B);
p1 is 1; and
each —$R^{NN1}$ is independently —H or saturated aliphatic $C_{1-4}$alkyl.

16. A compound of the following formula, or a pharmaceutically acceptable salt thereof:

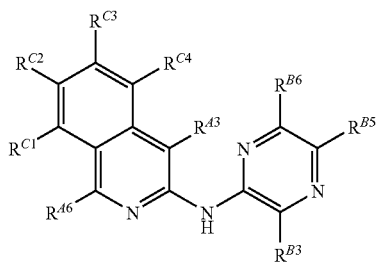

wherein:
—$R^{C1}$ is -$Q^C$;
each of —$R^{C2}$, —$R^{C3}$, and —$R^{C4}$ is —H;
—$R^{A3}$ is —H;
—$R^{A6}$ is —H;
—$R^{B3}$ is —H;
—$R^{B5}$ is -$Q^{B5}$;
—$R^{B6}$ is -$Q^{B6}$;
-$Q^{B5}$ is —CN;
-$Q^{B6}$ is —O—$R^{QB6}$;
—$R^{QB6}$ is:

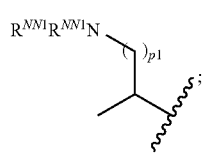
(B6-1B)

p1 is 1;
each —$R^{NN1}$ is independently —H or saturated aliphatic $C_{1-4}$alkyl;
-$Q^C$ is independently —$R^{X1}$, —F, —Cl, —Br, —I, —$CF_3$, —$OCF_3$, —OH, —$OR^{X1}$, —$NH_2$, —$NHR^{X1}$, —$NR^{X1}{}_2$, —$R^{M1}$, —NH—$(CH_2)_z$—OH, —NH—$(CH_2)_z$—$OR^{X1}$, —NH—$(CH_2)_z$—$NH_2$, —NH—$(CH_2)_z$—$NHR^{X1}$, —NH—$(CH_2)_z$—$NR^{X1}{}_2$, or —NH—$(CH_2)_z$—$R^{M1}$;
each z is independently 2 or 3;
each —$R^{X1}$ is saturated aliphatic $C_{1-4}$alkyl; and
each —$R^{M1}$ is independently piperidino, piperizino, or morpholino, and is optionally substituted with one or more saturated aliphatic $C_{1-4}$alkyl groups.

17. A compound according to claim 1, which is a compound selected from the following compounds, or a pharmaceutically acceptable salt thereof:

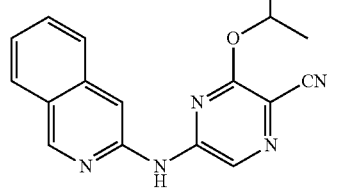
(AA-001)

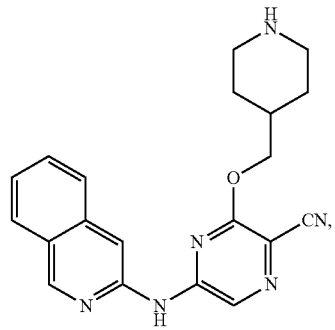
(AA-003)

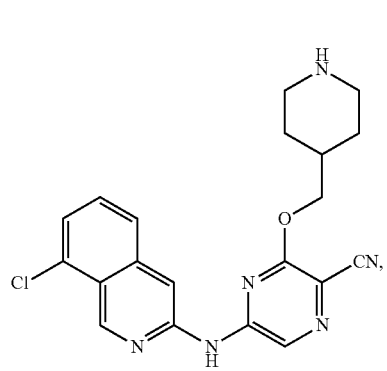
(AA-006)

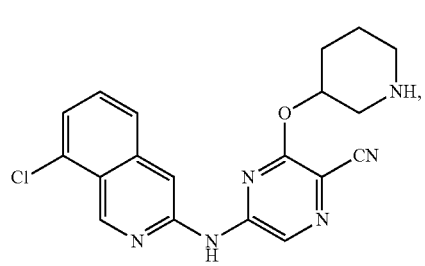
(AA-007)

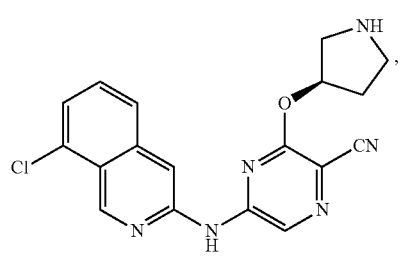
(AA-008)

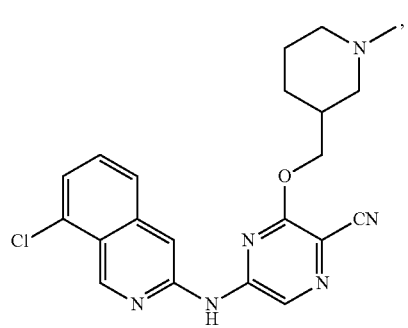
(AA-009)

-continued
(AA-010)
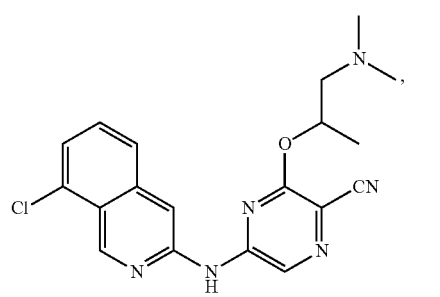
(AA-012)
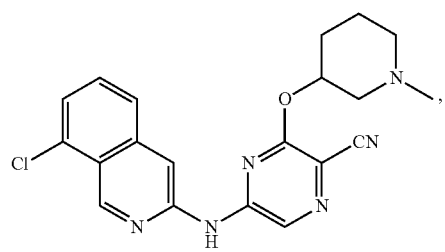
(AA-013)
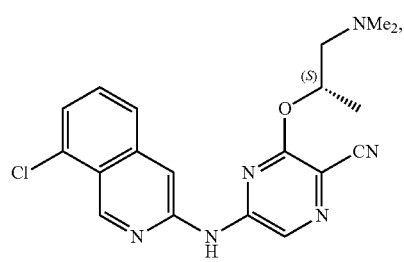
(AA-014)
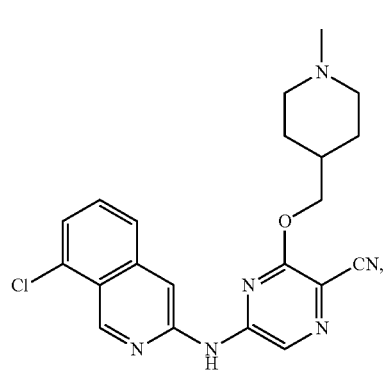
(AA-015)
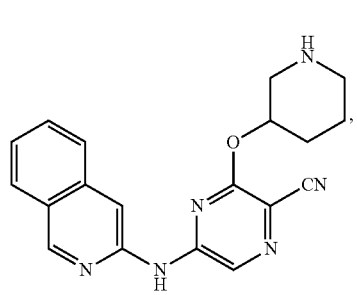
-continued
(AA-016)
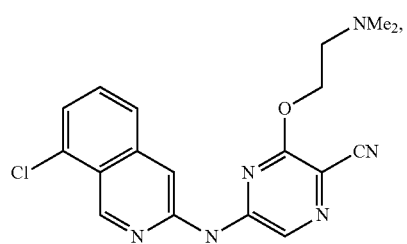
(AA-022)
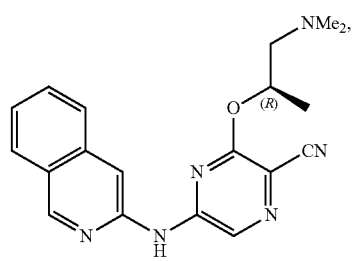
(AA-023)
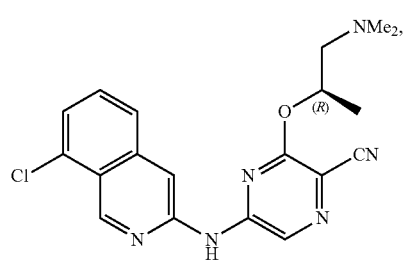
(AA-025)
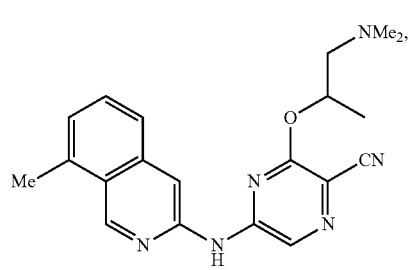
(AA-026)
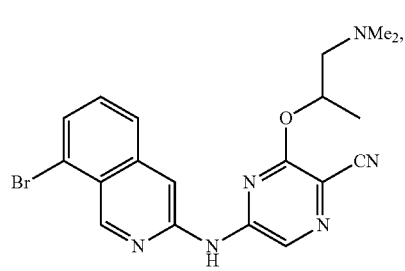
(AA-028)
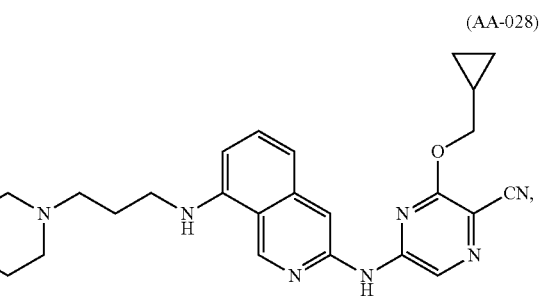

(AA-029)
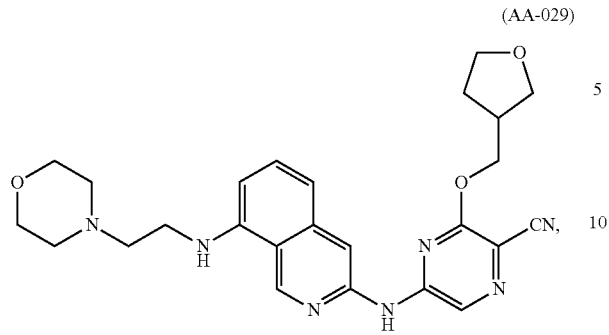
(AA-030)
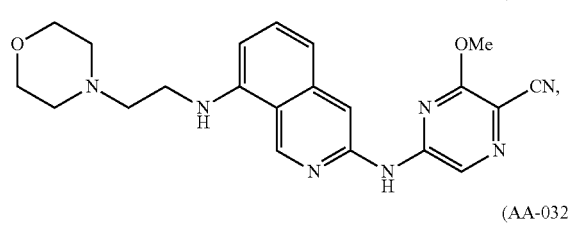
(AA-032)
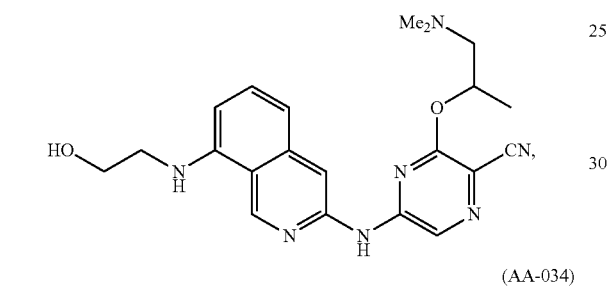
(AA-034)
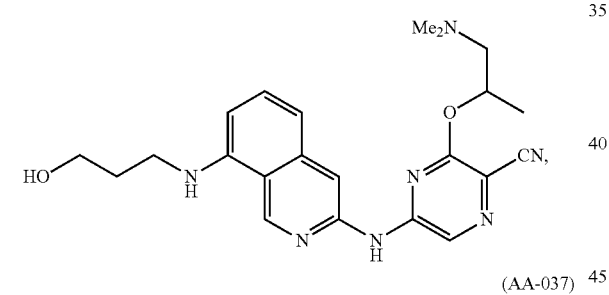
(AA-037)
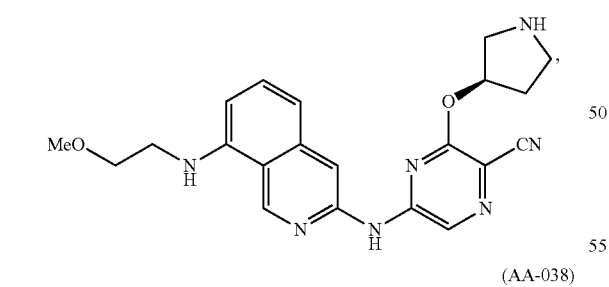
(AA-038)
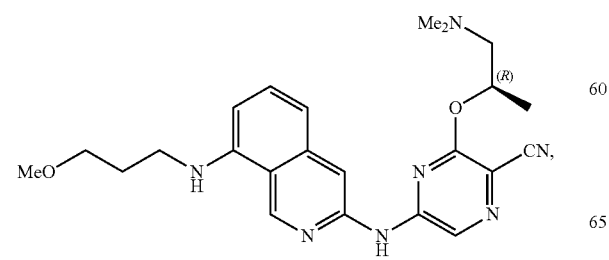
(AA-039)
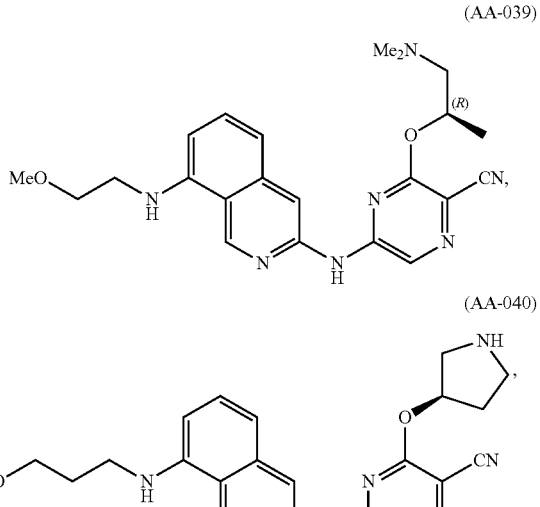
(AA-040)
(AA-041)
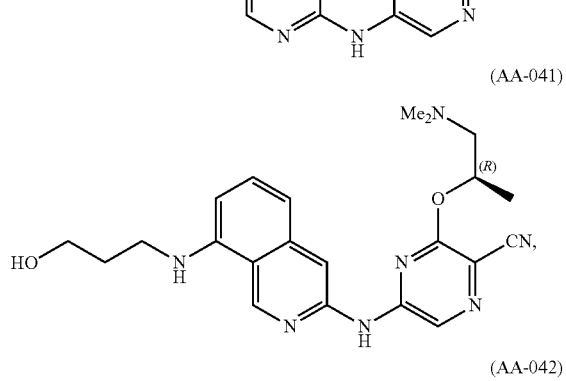
(AA-042)
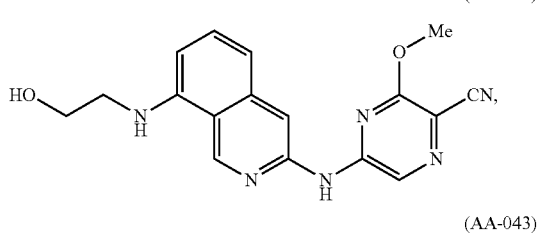
(AA-043)
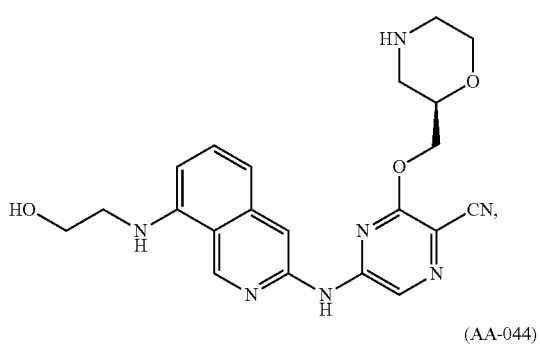
(AA-044)
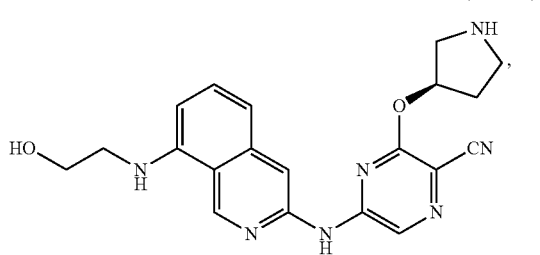

(AA-045)
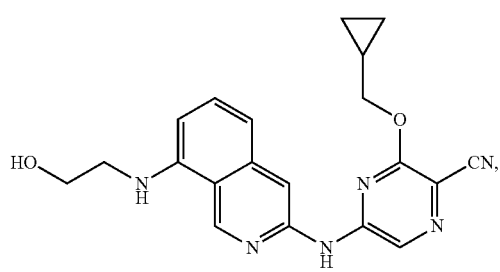
(AA-046)
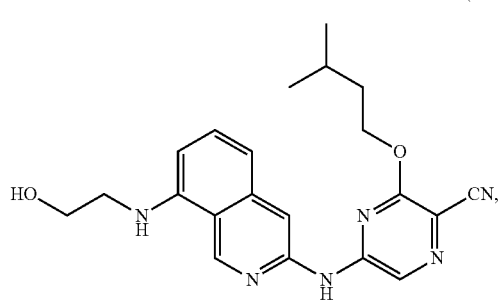
(AA-047)
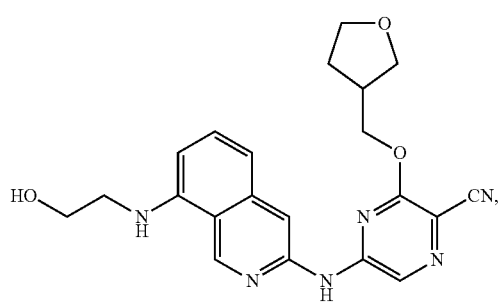
(AA-048)
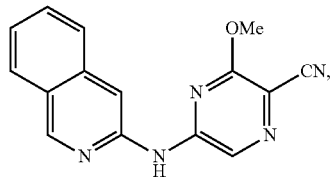
(AA-049)
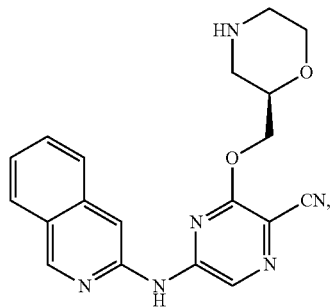
(AA-050)
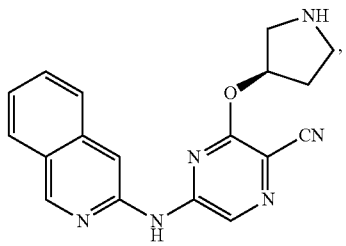
(AA-051)
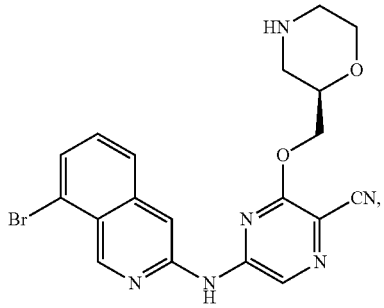
(AA-052)
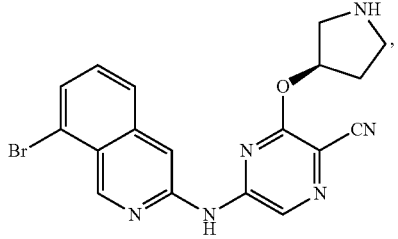
(AA-053)
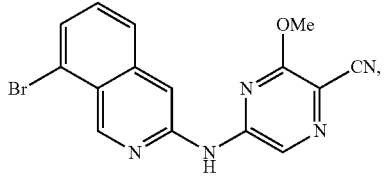
(AA-054)
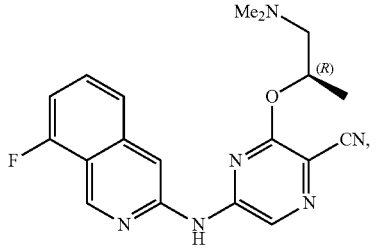
(AA-055)
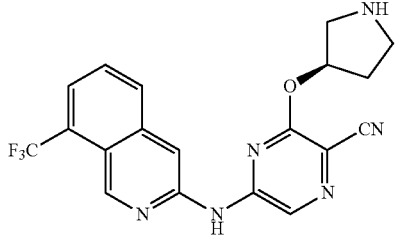

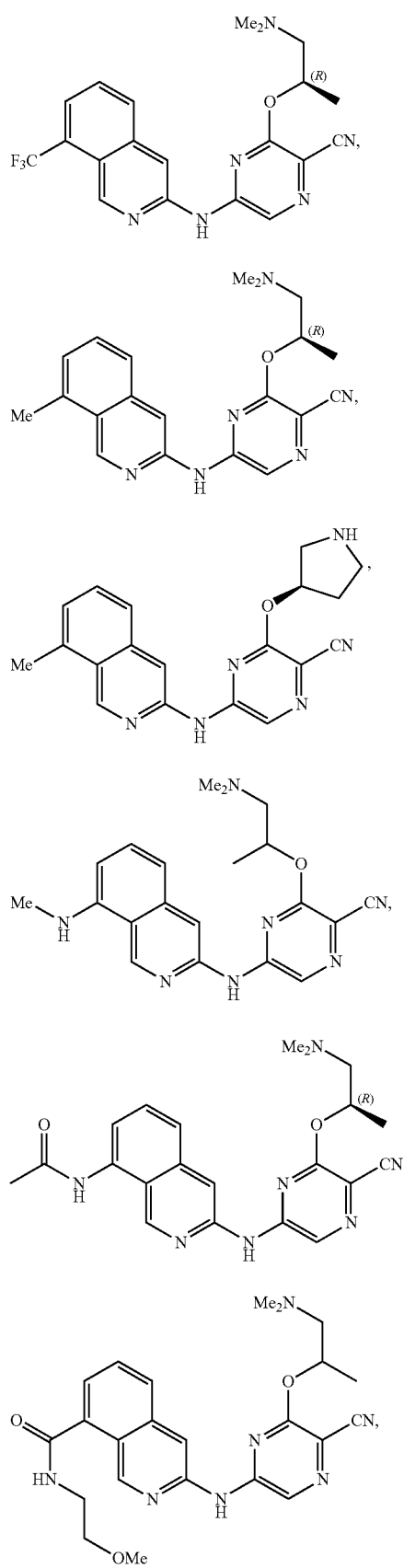
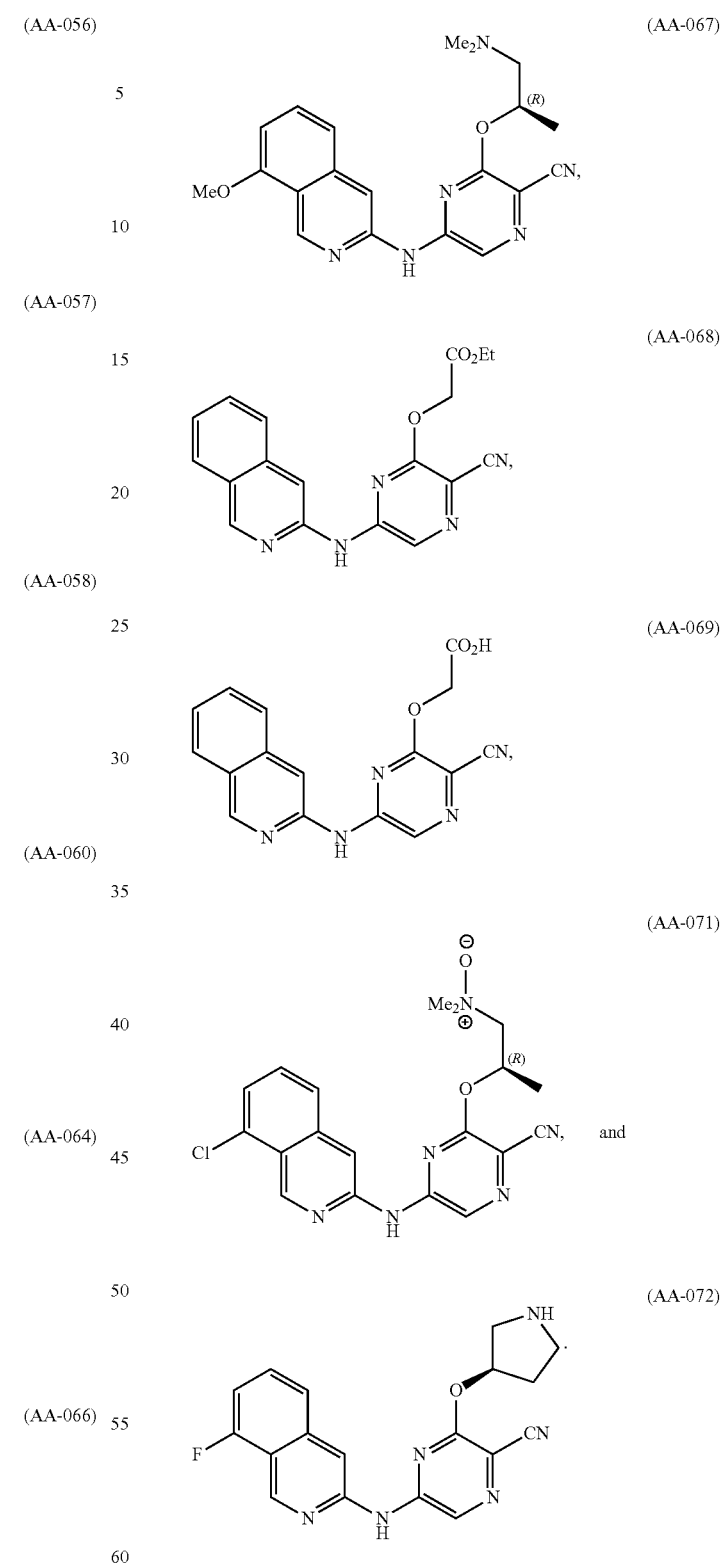
18. A compound according to claim 16, which is a compound selected from the following compounds, or a pharmaceutically acceptable salt thereof:

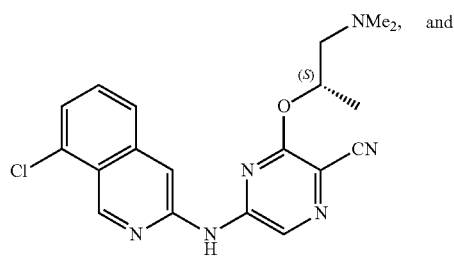
(AA-013)
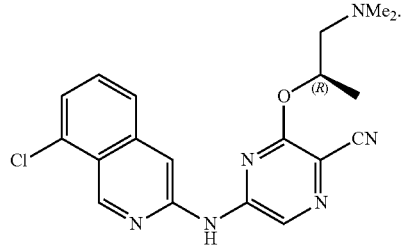
(AA-023)
19. A pharmaceutical composition comprising a compound according to claim 1, and a pharmaceutically acceptable carrier or diluent.